(12) United States Patent
Braithwaite et al.

(10) Patent No.: US 11,382,907 B2
(45) Date of Patent: *Jul. 12, 2022

(54) METHODS AND COMPOSITIONS FOR TREATING AGING-ASSOCIATED IMPAIRMENTS USING CCR3-INHIBITORS

(71) Applicant: Alkahest, Inc., San Carlos, CA (US)

(72) Inventors: Steven P. Braithwaite, Redwood City, CA (US); S. Sakura Minami, San Francisco, CA (US); Karoly Nikolich, Emerald Hills, CA (US)

(73) Assignee: Alkahest, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/945,664

(22) Filed: Apr. 4, 2018

(65) Prior Publication Data
US 2019/0105314 A1 Apr. 11, 2019

Related U.S. Application Data

(60) Provisional application No. 62/620,921, filed on Jan. 23, 2018, provisional application No. 62/560,940, filed on Sep. 20, 2017, provisional application No. 62/482,137, filed on Apr. 5, 2017.

(51) Int. Cl.
| | | |
|---|---|---|
| *A61K 31/4545* | (2006.01) | |
| *A61P 25/00* | (2006.01) | |
| *A61P 25/16* | (2006.01) | |
| *A61K 9/20* | (2006.01) | |
| *A61K 47/02* | (2006.01) | |
| *A61K 9/00* | (2006.01) | |
| *A61K 9/08* | (2006.01) | |
| *A61K 47/26* | (2006.01) | |
| *A61K 47/18* | (2017.01) | |
| *A61K 9/16* | (2006.01) | |
| *A61K 47/40* | (2006.01) | |
| *A61K 9/28* | (2006.01) | |
| *A61K 9/48* | (2006.01) | |

(52) U.S. Cl.
CPC ............ *A61K 31/4545* (2013.01); *A61K 9/00* (2013.01); *A61K 9/0004* (2013.01); *A61K 9/008* (2013.01); *A61K 9/0075* (2013.01); *A61K 9/08* (2013.01); *A61K 9/1617* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 9/2077* (2013.01); *A61K 9/2095* (2013.01); *A61K 9/2813* (2013.01); *A61K 9/2866* (2013.01); *A61K 9/4858* (2013.01); *A61K 47/02* (2013.01); *A61K 47/183* (2013.01); *A61K 47/26* (2013.01); *A61K 47/40* (2013.01); *A61P 25/00* (2018.01); *A61P 25/16* (2018.01)

(58) Field of Classification Search
CPC combination set(s) only.
See application file for complete search history.

(56) References Cited

U.S. PATENT DOCUMENTS

| | | | |
|---|---|---|---|
| 6,946,546 B2 | 9/2005 | Vaughan et al. | |
| 8,278,302 B2 * | 10/2012 | Grundl | A61K 31/4523 514/237.2 |
| 8,680,280 B2 | 3/2014 | Duran et al. | |
| 8,742,115 B2 * | 6/2014 | Frank | C07D 211/58 546/193 |
| 2002/0151064 A1 | 10/2002 | Rothenberg et al. | |
| 2004/0254152 A1 | 12/2004 | Monje et al. | |
| 2005/0142101 A1 | 5/2005 | Forssmann et al. | |
| 2006/0094064 A1 | 5/2006 | Ray et al. | |
| 2007/0155725 A1 | 7/2007 | Li et al. | |
| 2007/0190055 A1 | 8/2007 | Ambati | |
| 2008/0026485 A1 | 1/2008 | Hueber et al. | |
| 2008/0057590 A1 | 3/2008 | Urdea et al. | |
| 2010/0261687 A1 | 10/2010 | Grundl et al. | |
| 2010/0310609 A1 | 12/2010 | Watson et al. | |
| 2012/0264729 A1 | 10/2012 | Frank et al. | |
| 2013/0261153 A1 | 10/2013 | Nivens et al. | |

(Continued)

FOREIGN PATENT DOCUMENTS

| | | |
|---|---|---|
| JP | 2012-514024 A | 6/2012 |
| JP | 2012-524790 A | 10/2012 |

(Continued)

OTHER PUBLICATIONS

Britschgi et al., "Blood Protein Signature for the Early Diagnosis of Alzheimer Disease," Arch Neural., 2009, 66(2), 161-165.
Manzo et al., "Role of Chemokines and Chemokine Receptors in Regulating Specific Leukocyte Trafficking in the Immune/Inflammatory Response," Clinical and Experimental Rheumatology, 2003, 21, 501-508. (Year: 2003).
Palop et al., "A Network Dysfunction Perspective on Neurodegenerative Diseases," Nature, 2006 ,443, 768-773 (Year: 2006).
Prakasam et al., "Amyloid and Neurodegeneration: Alzheimer's Disease and Retinal Degeneration," Chapter 7, Handbook of Neurochemistry and Molecular Neurobiology, Lajtha ed., 2009, 131-163. (Year: 2009).

(Continued)

*Primary Examiner* — Shobha Kantamneni
(74) *Attorney, Agent, or Firm* — Mandar A. Joshi; Bret E. Field; Bozicevic, Field & Francis LLP

(57) ABSTRACT

Methods of improving neurodegenerative disease with CCR3 modulating agents are provided. The methods include administering a therapeutically effective amount of the CCR3 modulating agent to the subject, with a concomitant improvement in cognition, motor, or other neurodegenerative-affected function. Cognitive and motor diseases upon which the methods of the invention can improve cognition include Alzheimer's disease, Parkinson's disease, frontotemporal dementia, Huntington's disease, amyotrophic lateral sclerosis, multiple sclerosis, glaucoma, myotonic dystrophy, vascular dementia, progressive supranuclear palsy.

16 Claims, 34 Drawing Sheets

(56) References Cited

U.S. PATENT DOCUMENTS

| | | | |
|---|---|---|---|
| 2013/0261553 A1 | 10/2013 | Nivens et al. | |
| 2013/0266646 A1 | 10/2013 | Fetscher et al. | |
| 2015/0105371 A1 | 4/2015 | Frank et al. | |
| 2016/0208011 A1* | 7/2016 | Wyss-Coray | C12Q 1/6883 |
| 2017/0319567 A1 | 11/2017 | Nivens et al. | |

FOREIGN PATENT DOCUMENTS

| | | |
|---|---|---|
| JP | 2013-542207 A | 11/2013 |
| JP | 2015-512433 A | 4/2015 |
| WO | WO2005090330 A1 | 9/2005 |
| WO | WO2005106492 A2 | 11/2005 |
| WO | WO2006133423 A1 | 12/2006 |
| WO | WO2007102769 A2 | 9/2007 |
| WO | WO2009055729 A1 | 4/2009 |
| WO | WO2011115836 A1 | 10/2010 |
| WO | WO2018187473 A1 | 10/2018 |
| WO | WO2018187503 A1 | 10/2018 |

OTHER PUBLICATIONS

Royer et al., "A novel antagonist of prostaglandin D2 blocks the locomotion of eosinophils and basophils." Eur J Clin nvesl. Sep. 2008;38(9):663-71.

Sellebjerg et al., "Identification of new sensitive biomarkers for the in vivo response to interferon-beta treatment in multiple sclerosis using DNA-array evaluation." European J. of Neurology (Dec. 2009), 16(12):1291-8.

Shin et al., "Association of Eotaxin Gene Family with Asthma and Serum Total IgE," Human Molecular Genetics (Jun. 2003), 12(11):1279-85.

Skovronsky et al., "Neurodegenerative Diseases: New Concepts of Pathogenesis and their Therapeutic Implications," Annual Review of Pathology: Mechanisms of Disease, 2006, 1, 151-170. (Year: 2006).

Strobel et al., "Chicago: The Vampire Principle—Young Blood Rejuvenates Aging Brain?" Alzheimer Research Forum (Nov. 2009), p. 1-3.

Stubbs et al., "Indomethacin causes prostaglandin D(2)-like and eotaxin-like selective responses in eosinophils and basophils." J Biol Chem. Jul. 19, 2002;277(29):26012-20.

Teixeira et al., "Increased serum levels CCL11/eotaxin in schizophrenia," Process in Neuro-Psychopharmacology & Biological Psychiatry (Apr. 2008), 32(3):710-4.

Villeda et al., "Changes in the Systemic Milieu Modulate Neurogenesis During Aging," Abstract, 39th Annual Neuroscience Meeting, Society for Neuroscience, Chicago, IL, 2009, 1-2. (Year: 2009).

Wilson et al., "Beta2-microglobulin as a biomarker in peripheral arterial disease: proteomic profiling and clinical studies." Circulation (Sep. 2007), 116(12):1396-403.

Ye et al., "Haptoglobin-alpha subunit as potential serum biomarker in ovarian cancer: identification and characterization using proteomic profiling and mass spectrometry." Clinical Cancer Research (Aug. 2003), 9(8):2904-11.

Zhang et al., High-Content Genome-Wide RNAi Screen Reveals CCR3 as a Key Mediator of Neuronal Cell Death. eNeuro, Oct. 7, 2016, vol. 3, No. 5, e0185-16.2016, pp. 1-13.

Banisadr et al., Chemokines and Brain Functions, Current Drug Targets—Inflammation & Allergy, 2005, 4, 387-399.

\* cited by examiner

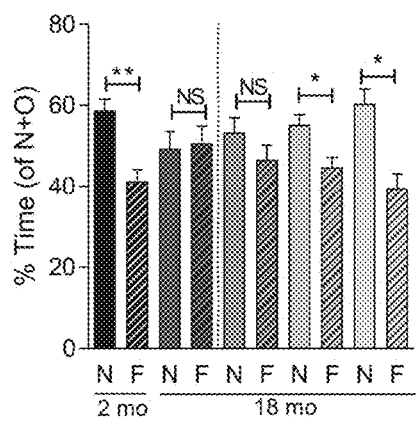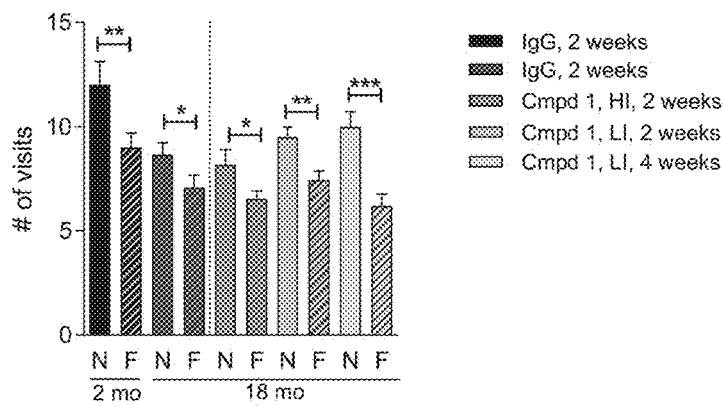
Figure 2A
Figure 2B

Figure 7

| Tissue | AUC$_{(0-168h)}$ (nmol·h/kg) |
|---|---|
| Data determined by QWBA | |
| Adrenal glands | 34128 |
| Blood | 17120 |
| Bone marrow | 22590 |
| Brain | <LOQ |
| Epididymis | 105032 |
| Fat (brown) | 73689 |
| Fat (white) | 67348 |
| Harderian Gland | 562921 |
| Kidney (cortical) | 110093 |
| Kidney (medullary) | 81568 |
| Liver | 282564 |
| Lung | 22893 |
| Muscle | 8028 |
| Pituitary | 28023 |
| Pancreas | 70076 |
| Prostate | 8758 |
| Spleen | 20446 |
| Salivary Gland | 54131 |
| Skin | 11086 |
| Spinal Cord | <LOQ |
| Testis | 15715 |
| Thyroid | 44579 |
| Thymus | 15201 |
| Uveal Tract | 2040984 |
| Data Determined by LSC | |
| Blood | 11462 |
| Plasma | 11699 |
| Eye | 722613 |

LOQ = Below the limit of quantification

Figure 30A

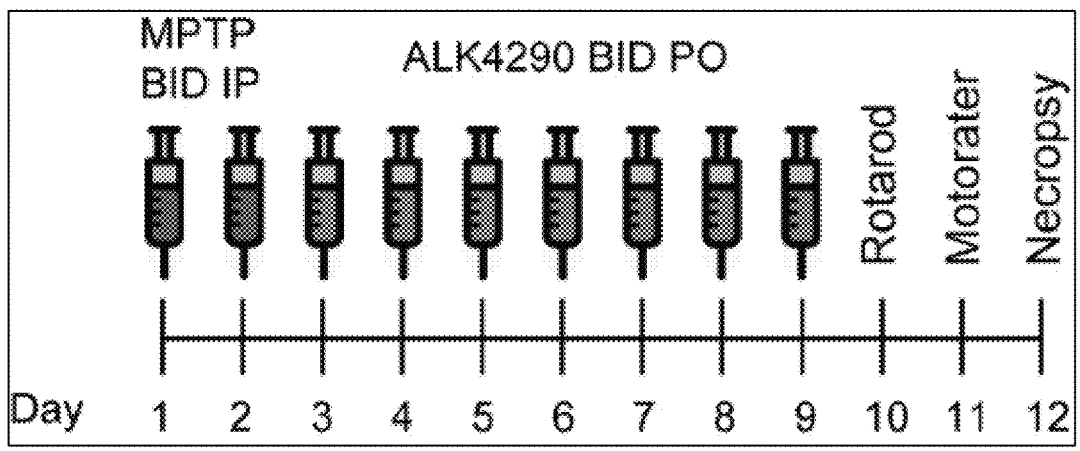

Figure 30B

| Outcome measure | Assay |
|---|---|
| Motor function (gross) | Rotarod |
| Motor function (fine) | Motorater |
| Transporter levels (DA, DOPAC, HVA), striatum | HPLC |
| TH-positive cells, substantia nigra | IHC, stereology |
| CD4+ and CD8+ T cell infiltration, substantia nigra | IHC |
| Eosinophil infiltration, substantia nigra | IHC |
| CD68+ and GFAP+ gliosis, substantia nigra | IHC |
| Cytokine and chemokine levels, plasma | Luminex |
| Eosinophil counts, blood | FACS |

Figure 32

| Outcome measure | Assay |
|---|---|
| Motor function (gross) | Rotarod |
| Motor function (fine) | Pasta Gnawing |
| Motor function (strength) | Wire suspension |
| Motor function (gross) | Beam walk |
| Motor function (ADL) | Nest building |
| CD4+ and CD8+ T cell infiltration, substantia nigra | IHC |
| Eosinophil infiltration, substantia nigra | IHC |
| CD68+ and GFAP+ gliosis, substantia nigra | IHC |
| Synuclein levels, striatum and hippocampus | IHC |
| Cytokine and chemokine levels, substantia nigra | Luminex |
| Cytokine and chemokine levels, plasma | Luminex |
| Eosinophil counts, blood | FACS |

METHODS AND COMPOSITIONS FOR TREATING AGING-ASSOCIATED IMPAIRMENTS USING CCR3-INHIBITORS

I. CROSS-REFERENCE TO RELATED APPLICATIONS

Pursuant to 35 U.S.C. § 119 (e), this application claims priority to the filing dates of: U.S. Provisional Patent Application No. 62/482,137, filed Apr. 5, 2017; U.S. Provisional Patent Application No. 62/560,940, filed Sep. 20, 2017; and U.S. Provisional Patent Application No. 62/620,921, filed Jan. 23, 2018; the disclosures of which applications are herein incorporated by reference.

II. INTRODUCTION

The following is offered as background information only and is not admitted to be prior art to the present invention.

Aging is an important risk factor for multiple human diseases including cognitive impairment, cancer, arthritis, vision loss, osteoporosis, diabetes, cardiovascular disease, and stroke. In addition to normal synapse loss during natural aging, synapse loss is an early pathological event common to many neurodegenerative conditions and is the best correlate to the neuronal and cognitive impairment associated with these conditions. As such, aging remains the single most dominant risk factor for dementia-related neurodegenerative diseases such as Alzheimer's disease (AD) (Bishop, N. A. et al., Neural mechanisms of ageing and cognitive decline. Nature 464(7288), 529-535 (2010); Heeden, T. et al., Insights into the ageing mind: a view from cognitive neuroscience. Nat. Rev. Neurosci. 5(2), 87-96 (2004); Mattson, M. P., et al., Ageing and neuronal vulnerability. Nat. Rev. Neurosci. 7(4), 278-294 (2006)). Aging affects all tissues and functions of the body including the central nervous system, and a decline in functions such as cognition and motor activity can severely impact quality of life.

Treatment for cognitive and motor decline associated with neurodegeneration has achieved limited success in preventing and reversing impairment. It is therefore important to identify new treatments for maintaining cognitive integrity by protecting against, countering, or reversing the effects of aging. Unfortunately, drug treatments for cognitive and motor impairment face significant hurdles. For example, it is thought that for treatments such as small molecules to be effective in treating cognitive decline and motor activity, they must cross the blood-brain barrier (BBB). Transport across the BBB is the exception not the rule, and 98% of all small molecules do not cross it. (Pardridge, William M, *The Blood-Brain Barrier. Bottleneck in Brain Drug Development*, NeuroRx: The J. of the Am. Society for Experimental NeuroTherapeutics, 2:3-14, 2005). As a result, therapies for neurodegenerative diseases, such as Alzheimer's disease, Huntington's disease, Parkinson's disease, and amyotrophic lateral sclerosis (ALS), are limited; in fact, Alzheimer's has one of the highest failure rates for clinical development of any disease area (99.6% failure in the last 20 years). (Id.; and Burke, M., *Renewed focus on dementia checked by drug challenges*, ChemistryWorld, Jul. 3, 2014). Those BBB-permeable drugs that are approved for treatment of cognitive disease like Alzheimer's, such as donepezil, exhibit temporary effects and do not work on all patients. (Banks, W. A., *Drug Delivery to the Brain in Alzheimer's Disease. Consideration of the Blood-brain Barrier*, Adv. Drug. Deliv. Rev. 64(7):629-39 (2012); and Burke, M. supra). Similarly, levodopa which treats Parkinson's disease symptoms like motor deficits and crosses the BBB, eventually loses its efficacy. An additional hurdle for treatments that do cross the BBB is that making compounds more lipophilic (which tends to make them more BBB-penetrating) also often results in increased removal from the blood, leading to decreased bioavailability. Hence, the increase in lipophilicity offsets the plasma area under the curve (AUC), minimizing brain uptake. (Pardridge, William M, supra).

III. SUMMARY

The present invention overcomes these drawbacks. For example, Compound 1, a compound of the invention, has exhibited resistance in crossing the BBB in significant concentrations yet unexpectedly results in improvement of symptoms associated with age-related neurodegeneration and age-related motor decline. Thus, the present invention can act in a peripheral manner, forgoing what was considered to be a requirement for effective cognitive-acting pharmaceuticals, i.e. to work directly on central nervous system. And although certain embodiments of the invention may cross the BBB in significant concentrations, their ability to antagonize the CCL11/CCR3 pathway offers an alternative mechanism of action to current therapy for cognitive and motor defects.

The compounds of the invention act as antagonists of c-c motif chemokine receptor 3 (CCR3), the receptor for Eotaxin-1. Eotaxin-1 (CCL11) is a protein that is increased in levels in blood plasma with aging and which has been shown to cause decreases in cognitive function. (Villeda et al., *The aging systemic milieu negatively regulates neurogenesis and cognitive function*, Nature, 477(7362):90-94 (2011)). Eotaxin/CC11 acts primarily on the G-protein coupled receptor CCR3 which is expressed on eosinophils in the periphery and on neurons and glial cells in the central nervous system. (Xia, M, et al., *Immunohistochemical Study of the β-Chemokine Receptors CCR3 and CCR5 and Their Ligands in the Normal and Alzheimer's Disease Brains*, Am. J. Pathol. 153(1); 31-37 (1998)). In Alzheimer's disease, it has been observed that CCR3 levels are increased in the CNS. (Id.) The cognitive effects of antagonizing CCR3 in Alzheimer's disease and related disorders would thus be expected to be mediated by centrally located eotaxin-1/CCR3 interaction. However, Compound 1 (a compound of the invention), unexpectedly resulted in improving cognitive function and stimulating neurogenesis despite its inability to cross the BBB in significant concentrations.

Methods of treating patients for aging-associated impairments, neurodegenerative disease and associated cognitive and motor decline are provided, including by way of example and not limitation, Alzheimer's disease, Parkinson's disease, Dementia with Lewy Bodies, frontotemporal dementia, Huntington disease, amyotrophic lateral sclerosis, multiple sclerosis, glaucoma, myotonic dystrophy, vascular dementia, progressive supranuclear palsy, and the like. Aspects of the methods include modulation of CCR3, the principal receptor of CCL11/eotaxin-1 through the administration of a therapeutically effective amount of CCR3 antagonists of the invention. The methods include administering an effective therapeutic dose of CCR3 antagonists to subjects or patients as well as monitoring for specific clinical endpoints. Also included are methods of treating neurodegenerative disease and associated cognitive and motor decline with an agent that acts peripherally, i.e. does not cross the blood-brain barrier in significant concentrations, yet exhibits improvement in the disease, such as improved cognition or motor activity.

IV. INCORPORATION BY REFERENCE

All publications, patents and patent applications mentioned in this specification are herein incorporated by reference to the same extent as if each individual publication or patent application was specifically and individually indicated to be incorporated by reference.

V. BRIEF DESCRIPTION OF THE FIGURES

FIG. 1A depicts the sum of doublecortin (DCX) positive cells in the hippocampus of: 2-month-old and 18-month-old C57Bl/6 mice treated with IgG (n=18 for both groups); 18-month-old mice treated with Compound 1 for 2 weeks at either a high (n=16) or low dose (n=31); and 18-month-old mice treated with Compound 1 ("Cmpd 1") for 4 weeks at a low dose (n=16). Data shown are the mean±s.e.m., where *P<0.05, ***P<0.001.

FIG. 1B depicts the sum of 5-bromo-2'-deoxyuridine (BrdU) positive cells in the hippocampus of: 2-month-old and 18-month-old C57Bl/6 mice treated with IgG (n=19 for both groups); 18-month-old mice treated with Compound 1 for 2 weeks at either a high (n=16) or low dose (n=24). Data shown are the mean±s.e.m., where ***P<0.001.

FIG. 2A depicts the effect of Compound 1 on the time spent by young and old C57Bl/6 mice in the novel (N) versus familiar/old ("F" or "O") arm during a Y-maze test. 2-month-old mice were treated for 2 weeks with IgG (n=18). 18-month-old mice were treated with: IgG for 2 weeks (n=18); Compound 1 at a high dose for 2 weeks (n=15); Compound 1 at a low dose for 2 weeks (n=31); or Compound 1 at a low dose for 4 weeks (n=16). Data shown are the mean±s.e.m., where P<0.05, *P<0.01

FIG. 2B depicts the effect of Compound 1 on the total number of visits made by young and old C57Bl/6 mice into the novel (N) versus familiar (F) arm during a Y-maze test. 2-month-old mice were treated for 2 weeks with IgG (n=18). 18-month-old mice were treated with: IgG for 2 weeks (n=18); Compound 1 at a high dose for 2 weeks (n=15); Compound 1 at a low dose for 2 weeks (n=31); or Compound 1 at a low dose for 4 weeks (n=16). Data shown are the mean±s.e.m., where *P<0.05, P<0.01, *P<0.001.

FIG. 3 depicts the effect of Compound 1 on bouts of entry ("number of visits") into the novel and familiar arms by C57Bl/6 mice in the Y-maze test. The number of visits to each arm was plotted for each treatment group and subjected to paired t-test. 3-month-old mice (n=15) received an infusion of vehicle (veh) subcutaneously by Alzet mini-pump (0.5 µL/hour) for four weeks, with one replacement. 16.5-month-old mice were infused subcutaneously with either vehicle (veh, n=16) or 50 mg/mL Compound 1 (n=16) by Alzet mini-pump (0.5 µL/hour) for four weeks with one replacement. Data shown are mean±s.e.m.; *P<0.05.

FIG. 4A depicts the effect of Compound 1 on average time taken by C57Bl/6 mice to find the target hole in the Barnes Maze test. Average times were plotted for each treatment group. 3-month-old mice (n=18) received an infusion of vehicle (veh) subcutaneously by Alzet mini-pump (0.5 µL/hour) for four weeks, with one replacement. 16.5-month-old mice were infused subcutaneously with either vehicle (veh, n=15) or 50 mg/mL Compound 1 (n=15) by Alzet mini-pump (0.5 µL/hour) for four weeks with one replacement. Data shown are mean±s.e.m.

FIG. 4B depicts the effect of Compound 1 on the difference in latency to find the target hole between the last and first trial of the last day of the Barnes Maze test in C57Bl/6 mice. The differences were plotted for each treatment group and the data subjected to an unpaired t-test. 3-month-old mice (n=18) received an infusion of vehicle (veh) subcutaneously by Alzet mini-pump (0.5 µL/hour) for four weeks, with one replacement. 16.5-month-old mice were infused subcutaneously with either vehicle (veh, n=15) or 50 mg/mL Compound 1 (n=15) by Alzet mini-pump (0.5 µL/hour) for four weeks with one replacement. Data shown are mean±s.e.m.

FIG. 5 depicts the effect of Compound 1 on neurogenesis in C57Bl/6 mice by detection of BrdU positive cells from all sections in the dentate gyrus. The number of cells positive for BrdU from the dentate gyrus were plotted for each treatment group and the data subjected to an unpaired t-test between the 16.5-month-old groups. 3-month-old mice (n=17) received an infusion of vehicle (veh) subcutaneously by Alzet mini-pump (0.5 µL/hour) for four weeks, with one replacement. 16.5-month-old mice were infused subcutaneously with either vehicle (veh, n=17) or 50 mg/mL Compound 1 (n=17) by Alzet mini-pump (0.5 µL/hour) for four weeks with one replacement. Data shown are mean±s.e.m.; *P<0.05.

FIG. 7 depicts the distribution (measured as area under the curve (AUC)) of Compound 1 in C57BL/6JOlaHsd mouse tissues over a time course. Compound was tagged with carbon-14 label, and measurements taken at 1, 24, and 168 hours.

Figure 8:
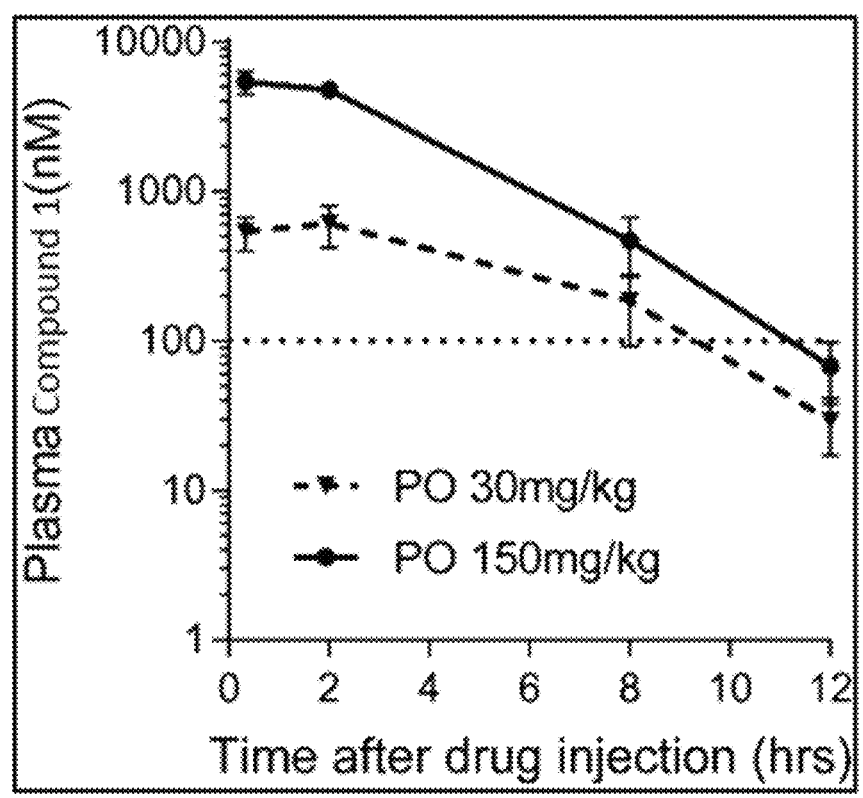

FIG. 8 depicts the pharmacokinetic profiles of Compound 1 after per os (P.O.) dosing. Blood plasma from male 2-month-old C57Bl/6 mice receiving either 30 mg/kg or 150 mg/kg by oral gavage was measured for Compound 1 at 20 minutes, 2 hours, 8 hours, and 12 hours after administration. Plasma concentration after drug administration was plotted over time.

Figure 9:
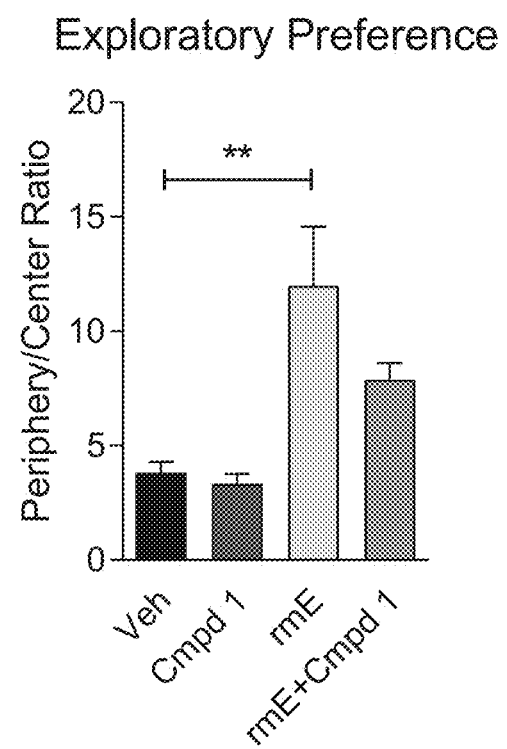

FIG. 9 depicts the effect of Compound 1 on exploratory preference during the Open Field test in young C57Bl/6 mice. Exploratory preference was plotted as the ratio of time spent in the periphery vs. center and data was subjected to a one-way ANOVA. 2-month-old mice were treated with: vehicle p.o. b.i.d. (n=1); Compound 1 p.o. b.i.d. 30 mg/kg (n=12); vehicle p.o. b.i.d. plus recombinant mouse CCL11 (eotaxin-1, or "rmE") i.p. (n=14); or Compound 1 p.o. b.i.d. 30 mg/kg plus recombinant mouse CCL11 (n=14). Data shown are mean±s.e.m.; **P<0.01.

Figure 10A:
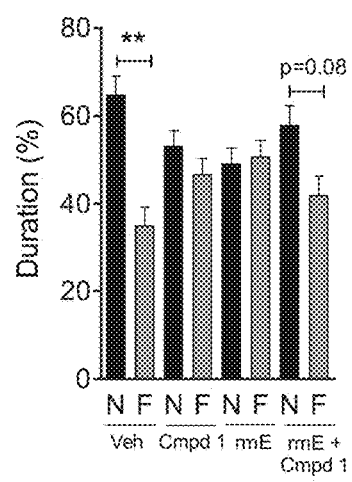

FIG. 10A depicts the effect of Compound 1 on the time spent in the novel versus familiar arms of the Y-maze test in young C57Bl/6 mice. The time spent in the novel versus familiar arms were plotted for each treatment group and data was subjected to a paired t-test. 2-month-old mice were treated with: vehicle p.o. b.i.d. (n=13); Compound 1 p.o. b.i.d. 30 mg/kg (n=14); vehicle p.o. b.i.d. plus recombinant mouse CCL11 (eotaxin-1) i.p. (n=15); or Compound 1 p.o. b.i.d. 30 mg/kg plus recombinant mouse CCL11 (n=15). Data shown are mean±s.e.m.; **P<0.01.

Figure 10B:
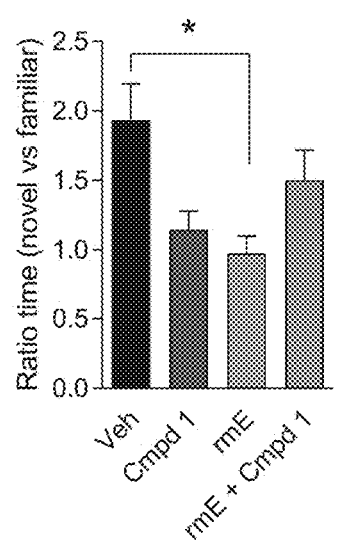

FIG. 10B depicts the effect of Compound 1 on the ratio of time spent in the novel versus familiar arm of the Y-maze test in young C57Bl/6 mice. Ratios were plotted for each treatment group and data was subjected to an ANOVA Kruskal-Wallis test post-hoc. 2-month-old mice were treated with: vehicle p.o. b.i.d. (n=12); Compound 1 p.o. b.i.d. 30 mg/kg (n=14); vehicle p.o. b.i.d. plus recombinant mouse CCL11 (eotaxin-1) i.p. (n=15); or Compound 1 p.o. b.i.d. 30 mg/kg plus recombinant mouse CCL11 (n=15). Data shown are mean±s.e.m.; *P<0.05.

Figure 10C:
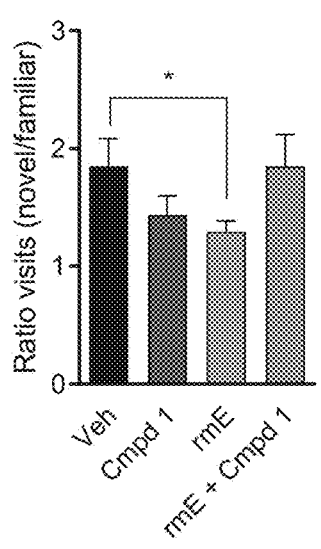

FIG. 10C depicts the effect of Compound 1 on the ratio of number of entries made into the novel versus familiar arm of the Y-maze test in young C57Bl/6 mice. Ratios were plotted for each treatment group and data was subject to a t-test between vehicle and recombinant mouse CCL11 treatment. 2-month-old mice were treated with: vehicle p.o. b.i.d. (n=13); Compound 1 p.o. b.i.d. 30 mg/kg (n=14); vehicle p.o. b.i.d. plus recombinant mouse CCL11 (eotaxin-1) i.p. (n=15); or Compound 1 p.o. b.i.d. 30 mg/kg plus recombinant mouse CCL11 (n=15). Data shown are mean±s.e.m.; *P<0.05.

Figure 11A:
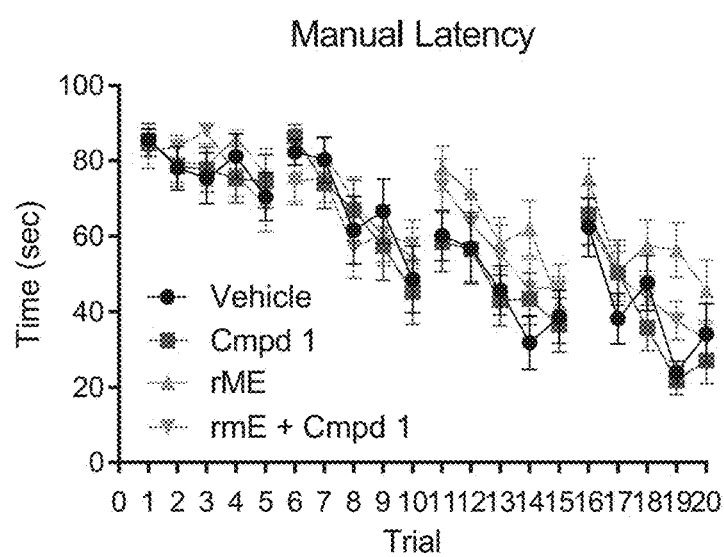

FIG. 11A depicts the effect of Compound 1 on the average latency to find the target hole during the Barnes Maze test in young C57Bl/6 mice. Average latencies were plotted as units of time for each treatment group on each trial. 2-month-old mice were treated with: vehicle p.o. b.i.d. (n=13); Compound 1 p.o. b.i.d. 30 mg/kg (n=14); vehicle p.o. b.i.d. plus recombinant mouse CCL11 (eotaxin-1) i.p. (n=15); or Compound 1 p.o. b.i.d. 30 mg/kg plus recombinant mouse CCL11 (n=15). Data shown are mean±s.e.m.

Figure 11B:
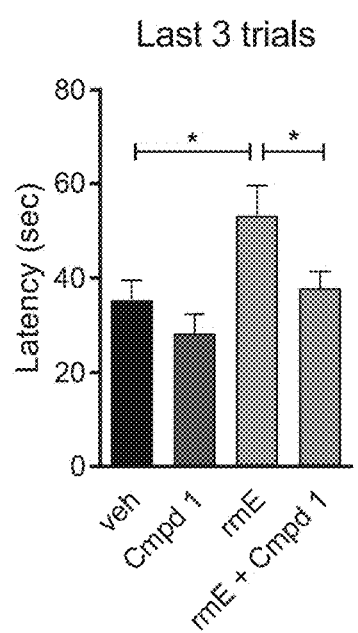

FIG. 11B depicts the effect of Compound 1 on the latency to find the target hole during the Barnes Maze test in young C57Bl/6 mice. Latencies averaged over the last three trials for each treatment group were plotted and data was subjected to an unpaired t-test. 2-month-old mice were treated with: vehicle p.o. b.i.d. (n=13); Compound 1 p.o. b.i.d. 30 mg/kg (n=14); vehicle p.o. b.i.d. plus recombinant mouse CCL11 (eotaxin-1) i.p. (n=15); or Compound 1 p.o. b.i.d. 30 mg/kg plus recombinant mouse CCL11 (n=15). Data shown are mean±s.e.m.; *P<0.05.

Figure 12A:
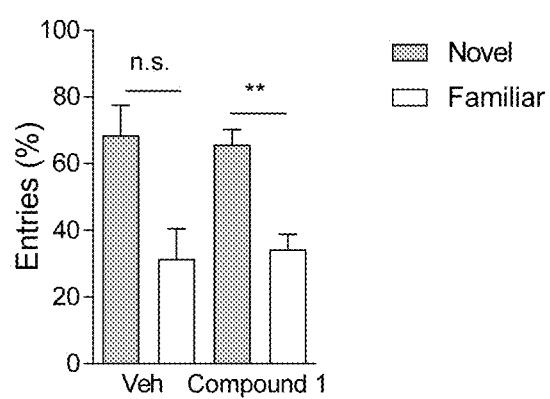

FIG. 12A depicts the effect of Compound 1 on memory for the novel arm in the Y maze, by number of entries made into the novel arm over the total entries. 24 month old mice were treated with Compound 1 p.o. b.i.d. 30 mg/kg or vehicle. Data shown are mean±s.e.m.; **P<0.01.

Figure 12B:
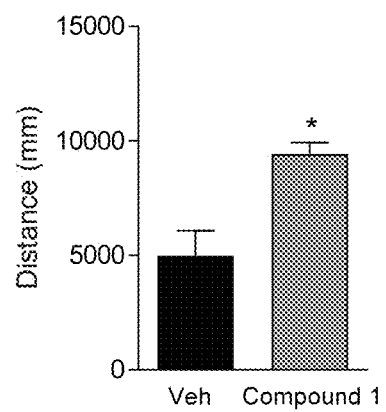

FIG. 12B depicts the effect of Compound 1 on total distance travelled in the Y maze, as a measure of locomotor activity. 24 month old mice were treated with Compound 1 p.o. b.i.d. 30 mg/kg or vehicle. Data shown are mean±s.e.m.; *P<0.05.

Figure 13A:
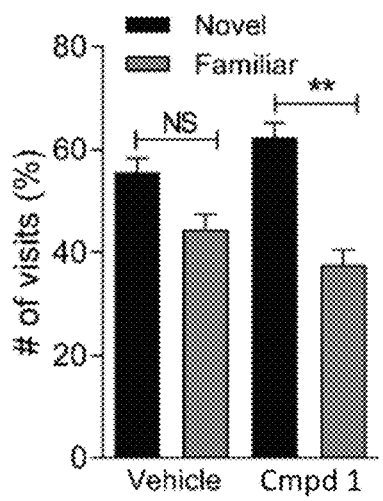

FIG. 13A depicts the effect of Compound 1 on bouts of entry ("number of visits") into the novel and familiar arms by C57Bl/6 mice in the Y-maze test in 24-month-old mice. The number of visits to each arm was plotted for each treatment group and subjected to a paired t-test. Mice 23 months-old were dosed with either vehicle control or Compound 1 subcutaneously BID (twice daily) for 21 days. Three weeks later, mice were subjected to Y-maze testing. All mice received 5 consecutive days of BrdU injection at 50 mg/kg IP immediately prior to start of treatment. Data shown are mean±s.e.m.; *P<0.05, P<0.01, *P<0.001 novel vs familiar arm by paired student's t-test.

Figure 13B:
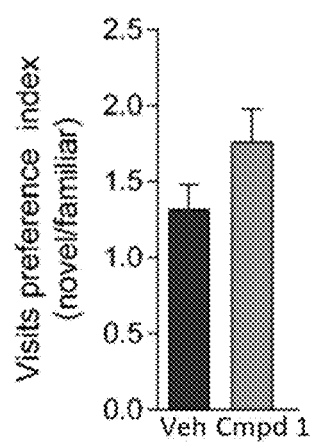

FIG. 13B depicts the effect of Compound 1 on the ratio of number of entries made into the novel versus familiar arm of the Y-maze test in 24-month-old mice. Ratios were plotted for each treatment group and data was subject to a t-test between vehicle and Compound 1 treatment. Mice 23 months-old were dosed with either vehicle control or Compound 1 subcutaneously BID (twice daily) for 21 days. Three weeks later, mice were subjected to Y-maze testing. All mice received 5 consecutive days of BrdU injection at 50 mg/kg IP immediately prior to start of treatment. Data shown are mean±s.e.m.; *P<0.05, P<0.01, *P<0.001 compared to control by student's t-test.

Figure 13C:
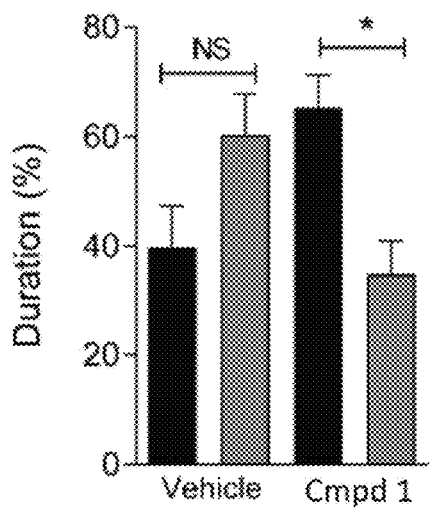

FIG. 13C depicts the effect of Compound 1 on the time spent in the novel versus familiar arms of the Y-maze test in 24-month-old C57Bl/6 mice. The time spent in the novel versus familiar arms were plotted for each treatment group and data was subjected to a paired t-test. Mice 23 months-old were dosed with either vehicle control or Compound 1 subcutaneously BID (twice daily) for 21 days. Three weeks later, mice were subjected to Y-maze testing. All mice received 5 consecutive days of BrdU injection at 50 mg/kg IP immediately prior to start of treatment. Data shown are mean±s.e.m.; *P<0.05, P<0.01, *P<0.001 novel vs familiar arm by paired student's t-test.

Figure 13D:
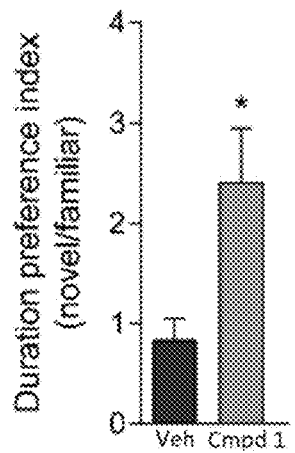

FIG. 13D depicts the effect of Compound 1 on the ratio of time spent ("duration") in the novel versus familiar arm of the Y-maze test in 24-month-old C57Bl/6 mice. Ratios were plotted for each treatment group and data was subjected to a t-test. Mice 23 months-old were dosed with either vehicle control or Compound 1 subcutaneously BID (twice daily) for 21 days. Three weeks later, mice were subjected to Y-maze testing. All mice received 5 consecutive days of BrdU injection at 50 mg/kg IP immediately prior to start of treatment. Data shown are mean±s.e.m.; *P<0.05, P<0.01, *P<0.001 compared to control by student's t-test.

Figure 13E:
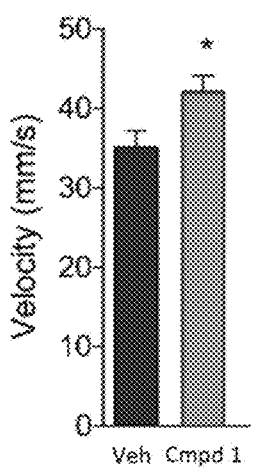

FIG. 13E depicts the effect of Compound 1 on the average velocity during the Y-Maze test of 24-month-old C57Bl/6 mice. Average velocities were plotted for each treatment group and data was subject to a t-test. Mice 23 months-old were dosed with either vehicle control or Compound 1 subcutaneously BID (twice daily) for 21 days. Three weeks later, mice were subjected to Y-maze testing. All mice received 5 consecutive days of BrdU injection at 50 mg/kg IP immediately prior to start of treatment. Data shown are mean±s.e.m.; *P<0.05, P<0.01, *P<0.001 compared to control by student's t-test.

Figure 14A:
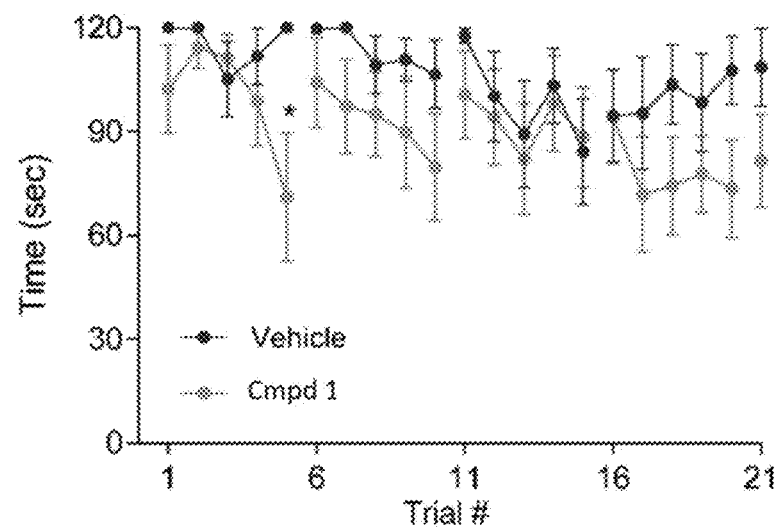

FIG. 14A depicts the effect of Compound 1 on average time taken by 24-month-old C57Bl/6 mice to find the target hole in the Barnes Maze test. Average times were plotted for each treatment group. Mice 23 months-old were dosed with either vehicle control or Compound 1 subcutaneously BID (twice daily) for 21 days. Three weeks later, mice were subjected to Barnes Maze testing. Data shown are mean±s.e.m.; *P<0.05 compared to control by student's t-test.

Figure 14B:
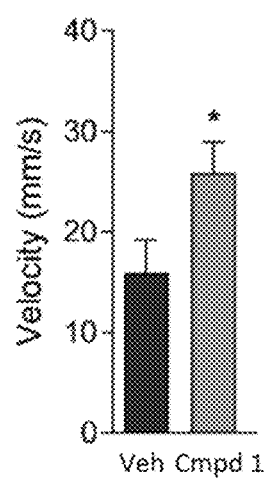

FIG. 14B depicts the effect of Compound 1 on velocity in 24-month-old C57Bl/6 mice in Barnes Maze test, averaged over all trials for each treatment group. Mice 23 months-old were dosed with either vehicle control or Compound 1 subcutaneously BID (twice daily) for 21 days. Three weeks later, mice were subjected to Barnes Maze testing. Data shown are mean±s.e.m.; *P<0.05 compared to control by student's t-test.

Figure 15A:
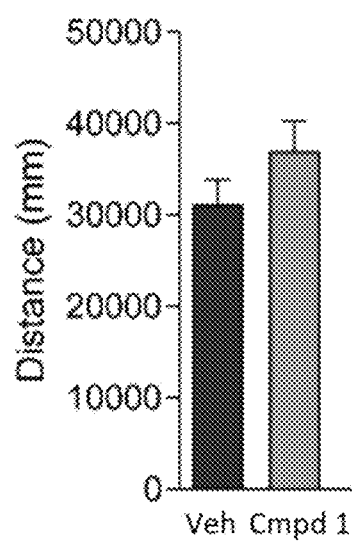

FIG. 15A depicts the effect of Compound 1 on distance traveled in the Open Field test in 24-month-old C57Bl/6 mice. Average distance traveled was plotted for each treatment group. Mice 23 months-old were dosed with either vehicle control or Compound 1 subcutaneously BID (twice daily) for 21 days. Three weeks later, mice were subjected to Open Field testing. Data shown are mean±s.e.m.

Figure 15B:
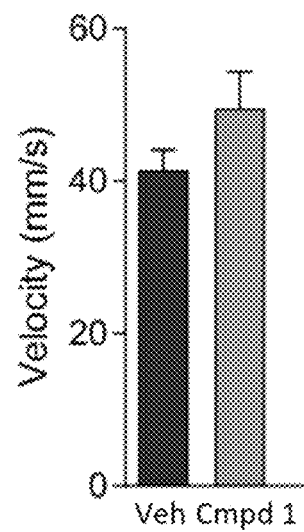

FIG. 15B depicts the effect of Compound 1 on velocity in the Open Field test in 24-month-old C57Bl/6 mice. Average velocity of the mice was plotted for each treatment group. Mice 23 months-old were dosed with either vehicle control or Compound 1 subcutaneously BID (twice daily) for 21 days. Three weeks later, mice were subjected to Open Field testing. Data shown are mean±s.e.m.

Figure 16A:
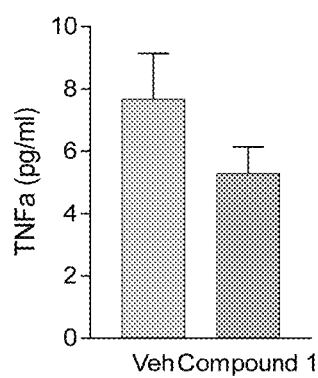

FIG. 16A depicts the effect of Compound 1 on TNFalpha cytokine levels in the plasma of 24-month-old C57Bl/6 mice. Mice 23 months-old were dosed with either vehicle control or Compound 1 subcutaneously BID (twice daily) for 21 days. Levels of the inflammatory cytokine trend lower in Compound 1 treated mice than in vehicle treated mice.

Figure 16B:
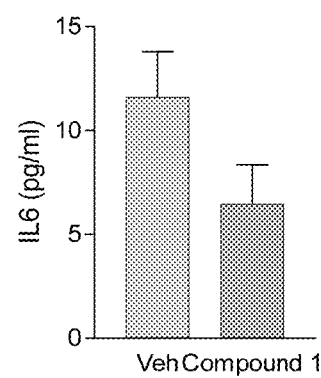

FIG. 16B depicts the effect of Compound 1 on IL6 cytokine levels in the plasma of 24-month-old C57Bl/6 mice. Mice 23 months-old were dosed with either vehicle control or Compound 1 subcutaneously BID (twice daily) for 21 days. Levels of the inflammatory cytokine trend lower in Compound 1 treated mice than in vehicle treated mice.

Figure 16C:
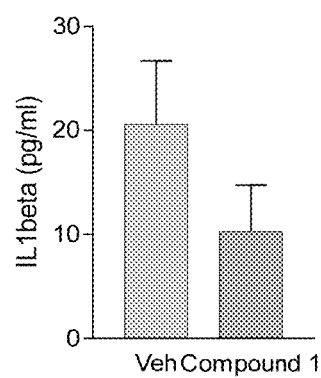

FIG. 16C depicts the effect of Compound 1 on IL1beta cytokine levels in the plasma of 24-month-old C57Bl/6 mice. Mice 23 months-old were dosed with either vehicle control or Compound 1 subcutaneously BID (twice daily) for 21 days. Levels of the inflammatory cytokine trend lower in Compound 1 treated mice than in vehicle treated mice.

Figure 16D:
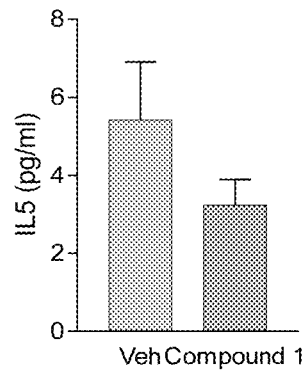

FIG. 16D depicts the effect of Compound 1 on IL5 cytokine levels in the plasma of 24-month-old C57Bl/6 mice. Mice 23 months-old were dosed with either vehicle control or Compound 1 subcutaneously BID (twice daily) for 21 days. Levels of the inflammatory cytokine trend lower in Compound 1 treated mice than in vehicle treated mice.

Figure 16E:
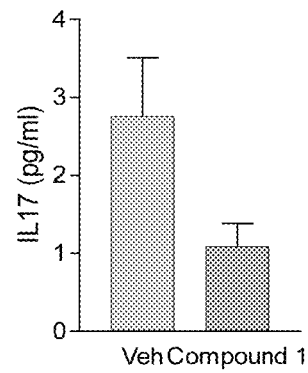

FIG. 16E depicts the effect of Compound 1 on IL17 cytokine levels in the plasma of 24-month-old C57Bl/6 mice. Mice 23 months-old were dosed with either vehicle control or Compound 1 subcutaneously BID (twice daily) for 21 days. Levels of the inflammatory cytokine trend lower in Compound 1 treated mice than in vehicle treated mice.

Figure 17:
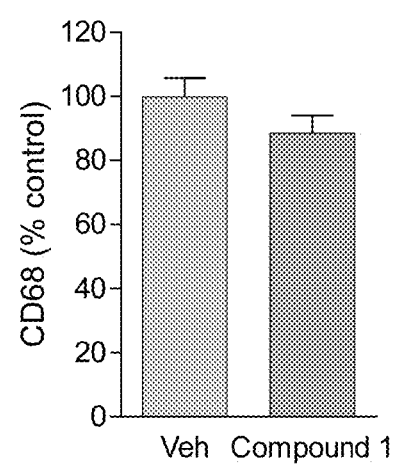

FIG. 17 depicts the effect of Compound 1 on activated microglia in 24-month-old C57Bl/6 mice. Mice 23 months-old were dosed with either vehicle control or Compound 1 subcutaneously BID (twice daily) for 21 days. Levels of CD68+ activated microglia trend lower in Compound 1 treated mice than in vehicle treated mice.

Figure 18:
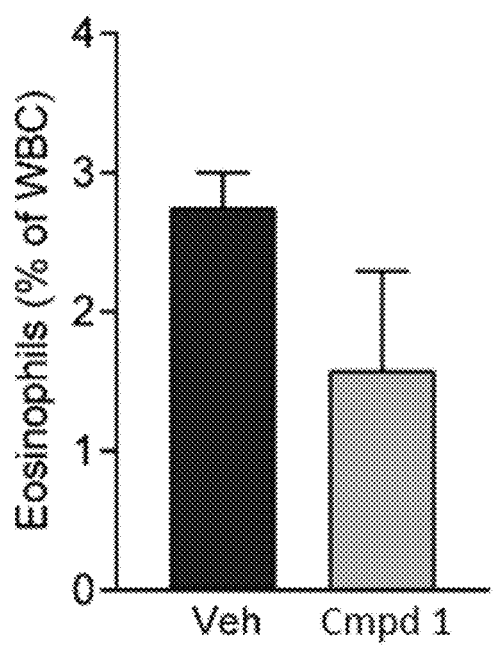

FIG. 18 depicts the effect of Compound 1 on the percentage of eosinophils in complete white blood cell (WBC) count, in 24-month-old C57Bl/6 mice treated with control saline or 30 mg/kg of Compound 1 for 3 weeks BID, SQ. Compound 1 decreased an endogenous age-related increase in blood eosinophils.

Figure 19:
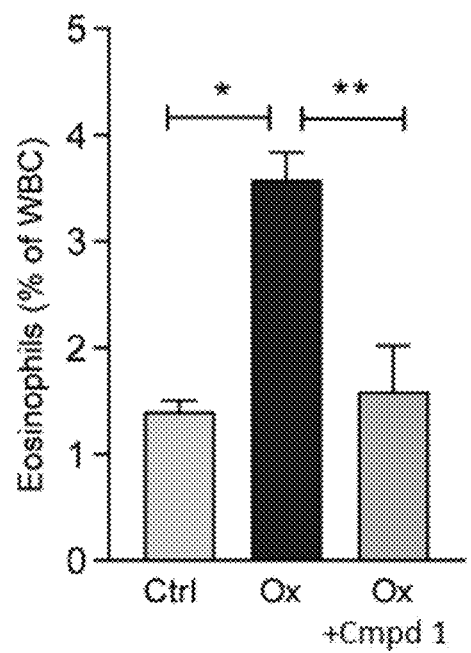

FIG. 19 depicts the effect of Compound 1 on the percentage of eosinophils in complete white blood cell (WBC) count, in 3-month-old hairless mice treated with control saline or 30 mg/kg of Compound 1 for 2 weeks BID, PO. Compound 1 decreased an oxazolone-induced increase in blood eosinophils.

Figure 20:
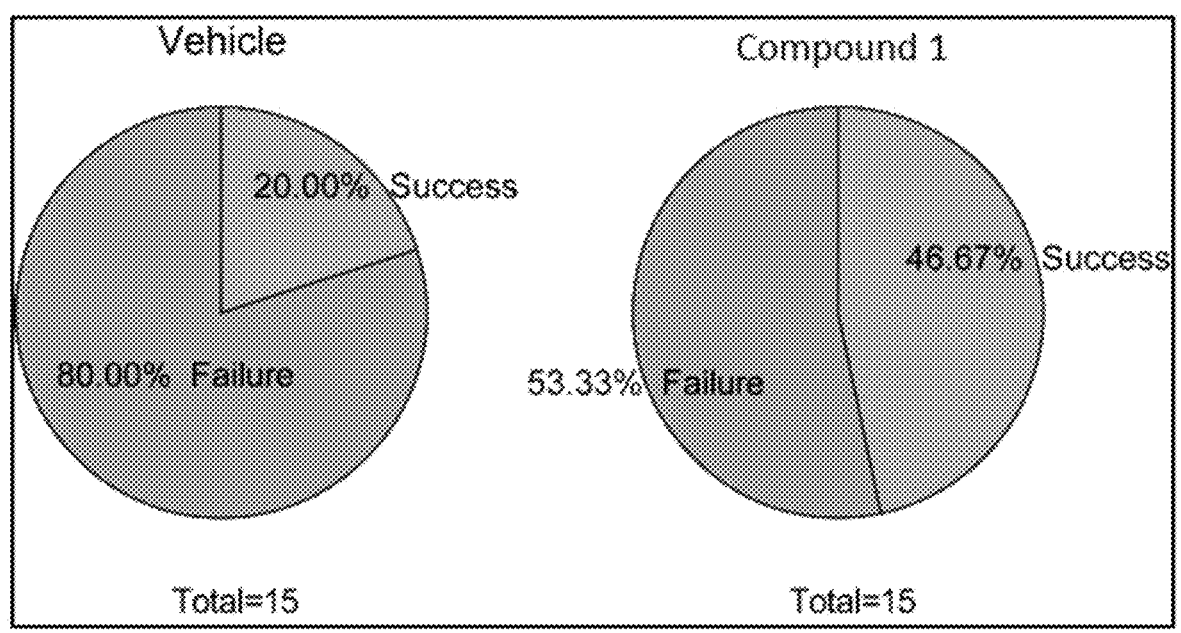

FIG. 20 shows the results of Compound 1 on a rotarod test for motor coordination. Twenty-four-month-old C57 mice were treated for 4 weeks with continuous infusion of Compound 1 or vehicle by osmotic pump. Treated mice succeeded more than vehicle-treated mice in a binomial test, *P<0.05.

Figure 21:
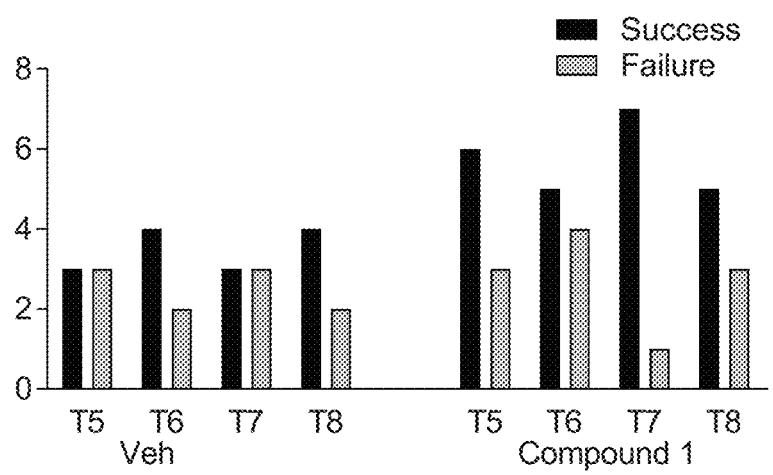

FIG. 21 shows the results of Compound 1 on the T maze test for memory. Twenty-four-month-old C57 mice were treated for 4 weeks with continuous infusion of Compound 1 or vehicle by osmotic pump. Treated mice succeeded more than vehicle-treated mice in a binomial test, *P<0.05.

Figure 22A:
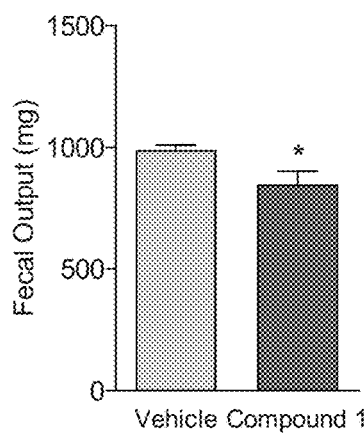

FIG. 22A shows the results of Compound 1 on fecal output overnight. Twenty-four-month-old C57 mice were treated for 4 weeks with continuous infusion of Compound 1 or vehicle by osmotic pump. The weight of fecal pellets was measured overnight. Compound 1 treated mice had significantly lower fecal output compared to vehicle treated mice by student's t-test, *P<0.05.

Figure 22B:
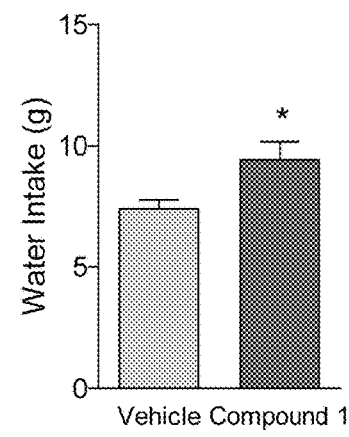

FIG. 22B shows the results of Compound 1 on water drinking overnight. Twenty-four-month-old C57 mice were treated for 4 weeks with continuous infusion of Compound 1 or vehicle by osmotic pump. The total water drank was measured overnight. Compound 1 treated mice drank significantly more water compared to vehicle treated mice by student's t-test, *P<0.05.

Figure 22C:
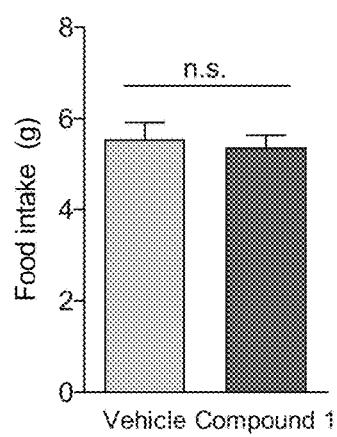

FIG. 22C shows the results of Compound 1 on food intake overnight. Twenty-four-month-old C57 mice were treated for 4 weeks with continuous infusion of Compound 1 or vehicle by osmotic pump. The total food eaten was measured overnight. There were no differences in total food intake overnight between the two groups.

Figure 23:
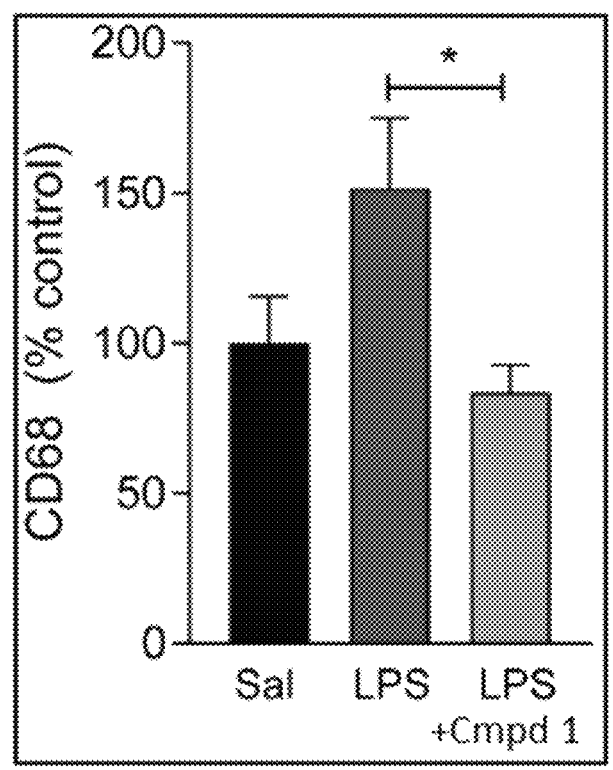

FIG. 23 depicts the effect of Compound 1 (Cmpd 1) on the numbers of CD68-positive (CD68+) activated microglia within the brains of three-month-old mice treated with LPS and treated with Compound 1 for 18 days. Compound 1-treated mice exhibited decreased CD68+ immunoreactivity, and thus decreased gliosis.

Figure 24A:
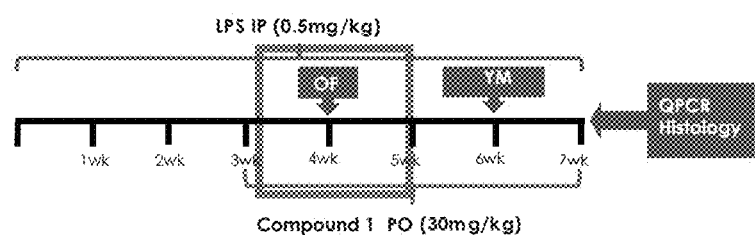
Figure 24B:
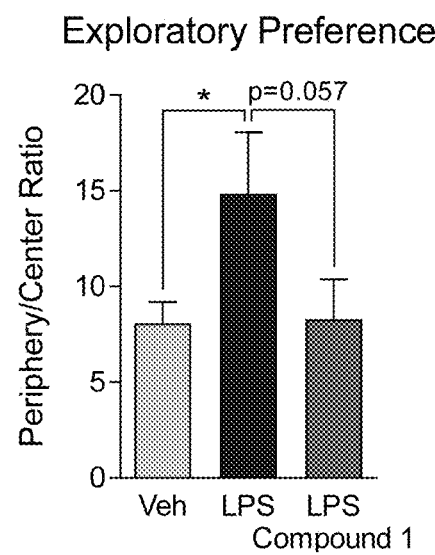

FIGS. 24A-24B depict the effect of Compound 1 on anxiety in the Open Field test in three-month-old mice treated with LPS IP for 4 weeks and treated with Compound 1 per orally BID (twice daily) for 1 week. LPS treatment increased the preference for the periphery of the Open Field, indicating increased anxiety. Compound 1 treatment decreased the LPS-induced anxiety in the Open Field. Data shown are mean±s.e.m; *P<0.05 by student's t-test.

Figure 25A:
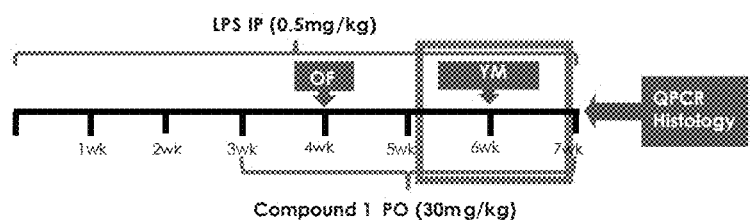
Figure 25B:
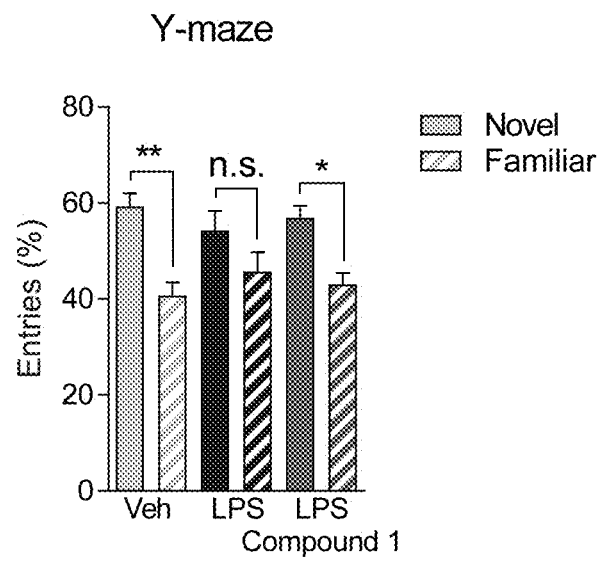

FIGS. 25A-25B depict the effect of Compound 1 on number of entries into the novel and familiar arms in the Y-maze test by 3-month-old C57Bl/6 mice treated with LPS. The number of visits to each arm was plotted for each treatment group and subjected to a paired t-test. Mice 3 months-old were dosed with either vehicle or LPS IP for 6 weeks, and dosed with vehicle control or Compound 1 per orally BID (twice daily) for 3 weeks. Compound 1-treated mice showed a significant preference for the novel arm while vehicle-treated mice did not. Data shown are mean±s.e.m.; **P<0.01, *P<0.05, novel vs familiar arm by paired student's t-test.

Figure 26A:
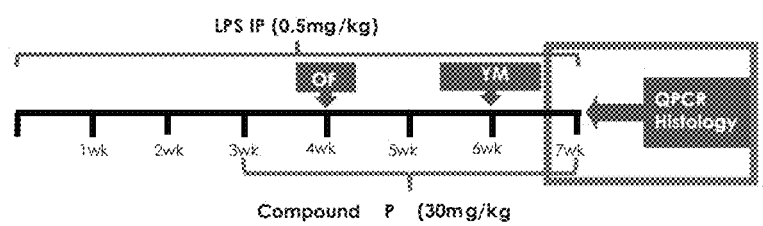
Figure 26B:
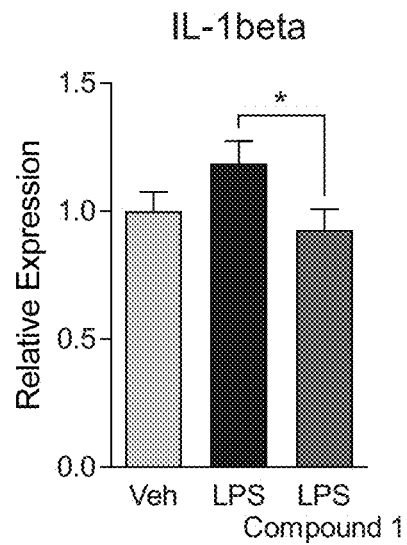

FIGS. 26A-26B depict the effect of Compound 1 on IL1beta mRNA in the brains from 3-month-old C57Bl/6 mice treated with LPS and/or Compound 1. Mice were dosed with either vehicle control or LPS IP for 7 weeks, and dosed with vehicle or Compound 1 per orally BID (twice daily) for 4 weeks. Tissues were harvested and RNA was prepared from cortical brain tissues. Levels of IL1beta mRNA were measured by qPCR and data are presented relative to vehicle control. There was a trend towards increased levels of IL1beta mRNA with LPS treatment and a significant decrease with Compound 1 treatment. Data shown are mean±s.e.m; *P<0.05 by student's t-test.

Figure 27A:
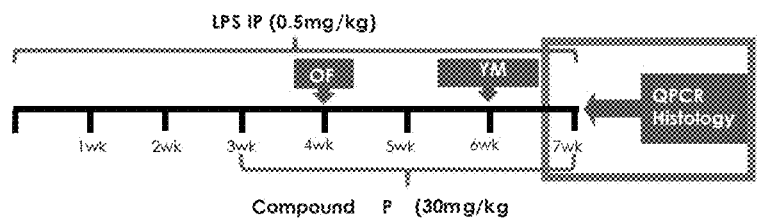
Figure 27B:
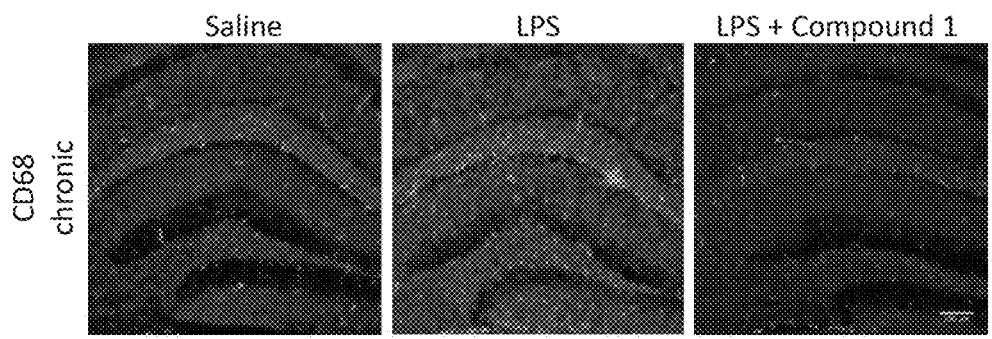
Figure 27C:
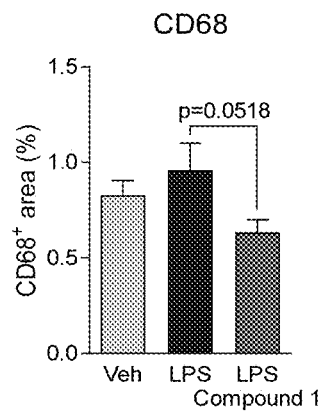

FIGS. 27A-27C depict the effect of Compound 1 on microglia activation in the hippocampus from 3-month-old C57Bl/6 mice treated with LPS and/or Compound 1. Mice were dosed with either vehicle control or LPS IP for 7 weeks, and dosed with vehicle or Compound 1 per orally BID (twice daily) for 4 weeks. Tissues were harvested and brain sections were subjected to immunohistochemistry for CD68, a marker for activated microglia. There was a trend towards increased levels of CD68 with LPS treatment and a robust trend towards decrease with Compound 1 treatment. Data shown are mean±s.e.m.

Figure 28A:
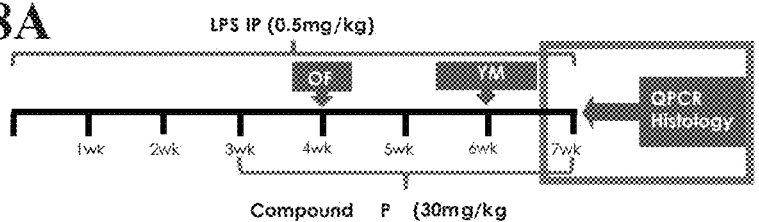
Figure 28B:
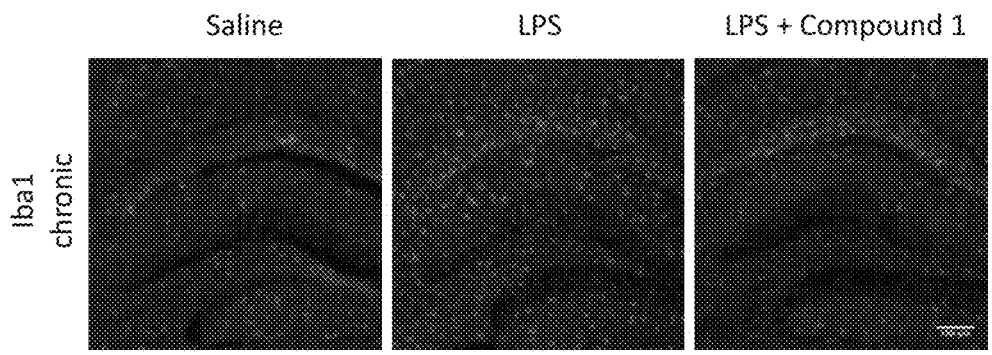
Figure 28C:
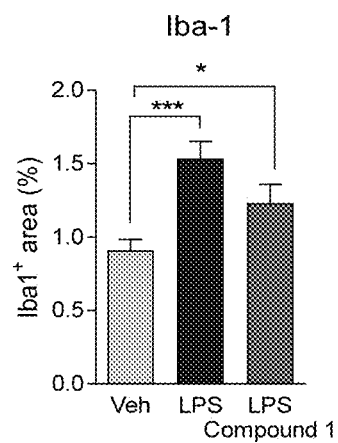

FIGS. 28A-28C depict the effect of Compound 1 on total microglia in the hippocampus from 3-month-old C57Bl/6 mice treated with LPS and/or Compound 1. Mice were dosed with either vehicle control or LPS IP for 7 weeks, and dosed with vehicle or Compound 1 per orally BID (twice daily) for 4 weeks. Tissues were harvested and brain sections were subjected to immunohistochemistry for Iba1, a marker for microglia. There was a significant increase in Iba1 with LPS treatment and a trend towards decrease with Compound 1 treatment. Data shown are mean±s.e.m.; ***P<0.001, *P<0.05, by student's t-test.

Figure 29A:
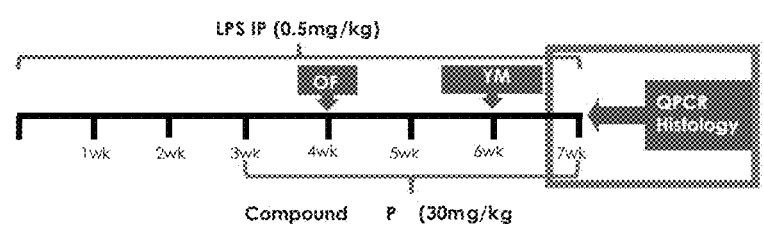
Figure 29B:
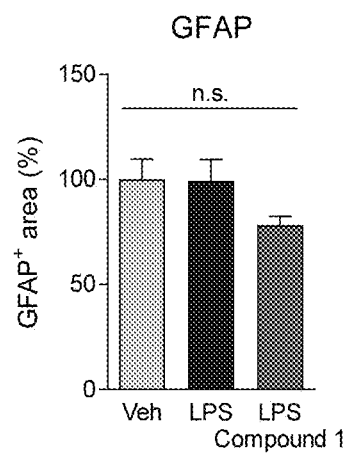

FIGS. 29A-29B depict the effect of Compound 1 on total astrocytes in the hippocampus from 3-month-old C57Bl/6 mice treated with LPS and/or Compound 1. Mice were dosed with either vehicle control or LPS IP for 7 weeks and dosed with vehicle or Compound 1 per orally BID (twice daily) for 4 weeks. Tissues were harvested, and brain sections were subjected to immunohistochemistry for GFAP, a marker for astrocytes. There was a trend towards decrease with Compound 1 treatment. Data shown are mean±s.e.m.

FIG. 30A depicts the treatment study timeline for a mouse MPTP model of Parkinson's Disease.

FIG. 30B summarizes the behavioral, biochemical, and histological endpoints for a mouse MPTP model of Parkinson's Disease.

Figure 31:
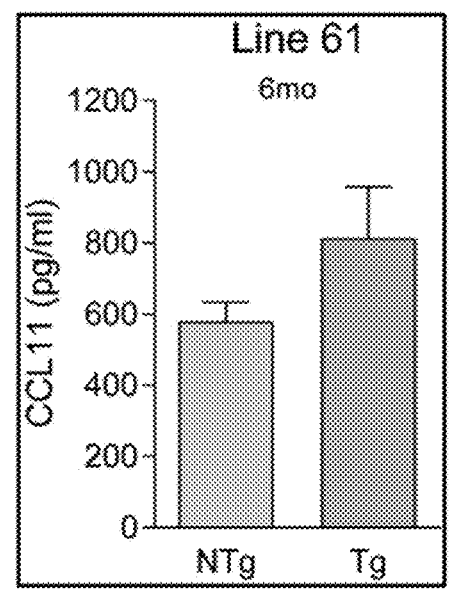

FIG. 31 depicts plasma eotaxin-1 levels in 6-month-old Line 61 synuclein-overexpressing transgenic mice. Eotaxin-1 levels (CCL11) in Non-transgenic (NTg) versus transgenic Line 61 synuclein mice (Tg) were plotted at pg/mL concentrations.

FIG. 32 summarizes behavioral, biochemical, and histological endpoints for synuclein transgenic mouse models treated with vehicle and Compound 1.

Figure 33:
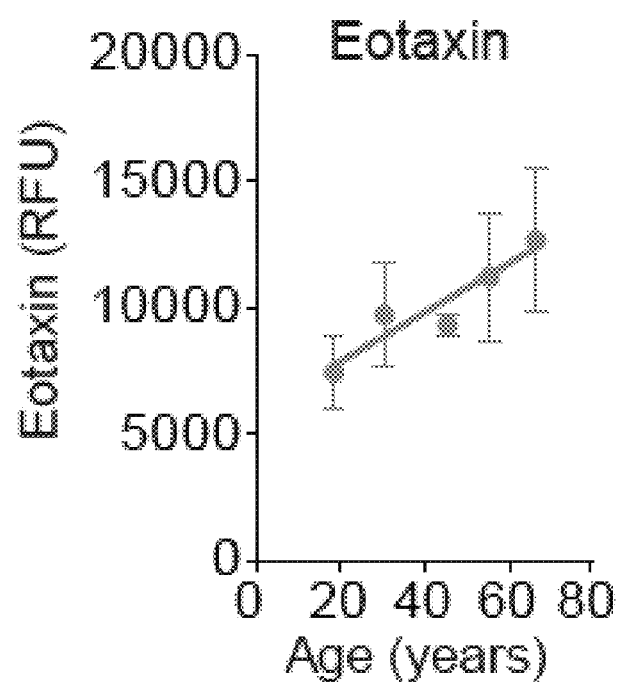

FIG. 33 depicts the concentrations of human eotaxin-1 in a proteomic screen. Relative concentrations of human eotaxin-1 were measured in a commercially-available affinity-based assay (SomaLogic). Plasma samples from each of 18, 30, 45, 55, and 66-year-old donors were plotted.

Figure 34A:
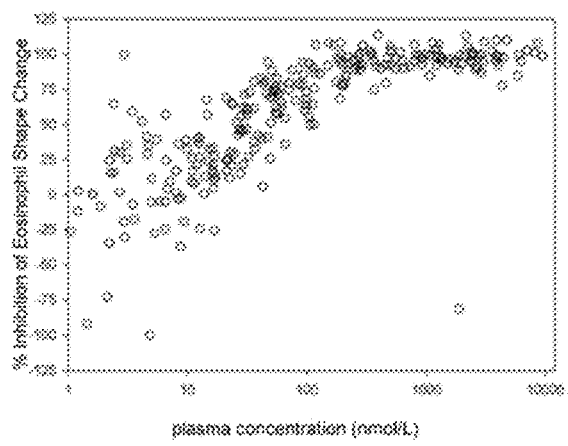

FIG. 34A depicts the effect of Compound 1 on inhibition of eosinophil shape change. Whole blood from humans treated with Compound 1 was incubated with recombinant eotaxin to trigger eosinophil shape change. Inhibition of shape change was plotted against plasma Compound 1 concentrations.

Figure 34B:
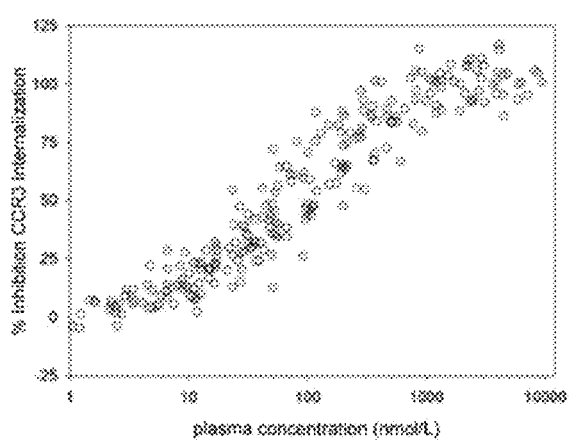

FIG. 34B depicts the effect of Compound 1 on CCR3 internalization. Whole blood from humans treated with Compound 1 was incubated with recombinant eotaxin to trigger CCR3 internalization and labeled with anti-CCR3 antibody. Inhibition of CCR3 internalization by Compound 1 was plotted against plasma Compound 1 concentrations.

VI. DETAILED DESCRIPTION

Aspects of the invention include methods of treating aging-associated impairments/neurodegenerative diseases. The aging-associated impairment may manifest in a number of different ways, e.g., as aging-associated cognitive impairment and/or physiological impairment, e.g., in the form of damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone; in the form of decreased neurogenesis, etc.

In some embodiments, the aging-associated impairment is an aging-associated impairment in cognitive ability in an individual, i.e., an aging-associated cognitive impairment. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. Aging-associated cognitive impairments include impairments in cognitive ability that are typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, Dementia with Lewy Bodies, frontotemporal dementia, Huntington's disease, amyotrophic lateral sclerosis, multiple sclerosis, glaucoma, myotonic dystrophy, vascular dementia, and the like.

By "treatment" it is meant that at least an amelioration of one or more symptoms associated with an aging-associated impairment afflicting the subject is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a subject, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

In some instances where the aging-associated impairment is aging-associated cognitive decline, treatment by methods of the present disclosure slows, or reduces, the progression of aging-associated cognitive decline. In other words, cognitive abilities in the individual decline more slowly, if at all, following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual, e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than they were prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In some instances where the aging-associated impairment is aging-associated motor impairment or decline, treatment by methods of the present disclosure slows, or reduces, the progression of aging-associated impairment or decline. In other words, motor abilities in the individual decline more slowly, if at all, following treatment by the disclosed methods than prior to or in the absence of treatment by the disclosed methods. In some instances, treatment by methods of the present disclosure stabilizes the motor abilities of an individual. For example, the progression of motor decline in an individual suffering from aging-associated motor decline is halted following treatment by the disclosed methods. As another example, motor decline in an individual, e.g., an individual 40 years old or older, that is projected to suffer from aging-associated motor decline, is prevented following treatment by the disclosed methods. In other words, no (further) motor impairment is observed. In some instances, treatment by methods of the present disclosure reduces, or reverses, motor impairment, e.g., as observed by improving motor coordination or abilities in an individual suffering from aging-associated motor decline. In other words, the motor abilities of the individual suffering from aging-associated motor decline following treatment by the disclosed methods are better than they were prior to treatment by the disclosed methods, i.e., they improve upon treatment. In some instances, treatment by methods of the present disclosure abrogates motor impairment. In other words, the motor coordination or abilities of the individual suffering from aging-associated motor decline are restored, e.g., to their level when the individual was about 40 years old or less, following treatment by the disclosed methods, e.g., as evidenced by improved motor coordination or abilities in an individual suffering from aging-associated motor decline.

In some instances, treatment of an adult mammal in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional, e.g., in the form of enhanced neurogenesis.

Methods of treating dysfunction caused by neurodegenerative disease are provided, the method comprising administering compounds from the formulae discussed below. An embodiment of the invention comprises a method of improving cognition or motor activity in subjects with brain-associated, cognitive-associated, or motor disease, the method comprising administering a therapeutically effective amount of a compound from the chemical formulae discussed below. Additional embodiments of the invention comprise a method of increasing neurogenesis in subjects with brain- or cognitive-associated disease, the method comprising administering a therapeutically effective amount of a compound from the chemical formulae discussed below. Additional embodiments of the invention comprise a method of alleviating or treating symptoms of brain- or cognitive-associated disease, the method comprising administering a therapeutically effective amount of a compound from the chemical formulae below. Additional embodiments of the invention include methods of alleviating symptoms of central nervous system-associated disease, the method comprising administering a therapeutically effective amount of a primarily peripheral-acting agent from the chemical formulae below. Further additional embodiments of the invention include methods of improving motor activity in a subject with age-related motor dysfunction, the method comprising administering a therapeutically effective amount of a compound from the chemical formulae discussed below. The methods of the invention may also comprise monitoring improvement in age-related disease, including for example, improvement in cognition, motor activity, neurogenesis and the like in a subject diagnosed with one or more such disease or dysfunction.

Additional embodiments of the invention include administering a therapeutically effective amount of a compound wherein the compound is in the form of the co-crystals or salts of the formulae discussed below. Further embodiments of the invention include administering a therapeutically effective amount of a compound wherein the compound is in the form of individual optical isomers, a mixture of the individual enantiomers, a racemate or enantiomerically pure compounds. Additional embodiments of the invention also include administering a therapeutically effective amount of a compound wherein the compound is in the form of the pharmaceutical compositions and formulations further discussed below.

Additional embodiments of the invention that treat aging-associated motor impairment or decline include modifying agents which inhibit the eotaxin/CCR3 pathway. Such modifying agents include not only compounds from the formulae discussed below, but other eotaxin and CCR3 inhibiting agents. Modifying agents that are contemplated include by way of example and not of limitation: the compounds of the formulae discussed below and other CCR3 small molecule inhibitors (e.g. bipiperidine derivatives described for example in U.S. Pat. No. 7,705,153, cyclic amine derivatives described for example in U.S. Pat. No. 7,576,117, and the CCR3 antagonists described in Pease J E and Horuk R, Expert Opin Drug Discov (2014) 9(5):467-83, all herein incorporated by reference in their entirety); anti-eotaxin antibodies; anti-CCR3 antibodies; aptamers that inhibit either eotaxin or CCR3 expression or function (methods of producing such aptamers include U.S. Pat. Nos. 5,270,163, 5,840,867, 6,180,348); antisense oligonucleotides or siRNAs that inhibit expression or function of either eotaxin or CCR3 (e.g. described in U.S. Pat. No. 6,822,087); soluble CCR3 receptor protein (e.g. decoys); and the like.

a. Compounds

The methods of the invention further comprise administration to a subject of the compounds that follow. In the groups, radicals, or moieties defined in this "Compounds" section, the number of carbon atoms is often specified preceding the group, for example, $C_{1-6}$ alkyl means an alkyl group or radical having 1 to 6 carbon atoms. In general, for groups comprising two or more subgroups which are disclosed in this "Compounds" section, the last-named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

An embodiment of the invention further comprises administration to a subject of the compounds of formula 1, wherein

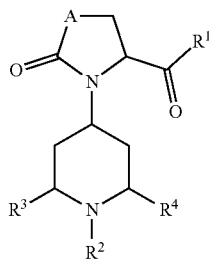

1

A is $CH_2$, O or $N-C_{1-6}$-alkyl;
$R^1$ is selected from
  $NHR^{1.1}$, $NMeR^{1.1}$;
  $NHR^{1.2}$, $NMeR^{1.2}$;
  $NHCH_2-R^{1.3}$;
  $NH-C_{3-6}$-cycloalkyl, whereas optionally one carbon atom is replaced by a nitrogen atom, whereas the ring is optionally substituted with one or two residues selected from the group consisting of $C_{1-6}$-alkyl, $O-C_{1-6}$-alkyl, $NHSO_2$-phenyl, $NHCONH$-phenyl, halogen, CN, $SO_2-C_{1-6}$-alkyl, $COO-C_{1-6}$-alkyl;
  a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, $COO-C_{1-6}$-alkyl, $C_{1-6}$-haloalkyl, $O-C_{1-6}$-alkyl, $NO_2$, halogen, CN, $NHSO_2-C_{1-6}$-alkyl, methoxy-phenyl;
  a group selected from $NHCH$(pyridinyl)$CH_2COO-C_{1-6}$-alkyl, $NHCH(CH_2O-C_{1-6}$-alkyl)-benzoimidazolyl, optionally substituted with halogen or CN;
  or 1-aminocyclopentyl, optionally substituted with methyl-oxadiazole
$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl)$_2$, $CH_2NHCONH-C_{3-6}$-cycloalkyl, CN, CO-pyridinyl, $CONR^{1.1.1}R^{1.1.2}$, $COO-C_{1-6}$-alkyl, $N(SO_2-C_{1-6}$-alkyl)($CH_2CON(C_{1-4}$-alkyl)$_2$) $O-C_{1-6}$-alkyl, O-pyridinyl, $SO_2-C_{1-6}$-alkyl, $SO_2-C_{1-6}$-alkylen-OH, $SO_2-C_{3-6}$-cycloalkyl, $SO_2$-piperidinyl, $SO_2NH-C_{1-6}$-alkyl, $SO_2N(C_{1-6}$-alkyl)$_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;
$R^{1.1.1}$ H, $C_{1-6}$-alkyl, $C_{3-6}$-cycloalkyl, $C_{1-6}$-haloalkyl, $CH_2CON(C_{1-6}$-alkyl)$_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;
$R^{1.1.2}$ H, $C_{1-6}$-alkyl, $SO_2C_{1-6}$-alkyl;
or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;
or
$R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;
$R^{1.2}$ is selected from
  heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO-C_{1-6}$-alkyl, $CONR^{1.2.1}R^{1.2.2}$, $COR^{1.2.3}$, $COO-C_{1-6}$-alkyl, $CONH_2$, $O-C_{1-6}$-alkyl, halogen, CN, $SO_2N(C_{1-6}$-alkyl)$_2$ or heteroaryl optionally substituted with one or two residues selected from the group consisting of $C_{1-6}$-alkyl;
  heteroaryl, optionally substituted with a five- or six-membered carbocyclic non-aromatic ring containing independently from each other two N, O, S, or $SO_2$, replacing a carbon atom of the ring;
  a aromatic or non-aromatic $C_{9\ or\ 10}$-bicyclic-ring, whereas one or two carbon atoms are replaced by N, O or S each optionally substituted with one or two residues selected from the group consisting of $N(C_{1-6}$-alkyl)$_2$, $CONH-C_{1-6}$-alkyl, =O;
  a heterocyclic non-aromatic ring, optionally substituted with pyridinyl;
  4,5-dihydro-naphtho[2,1-d]thiazole, optionally substituted with $NHCO-C_{1-6}$-alkyl,
$R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-$O-C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl
$R^{1.2.2}$ H, $C_{1-6}$-alkyl;
$R^{1.2.3}$ a five- or six-membered carbocyclic non-aromatic ring, optionally containing independently from each other one or two N, O, S, or $SO_2$, replacing a carbon atom of the ring;
$R^{1.3}$ is selected from phenyl, heteroaryl or indolyl, each optionally substituted with one or two residues selected from the group consisting of $C_{1-6}$-alkyl, $C_{3-6}$-cycloalkyl, $O-C_{1-6}$-alkyl, $O-C_{1-6}$-haloalkyl, phenyl, heteroaryl;
$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-6}$-alkyl;

$R^4$ is H, $C_{1-6}$-alkyl;

or $R^3$ and $R^4$ together are forming a $CH_2$—$CH_2$ group.

Another embodiment of the present invention further comprises administration to a subject of the compounds of formula 1 (above), wherein A is $CH_2$, O or N—$C_{1-4}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl$)_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2CON(C_{1-4}$-alkyl$)_2$) O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}$-alkyl$)_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

$R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, heteroaryl; where in some instances $R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, pyrrolidinyl;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1 (above), wherein A is $CH_2$, O or N—$C_{1-4}$-alkyl;

$R^1$ is selected from $NHR^{1.1}$, $NMeR^{1.1}$;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl$)_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2CON(C_{1-4}$-alkyl$)_2$) O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}$-alkyl$)_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1, wherein A is $CH_2$, O or N—$C_{1-4}$-alkyl;

$R^1$ is selected from
  $NHR^{1.2}$, $NMeR^{1.2}$;
  $R^{1.2}$ is selected from
    heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, $COO$—$C_{1-6}$-alkyl, $CONH_2$, O—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl;
    heteroaryl, optionally substituted with a five- or six-membered carbocyclic non-aromatic ring containing independently from each other two N, O, S, or $SO_2$, replacing a carbon atom of the ring;
    benzothiazolyl, indazolyl, dihydro-indolyl, indanyl, tetrahydro-quinolinyl, each optionally substituted with one or two residues selected from the group consisting of $N(C_{1-6}$-alkyl$)_2$, $CONH$—$C_{1-6}$-alkyl, =O;
    piperidinyl, optionally substituted with pyridinyl;
    4,5-dihydro-naphtho[2,1-d]thiazole, optionally substituted with NHCO—$C_{1-6}$-alkyl,
    $R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl
    $R^{1.2.2}$ H, $C_{1-6}$-alkyl;
    $R^{1.2.3}$ a five- or six-membered carbocyclic non-aromatic ring, optionally containing independently from each other one or two N, O, S, or $SO_2$, replacing a carbon atom of the ring;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1 (above), wherein A is $CH_2$, O or N—$C_{1-4}$-alkyl;

$R^1$ is selected from
  $NHR^{1.2}$, $NMeR^{1.2}$;
  $R^{1.2}$ is selected from
    heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, $COO$—$C_{1-6}$-alkyl, $CONH_2$, O—$C_{1-6}$-alkyl, halogen, CN, $SO_2N(C_{1-4}$-alkyl$)_2$ or heteroaryl optionally substituted with one or two residues selected from the group consisting of $C_{1-6}$-alkyl;
    heteroaryl, optionally substituted with a five- or six-membered carbocyclic non-aromatic ring containing independently from each other two N, O, S, or $SO_2$, replacing a carbon atom of the ring;
    $R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl
    $R^{1.2.2}$ H, $C_{1-6}$-alkyl;
    $R^{1.2.3}$ a five- or six-membered carbocyclic non-aromatic ring, optionally containing independently from each other one or two N, O, S, or $SO_2$, replacing a carbon atom of the ring;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1, wherein A is $CH_2$, O or N—$C_{1-4}$-alkyl;

$R^1$ is selected from
  $NHCH_2$—$R^{1.3}$;
  $R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, pyrrolidinyl;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1, wherein A is $CH_2$, O or N—$C_{1-4}$-alkyl;

$R^1$ is selected from
  $NHR^{1.1}$, $NMeR^{1.1}$;
  $NHR^{1.2}$, $NMeR^{1.2}$;
  $NHCH_2$—$R^{1.3}$;
  NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl;
  a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, m-methoxyphenyl;

a group selected from NHCH(pyridinyl)$CH_2$COO—$C_{1-6}$-alkyl, NHCH($CH_2$O—$C_{1-6}$-alkyl)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-6}$-alkyl, $C_{1-6}$-haloalkyl, $CH_2CON(C_{1-6}$-alkyl$)_2$, $CH_2NHCONH$—$C_{3-6}$-cycloalkyl, CN, $CONR^{1.1.1}R^{1.1.2}$, COO—$C_{1-6}$-alkyl, O—$C_{1-6}$-alkyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}$-alkyl$)_2$, $CH_2$CO-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from heteroaryl, optionally substituted with one or two residues selected from the group consisting of $C_{1-6}$-alkyl, $C_{3-6}$-cycloalkyl, $CH_2$COO—$C_{1-6}$-alkyl, $CONR^{1.2.1}R^{1.2.2}$, COO—$C_{1-6}$-alkyl, $CONH_2$, O—$C_{1-6}$-alkyl, halogen, CN, CO-pyrrolidinyl, CO-morpholinyl or heteroaryl optionally substituted with one or two residues selected from the group consisting of $C_{1-6}$-alkyl;

benzothiazolyl, indazolyl, dihydro-indolyl, indanyl, tetrahydro-quinolinyl, each optionally substituted with one or two residues selected from the group consisting of $N(C_{1-6}$-alkyl$)_2$, CONH—$C_{1-6}$-alkyl, =O;

piperidinyl, optionally substituted with pyridinyl;

4,5-dihydro-naphtho[2,1-d]thiazole, optionally substituted with NHCO—$C_{1-6}$-alkyl, $R^{1.2.1}$ H, $C_{1-6}$-alkyl;

$R^{1.2.2}$ H, $C_{1-6}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl;

$R^2$ is selected from $C_{1-6}$-alkylene-phenyl or $C_{1-6}$-alkylene-naphthyl, both optionally substituted with one or two residues selected from the group consisting of $C_{1-6}$-alkyl, $C_{1-6}$-haloalkyl, O—$C_{1-6}$-alkyl, O—$C_{1-6}$-haloalkyl, halogen; or $CH_2$-thiophenyl, optionally substituted with one or two residues selected from the group consisting of halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from $NHR^{1.1}$, $NMeR^{1.1}$;

$NHR^{1.2}$, $NMeR^{1.2}$;

$NHCH_2$—$R^{1.3}$;

NH-cyclohexyl, optionally substituted with one or two residues selected from the group consisting of $C_{1-4}$-alkyl, $NHSO_2$-phenyl, NHCONH-phenyl, halogen;

NH-pyrrolidinyl, optionally substituted with one or two residues selected from the group consisting of $SO_2$—$C_{1-4}$-alkyl, COO—$C_{1-4}$-alkyl;

piperidinyl, optionally substituted with one or two residues selected from the group consisting of $NHSO_2$—$C_{1-4}$-alkyl, m-methoxyphenyl;

dihydro-indolyl, dihydro-isoindolyl, tetrahydro-quinolinyl or tetrahydro-isoquinolinyl, optionally substituted with one or two residues selected from the group consisting of $C_{1-4}$-alkyl, COO—$C_{1-4}$-alkyl, $C_{1-4}$-haloalkyl, O—$C_{1-4}$-alkyl, $NO_2$, halogen;

a group selected from NHCH(pyridinyl)$CH_2$COO—$C_{1-4}$-alkyl, NHCH($CH_2$O—$C_{1-4}$-alkyl)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-4}$-alkyl, $C_{1-4}$-haloalkyl, $CH_2CON(C_{1-4}$-alkyl$)_2$, $CH_2NHCONH$—$C_{3-6}$-cycloalkyl, CN, $CONR^{1.1.1}R^{1.1.2}$, COO—$C_{1-4}$-alkyl, O—$C_{1-4}$-alkyl, $SO_2$—$C_{1-4}$-alkyl, $SO_2$—$C_{1-4}$-alkylen-OH, $SO_2$—$C_{3-6}$-cycloalkyl, $SO_2$-piperidinyl, $SO_2NH$—$C_{1-4}$-alkyl, $SO_2N(C_{1-4}$-alkyl$)_2$, halogen, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of $C_{1-4}$-alkyl, $NHC_{1-4}$-alkyl, =O;

$R^{1.1.1}$ H, $C_{1-6}$-alkyl, $C_{3-6}$-cycloalkyl, $C_{1-4}$-haloalkyl, $CH_2CON(C_{1-4}$-alkyl$)_2$, $CH_2$CO-azetindinyl, $C_{1-4}$-alkylen-$C_{3-6}$-cycloalkyl, $CH_2$-pyranyl, $CH_2$-tetrahydrofuranyl, $CH_2$-furanyl, $C_{1-4}$-alkylen-OH or thiadiazolyl, optionally substituted with $C_{1-4}$-alkyl;

$R^{1.1.2}$ H, $C_{1-4}$-alkyl, $SO_2C_{1-4}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyridazinyl, pyrrolyl, pyrazolyl, isoxazolyl, thiazolyl, thiadiazolyl, optionally substituted with one or two residues selected from the group consisting of $C_{1-4}$-alkyl, $C_{3-6}$-cycloalkyl, $CH_2$COO—$C_{1-4}$-alkyl, $CONR^{1.2.1}R^{1.2.2}$, COO—$C_{1-4}$-alkyl, $CONH_2$, O—$C_{1-4}$-alkyl, halogen, CO-pyrrolidinyl, CO-morpholinyl or pyrazolyl, triazolyl, tetrazolyl, isoxazolyl, oxadiazolyl, each optionally substituted with one or two residues selected from the group consisting of $C_{1-4}$-alkyl;

benzothiazolyl, indazolyl, dihydro-indolyl, indanyl, tetrahydro-quinolinyl, each optionally substituted with one or two residues selected from the group consisting of $N(C_{1-4}$-alkyl$)_2$, CONH—$C_{1-4}$-alkyl, =O;

piperidinyl, optionally substituted with pyridinyl;
4,5-dihydro-naphtho[2,1-d]thiazole, optionally substituted with NHCO—$C_{1-4}$-alkyl,
$R^{1.2.1}$ H, $C_{1-4}$-alkyl;
$R^{1.2.2}$ H, $C_{1-4}$-alkyl;
$R^{1.3}$ is selected from phenyl, pyrazolyl, isoxazolyl, pyrimidinyl, indolyl or oxadiazolyl, each optionally substituted with one or two residues selected from the group consisting of $C_{1-4}$-alkyl, $C_{3-6}$-cycloalkyl, O—$C_{1-4}$-alkyl, O—$C_{1-4}$-haloalkyl;
$R^2$ is selected from $C_{1-6}$-alkylene-phenyl or $C_{1-6}$-alkylene-naphthyl, both optionally substituted with one or two residues selected from the group consisting of $C_{1-4}$-alkyl, $C_{1-4}$-haloalkyl, O—$C_{1-4}$-haloalkyl, halogen; or $CH_2$-thiophenyl, optionally substituted with one or two residues selected from the group consisting of halogen;
$R^3$ is H;
$R^4$ is H;
or $R^3$ and $R^4$ together are forming a $CH_2$—$CH_2$ group.

Another embodiment of the present invention further comprises administration to a subject of the compounds of formula 1, wherein
A is $CH_2$, O or NMe;
$R^1$ is selected from
NHR$^{1.1}$, NMeR$^{1.1}$;
NHR$^{1.2}$, NMeR$^{1.2}$;
NHCH$_2$—R$^{1.3}$;
NH-piperidinyl, optionally substituted with pyridinyl;
NH-cyclohexyl, optionally substituted with one or two residues selected from the group consisting of t-Bu, NHSO$_2$-phenyl, NHCONH-phenyl, F;
NH-pyrrolidinyl, optionally substituted with one or two residues selected from the group consisting of SO$_2$Me, COO-t-Bu;
piperidinyl, optionally substituted with one or two residues selected from the group consisting of NHSO$_2$-n-Bu, m-methoxyphenyl;
dihydro-indolyl, dihydro-isoindolyl, tetrahydro-quinolinyl or tetrahydro-isoquinolinyl, optionally substituted with one or two residues selected from the group consisting of Me, COOMe, CF$_3$, OMe, NO$_2$, F, Br;
a group selected from NHCH(pyridinyl)CH$_2$COOMe, NHCH(CH$_2$OMe)-benzoimidazolyl, optionally substituted with Cl;
or 1-aminocyclopentyl, optionally substituted with methyl-oxadiazolyl;
$R^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;
$R^{1.1.1}$ H, Me, Et, t-Bu, i-Pr, cyclopropyl, CH$_2$-i-Pr, CH$_2$-t-Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;
$R^{1.1.2}$ H, Me, Et, SO$_2$Me, SO$_2$Et
or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of CH$_2$OH
$R^{1.2}$ is selected from
pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me;
benzothiazolyl, indazolyl, dihydro-indolyl, indanyl, tetrahydro-quinolinyl, each optionally substituted with one or two residues selected from the group consisting of NMe$_2$, CONHMe, =O;
4,5-dihydro-naphtho[2,1-d]thiazole, optionally substituted with NHCOMe,
$R^{1.2.1}$ H, Me;
$R^{1.2.2}$ H, Me;
$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, OCHF$_2$;
$R^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;
$R^3$ is H;
$R^4$ is H;
or $R^3$ and $R^4$ together are forming a $CH_2$—$CH_2$ group.

Another embodiment of the present invention further comprises administration to a subject of the compounds of formula 1, wherein
A is $CH_2$, O or NMe;
$R^1$ is selected from
NHR$^{1.1}$
NHR$^{1.2}$,
$R^{1.1}$ is phenyl, optionally substituted with one or two residues selected from the group consisting of Me, Et, Pr, Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;
$R^{1.1.1}$ H, Me, Et, t-Bu, i-Pr, cyclopropyl, CH$_2$-i-Pr, CH$_2$-t-Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;
$R^{1.1.2}$ H, Me, Et, SO$_2$Me, SO$_2$Et
or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of CH$_2$OH
$R^{1.2}$ is selected from
pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of NMe$_2$, CONHMe, =O;

4,5-dihydro-naphtho[2,1-d]thiazole, optionally substituted with NHCOMe,

R$^{1.2.1}$ H, Me;

R$^{1.2.2}$ H, Me;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et R$^3$ is H;

R$^4$ is H.

Another embodiment of the present invention further comprises administration to a subject of the compounds of formula 1, wherein A is CH$_2$, O or NMe;

R$^1$ is selected from

NHR$^{1.1}$, NMeR$^{1.1}$;

NHR$^{1.2}$, NMeR$^{1.2}$;

NHCH$_2$—R$^{1.3}$;

R$^{1.1}$ is phenyl, optionally substituted with one or two residues selected from the group consisting of Me, Et, Pr, Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

R$^{1.1.1}$ H, Me, Et, Pr, Bu, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ H, Me, Et, SO$_2$Me, SO$_2$Et or R$^{1.1.1}$ and R$^{1.1.2}$ together are forming a four-, five- or six-membered carbocyclic ring, optionally containing one O, replacing a carbon atom of the ring, optionally substituted with one or two residues selected from the group consisting of CH$_2$OH R$^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of NMe$_2$, CONHMe, =O;

4,5-dihydro-naphtho[2,1-d]thiazole, optionally substituted with NHCOMe,

R$^{1.2.1}$ H, Me;

R$^{1.2.2}$ H, Me;

R$^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, OCHF$_2$;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

Another embodiment of the present invention further comprises administration to a subject of the compounds of formula 1, wherein A is CH$_2$, O or NMe;

R$^1$ is selected from

NHR$^{1.1}$, NMeR$^{1.1}$;

R$^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

R$^{1.1.1}$ H, Me, Et, Bu, Pr, cyclopropyl, CH$_2$—Pr, CH$_2$—Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ H, Me, Et, SO$_2$Me, SO$_2$Et or R$^{1.1.1}$ and R$^{1.1.2}$ together are forming a four-, five- or six-membered carbocyclic ring, optionally containing one O, replacing a carbon atom of the ring, optionally substituted with one or two residues selected from the group consisting of CH$_2$OH;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

Another embodiment of the present invention further comprises administration to a subject of the compounds of formula 1, wherein A is CH$_2$, O or NMe;

R$^1$ is selected from

NHR$^{1.1}$, NMeR$^{1.1}$;

R$^{1.1}$ is phenyl, optionally substituted with one or two residues selected from the group consisting of Me, Et, t-Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^2$ is defined as in Table 1 shown below;

$R^3$ is H;

$R^4$ is H;

Another embodiment of the present invention further comprises administration to a subject of the compounds of formula 1, wherein A is $CH_2$, O or NMe;

$R^1$ is selected from
  $NHR^{1.1}$, $NMeR^{1.1}$;
  $R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;
  and $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^2$ is defined as in Table 1 shown below;

$R^3$ is H;

$R^4$ is H;

Another embodiment of the present invention further comprises administration to a subject of the compounds of formula 1, wherein A is $CH_2$, O or NMe;

$R^1$ is selected from
  $NHR^{1.1}$, $NMeR^{1.1}$;
  $R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, F, Cl;
  $R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;
  $R^{1.1.2}$ H, Me, Et, $SO_2Me$, $SO_2Et$ $R^2$ is defined as in Table 1 shown below;

$R^3$ is H;

$R^4$ is H;

Another embodiment of the present invention further comprises administration to a subject of the compounds of formula 1, wherein A is $CH_2$, O or NMe;

$R^1$ is selected from
  $NHR^{1.1}$, $NMeR^{1.1}$;
  $R^{1.1}$ is phenyl, optionally substituted with one or two residues selected from the group consisting of $SO_2Me$, $SO_2CH_2CH_2OH$, $SO_2Et$, $SO_2$-cyclopropyl, $SO_2$-piperidinyl, $SO_2NHEt$, $SO_2NMeEt$;
  $R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;
  $R^{1.1.2}$ H, Me, Et, $SO_2Me$, $SO_2Et$ $R^2$ is defined as in Table 1 shown below;

$R^3$ is H;

$R^4$ is H;

Another embodiment of the present invention further comprises administration to a subject of the compounds of formula 1, wherein A is $CH_2$, O or NMe;

$R^1$ is selected from
  $NHR^{1.1}$, $NMeR^{1.1}$;
  $R^{1.1}$ is phenyl, optionally substituted with one residue selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, and additionally with one residue selected from the group consisting of CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;
  $R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;
  $R^{1.1.2}$ H, Me, Et, $SO_2Me$, $SO_2Et$ $R^2$ is defined as in Table 1 shown below;

$R^3$ is H;

$R^4$ is H;

Another embodiment of the present invention further comprises administration to a subject of the compounds of formula 1, wherein A is $CH_2$, O or NMe;

$R^1$ is selected from
  $NHR^{1.2}$, $NMeR^{1.2}$;
  $R^{1.2}$ is selected from
    pyridinyl, pyridazinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;
    benzothiazolyl, indazolyl, dihydro-indolyl, indanyl, tetrahydro-quinolinyl, each optionally substituted with one or two residues selected from the group consisting of $NMe_2$, CONHMe, =O;
    4,5-dihydro-naphtho[2,1-d]thiazole, optionally substituted with NHCOMe,
  $R^{1.2.1}$ H, Me;
  $R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from $NHR^{1.2}$, $NMeR^{1.2}$;

$R^{1.2}$ is selected from pyridinyl, pyridazinyl, pyrrolyl, pyrazolyl, isoxazolyl, thiazolyl, thiadiazolyl, optionally substituted with one or two residues selected from the group consisting of Me, Et, n-Pr, i-Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

$R^{1.2.1}$ H, Me;

$R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from $NHCH_2$—$R^{1.3}$;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention further comprises administration to a subject of the compounds of formula 1, wherein A is $CH_2$, O or NMe;

$R^1$ is selected from

NH-piperidinyl, optionally substituted with pyridinyl;

NH-cyclohexyl, optionally substituted with one or two residues selected from the group consisting of t-Bu, $NHSO_2$-phenyl, NHCONH-phenyl, F;

NH-pyrrolidinyl, optionally substituted with one or two residues selected from the group consisting of $SO_2Me$, COO-t-Bu;

piperidinyl, optionally substituted with one or two residues selected from the group consisting of $NHSO_2$-n-Bu, m-methoxyphenyl;

dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br;

a group selected from $NHCH(pyridinyl)CH_2COOMe$, $NHCH(CH_2OMe)$-benzoimidazolyl, optionally substituted with Cl;

or 1-aminocyclopentyl, optionally substituted with Methyl-Oxadiazolyl;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention further comprises administration to a subject of the compounds of formula 1, wherein A is $CH_2$, O or NMe, $R^1$ is selected from $NHR^{1.2}$, $NMeR^{1.2}$; $R^2$ is defined as in Table 1 shown below; $R^3$ is H; $R^4$ is and $R^{1.2}$ is selected from pyridinyl, optionally substituted with one or two residues selected from the group consisting of Me, Et, i-Pr, n-Bu, cyclopropyl, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

pyrrolyl, optionally substituted with one or two residues selected from the group consisting of Me, Et, COOMe, COOEt;

pyrazolyl, optionally substituted with one or two residues selected from the group consisting of Me, Et, cyclopropyl, COOEt, CO-pyrrolidinyl;

isoxazolyl, optionally substituted with one or two residues selected from the group consisting of t-Bu, COOEt;

thiazolyl, optionally substituted with one or two residues selected from the group consisting of Me, n-Pr, i-Pr, Bu, COOMe, COOEt, $CH_2COOEt$, $CONR^{1.2.1}R^{1.2.2}$;

thiadiazolyl, optionally substituted with one or two residues selected from the group consisting of COOEt;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, and $R^{1.2.1}$ is H or Me;

$R^{1.2.2}$ is H or Me.

Another embodiment of the present invention further comprises administration to a subject of the compounds of formula 1, wherein A is $CH_2$, O or NMe, $R^1$ is selected from $NHR^{1.2}$, $NMeR^{1.2}$; $R^2$ is defined as in Table 1 shown below; $R^3$ is H; $R^4$ is and $R^{1.2}$ is selected from pyridinyl, optionally substituted with one or two residues selected from the group consisting of Me, Et, i-Pr, n-Bu, $CONR^{1.2.1}R^{1.2.2}$, COOMe, COOEt, $CONH_2$, OMe, Cl, Br;

pyrrolyl, optionally substituted with one or two residues selected from the group consisting of Me, Et, COOMe, COOEt;

pyrazolyl, optionally substituted with one or two residues selected from the group consisting of Me, Et, cyclopropyl, COOEt, CO-pyrrolidinyl;

isoxazolyl, optionally substituted with one or two residues selected from the group consisting of t-Bu, COOEt;

thiazolyl, optionally substituted with one or two residues selected from the group consisting of Me, n-Pr, i-Pr, Bu, COOMe, COOEt, CONR$^{1.2.1}$R$^{1.2.2}$;

thiadiazolyl, optionally substituted with one or two residues selected from the group consisting of COOEt;

benzothiazolyl, indazolyl, dihydro-indolyl, indanyl, tetrahydro-quinolinyl, each optionally substituted with one or two residues selected from the group consisting of NMe$_2$, CONHMe, =O;

and

R$^{1.2.1}$ is H or Me;

R$^{1.2.2}$ is H or Me.

Another embodiment of the present invention further comprises administration to a subject of the compounds of formula 1, wherein A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is pyridinyl, optionally substituted with one or two residues selected from the group consisting of Me, Et, i-Pr, n-Bu, CONR$^{1.2.1}$R$^{1.2.2}$, COOMe, COOEt, CONH$_2$, OMe, Cl, Br; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is pyrrolyl, optionally substituted with one or two residues selected from the group consisting of Me, Et, COOMe, COOEt; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is pyrazolyl, optionally substituted with one or two residues selected from the group consisting of Me, Et, cyclopropyl, COOEt, CO-pyrrolidinyl; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is isoxazolyl, optionally substituted with one or two residues selected from the group consisting of t-Bu, COOE; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is thiazolyl, optionally substituted with one or two residues selected from the group consisting of Me, n-Pr, i-Pr, Bu, COOMe, COOEt, CONR$^{1.2.1}$R$^{1.2.2}$; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is thiadiazolyl, optionally substituted with one or two residues selected from the group consisting of COOEt; R$^{1.2.1}$ is H or Me and R$^{1.2.2}$ is H or Me.

A is CH$_2$, O or NMe, R$^1$ is selected from NHR$^{1.2}$, NMeR$^{1.2}$; R$^2$ is defined as in Table 1 shown below; R$^3$ is H; R$^4$ is H; R$^{1.2}$ is benzothiazolyl, indazolyl, dihydroindolyl, indanyl, tetrahydro-quinolinyl, each optionally substituted with one or two residues selected from the group consisting of NMe$_2$, CONHMe, =O; R$^{1.2.1}$ is H or Me and R$^{1.2.2}$ is H or Me.

Another embodiment of the present invention further comprises administration to a subject of the compounds of formula 1, wherein all groups are defined as above except R$^{1.3}$ is selected from phenyl, optionally substituted with OCHF$_2$;
pyrazolyl, optionally substituted with Me or Et;
isoxazolyl, optionally substituted with Pr;

pyrimidinyl, optionally substituted with two OMe;
indolyl;
oxadiazolyl, optionally substituted with cyclopentyl.

Another embodiment of the present invention further comprises administration to a subject of the compounds of formula 1, wherein all groups are defined as above except A is CH$_2$.

Another embodiment of the present invention further comprises administration to a subject of the compounds of formula 1, wherein all groups are defined as above except A is O.

Another embodiment of the present invention further comprises administration to a subject of the compounds of formula 1, wherein all groups are defined as above except A is NMe.

Another embodiment of the present invention are compounds of formula 1, wherein

A is CH$_2$, O or NMe;

R$^1$ is selected from

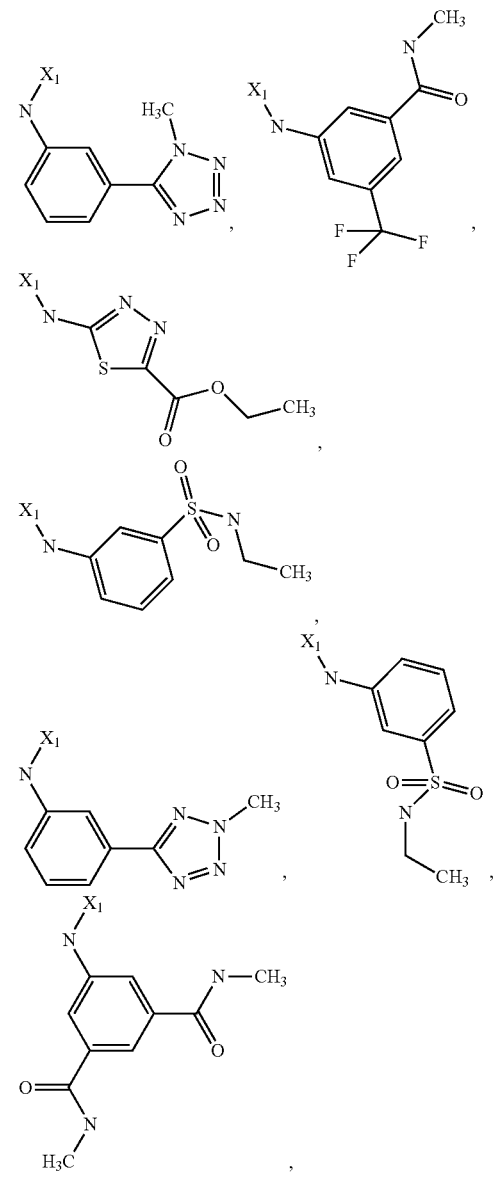

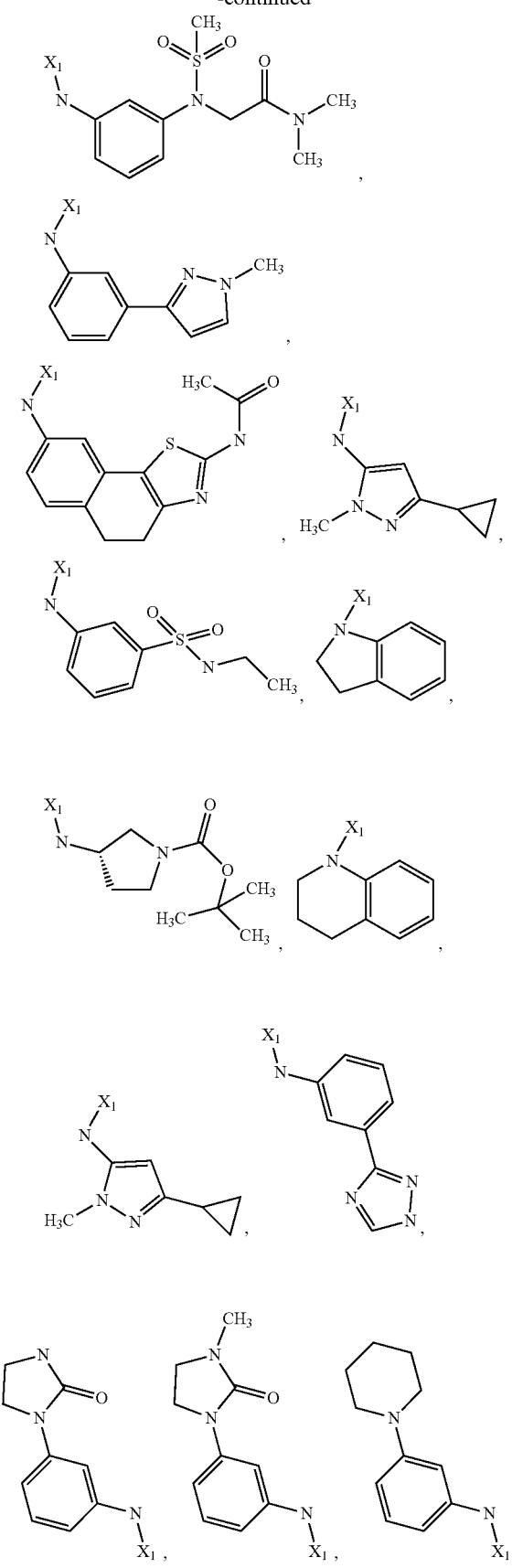
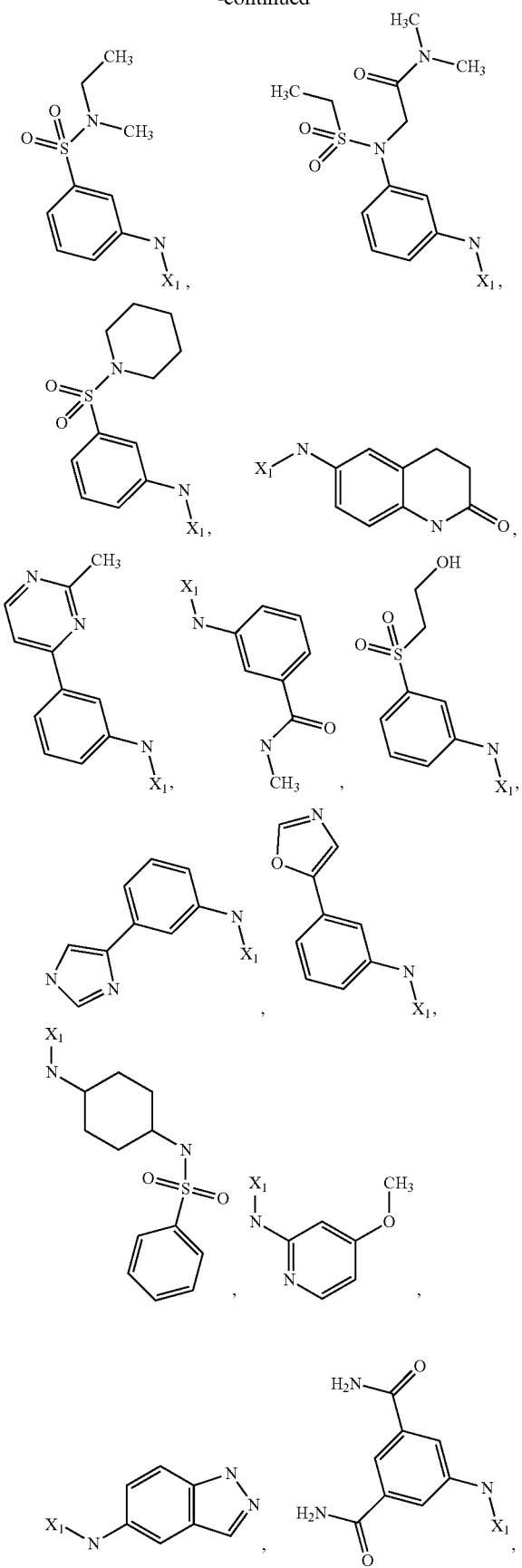

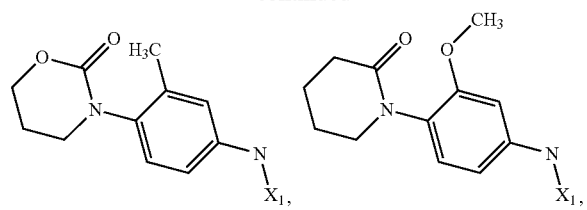
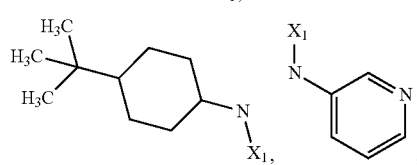
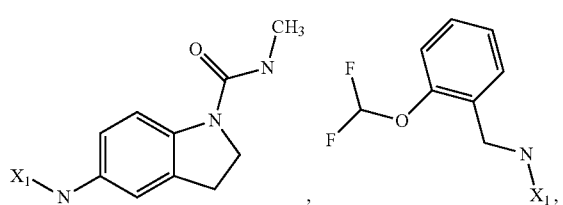
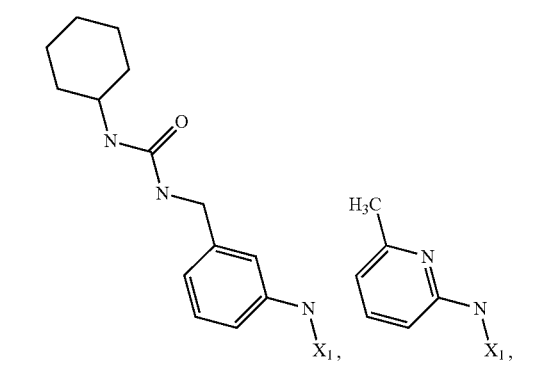
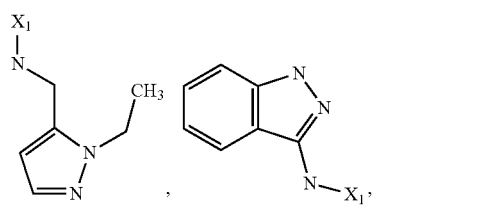
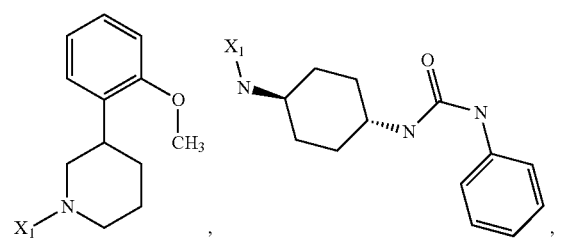
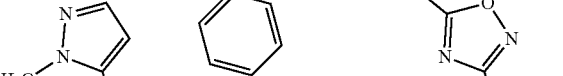
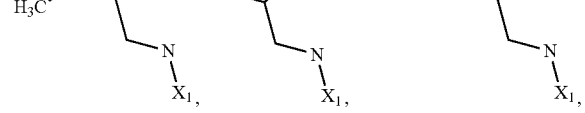
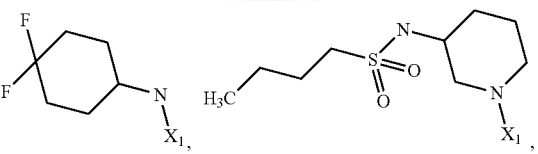
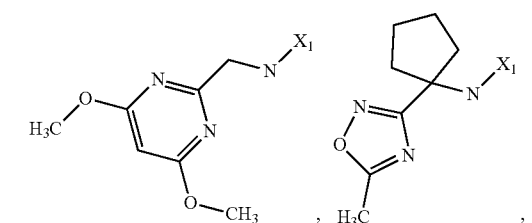
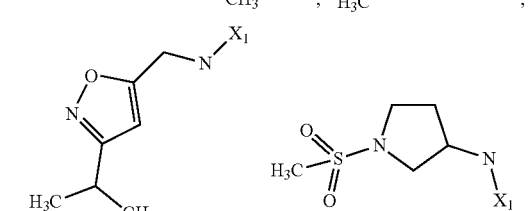
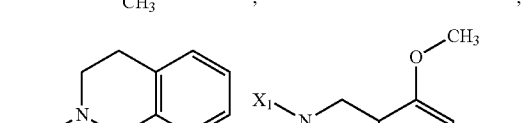
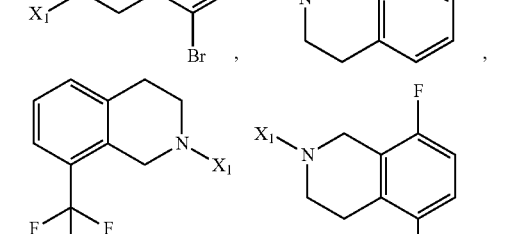
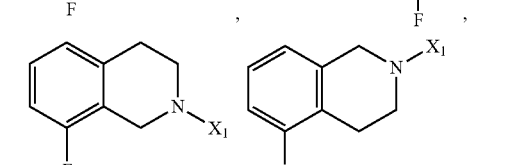
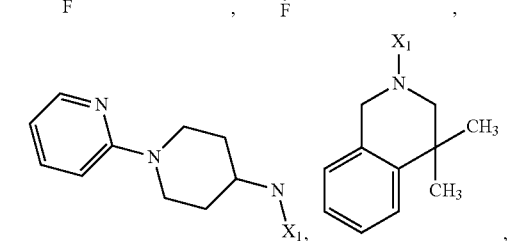
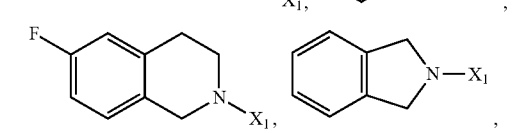
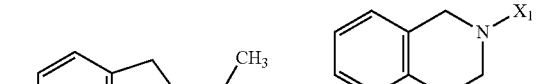
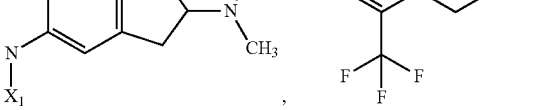

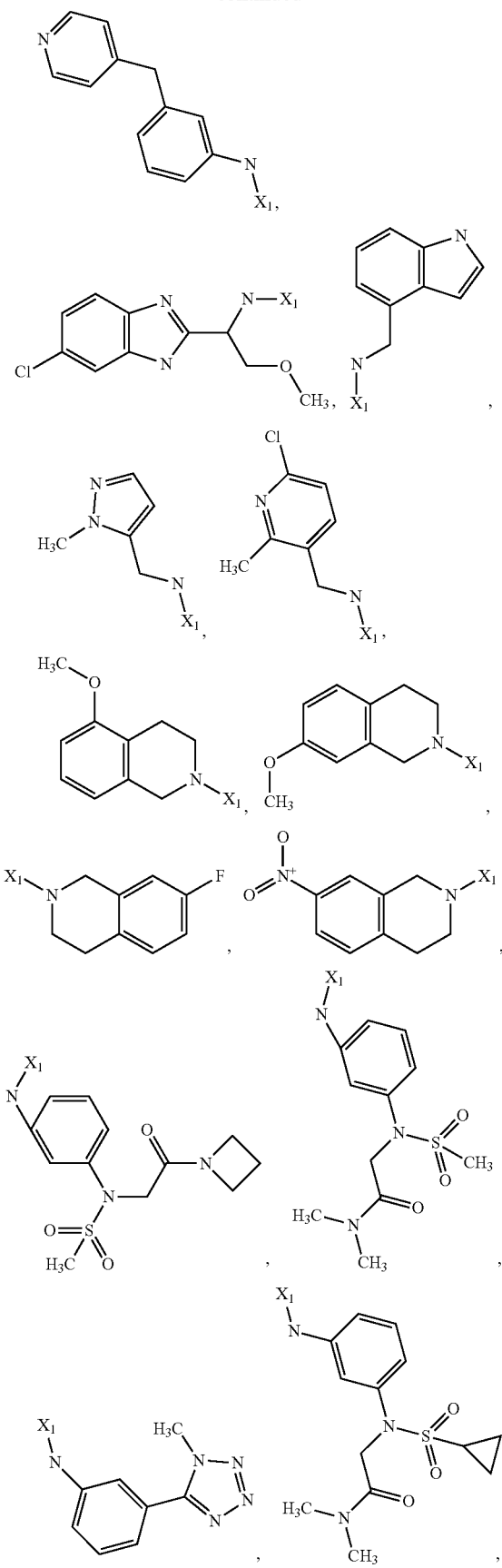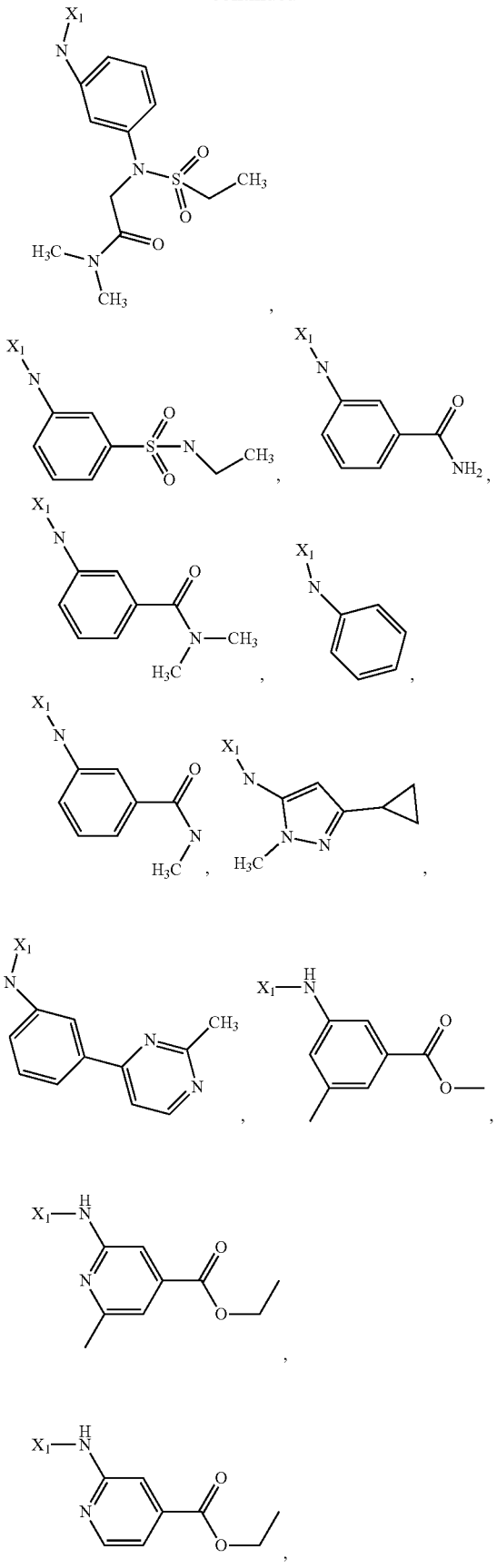

-continued
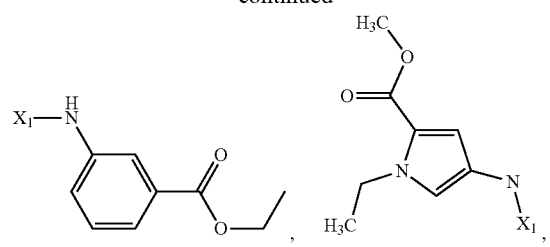
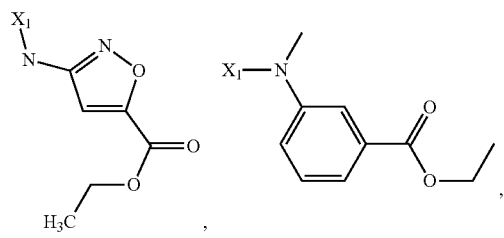
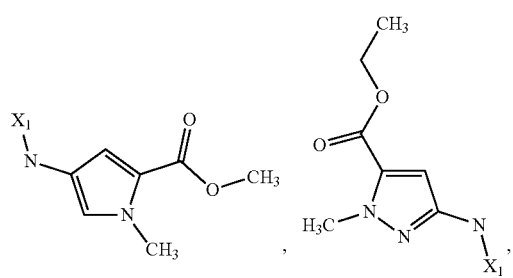
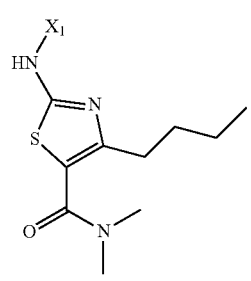
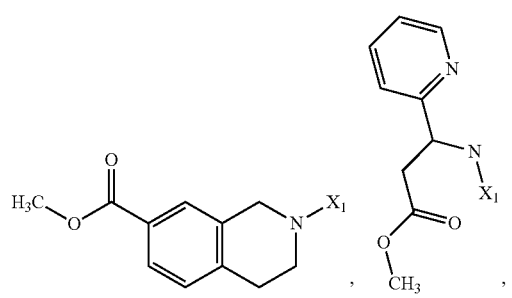
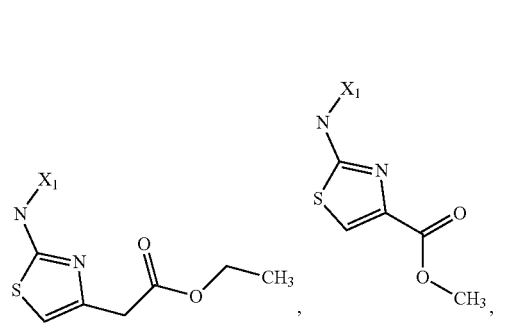
-continued
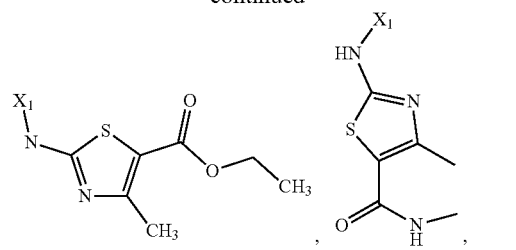
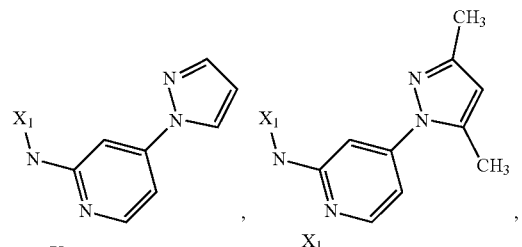
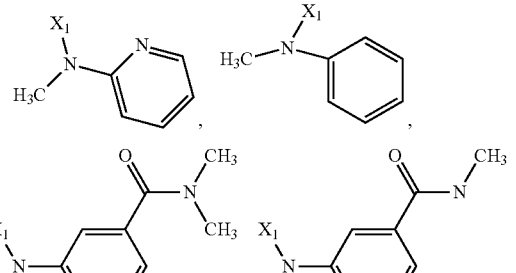
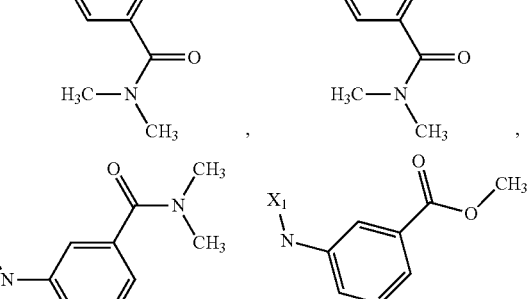
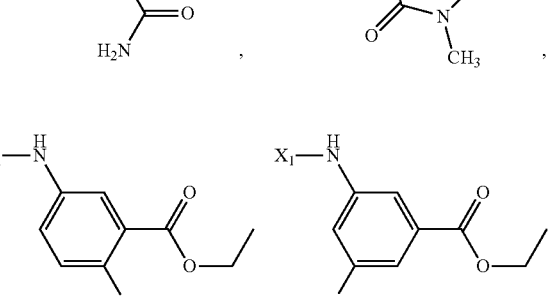
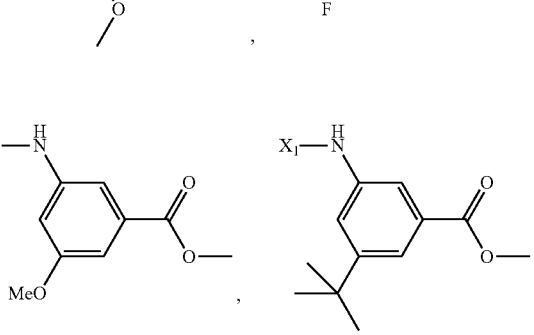

-continued
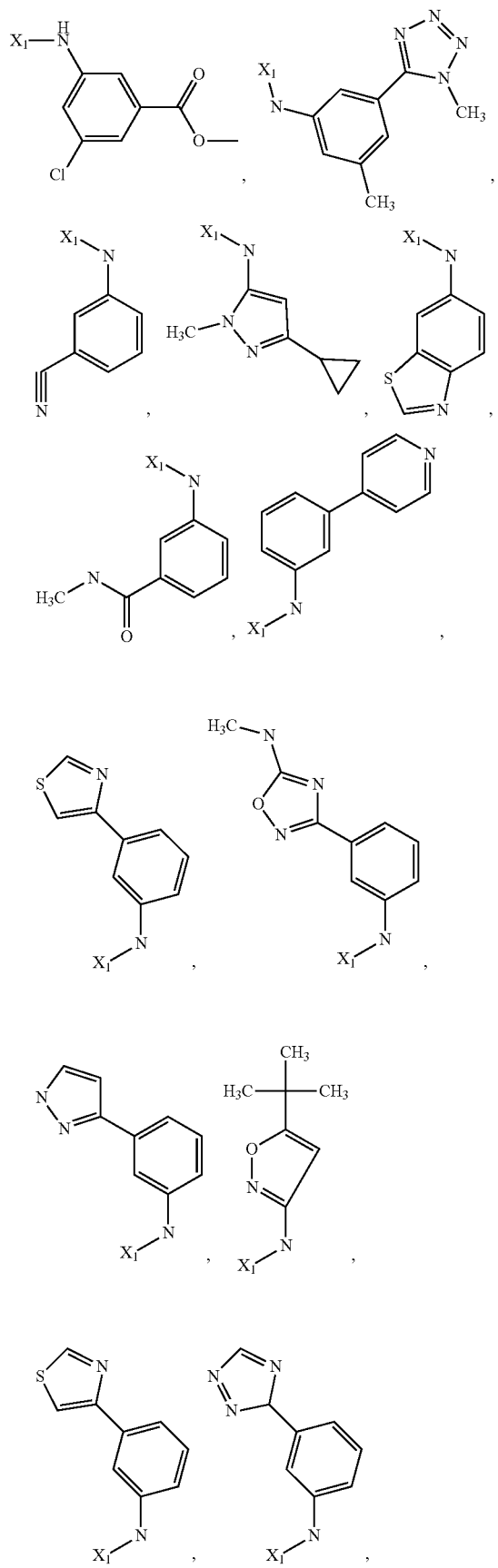
-continued
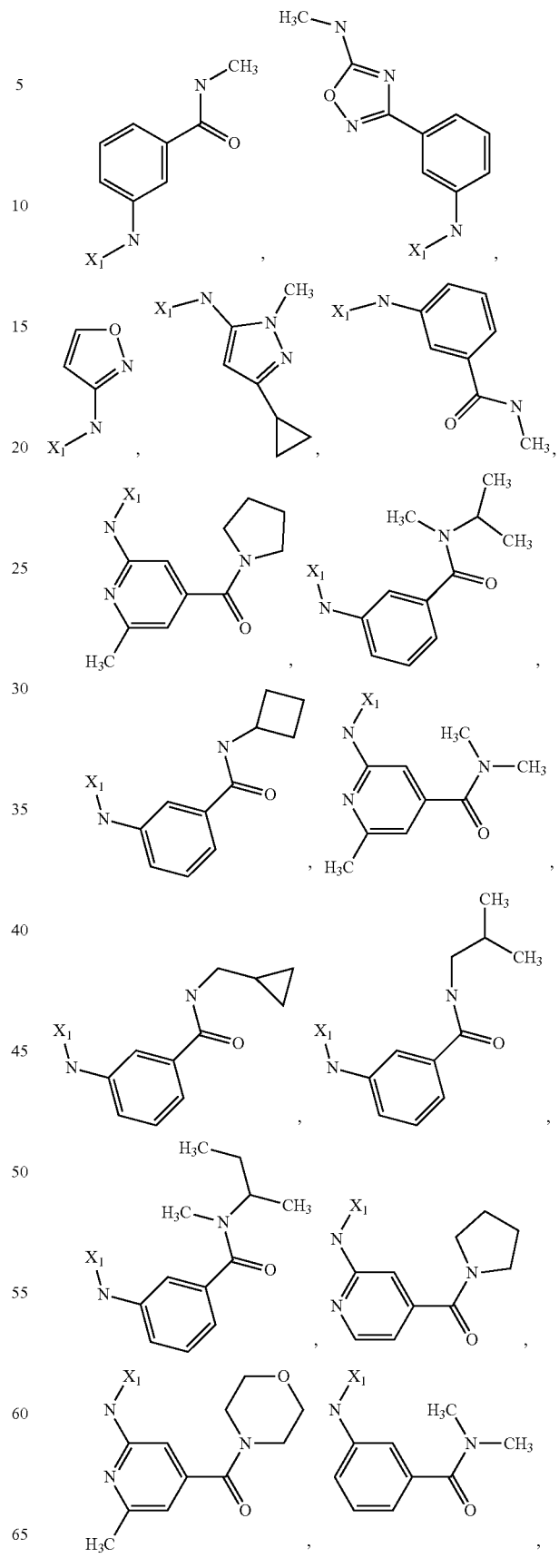

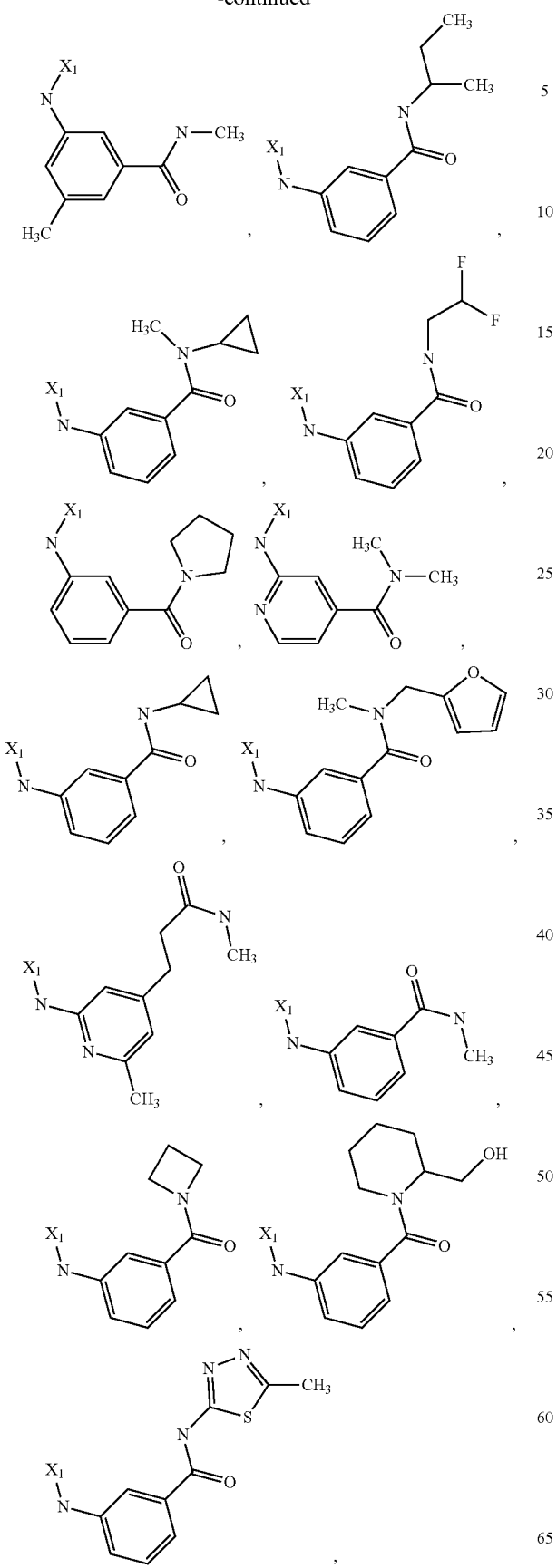
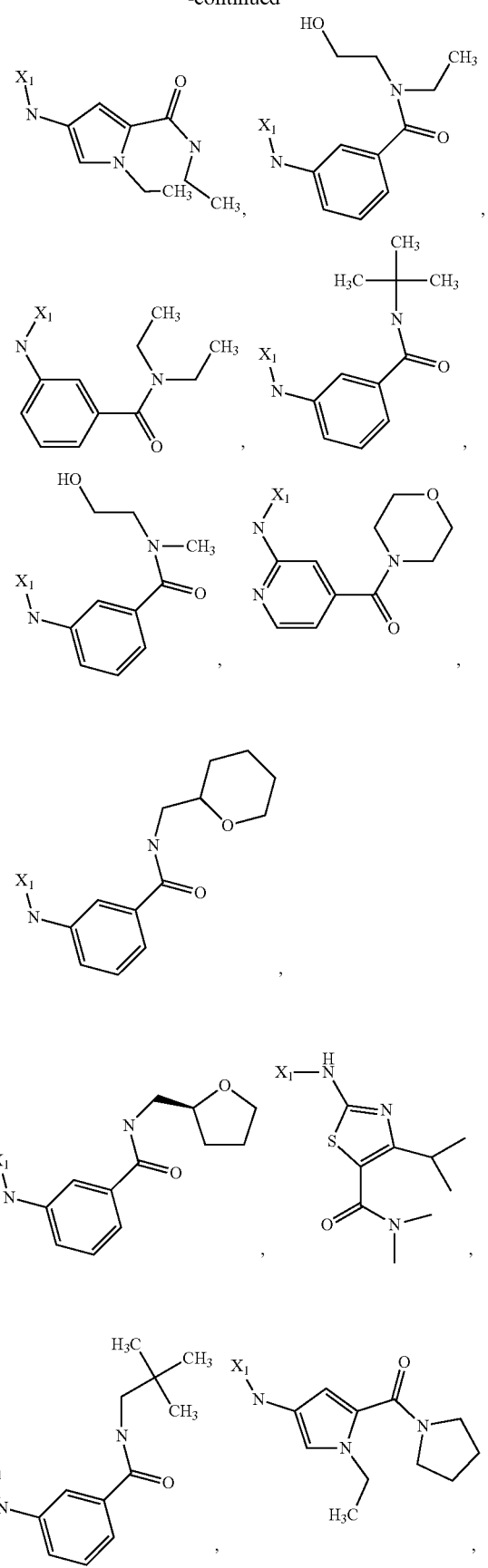

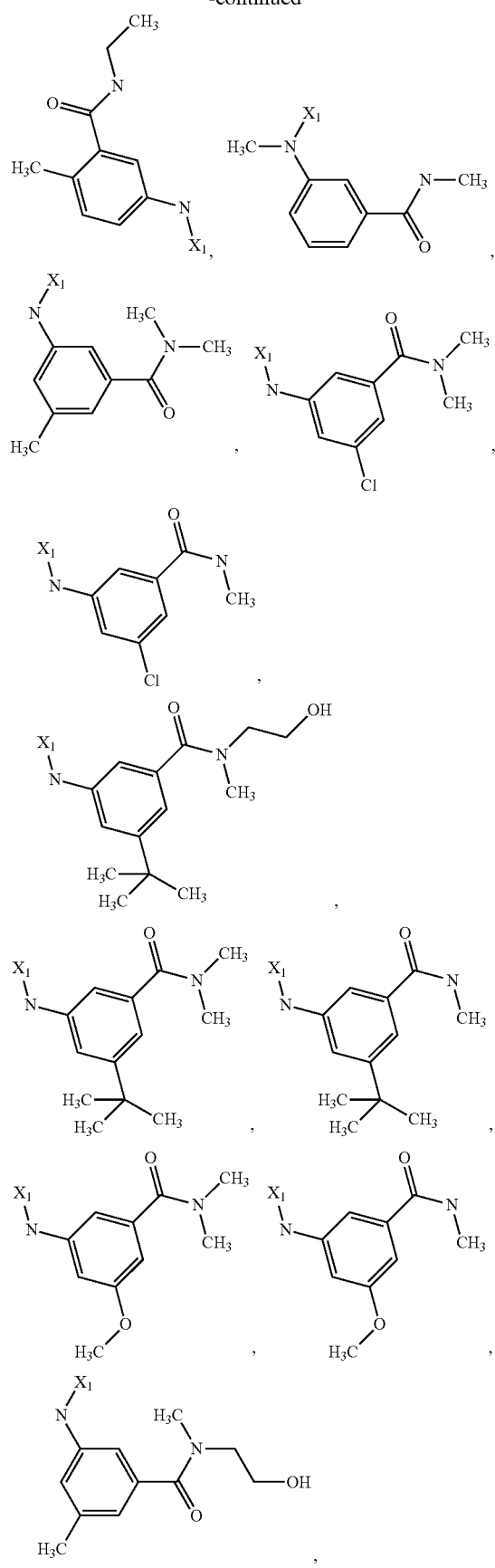
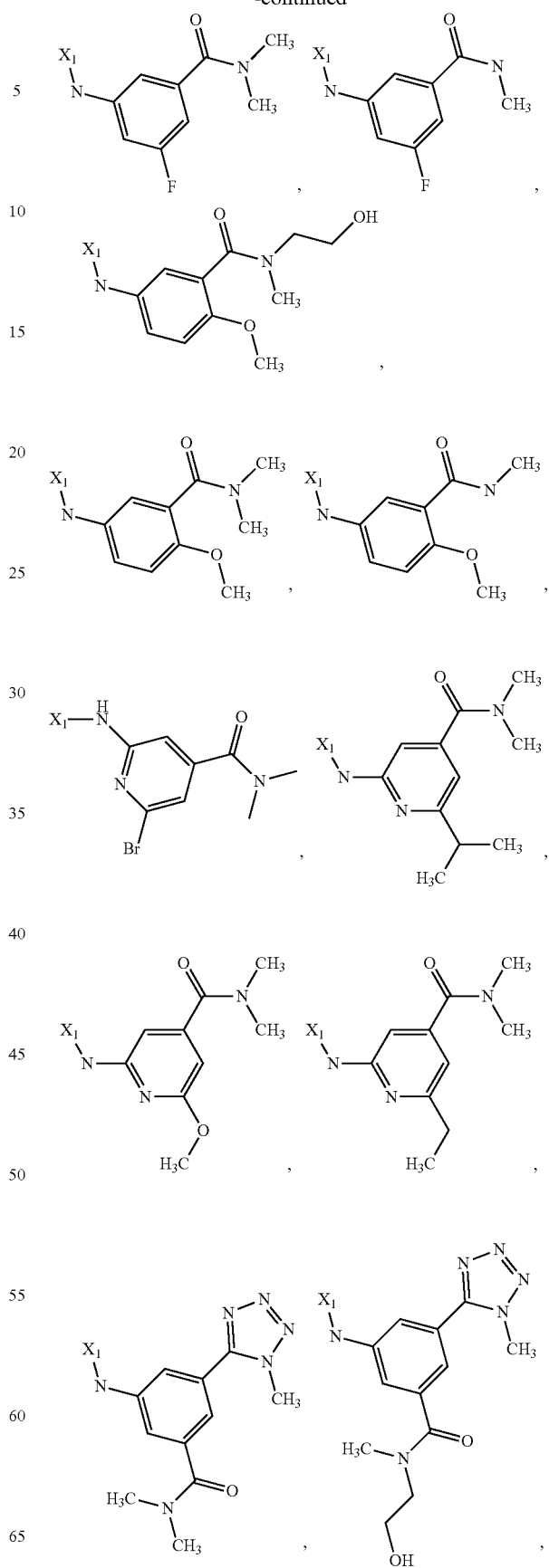

-continued
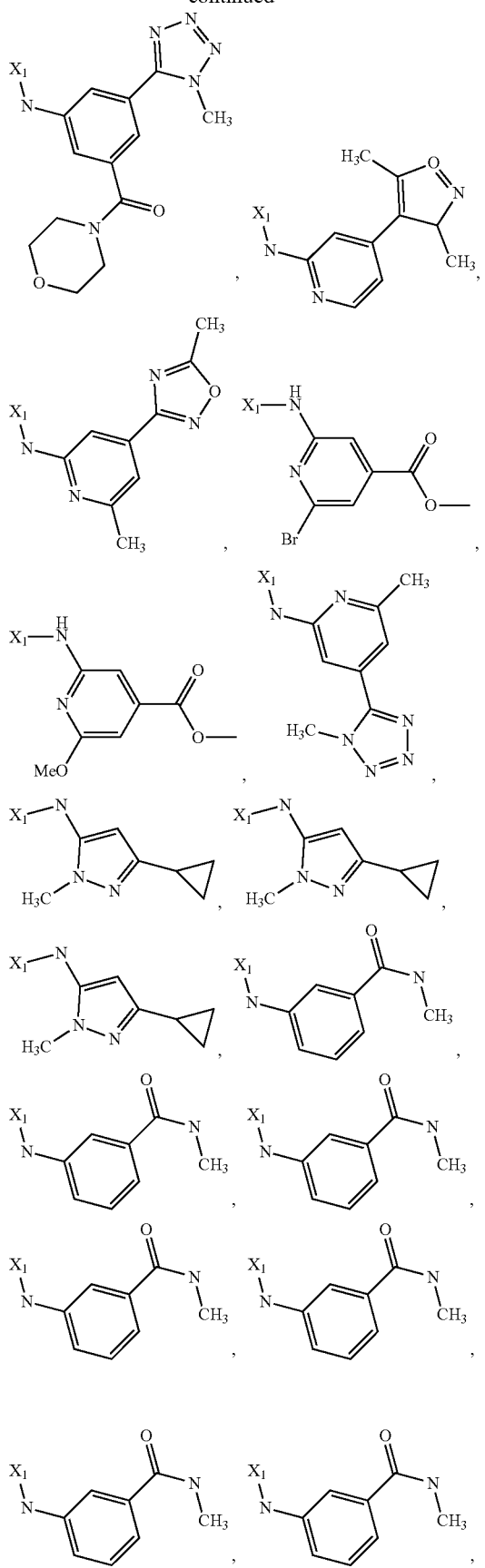
-continued
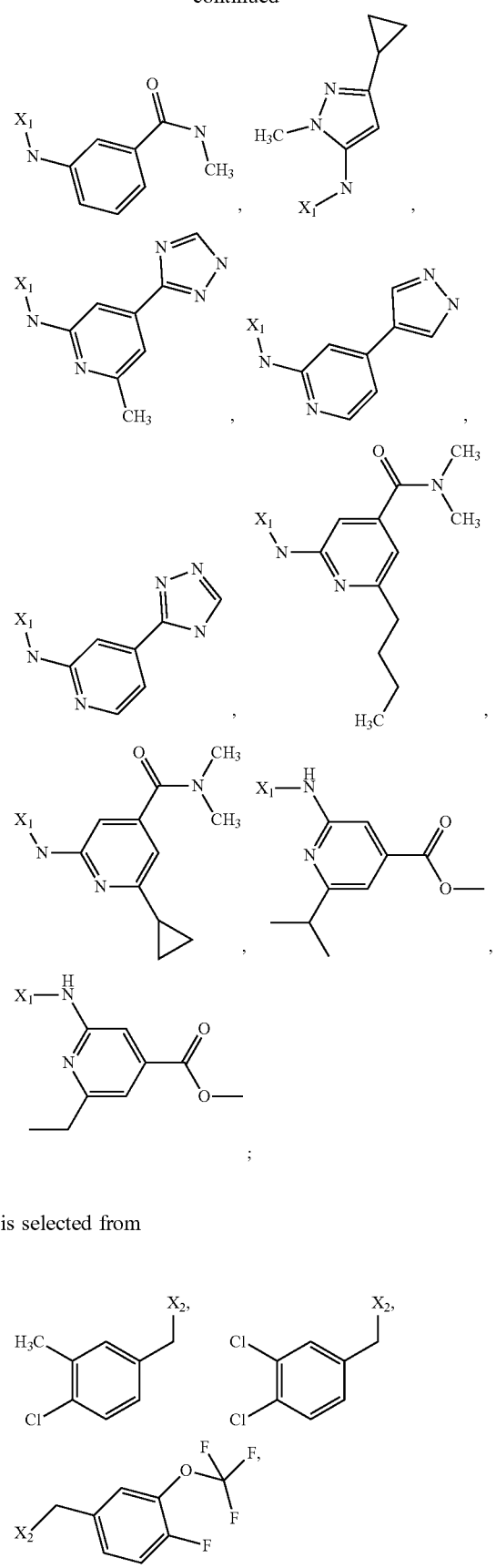
R² is selected from

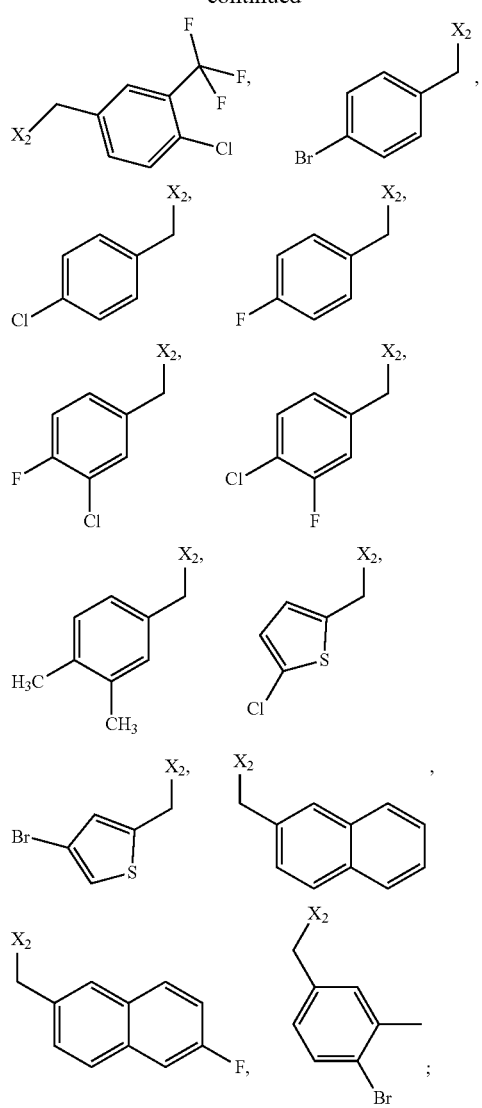
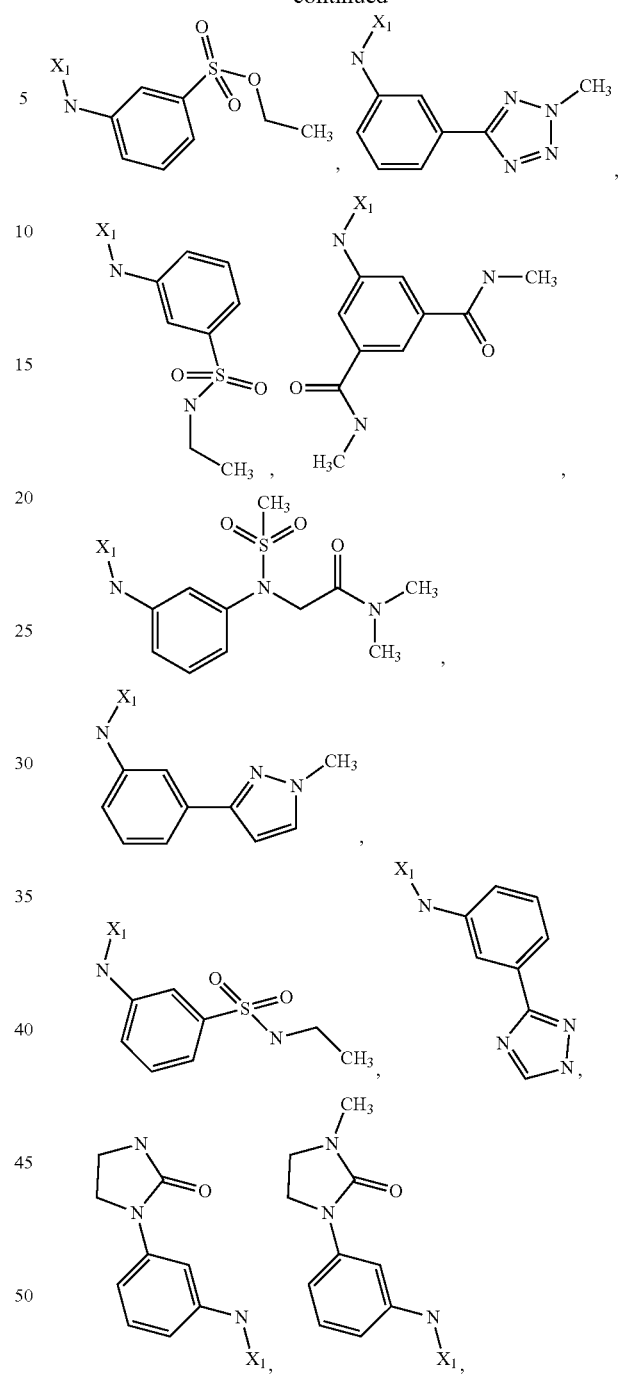
$R^3$ is H;
$R^4$ is H;
or $R^3$ and $R^4$ together are forming a $CH_2$—$CH_2$ group.
Another embodiment of the present invention are compounds of formula 1, wherein A is defined as above; $R^3$ is H; $R^4$ is H; and $R^2$ is defined as in Table 1 shown below; and $R^1$ is selected from
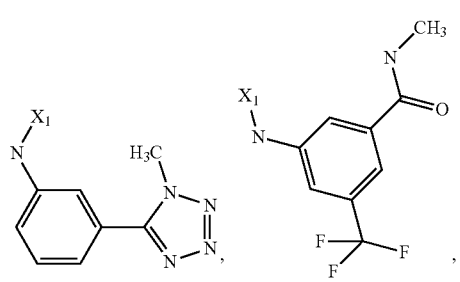
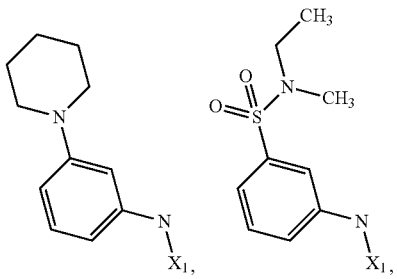

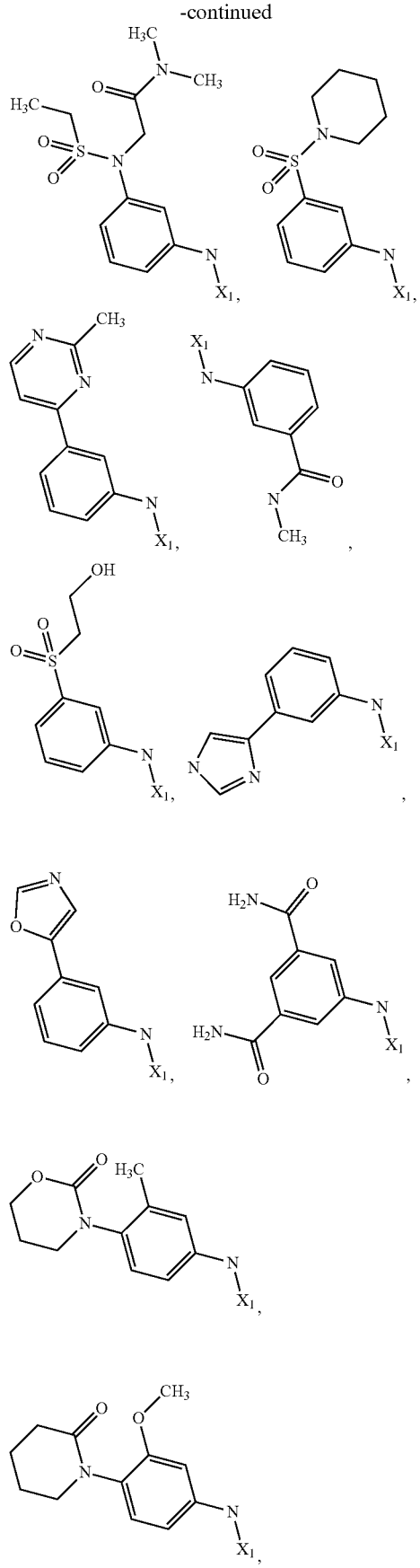
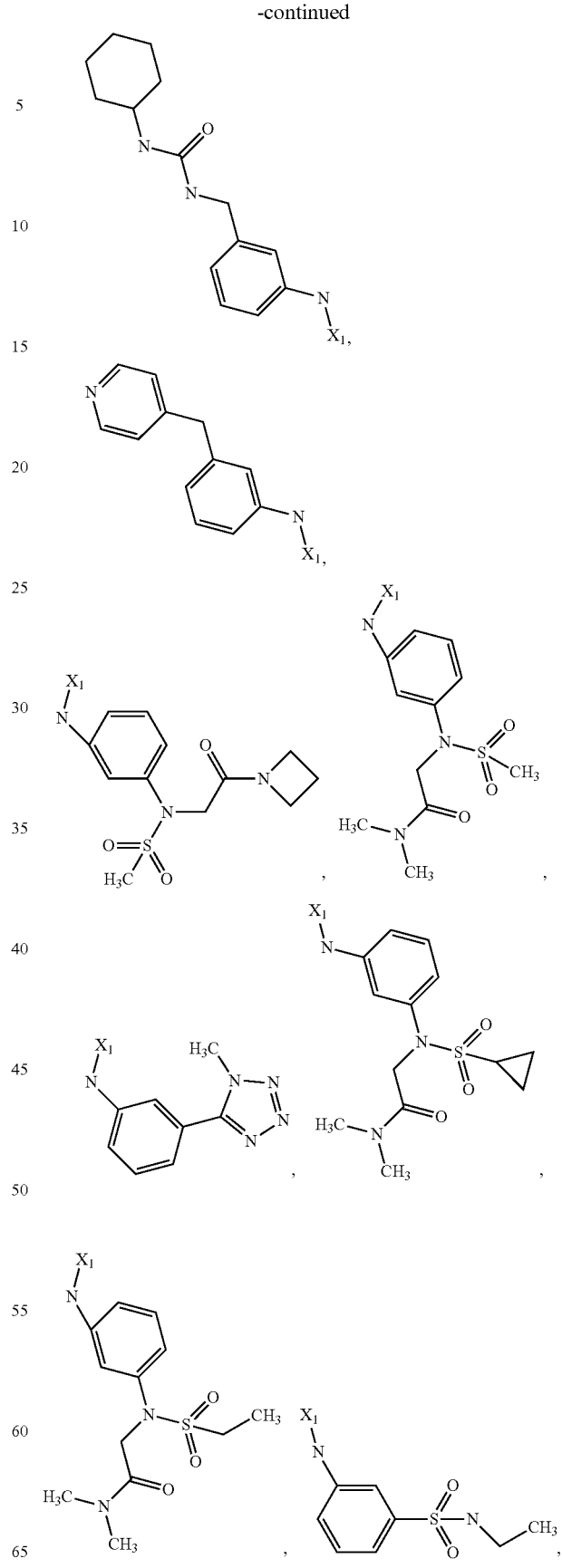

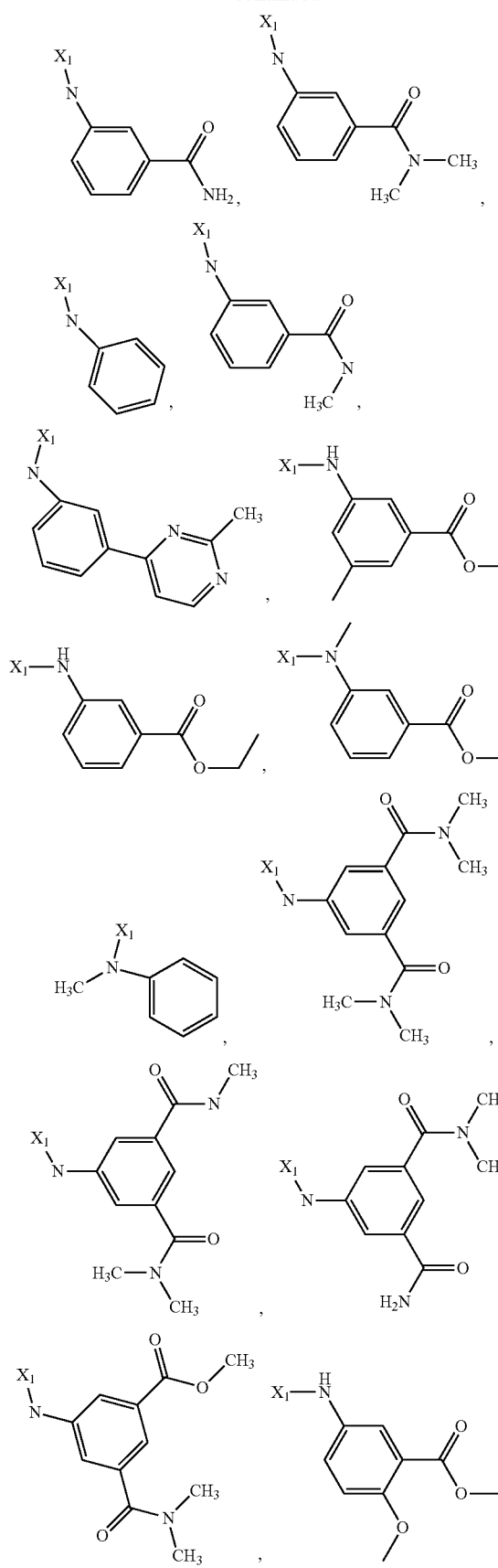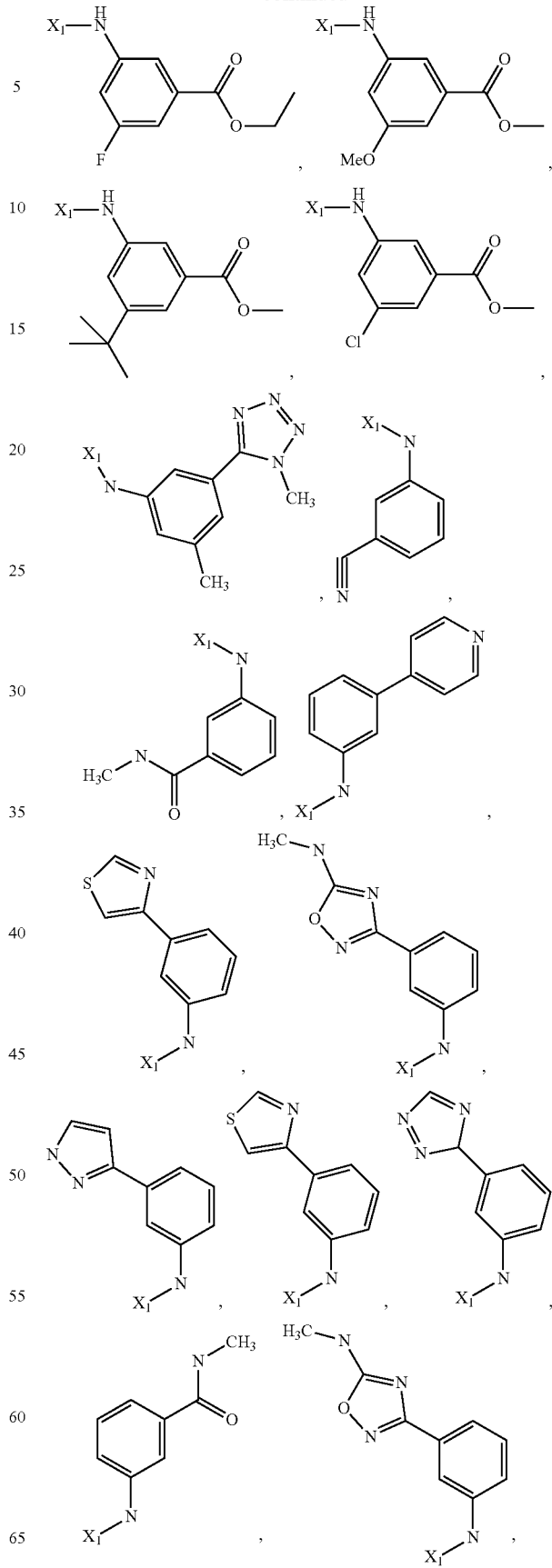

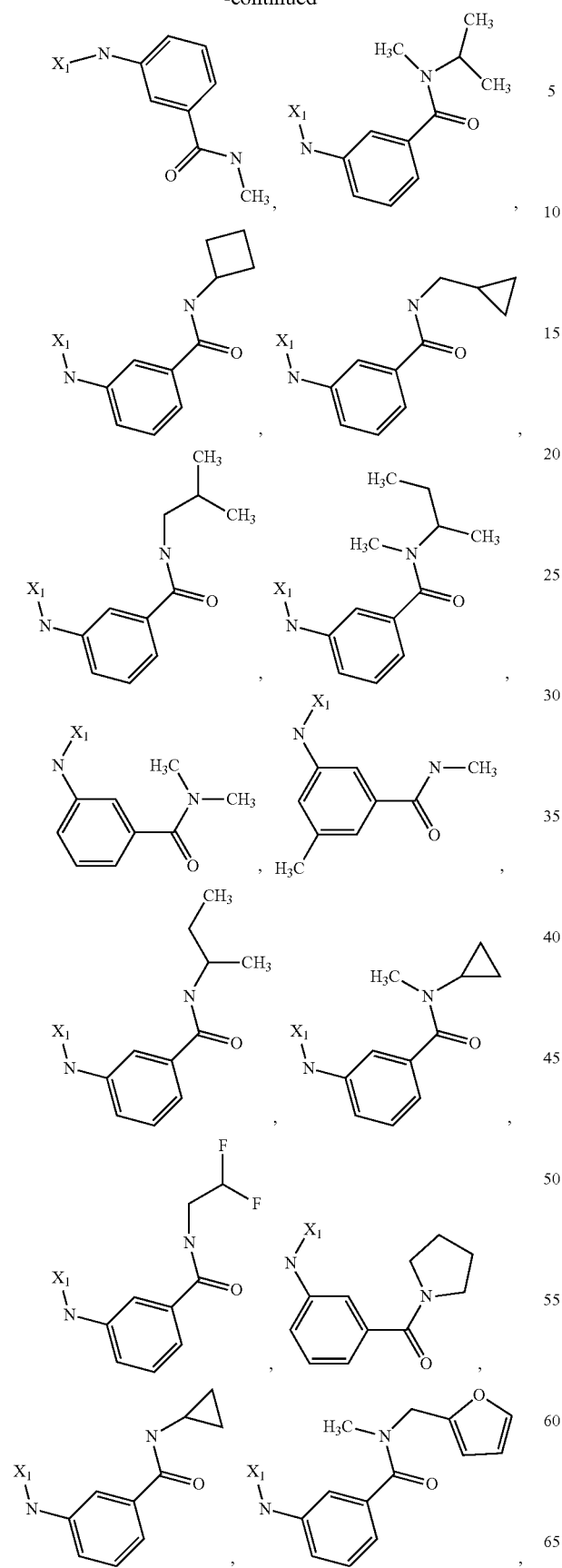
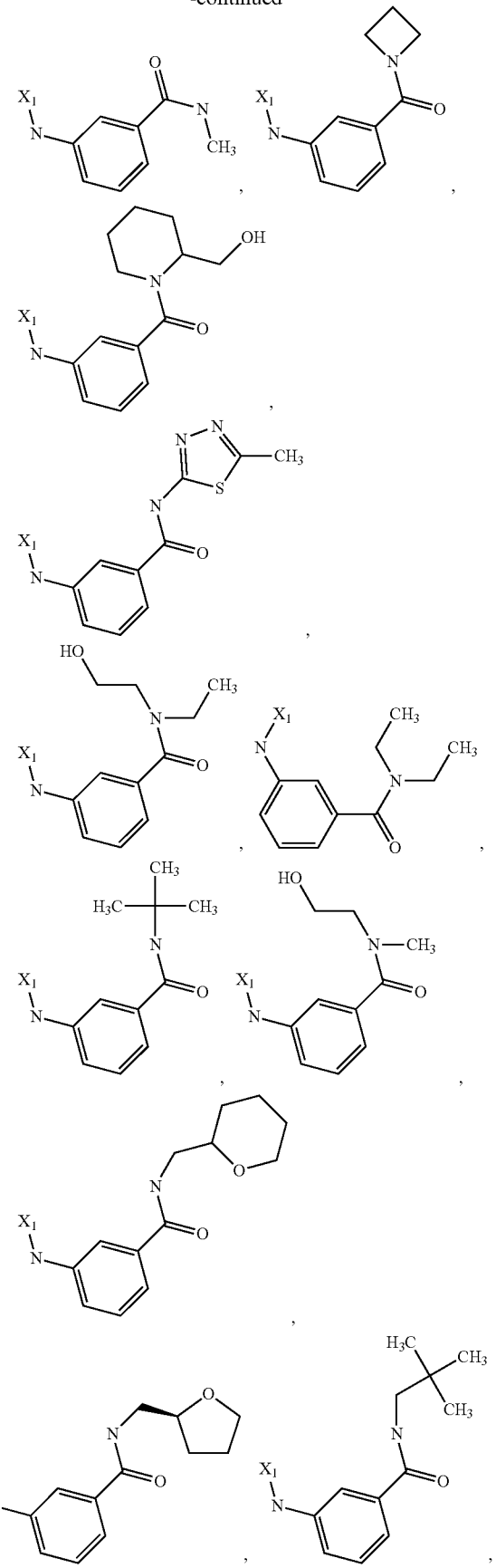

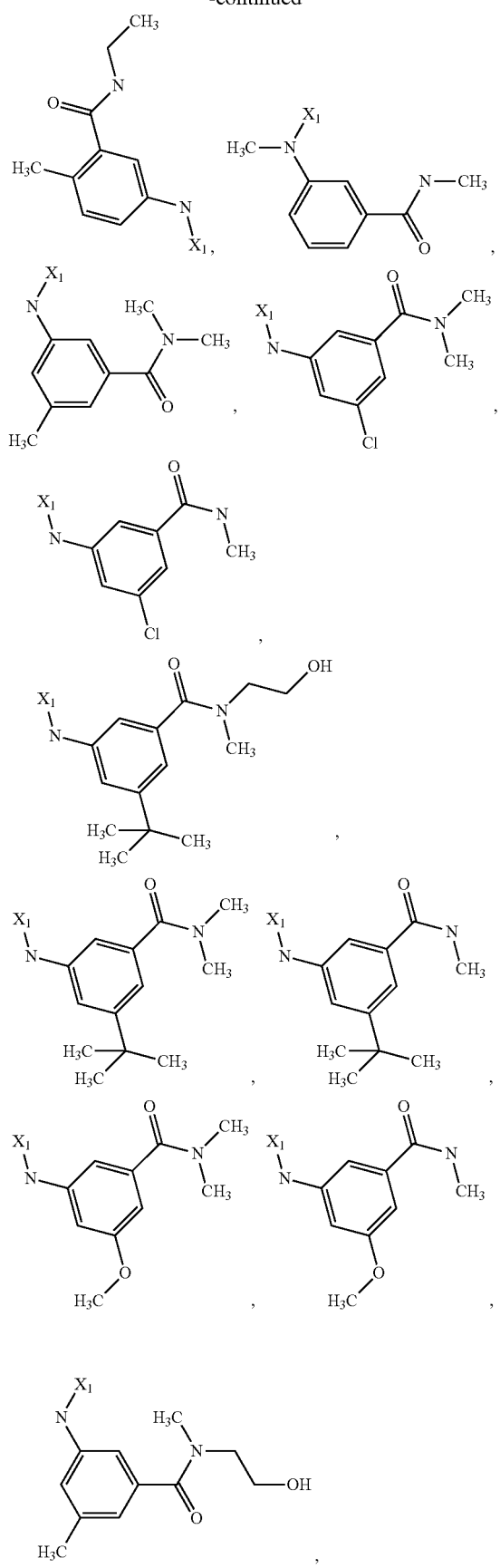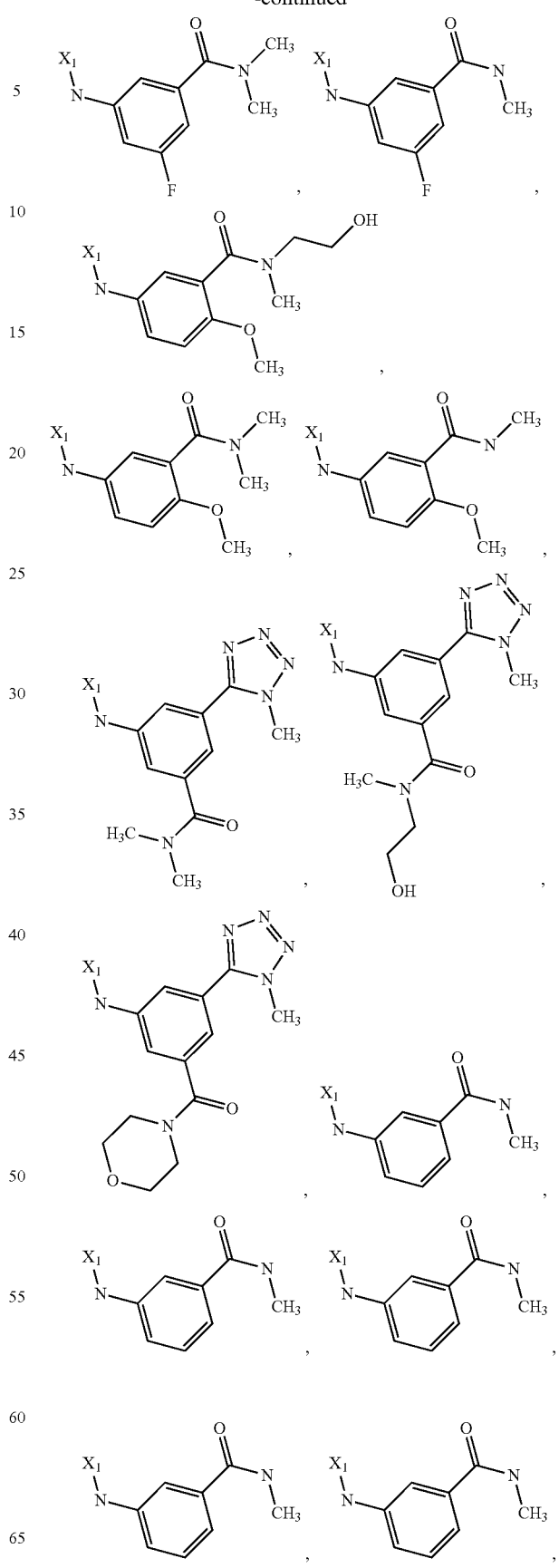

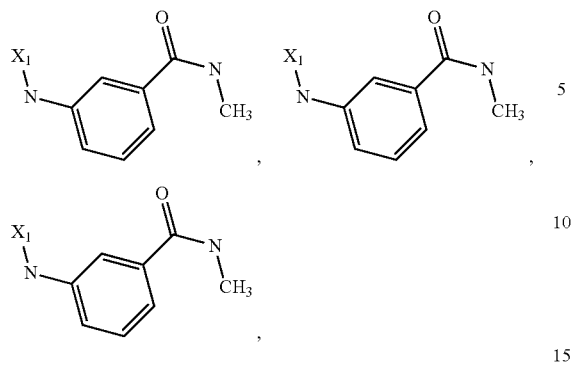
Another embodiment of the present invention further comprises administration to a subject of the compounds of formula 1, wherein A is defined as above; $R^3$ is H; $R^4$ is H; and $R^2$ is defined as in Table 1 shown below; and $R^1$ is selected from
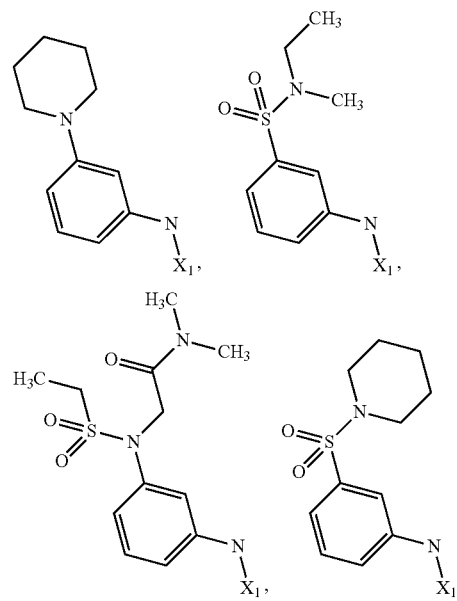
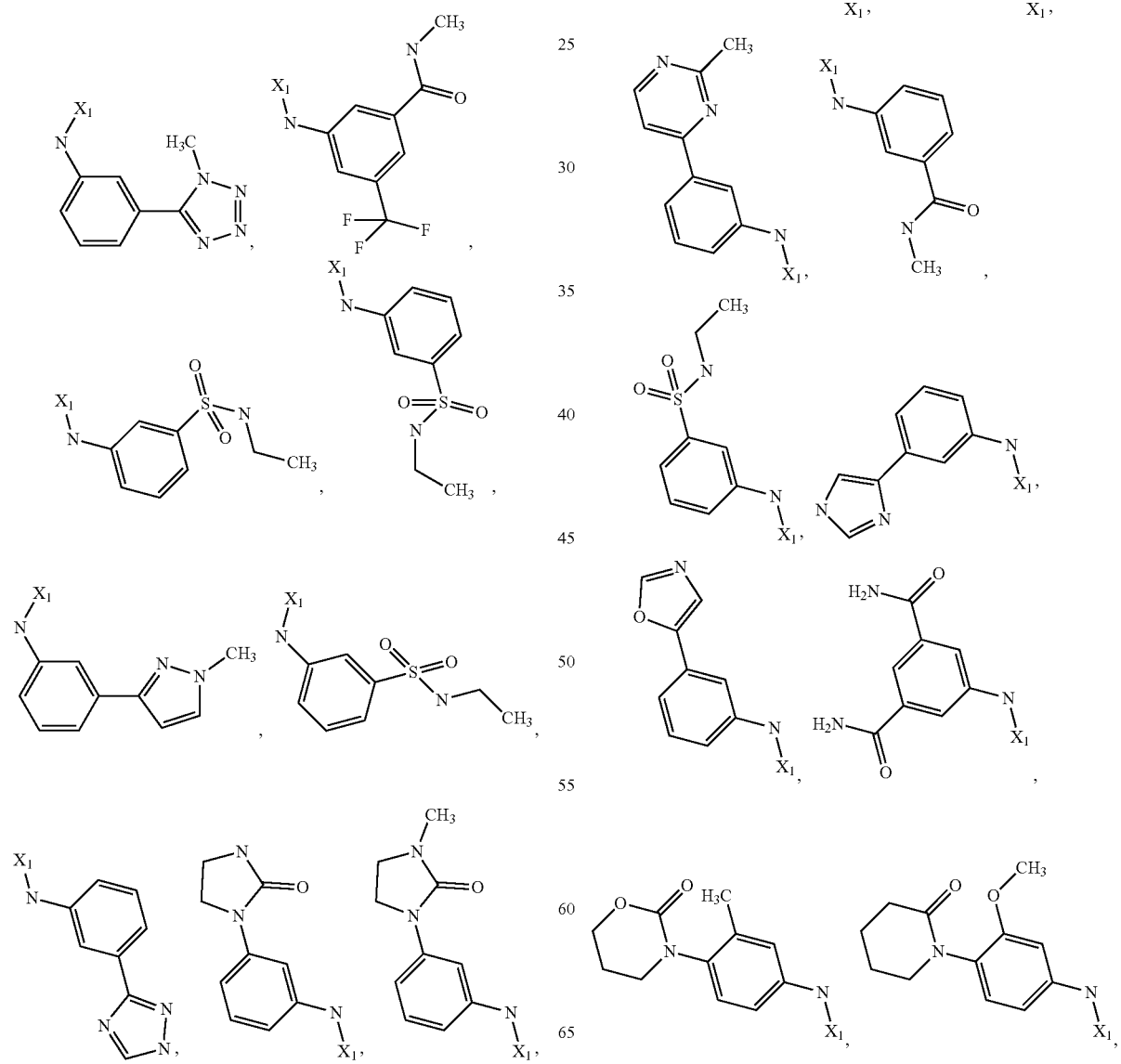

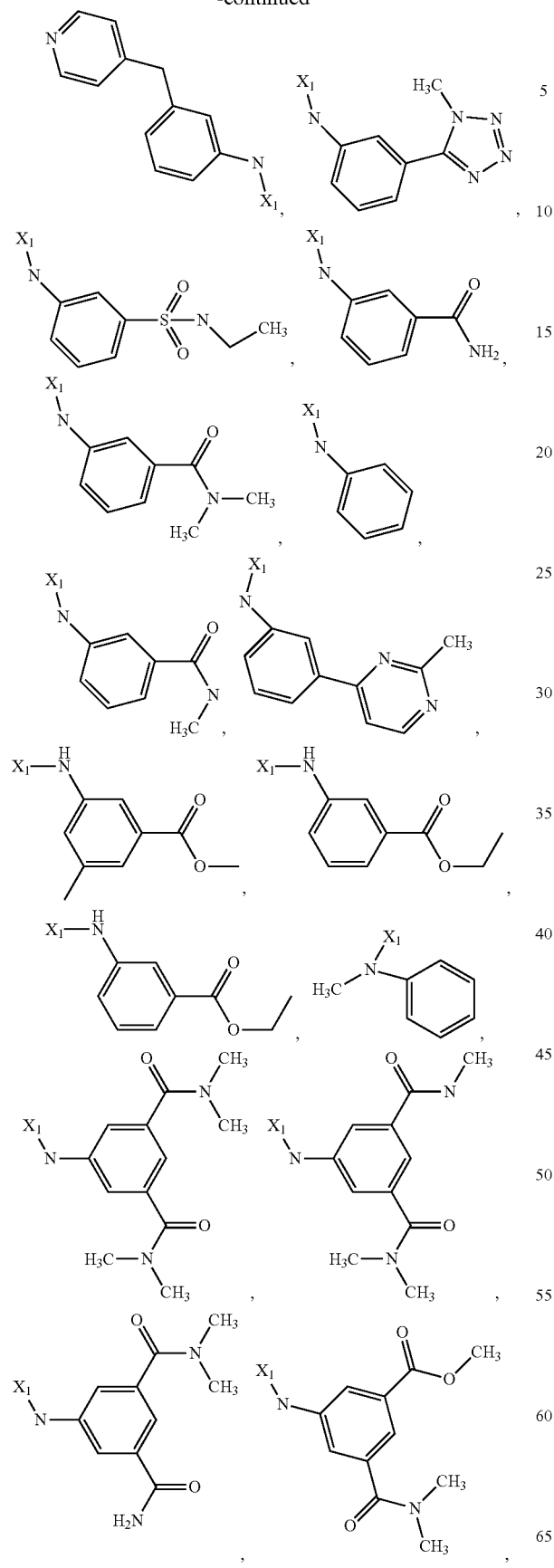
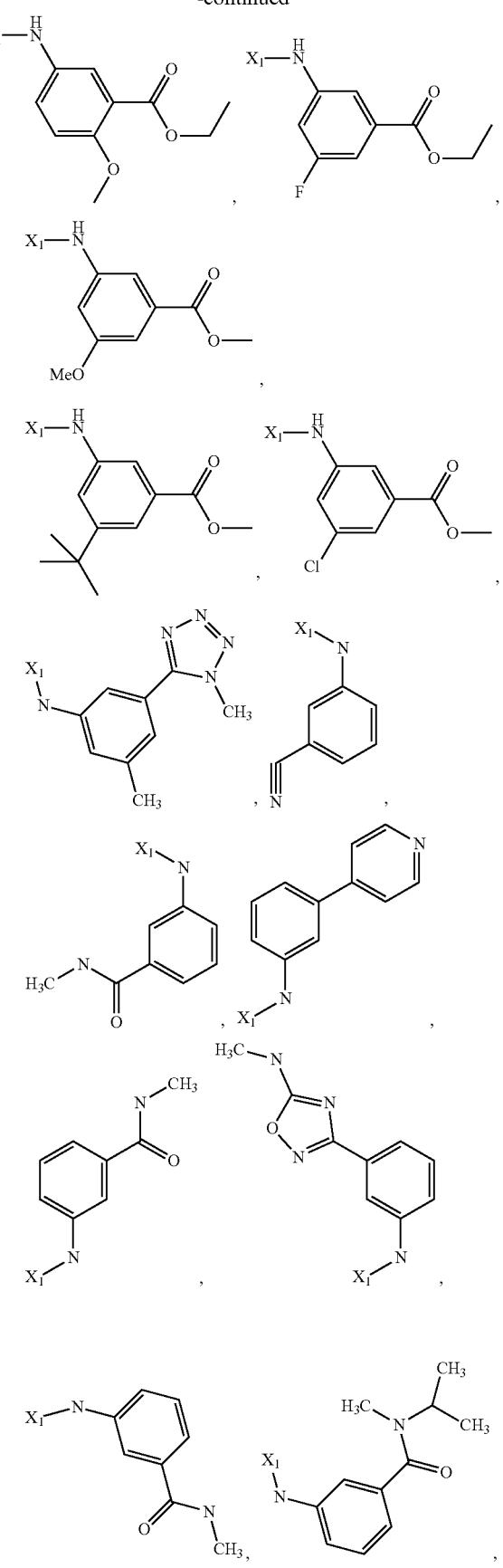

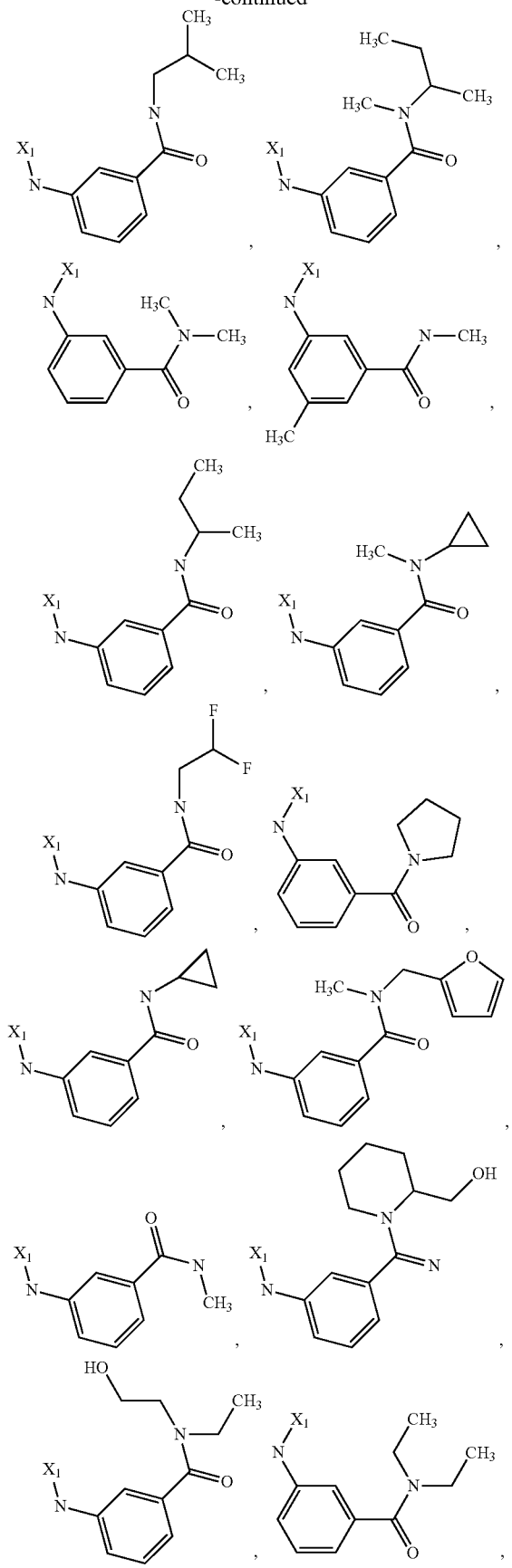
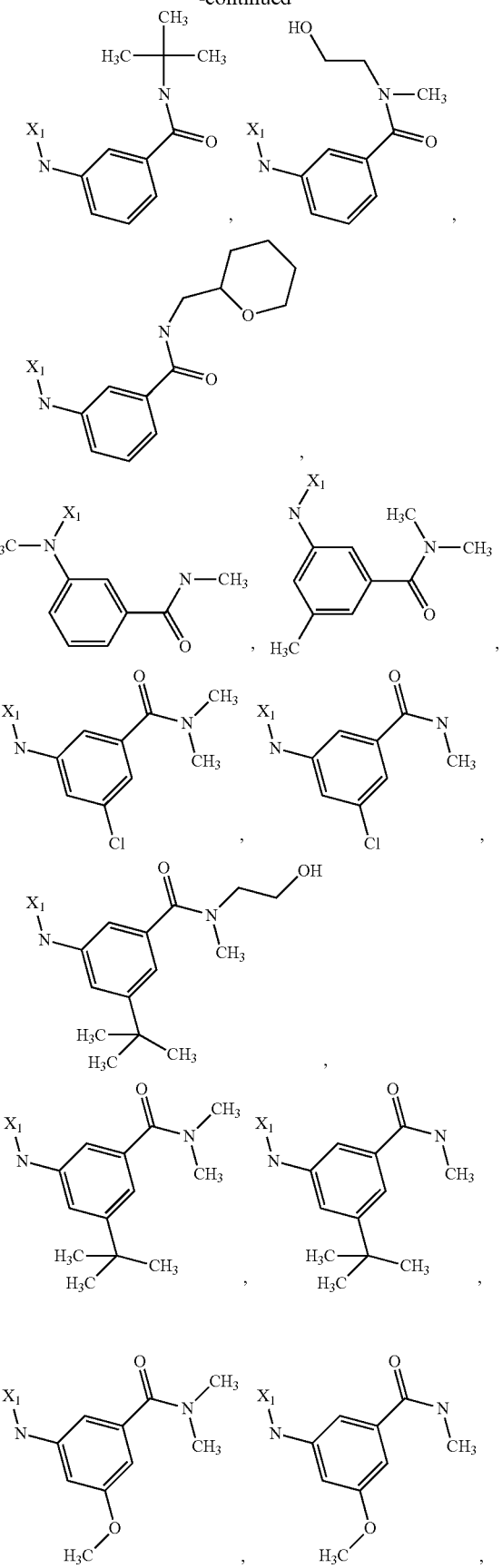

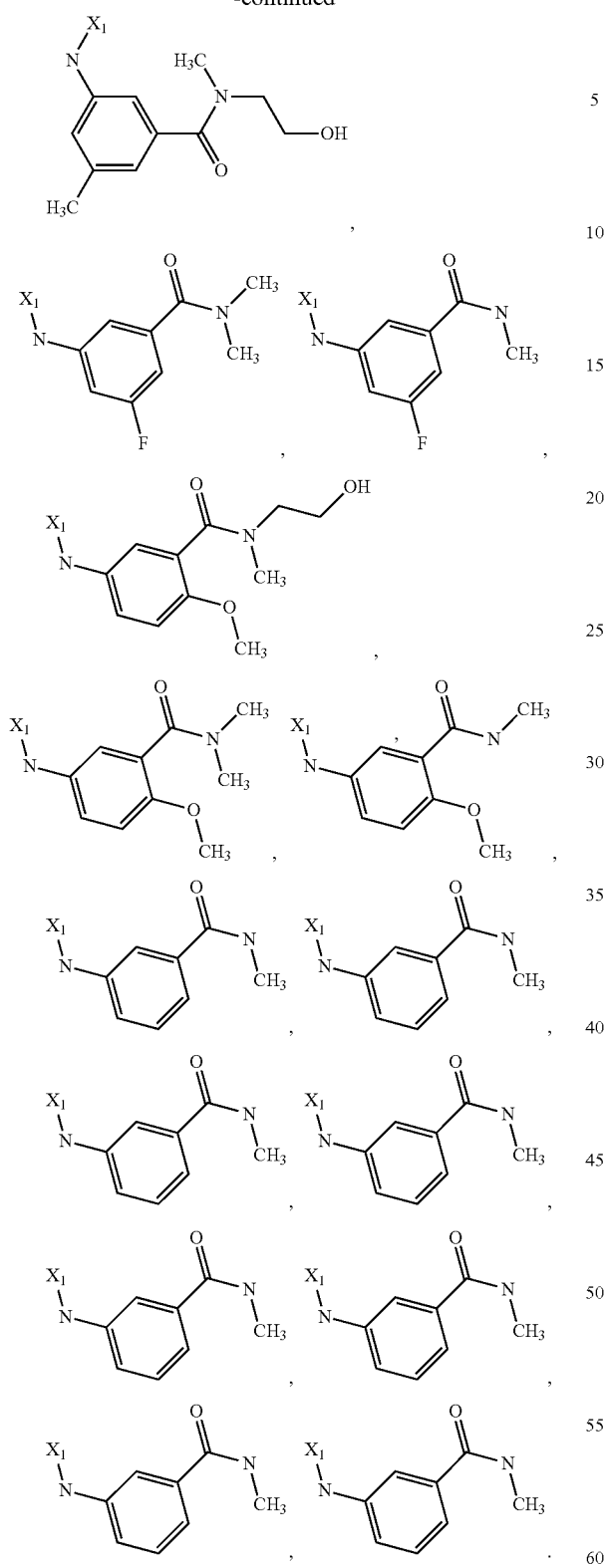
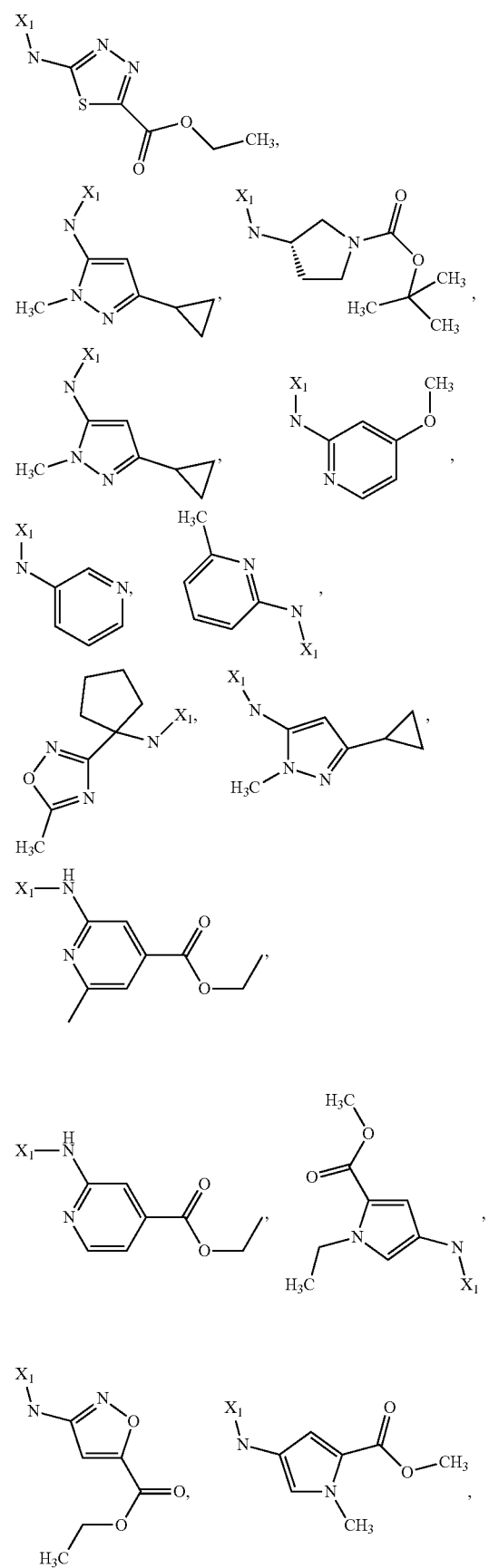
Another embodiment of the present invention further comprises administration to a subject of the compounds of formula 1, wherein A is defined as above; $R^3$ is H; $R^4$ is H; and $R^2$ is defined as in Table 1 shown below; $R^1$ is selected from

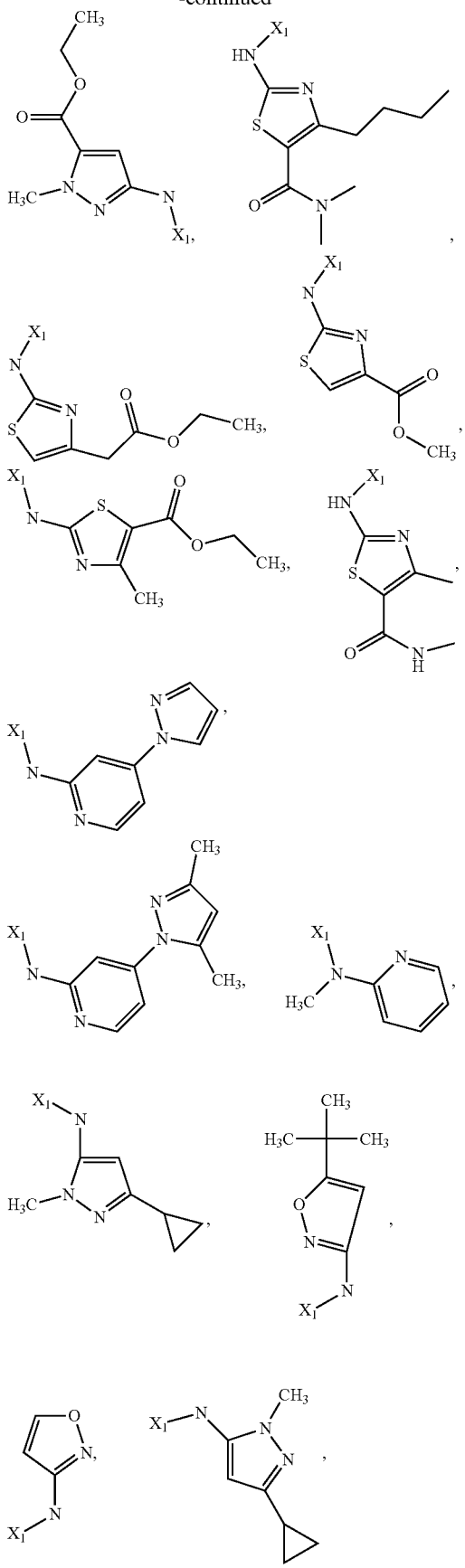
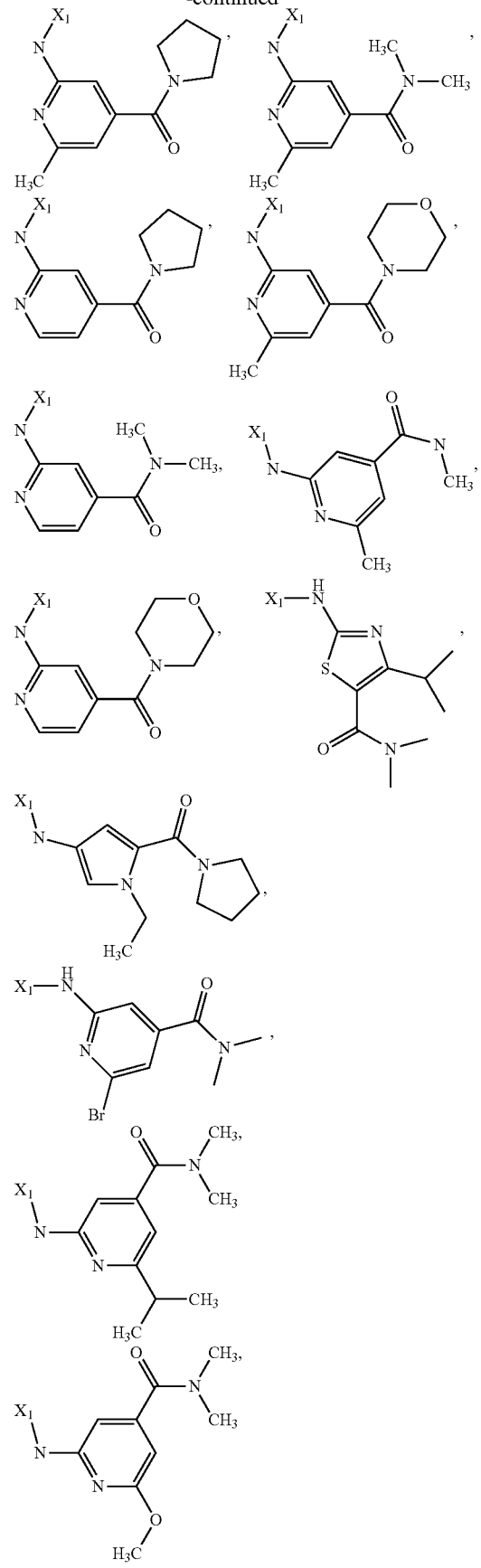

-continued
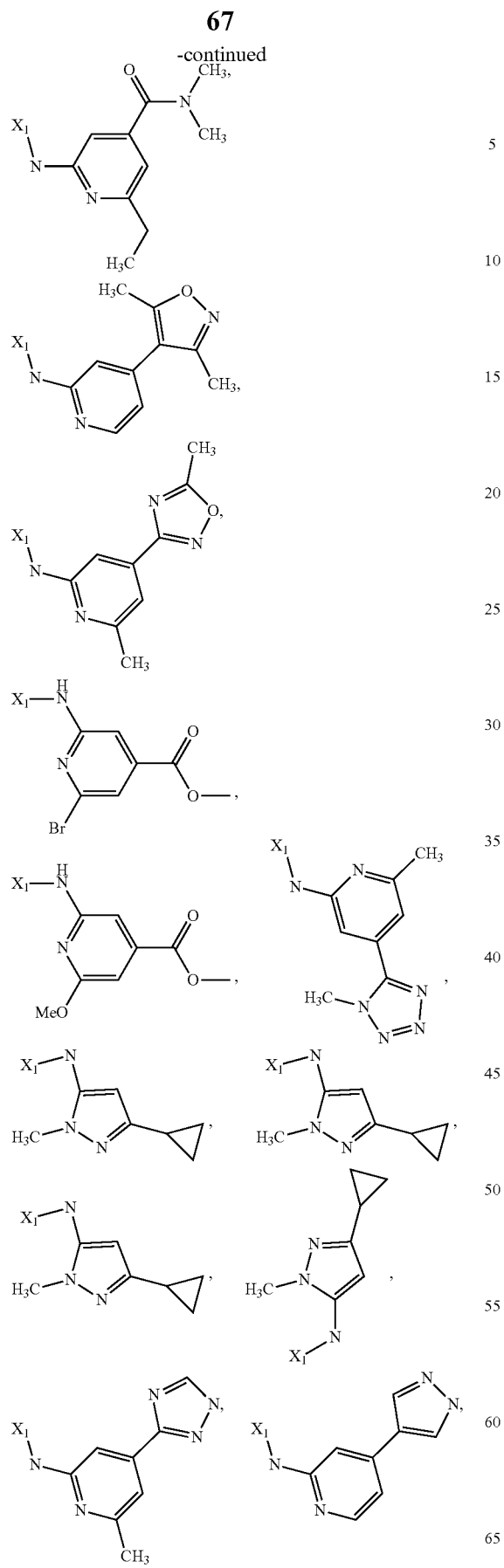
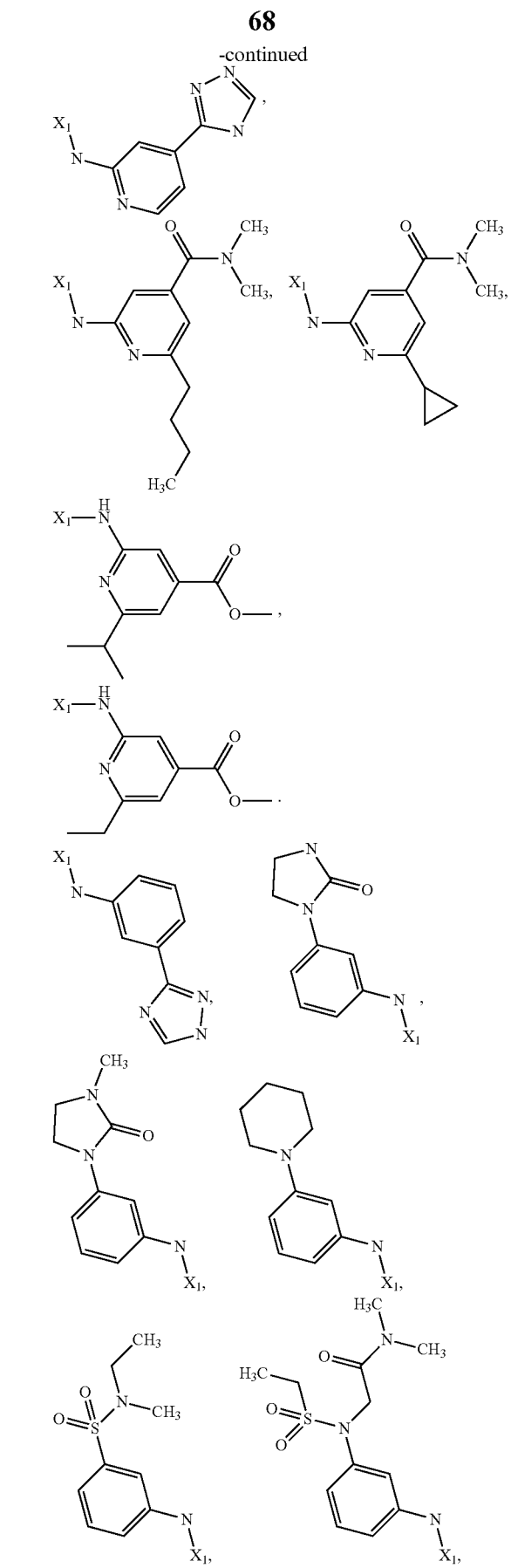

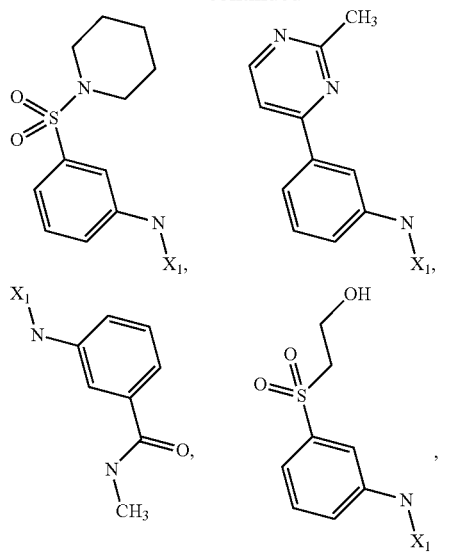
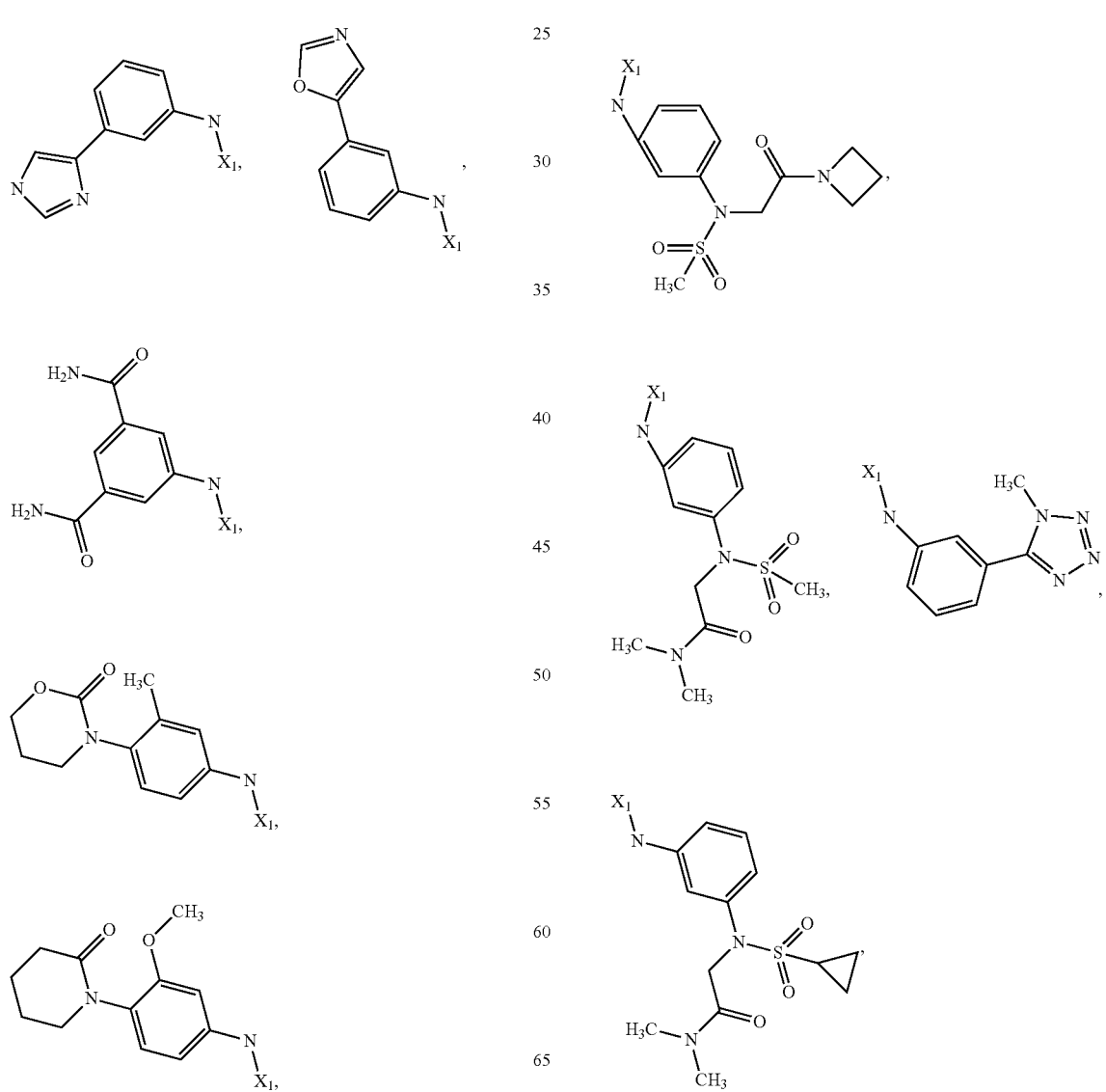

-continued
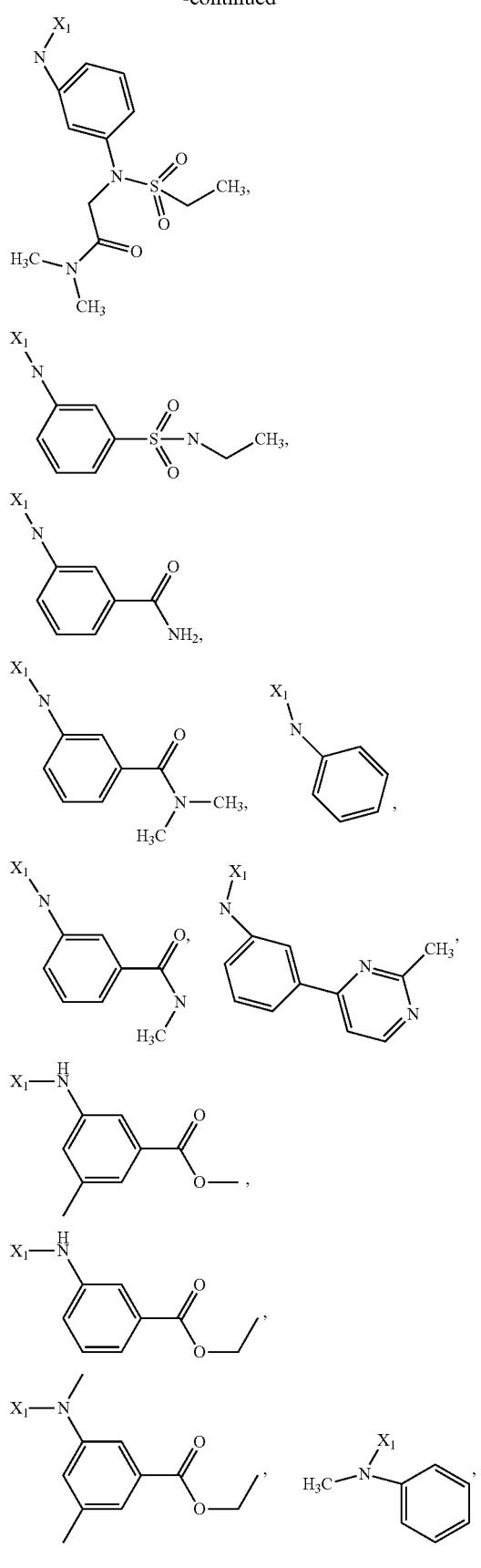
-continued
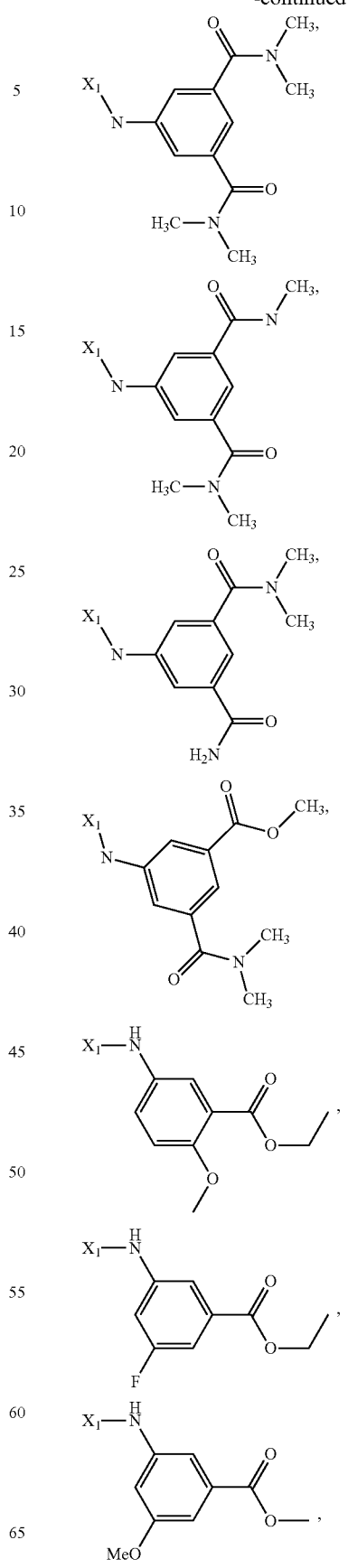

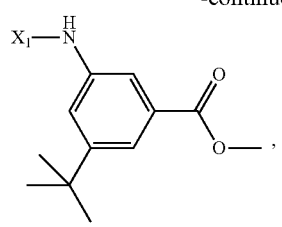
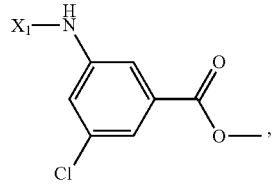
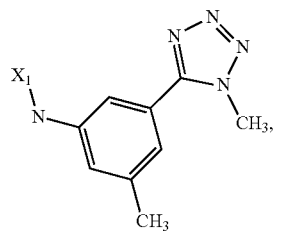
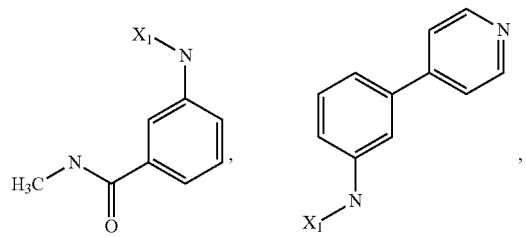
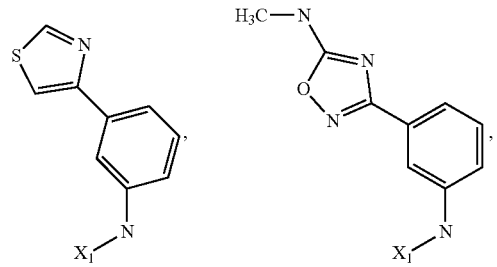
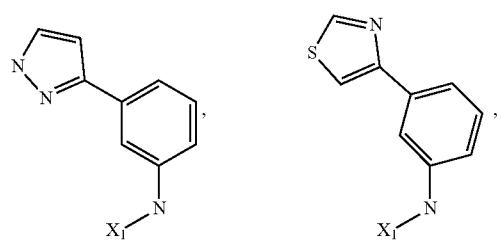
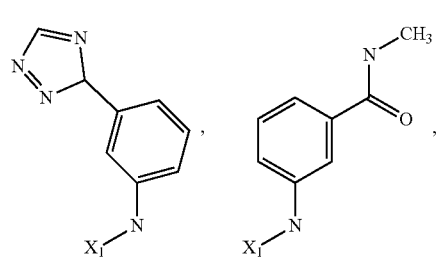
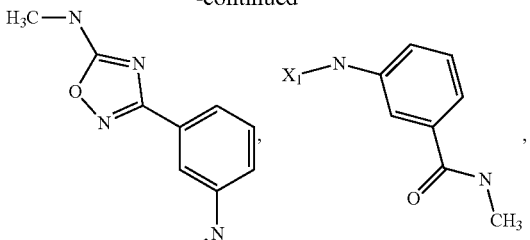
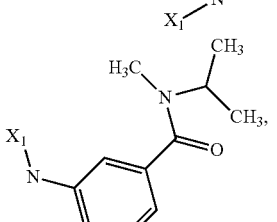
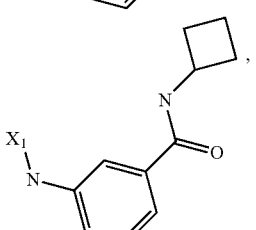
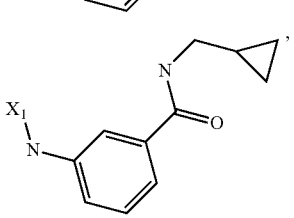
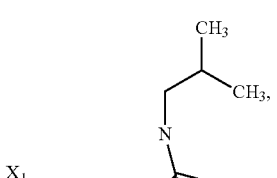
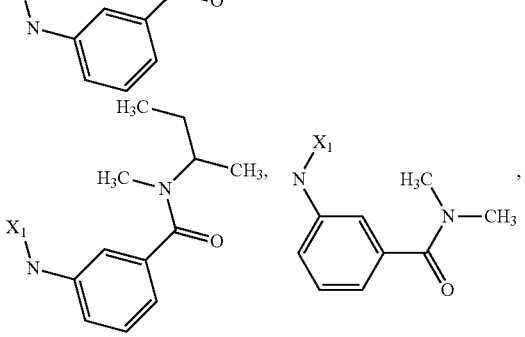
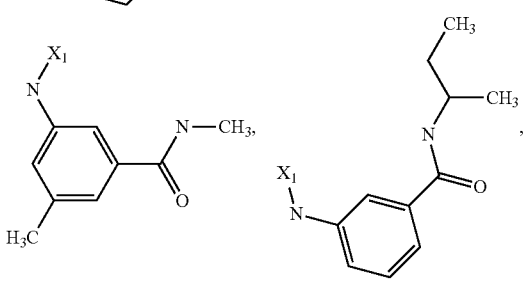

-continued
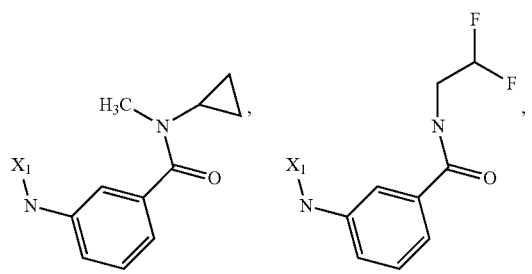
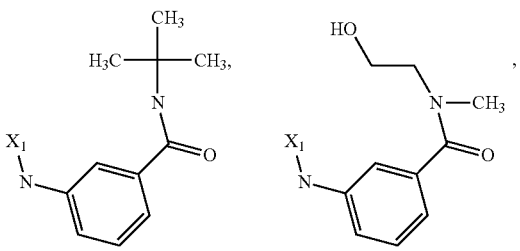
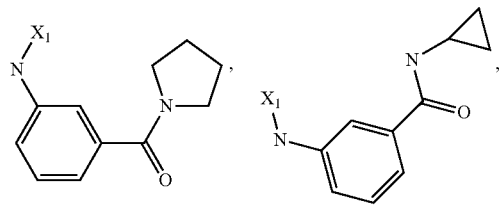
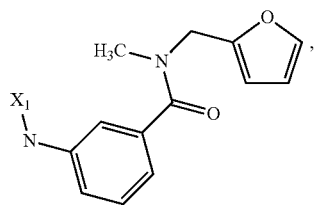
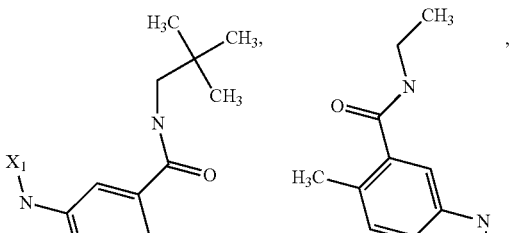
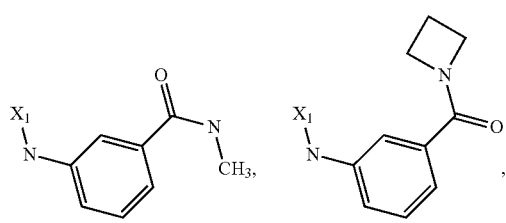
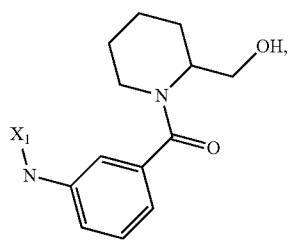
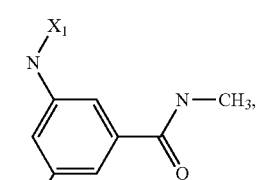
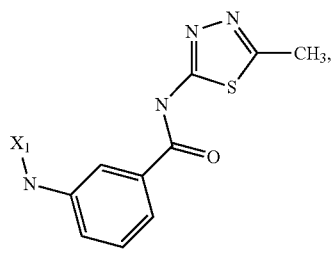
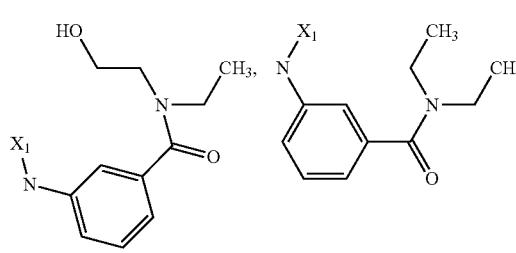
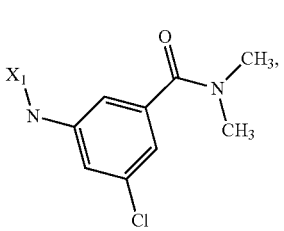

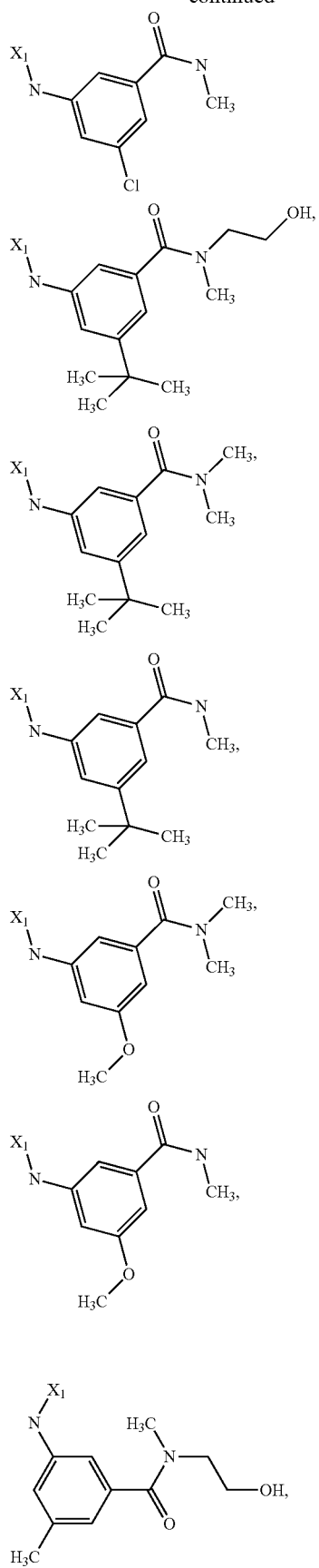
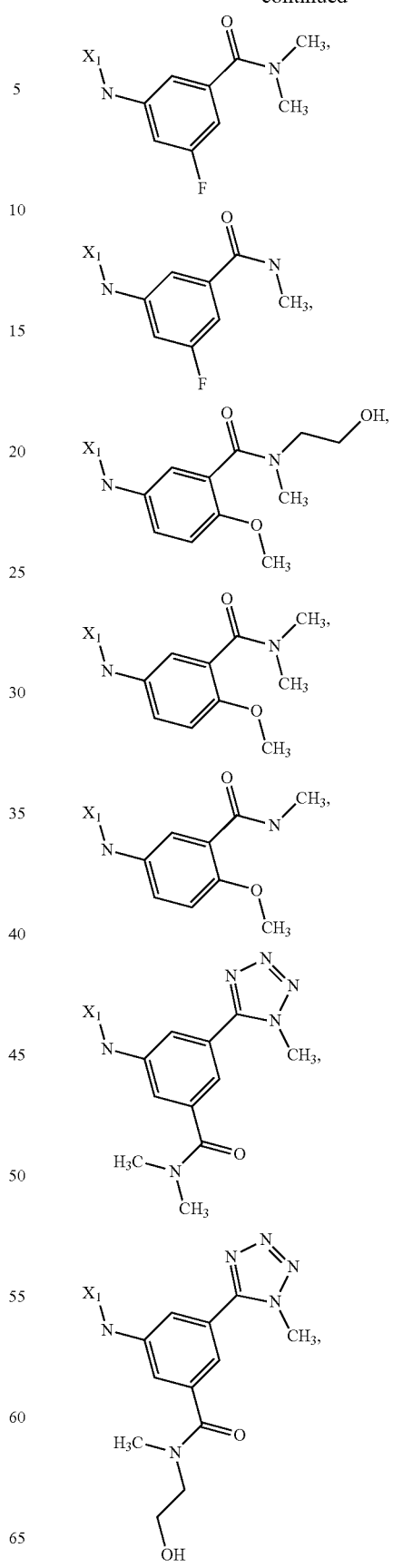

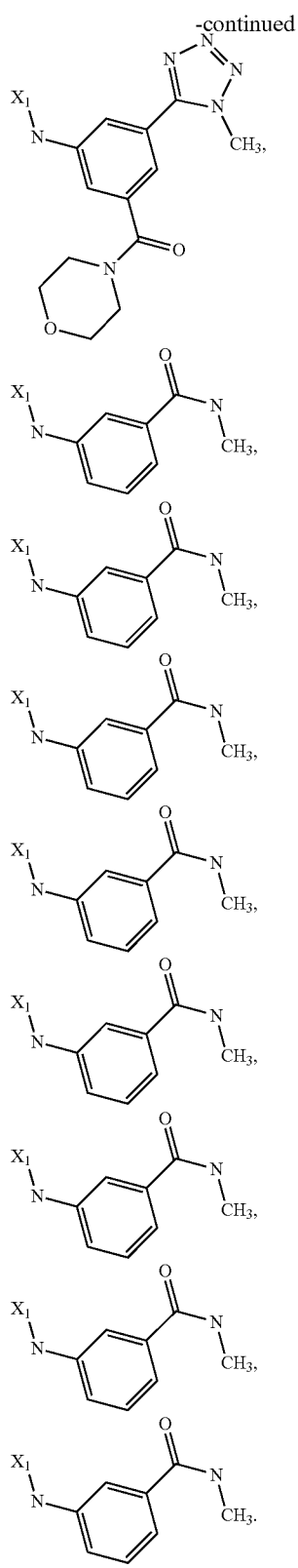
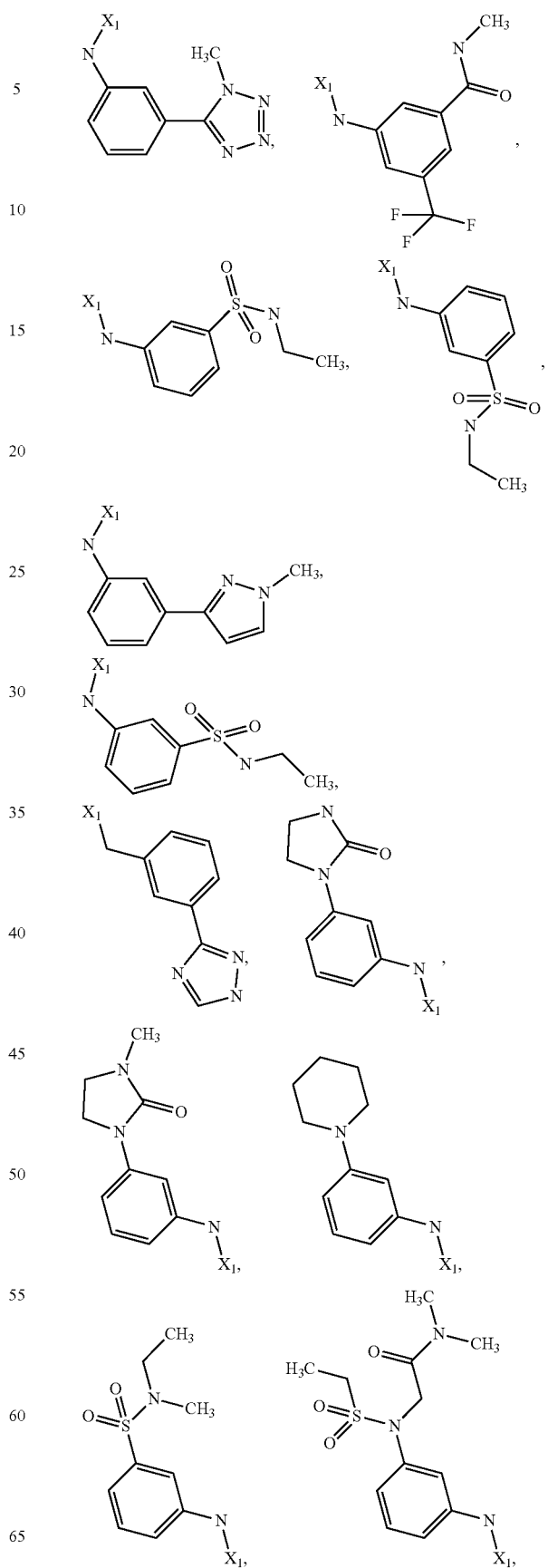
Another embodiment of the present invention further comprises administration to a subject of the compounds of formula 1, wherein A is defined as above; $R^3$ is H; $R^4$ is H; and $R^2$ is defined as in Table 1 shown below; and $R^1$ is selected from

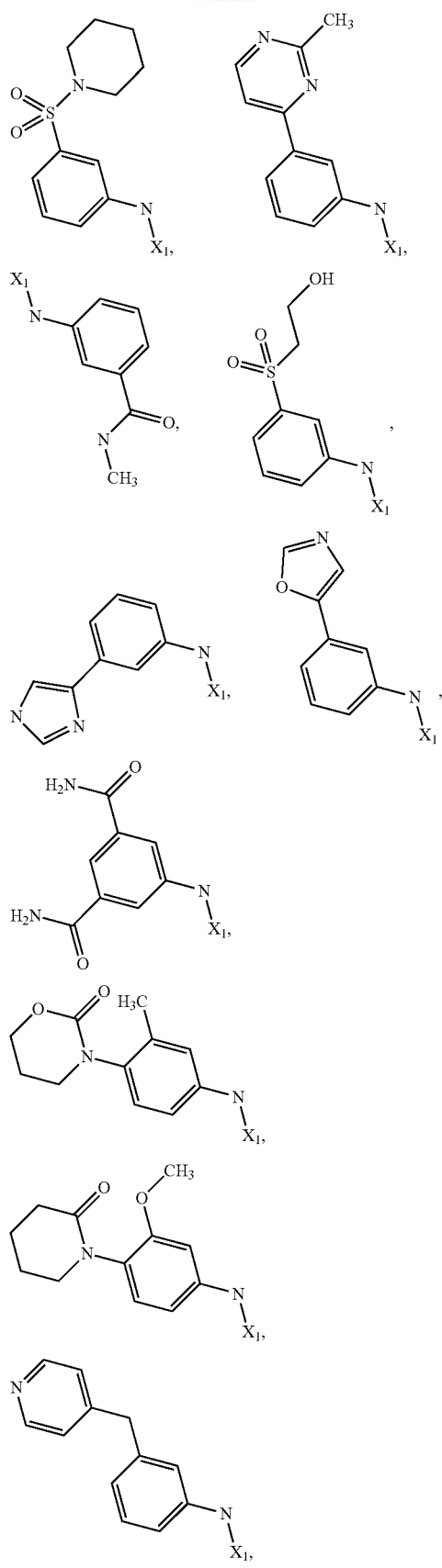
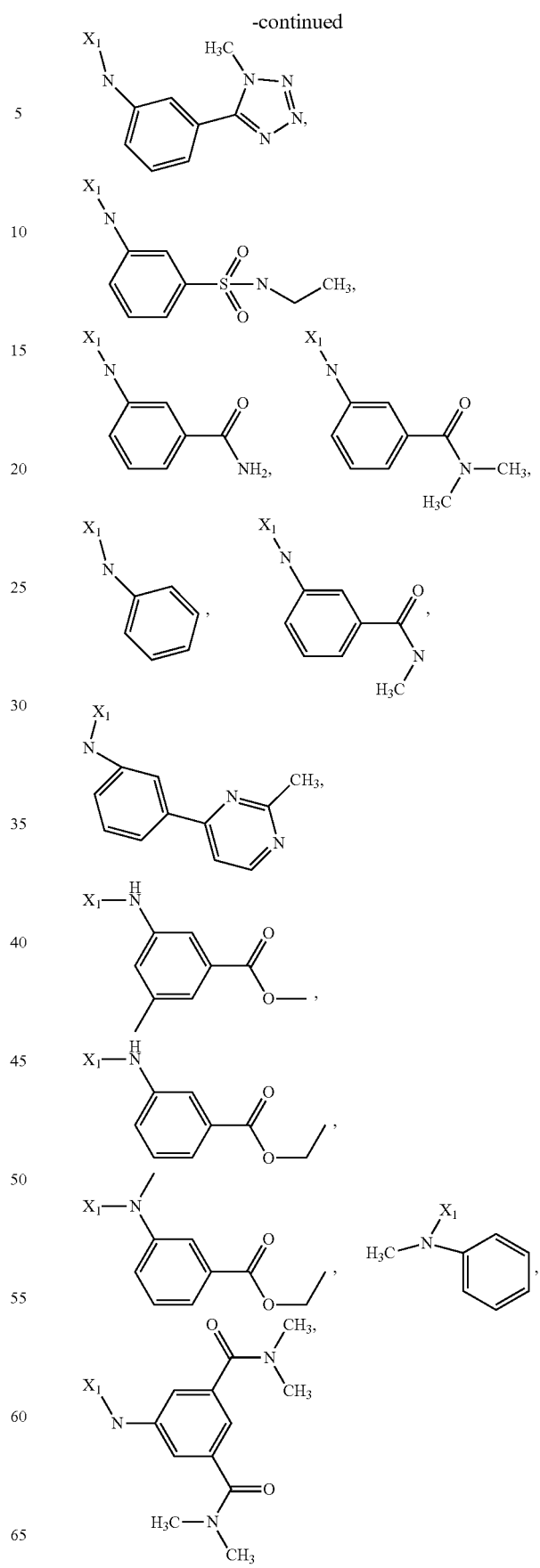

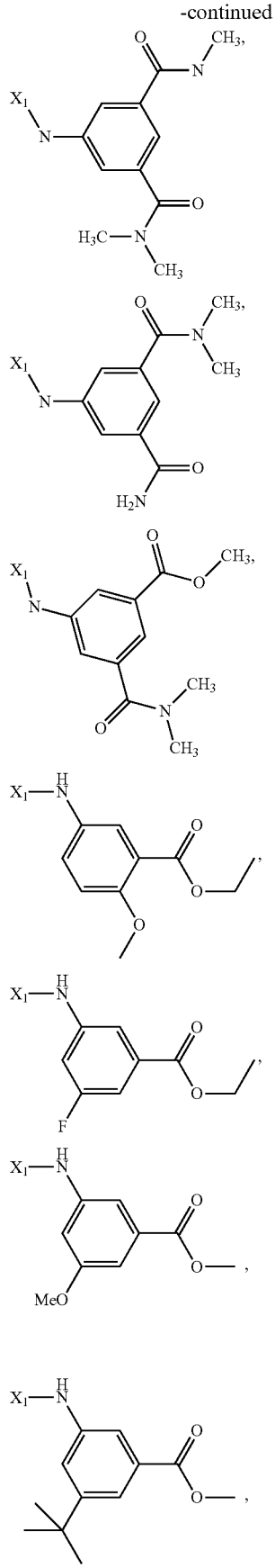
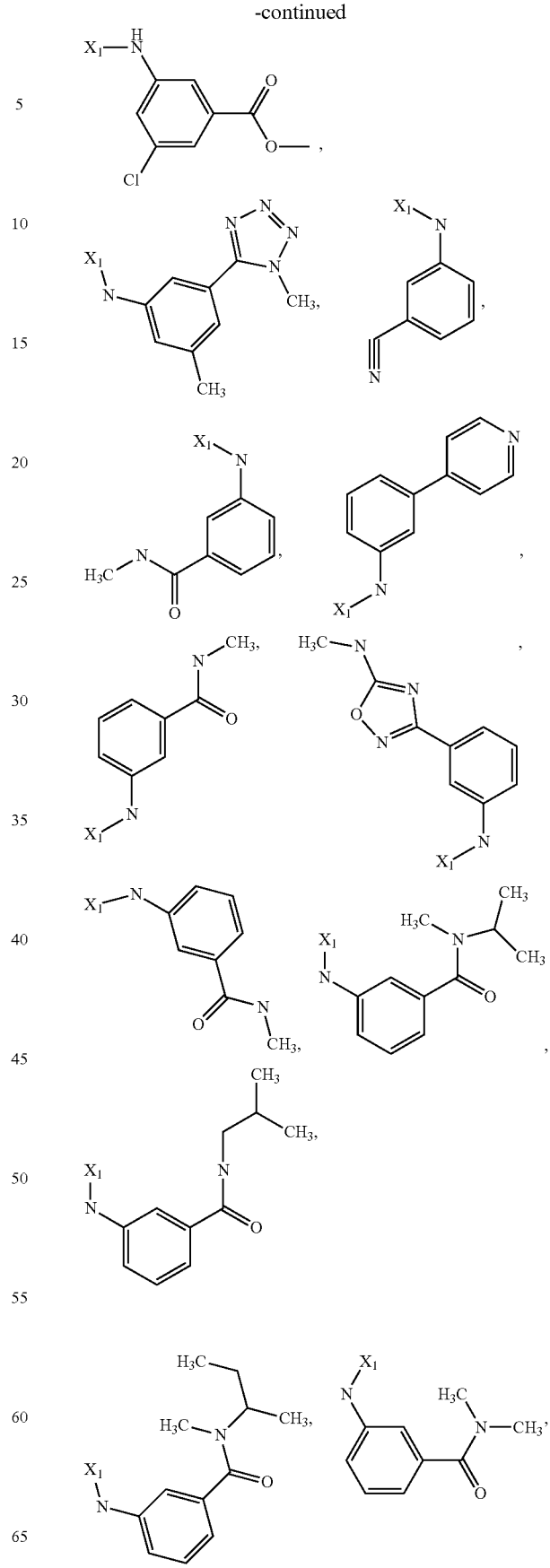

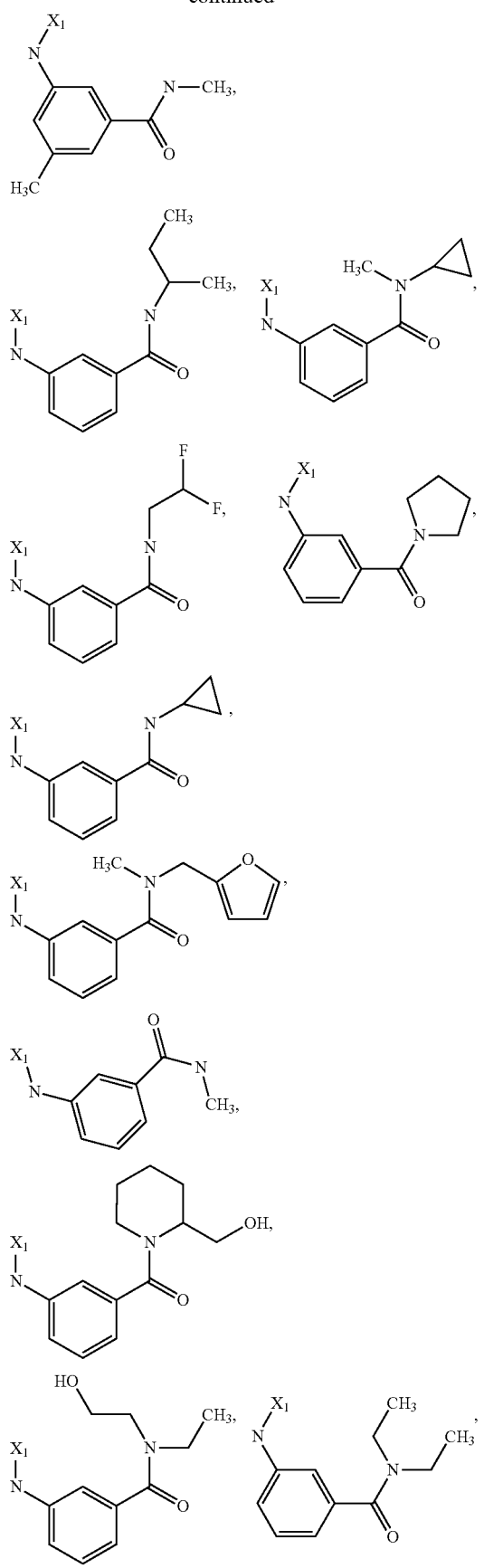
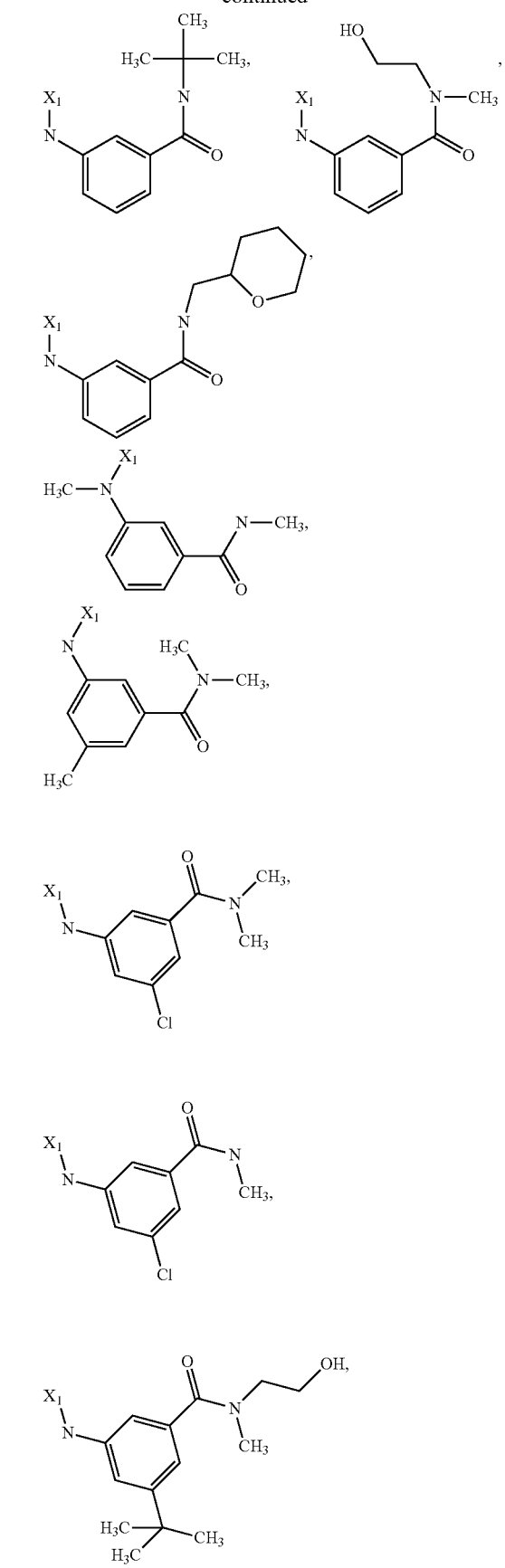

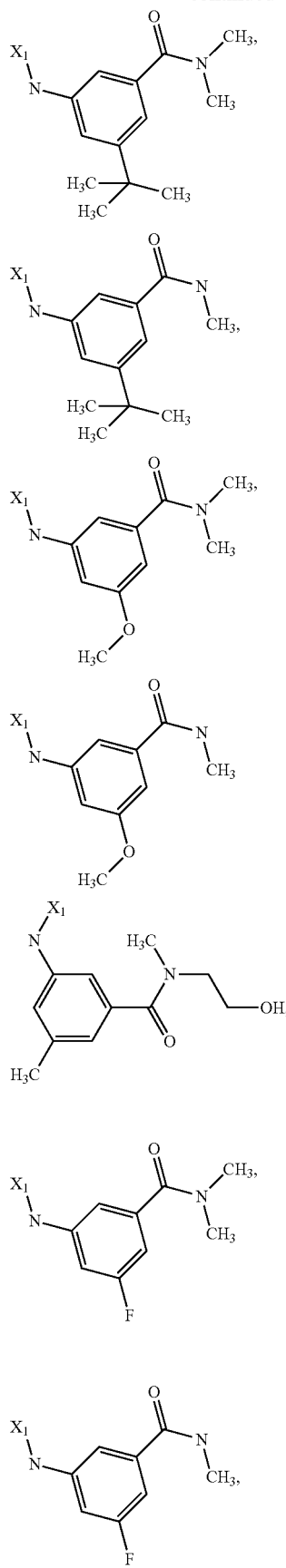

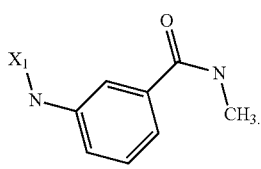
Another embodiment of the present invention further comprises administration to a subject of the compounds of formula 1, wherein A is defined as above; $R^3$ is H; $R^4$ is H; and $R^2$ is defined as in Table 1 shown below; $R^1$ is selected from
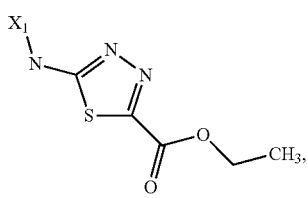
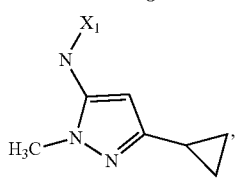
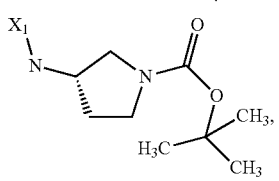
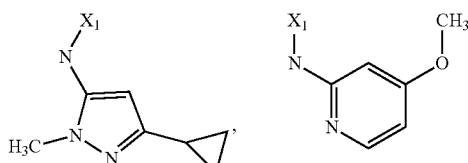
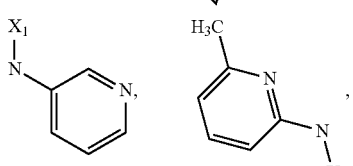
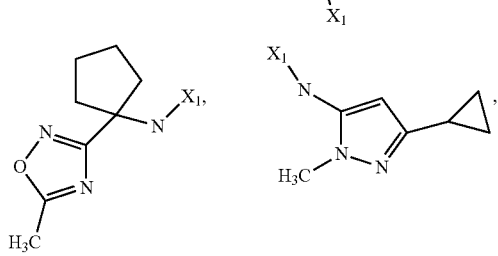
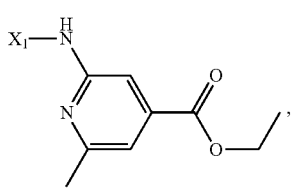
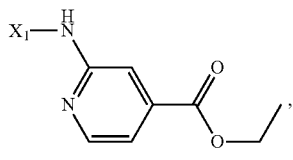
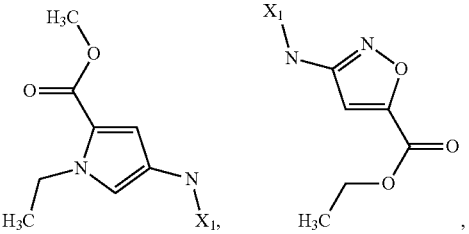
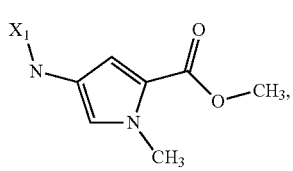
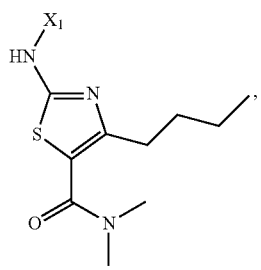
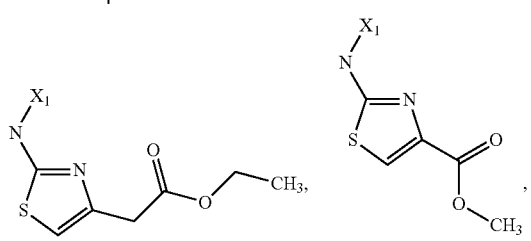
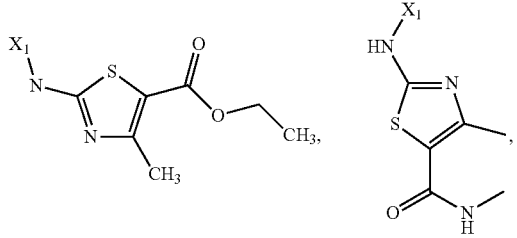
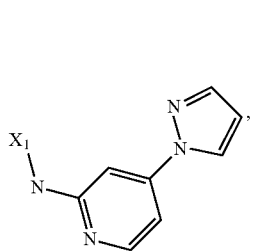

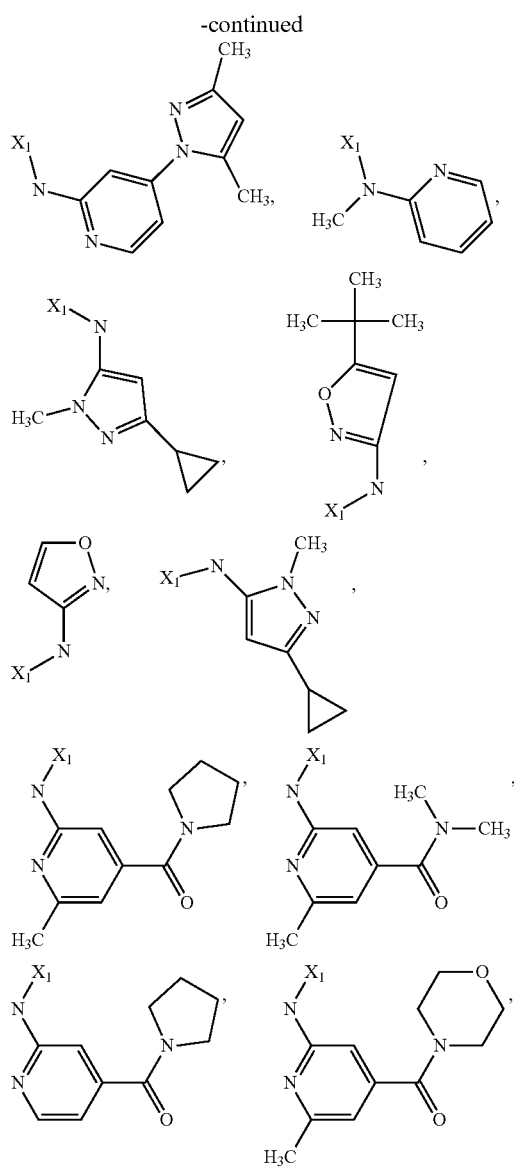
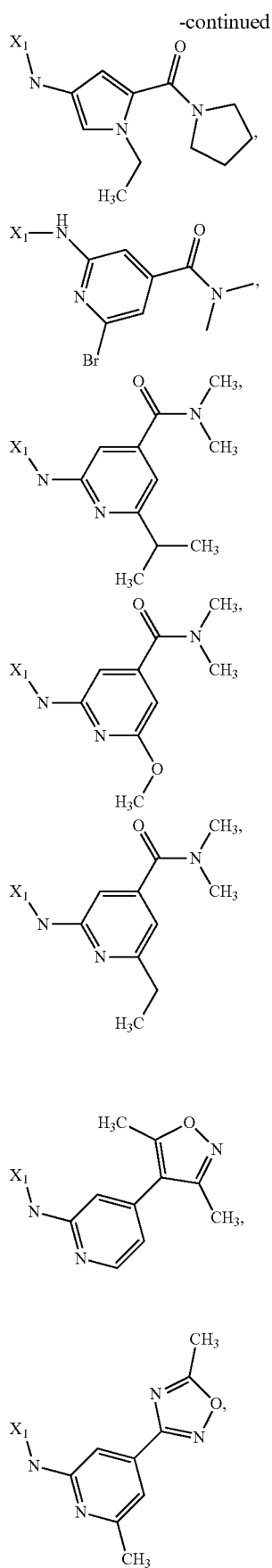

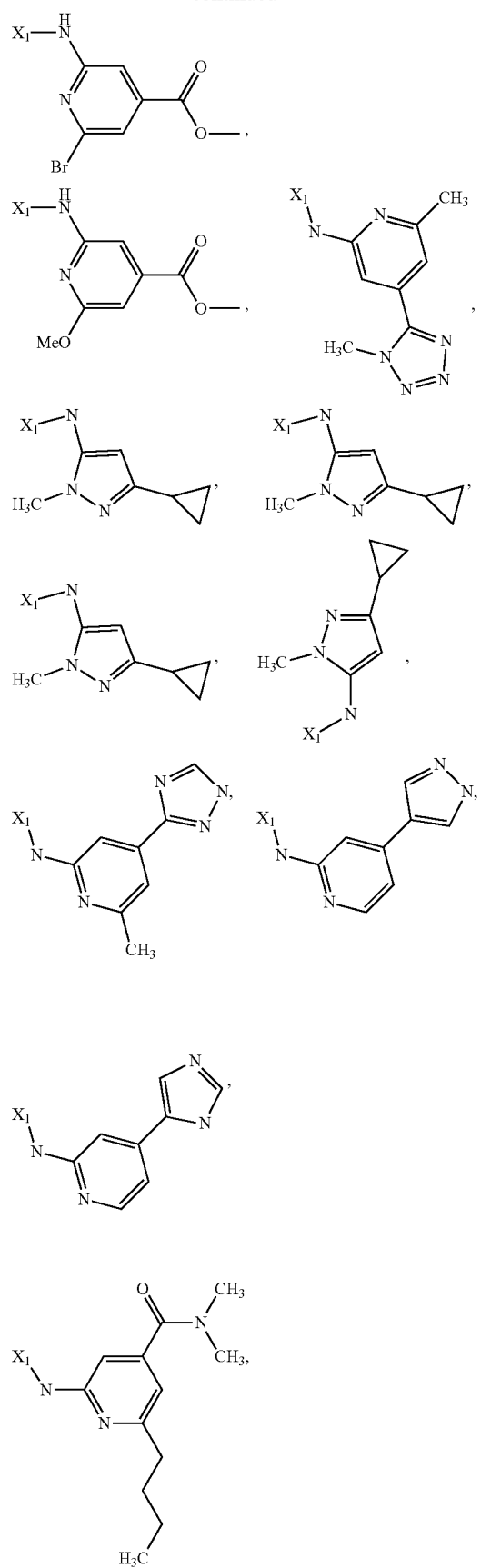
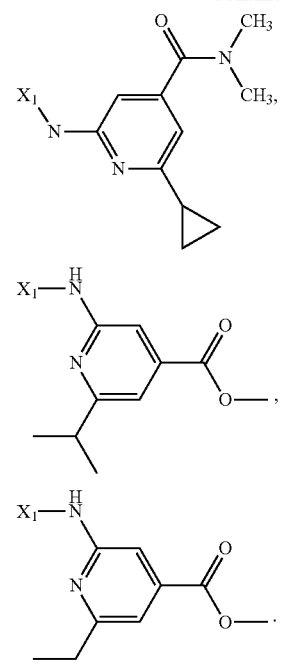
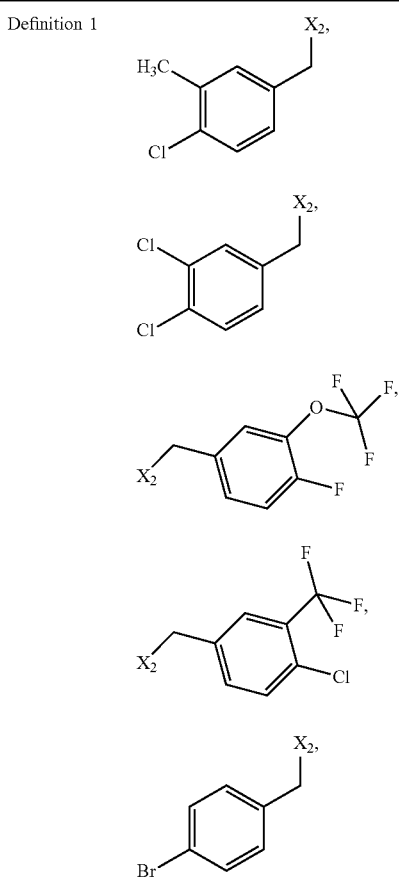
TABLE 1
R² is defined as one of the groups shown below in the definitions 1 to 4:
Definition 1

TABLE 1-continued
R² is defined as one of the groups shown below in the definitions 1 to 4:
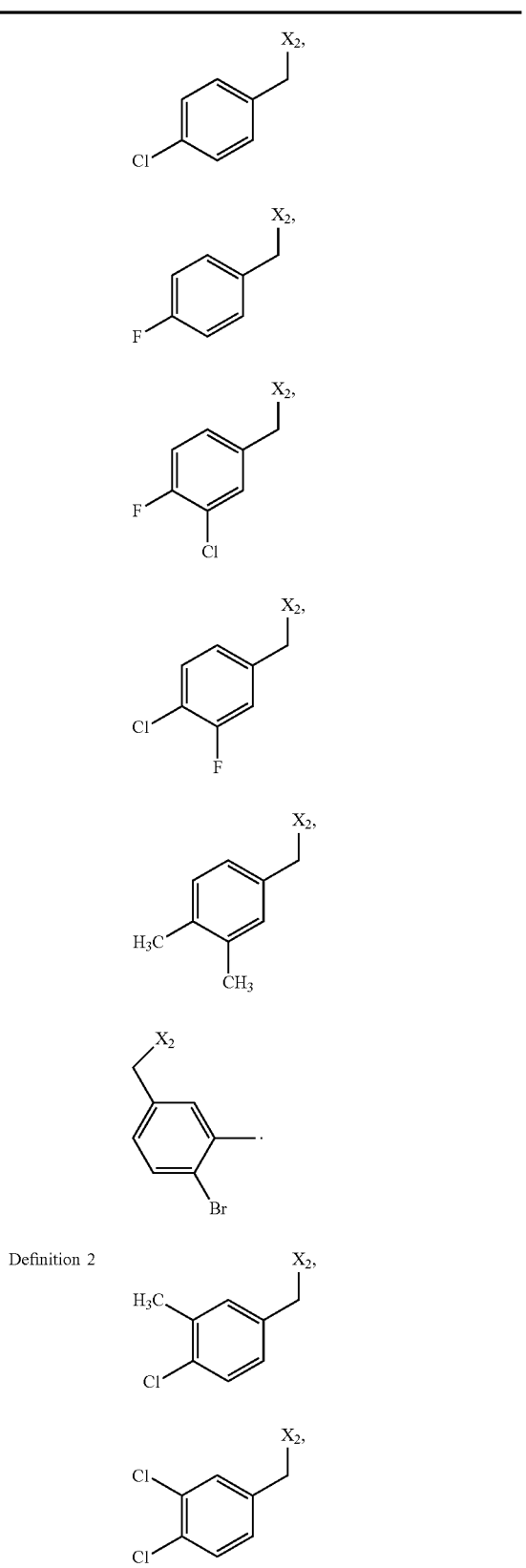
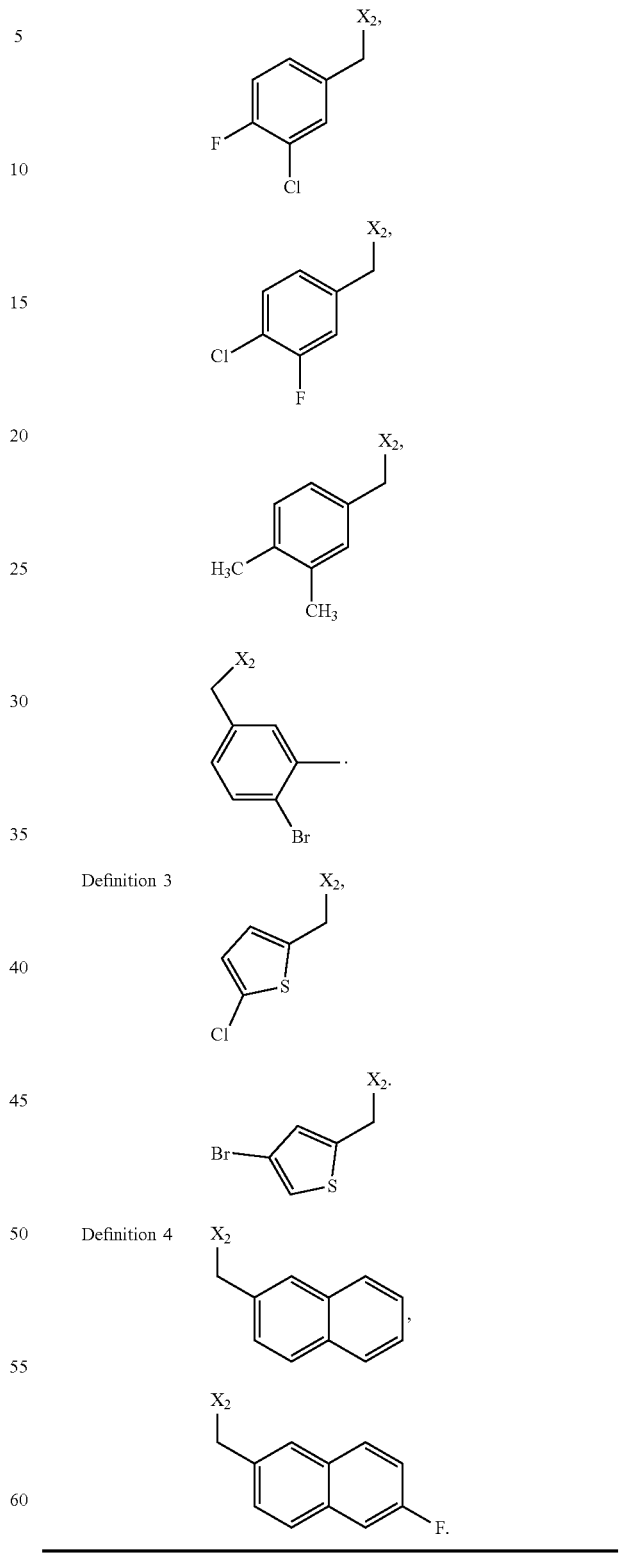
Another embodiment of the present invention further comprises administration to a subject of the compounds of formula 1, wherein the compounds of formula 1 are present in the form of the individual optical isomers, mixtures of the individual enantiomers or racemates, e.g., in the form of the enantiomerically pure compounds.

Another embodiment of the present invention further comprises administration to a subject of the compounds of formula 1, wherein the compounds of formula 1 are present in the form of the acid addition salts thereof with pharmacologically acceptable acids as well as optionally in the form of the solvates and/or hydrates.

b. Co-Crystals and Salts

Additional embodiments of the present invention further comprise administration to a subject of the co-crystals of the compounds of formula 2 (below). In general, for groups comprising two or more subgroups in this "Co-Crystals and Salts" section, the first named subgroup is the radical attachment point, for example, the substituent "$C_{1-3}$-alkyl-aryl" means an aryl group which is bound to a C1-3-alkyl-group, the latter of which is bound to the core or to the group to which the substituent is attached.

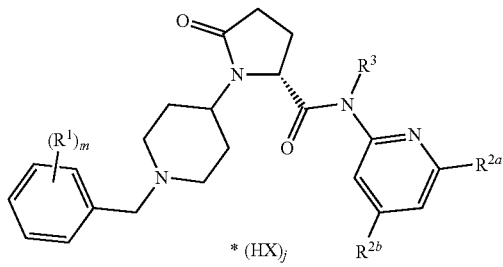

2 wherein
$R^1$ is $C_{1-6}$-alkyl, $C_{1-6}$-haloalkyl, O—$C_{1-6}$-haloalkyl, halogen;
m is 1, 2 or 3; and in some instances 1 or 2;
$R^{2a}$ and $R^{2b}$ are each independently selected from H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, $CONR^{2b.1}R^{2b.2}$, halogen;
$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
$R^3$ is H, $C_{1-6}$-alkyl;
X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; and in some instances chloride or dibenzoyltartrate
j is 0, 0.5, 1, 1.5 or 2; and in some instances 1 or 2;
with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-napthoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine, in some instances ascorbic acid, mucic acid, pamoic acid, succinamide, nicotinic acid, nicotinamide, isonicotinamide, 1-lysine, 1-proline.

Another aspect of the present invention further comprises administration to a subject of the co-crystals of the compounds of formula 2, wherein
$R^{2a}$ is H, $C_{1-6}$-alkyl, $C_{1-6}$-alkenyl, $C_{1-6}$-alkynyl, $C_{3-6}$-cycloalkyl, O—$C_{1-6}$-alkyl, $CONR^{2a.1}R^{2a.2}$;
$R^{2a.1}$ is H, $C_{1-6}$-alkyl, $C_{1-6}$-haloalkyl;
$R^{2a.2}$ is H, $C_{1-6}$-alkyl;
$R^{2b}$ is H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, $CONR^{2b.1}R^{2b.2}$, halogen;
$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
$R^{2a}$ is H, $C_{1-6}$-alkyl, $C_{1-6}$-alkynyl, $C_{3-6}$-cycloalkyl, O—$C_{1-6}$-alkyl, $CONR^{2a.1}R^{2a.2}$;
$R^{2a.1}$ is $C_{1-6}$-alkyl;
$R^{2a.2}$ is H;
$R^{2b}$ is H, $C_{1-6}$-alkyl, O—$C_{1-6}$-alkyl, $CONR^{2b.1}R^{2b.2}$;
$R^{2b.1}$ is $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
$R^{2a}$ is H, $C_{1-4}$-alkyl, $C_{1-4}$-alkynyl, $C_{3-6}$-cycloalkyl, O—$C_{1-4}$-alkyl, $CONR^{2a.1}R^{2a.2}$;
$R^{2a.1}$ is $C_{1-4}$-alkyl;
$R^{2a.2}$ is H;
$R^{2b}$ is H, $C_{1-4}$-alkyl, O—$C_{1-4}$-alkyl, $CONR^{2b.1}R^{2b.2}$;
$R^{2b.1}$ is $C_{1-4}$-alkyl, $C_{0-4}$-alkyl-$C_{3-6}$-cycloalkyl, $C_{1-4}$-haloalkyl;
$R^{2b.2}$ is H, $C_{1-4}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein
$R^{2a}$ is H, $C_{1-4}$-alkyl,
$R^{2b}$ is H, $CONR^{2b.1}R^{2b.2}$;
$R^{2b.1}$ is $C_{1-4}$-alkyl, $C_{0-4}$-alkyl-$C_{3-6}$-cycloalkyl, $C_{1-4}$-haloalkyl;
$R^{2b.2}$ is H, $C_{1-4}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein $R^1$ is $C_{1-6}$-alkyl, $C_{1-6}$-haloalkyl, O—$C_{1-6}$-haloalkyl, halogen;

m is 1 or 2;

$R^{2a}$ is H, $C_{1-4}$-alkyl;

$R^{2b}$ is H, $CONR^{2b.1}R^{2b.2}$;

$R^{2b.1}$ is $C_{1-4}$-alkyl, $C_{0-4}$-alkyl-$C_{3-6}$-cycloalkyl, $C_{1-4}$-haloalkyl;

$R^{2b.2}$ is H, $C_{1-4}$-alkyl;

or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom $R^3$ is H, $C_{1-6}$-alkyl;

X is an anion selected from the group consisting of chloride or dibenzoyltartrate j is 1 or 2.

Another aspect of the present invention further comprises administration to a subject of the co-crystals of the compounds of formula 2, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the co-crystals of the compounds of formula 2, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-haloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the co-crystals of the compounds of formula 2, wherein $R^1$, m, $R^{2a}$, $R^{2b}$, $R^3$, X and j are defined as above and the co-crystal former is selected from the group consisting of ascorbic acid, mucic acid, pamoic acid, succinamide, nicotinic acid, nicotinamide, isonicotinamide, l-lysine, l-proline, or hydrates or hydrochlorides of the same.

Another aspect of the present invention further comprises administration to a subject of the co-crystals of the compounds of formula 2a, wherein $R^{2a}$, $R^{2b}$, $R^3$, X and j are defined as above

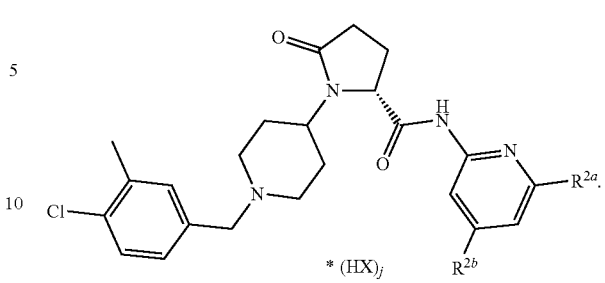

2a

Another aspect of the present invention further comprises administration to a subject of the co-crystals of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the co-crystals of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-haloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the co-crystals of the compounds of formula 2a, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

The free bases of compounds of formula 2 (j=0) are often amorphous and are used for a process of manufacturing co-crystal, nevertheless salts of compounds of formula 2 are employed in some instances for a process of manufacturing co-crystal. Thus, another aspect of the invention are salts of compounds of formula 2 wherein $R^1$, m, $R^{2a}$, $R^{2b}$, $R^3$ are defined as for the co-crystals above and X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate; in some instances chloride, or dibenzoyltartrate j is 0, 0.5, 1, 1.5 or 2; in some instances 1 or 2.

Another aspect of the present invention further comprises administration to a subject of the co-crystals of the compounds of formula 2, wherein $R^1$, m, $R^{2a}$, $R^{2b}$, $R^3$ are defined as for the co-crystals above and X is an anion selected from the group consisting of chloride or dibenzoyltartrate j is 1 or 2.

Another aspect of the present invention further comprises administration to a subject of the salts of the compounds of formula 2, wherein $R^1$, m, $R^{2a}$, $R^{2b}$, $R^3$ are defined as for the salts above and X is chloride and j is 2.

Another aspect of the present invention further comprises administration to a subject of the salts of the compounds of formula 2, wherein $R^1$, m, $R^{2a}$, $R^{2b}$, $R^3$ are defined as for the salts above and X is dibenzoyltartrate and j is 1.

Another aspect of the present invention further comprises administration to a subject of the salts of the compounds of formula 2a, wherein $R^{2a}$, $R^{2b}$, $R^3$, X and j are defined as above

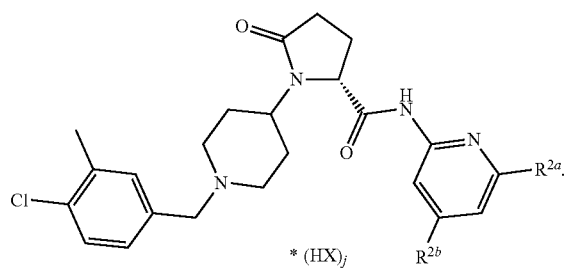

2a

Another aspect of the present invention further comprises administration to a subject of the salts of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-alkyl; in some instances Methyl, Ethyl, Propyl;

$R^{2b.2}$ is $C_{1-4}$-alkyl; in some instances Methyl, Ethyl, Propyl;

and the remaining residues are defined as above.

Another aspect of the present invention further comprises administration to a subject of the salts of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{0-4}$-alkyl-$C_{3-6}$-cycloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the salts of the compounds of formula 2a, wherein $R^{2a}$ is H, $C_{1-4}$-alkyl; in some instances Methyl, Ethyl, Propyl;

$R^{2b}$ is H, $CONR^{2b.1}R^{2b.2}$;

$R^{2b.1}$ is $C_{1-4}$-haloalkyl;

$R^{2b.2}$ is H, $C_{1-4}$-alkyl; in some instances H, Methyl, Ethyl, Propyl;

and the remaining residues are defined as above.

Another aspect of the present invention further comprises administration to a subject of the salts of the compounds of formula 2a, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom and the remaining residues are defined as above.

Another aspect of the present invention further comprises administration to a subject of the salts of the compounds of formula 2a, wherein $R^1$, m, $R^{2a}$, $R^{2b}$, $R^3$ are defined as for the salts above and X is chloride and j is 2.

Another aspect of the present invention further comprises administration to a subject of the salts of the compounds of formula 2a, wherein $R^1$, m, $R^{2a}$, $R^{2b}$, $R^3$ are defined as for the salts above and X is dibenzoyltartrate and j is 1. Another aspect of the invention are salts of compounds of formula 2a, wherein $R^1$, m, $R^{2a}$, $R^{2b}$, $R^3$ are defined as for the salts above and X is (S)—(S)-(+)-2,3-dibenzoyl-tartrate and j is 1.

c. Formulations

Additional embodiments of the present invention further comprise administration to a subject of a pharmaceutical composition containing compounds of formula 3

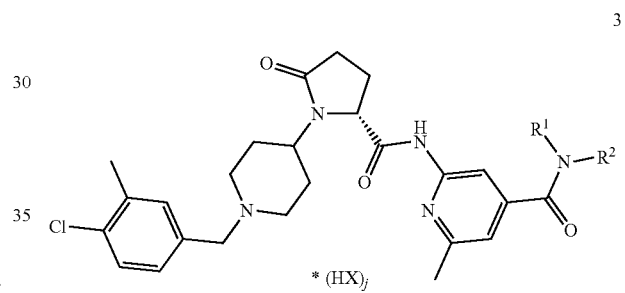

3 wherein $R^1$ is H, $C_{1-6}$-alkyl, $C_{0-4}$-alkyl-$C_{3-6}$-cycloalkyl, $C_{1-6}$-haloalkyl;

$R^2$ is H, $C_{1-6}$-alkyl;

X is an anion selected from the group consisting of chloride or ½ dibenzoyltartrate j is 1 or 2.

An embodiment of the present invention further comprises administration to a subject of a pharmaceutical composition containing compounds of formula 3 wherein $R^1$ is H, $C_{1-6}$-alkyl;

$R^2$ is H, $C_{1-6}$-alkyl;

X is an anion selected from the group consisting of chloride or ½ dibenzoyltartrate j is 1 or 2.

An embodiment of the present invention further comprises administration to a subject of a pharmaceutical composition containing compounds of formula 3 wherein $R^1$ is H, Methyl, Ethyl, Propyl, Butyl;

$R^2$ is H, Methyl, Ethyl, Propyl, Butyl;

X is an anion selected from the group consisting of chloride or ½ dibenzoyltartrate, such as chloride;

j is 1 or 2, in some instances 2.

An embodiment of the present invention further comprises administration to a subject of a pharmaceutical composition containing compounds of formula 3 wherein $R^1$ is H, Methyl, Ethyl, Propyl, Butyl;

$R^2$ is H, Methyl;

X is an anion selected from the group consisting of chloride or ½ dibenzoyltartrate, such as chloride;

j is 1 or 2, in some instances 2.

An embodiment of the present invention further comprises administration to a subject of a pharmaceutical composition containing compounds of formula 3 wherein R¹ is H, Methyl;

R² is H, Methyl;

X is an anion selected from the group consisting of chloride or ½ dibenzoyltartrate, such as chloride;

j is 1 or 2, in some instances 2.

An embodiment of the present invention further comprises administration to a subject of a pharmaceutical composition containing compounds described in Table 2 as a hydrochloride. An additional embodiment of the present invention further comprises administration to a subject of a pharmaceutical composition containing compounds describe in Table 2 as a di-hydrochloride.

TABLE 2

| # | Structure |
|---|-----------|
| 1 | 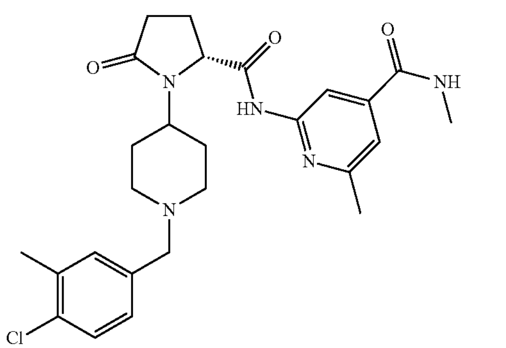 |
| 2 | 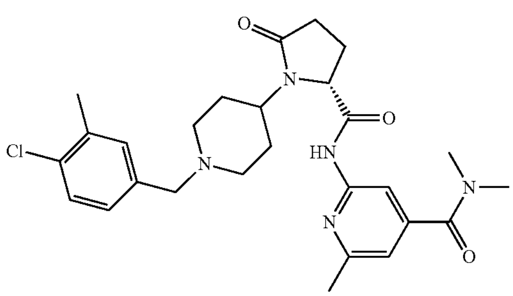 [SMILES: Cc1cc(C(=O)N(C)C)cc(NC(=O)[C@H]2CCC(=O)N2C2CCN(Cc3ccc(Cl)c(C)c3)CC2)n1] |
| 3 | 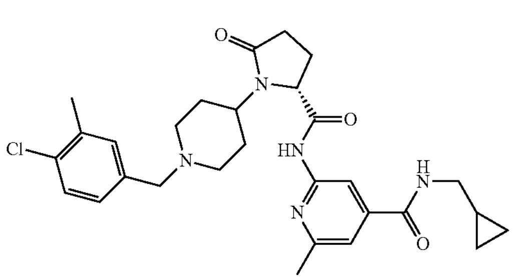 [SMILES: Cc1cc(C(=O)NCC2CC2)cc(NC(=O)[C@H]2CCC(=O)N2C2CCN(Cc3ccc(Cl)c(C)c3)CC2)n1] |

TABLE 2-continued

| # | Structure |
|---|-----------|
| 4 | 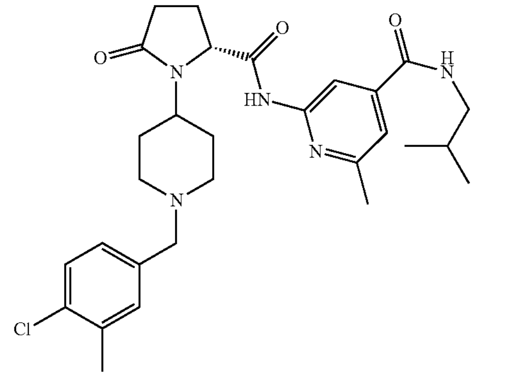 [SMILES: Cc1cc(C(=O)NCC(C)C)cc(NC(=O)[C@H]2CCC(=O)N2C2CCN(Cc3ccc(Cl)c(C)c3)CC2)n1] |
| 5 | 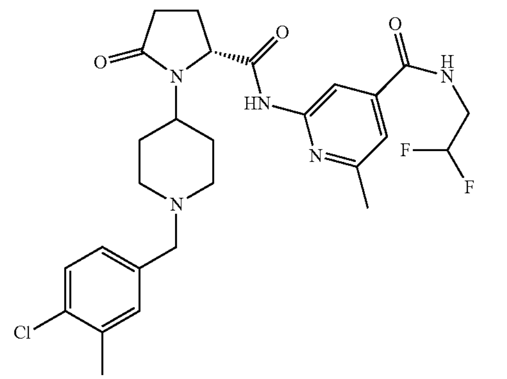 [SMILES: Cc1cc(C(=O)NCC(F)F)cc(NC(=O)[C@H]2CCC(=O)N2C2CCN(Cc3ccc(Cl)c(C)c3)CC2)n1] |
| 6 | 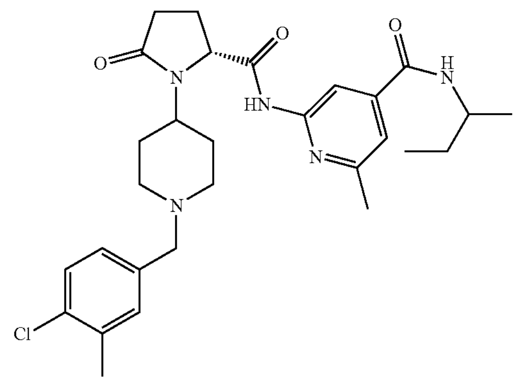 [SMILES: CCC(C)NC(=O)c1cc(C)nc(NC(=O)[C@H]2CCC(=O)N2C2CCN(Cc3ccc(Cl)c(C)c3)CC2)c1] |
| 7 | 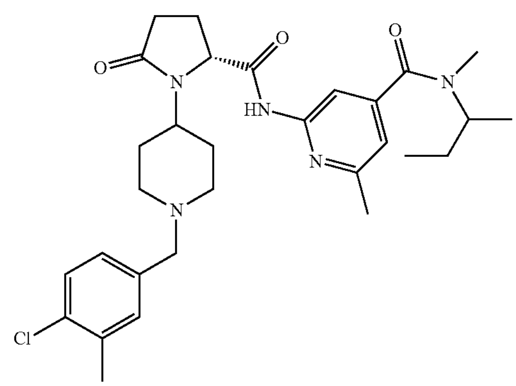 [SMILES: CCC(C)N(C)C(=O)c1cc(C)nc(NC(=O)[C@H]2CCC(=O)N2C2CCN(Cc3ccc(Cl)c(C)c3)CC2)c1] |

TABLE 2-continued

| # | Structure |
|---|---|
| 8 | 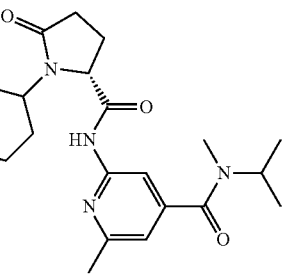 |
| 9 | 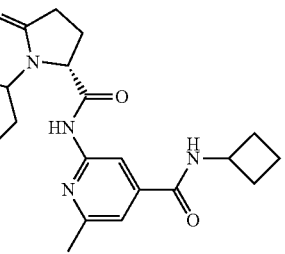 |
| 10 | 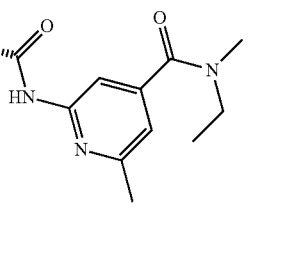 |

Another object of the present invention is administration to a subject of a pharmaceutical dosage form of the compounds described above, wherein the dosage is an orally deliverable dosage form.

Another object of the present invention is administration to a subject of a pharmaceutical dosage form of the compounds described above, which is in the form of a tablet, capsule, pellets, powder or granules.

Another object of the present invention is administration to a subject of the pharmaceutical dosage forms described above for use as medicament.

Another object of the present invention is the use of the above pharmaceutical dosage forms for the preparation of a medicament for the treatment of a neurodegenerative disease or condition selected from Alzheimer's disease, Parkinson's disease, frontotemporal dementia, Huntington disease, amyotrophic lateral sclerosis, multiple sclerosis, glaucoma, myotonic dystrophy, vascular dementia, and progressive supranuclear palsy.

Another object of the present invention is a process for the treatment and/or prevention of a disease or condition selected from neurodegenerative disease such as Alzheimer's disease, Parkinson's disease, frontotemporal dementia, Huntington disease, amyotrophic lateral sclerosis, multiple sclerosis, glaucoma, myotonic dystrophy, vascular dementia, and progressive supranuclear palsy, characterized in that an effective amount of the above defined pharmaceutical dosage form is administered orally to a subject or patient once, twice, thrice or several times daily.

d. Dosage Forms/Ingredients

Solid pharmaceutical compositions ready for use/ingestion made from a compound of formula 3 comprise powders, granules, pellets, tablets, capsules, chewable tablets, dispersible tables, troches and lozenges. In detail:

Capsule formulations according to the invention comprise the powdery intermediate of a compound of formula 3, an intermediate blend comprising the powdery intermediate, pellets or granules obtained by conventional wet-, dry or hot-melt granulation or hot-melt extrusion or spray-drying of a suitable intermediate blend, filled in conventional capsules, e.g. hard gelatin or HPMC capsules.

The Capsule formulations from above may also comprise the powdery intermediate of a compound of formula 3 in a compacted form.

Capsule formulations according to the invention comprise the compound of formula 3 suspended or diluted in a liquid or mixture of liquids.

Tablet formulations according to the invention comprise such tablets obtained by direct compression of a suitable final blend or by tableting of pellets or granules obtained by conventional wet-, dry or hot-melt granulation or hot-melt extrusion or spray-drying of a suitable intermediate blend.

Another object of the present invention is a dosage form where a pH-adjusting or buffering agent is added for stability improvement of the active ingredient. The pH-adjusting/buffering agent may be a basic amino acid, which has an amino group and alkaline characteristics (isoelectric point, pI: 7.59-10.76), such as e.g. L-arginine, L-lysine or L-histidine. A buffering agent within the meaning of this invention is L-arginine. L-arginine has a particular suitable stabilizing effect on the compositions of this invention, e.g. by suppressing chemical degradation of compounds of formula 3.

Thus, in an embodiment, the present invention is directed to a pharmaceutical composition (e.g. an oral solid dosage form, particularly a tablet) comprising a compound of formula 3 and L-arginine for stabilizing the composition, particularly against chemical degradation; as well as one or more pharmaceutical excipients.

Suitably the pharmaceutical excipients used within this invention are conventional materials such as cellulose and its derivates, D-mannitol, corn starch, pregelatinized starch as a filler, copovidone as a binder, crospovidone as disintegrant, magnesium stearate as a lubricant, colloidal anhydrous silica as a glidant, hypromellose as a film-coating agent, polyethylene glycol as a plasticizer, titanium dioxide, iron oxide red/yellow as a pigment, and talc, etc.

In detail pharmaceutical excipients can be a first and second diluent, a binder, a disintegrant and a lubricant; an additional disintegrant and an additional glidant are a further option.

Diluents suitable for a pharmaceutical composition according to the invention are cellulose powder, microcrystalline cellulose, lactose in various crystalline modifications, dibasic calcium phosphate anhydrous, dibasic calcium phosphate dihydrate, erythritol, low substituted hydroxypropyl cellulose, mannitol, starch or modified starch (eg pregelatinized or partially hydrolyzed) or xylitol. Among those diluents mannitol and microcrystalline cellulose are employed in some instances.

Diluents that find use as the second diluent are the above-mentioned diluents mannitol and microcrystalline cellulose.

Lubricants suitable for a pharmaceutical composition according to the invention are talc, polyethyleneglycol, calcium behenate, calcium stearate, sodium stearylfumarate, hydrogenated castor oil or magnesium stearate. The lubricant in some instances is magnesium stearate.

Binders suitable for a pharmaceutical composition according to the invention are copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, stearic-palmitic acid, low-substituted hydroxypropylcellulose (L-HPC), copovidone and pregelatinized starch being employed in some formulations. The above mentioned binders pregelatinized starch and L-HPC show additional diluent and disintegrant properties and can also be used as the second diluent or the disintegrant.

Disintegrants suitable for a pharmaceutical composition according to the present invention are corn starch, crospovidone, polacrilin potassium, croscarmellose sodium, low-substituted hydroxypropylcellulose (L-HPC) or pregelatinized starch; such as croscarmellose sodium.

As an optional glidant colloidal silicon dioxide can be used.

An exemplary composition according to the present invention comprises the diluent mannitol, microcrystalline cellulose as a diluent with additional disintegrating properties, the binder copovidone, the disintegrant croscarmellose sodium, and magnesium stearate as the lubricant.

Typical pharmaceutical compositions comprise (% by weight)

| | |
|---|---|
| 10-50% | active ingredient |
| 20-88% | diluent 1, |
| 5-50% | diluent 2, |
| 1-5% | binder, |
| 1-15% | disintegrant, and |
| 0.1-5% | lubricant. |

Pharmaceutical compositions according to some embodiments comprise (% by weight)

| | |
|---|---|
| 10-50% | active ingredient |
| 20-75% | diluent 1, |
| 5-30% | diluent 2, |
| 2-30% | binder, |
| 1-12% | disintegrant, and |
| 0.1-3% | lubricant |

Pharmaceutical compositions according to some embodiments comprise (% by weight)

| | |
|---|---|
| 10-90% | active ingredient |
| 5-70% | diluent 1, |
| 5-30% | diluent 2, |
| 0-30% | binder, |
| 1-12% | disintegrant, and |
| 0.1-3% | lubricant |

Pharmaceutical compositions according to some embodiments comprise (% by weight)

| | |
|---|---|
| 10-50% | active ingredient |
| 20-75% | diluent 1, |
| 5-30% | diluent 2, |
| 2-30% | binder, |
| 0.5-20% | buffering agent, |
| 1-12% | disintegrant, and |
| 0.1-3% | lubricant |

Pharmaceutical compositions according to some embodiments comprise (% by weight)

| | |
|---|---|
| 30-70% | active ingredient |
| 20-75% | diluent 1, |
| 5-30% | diluent 2, |
| 2-30% | binder, |
| 0.5-20% | buffering agent, |
| 1-12% | disintegrant, and |
| 0.1-3% | lubricant |

Pharmaceutical compositions containing 10-90% of active ingredient, such as 30-70% active ingredient (% by weight) are employed in some instances.

A tablet formulation according to the invention may be uncoated or coated, e.g. film-coated, using suitable coatings known not to negatively affect the dissolution properties of the final formulation. For instance the tablets can be provided with a seal coat for protection of the patients environment and clinical staff as well as for moisture protection purposes by dissolving a high molecular weight polymer as polyvinylpyrrolidone or hydroxypropyl-methylcellulose together with plasticizers, lubricants and optionally pigments and tensides in water or organic solvent as acetone and spraying this mixture on the tablet cores inside a coating equipment as a pan coater or a fluidized bed coater with wurster insert.

Additionally, agents such as beeswax, shellac, cellulose acetate phthalate, polyvinyl acetate phthalate, zein, film forming polymers such as hydroxypropyl cellulose, ethylcellulose and polymeric methacrylates can be applied to the tablets, provided that the coating has no substantial effect on the disintegration/dissolution of the dosage form and that the coated dosage form is not affected in its stability.

After the dosage form is film-coated, a sugar coating may be applied onto the sealed pharmaceutical dosage form. The sugar coating may comprise sucrose, dextrose, sorbitol and the like or mixtures thereof. If desired, colorants or opacifiers may be added to the sugar solution.

Solid formulations of the present invention tend to be hygroscopic. They may be packaged using PVC-blisters, PVDC-blisters or a moisture-proof packaging material such as aluminum foil blister packs, alu/alu blister, transparent or opaque polymer blister with pouch, polypropylene tubes, glass bottles and HDPE bottles optionally containing a child-resistant feature or may be tamper evident. The primary packaging material may comprise a desiccant such as molecular sieve or silica gel to improve chemical stability of the API. Opaque packaging such as colored blister materials, tubes, brown glass bottles or the like can be used to prolong shelf life of the API by reduction of photo degradation.

e. Dosages

A dosage range of the compound of formula 3 is usually between 100 and 1000 mg, in particular between 200 and 900 mg, 300 and 900 mg or 350 and 850 mg or 390 and 810 mg. It is possible to give one or two tablets, where in some instances two tablets for a daily oral dosage of 100, 200, 300, 350, 400, 450, 500, 550, 600, 650, 700, 750, 800, 850, 900 mg, and in some instances 350, 400, 450, 750, 800, 850 are employed.

The dosages range can be achieved by one tablet or by two tablets; in some instances two tablets are administered, each containing half of the dosage.

The application of the active ingredient may occur up to three times a day, such as one or two times a day. Particular dosage strengths are 400 mg or 800 mg.

f. Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term, "about" means 5% more or less of the specified value. Thus, about 100 minutes could also be read as from 95 to 105 minutes.

In case a compound of the present invention is depicted in form of a chemical name and as a formula in case of any discrepancy the formula shall prevail. An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Of interest are such groups that have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, Succinate, Sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl Sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N, N-dibenzylphenethylamine, 1-ephenamine, and N,P-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

"Heterocyclic rings" ("het") include five-, six- or seven-membered, saturated or unsaturated heterocyclic rings or 5-10 membered, bicyclic hetero rings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

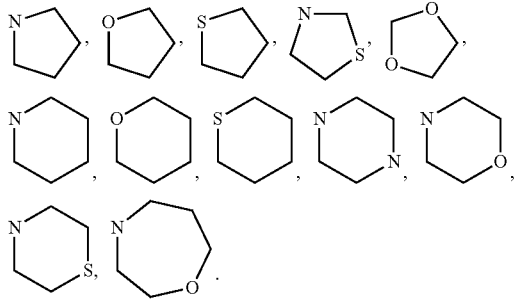

Unless stated otherwise, a heterocyclic ring may be provided with a keto group. Examples include:

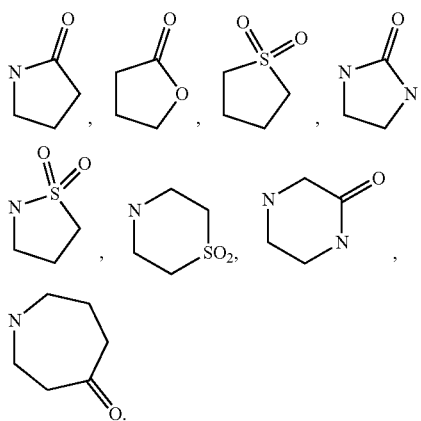

Examples of 5-10-membered bicyclic hetero rings are pyrrolizine, indole, indolizine, isoindole, indazole, purine, quinoline, isoquinoline, benzimidazole, benzofurane, benzopyrane, benzothiazole, benzoisothiazole, pyridopyrimidine, pteridine, pyrimidopyrimidine,

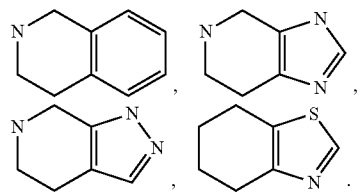

Although the term heterocyclic rings includes heterocyclic aromatic groups, the term heterocyclic aromatic groups ("hetaryl") denotes five- or six-membered heterocyclic aromatic groups or 5-10 membered, bicyclic hetaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

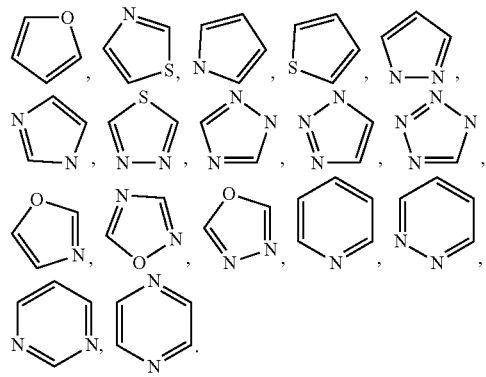

Examples of 5-10-membered bicyclic hetaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine, pyrimidopyrimidine.

The term "halogen" as used herein means a halogen substituent selected from fluoro, chloro, bromo or iodo.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are present in some instances. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are present in some instances. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Employed in some instances are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are present in some instances. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the respective groups with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are present in some instances. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are present in some instances. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the respective groups with the same number of carbons. Thus for example propynyl also includes 1-methylethynylene and butynylene includes 1-methylpropynylene, 1,1-dimethylethynylene, 1,2-dimethylethynylene.

The term "$C_{3-6}$-cycloalkyl" (including those which are part of other groups) as used herein means cyclic alkyl groups with 3 to 8 carbon atoms, where in some instances such groups are cyclic alkyl groups with 5 to 6 carbon atoms. Examples include: cyclopropyl, cyclobutyl, cyclopentyl or cyclohexyl.

By the term "$C_{1-6}$-haloalkyl" (including those which are part of other groups) are meant branched and unbranched alkyl groups with 1 to 6 carbon atoms wherein one or more hydrogen atoms are replaced by a halogen atom selected from among fluorine, chlorine or bromine, such as fluorine and chlorine, e.g., fluorine. By the term "$C_{1-4}$-haloalkyl" are meant correspondingly branched and unbranched alkyl groups with 1 to 4 carbon atoms, wherein one or more hydrogen atoms are replaced analogously to what was stated above. $C_{1-4}$-haloalkyl is present in some instances. Examples include: $CH_2F$, $CHF_2$, $CF_3$.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, —$H_3C$—$CH(CH_3)$—, —$H_3C$—$CH_2$—$CH_2$—$CH_2$—, —$H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-haloalkyl", wherein n is an integer from 2 to n, either alone or in combination with another radical denotes an acyclic, saturated, branched or linear hydrocarbon radical with 1 to n C atoms wherein one or more hydrogen atoms are replaced by a halogen atom selected from among fluorine, chlorine or bromine, such as fluorine and chlorine, e.g., fluorine. Examples include: $CH_2F$, $CHF_2$, $CF_3$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

By "an individual suffering from or at risk of suffering from an aging-associated cognitive impairment" is meant an individual that is about more than 50% through its expected lifespan, such as more than 60%, e.g., more than 70%, such as more than 75%, 80%, 85%, 90%, 95% or even 99% through its expected lifespan. The age of the individual will depend on the species in question. Thus, this percentage is based on the predicted life-expectancy of the species in question. For example, in humans, such an individual is 50 year old or older, e.g., 60 years old or older, 70 years old or older, 80 years old or older, 90 years old or older, and usually no older than 100 years old, such as 90 years old, i.e., between the ages of about 50 and 100, e.g., 50 ... 55 ... 60 ... 65 ... 70 ... 75 ... 80 ... 85 ... 90 ... 95 ... 100 years old or older, or any age between 50-1000, that suffers from an aging-associated condition as further described below, e.g., cognitive impairment associated with the natural aging process; an individual that is about 50 years old or older, e.g., 60 years old or older, 70 years old or older, 80 years old or older, 90 years old or older, and usually no older than 100 years old, i.e., between the ages of about 50 and 100, e.g., 50 ... 55 ... 60 ... 65 ... 70 ... 75 ... 80 ... 85 ... 90 ... 95 ... 100 years old, that has not yet begun to show symptoms of an aging-associated condition e.g., cognitive impairment; an individual of any age that is suffering from a cognitive impairment due to an aging-associated disease, as described further below, and an individual of any age that has been diagnosed with an aging-associated disease that is typically accompanied by cognitive impairment, where the individual has not yet begun to show symptoms of cognitive impairment. The corresponding ages for non-human subjects are known and are intended to apply herein.

As summarized elsewhere, in some instances the subject is a mammal. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations.

As used herein and as described above, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc. The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

In some embodiments, the condition that is treated is an aging-associated impairment in cognitive ability in an individual. By cognitive ability, or "cognition," it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, progressive supranuclear palsy, ataxia, associated frailty, and the like.

g. Combinations

The compounds of general formula 1 may be used on their own or combined with other active substances of formula 1 according to the invention. The compounds of general formula 1 may optionally also be combined with other pharmacologically active substances. These include, ß2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Nonsteroidal anti-inflammatory agents (NSAIDs), CRTH2 antagonists, DP1-receptor modulators, Thromboxane receptor antagonists, additional CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR$^2$ antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

In some embodiments, the other active substances are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, but also combinations of two or three active substances, i.e.:
  Betamimetics with corticosteroids, PDE4-inhibitors, CRTH2-inhibitors or LTD4-antagonists,
  Anticholinergics with betamimetics, corticosteroids, PDE4-inhibitors, CRTH2-inhibitors or LTD4-antagonists,
  Corticosteroids with PDE4-inhibitors, CRTH2-inhibitors or LTD4-antagonists
  PDE4-inhibitors with CRTH2-inhibitors or LTD4-antagonists
  CRTH2-inhibitors with LTD4-antagonists.
In these embodiments, the compounds that make up the combination are co-administered to a subject. The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent. "Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and compounds of the present disclosure. In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

h. Pharmaceutical Forms

Suitable preparations for administering the compounds of formula 1 and the co-crystal or salt forms of formulae 2 and 2a include for example tablets, capsules, suppositories, solutions and powders etc. The content of the pharmaceutically active compound(s) should be in the range from 0.05 to 90 wt.-%, such as 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, e.g., potato starch, gelatine and the like. Lubricants such as magnesium stearate, sodium laurylsulphate and talc may also be used to produce the tablets. In the case of aqueous suspensions the active substances may be combined with various flavor enhancers or colorings in addition to the abovementioned excipients.

For administering the compounds of formula 1 or the co-crystal or salt forms of formulae 2 and 2a preparations or pharmaceutical formulations which are suitable for inhalation may be employed. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain a compound of formula 1 or a co-crystal or salt form of formulae 2 and 2a either on their own or in admixture with suitable physiologically acceptable excipients.

If the active substances of the compounds of formula 1 or the co-crystal or salt forms of formulae 2 and 2a are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. In some instances, mono- or disaccharides are used, such as lactose or glucose, e.g., in the form of their hydrates, e.g., lactose, such as lactose monohydrate.

Within the scope of the inhalable powders according to the invention the excipients have a maximum average particle size of up to 250 µm, such as between 10 and 150 µm, and including between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronized active substance of the compounds of formula 1 or the co-crystal or salt forms of formulae 2 and 2a, such as with an average particle size of 0.5 to 10 µm, including from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain a compound of formula 1 or a co-crystal or salt form of formulae 2 and 2a dissolved in the propellant gas or in dispersed form. The compounds of formula 1 or the co-crystal or salt forms of formulae 2 and 2a may be contained in separate formulations or in a common formulation, in which they are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. In some instances, propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers). Moreover, the active substances of the compounds of formula 1 or the co-crystal or salt forms of formulae 2 and 2a according to the invention may be administered in the form of propellant-free inhalable solutions and suspensions. The solvent used may be an aqueous or alcoholic, such as an ethanolic solution. The solvent may be water on its own or a mixture of water and ethanol. The relative proportion of ethanol compared with water is not limited but the maximum is in some instances up to 70 percent by volume, such as up to 60 percent by volume and including up to 30 percent by volume. The remainder of the volume is made up of water. The solutions or suspensions containing a compound of formula 1 or a co-crystal or salt form of formulae 2 and 2a are adjusted to a pH of 2 to 7, such as 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. In some instances, the inorganic acids are hydrochloric and sulphuric acids. It is also possible to use the acids which have already formed an acid addition salt with one of the active substances. Of the organic acids, ascorbic acid, fumaric acid and citric acid are employed in some instances. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, in some instances hydrochloric acid is employed to adjust the pH.

If desired, the addition of edetic acid (EDTA) or one of the known salts thereof, sodium edetate, as stabilizer or complexing agent may be omitted in these formulations. Other embodiments may contain this compound or these compounds. In an embodiment the content based on sodium edetate is less than 100 mg/100 ml, such as less than 50 mg/100 ml, and including less than 20 mg/100 ml. Inhalable solutions in which the content of sodium edetate is from 0 to 10 mg/100 ml are employed in some instances. Co-solvents and/or other excipients may be added to the propellant-free inhalable solutions, such as those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. In some embodiments, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

In some embodiments excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly acetyl pyridinium chloride, benzalkonium chloride or benzoic acid or benzoates such as sodium benzoate in the concentration known from the prior art. The preservatives mentioned above may be present in concentrations of up to 50 mg/100 ml, such as between 5 and 20 mg/100 ml.

In some embodiments, the formulations contain, in addition to the solvent water and the compounds of formula 1 or the co-crystal or salt forms of formulae 2 and 2a, only benzalkonium chloride and sodium edetate. In an embodiment, no sodium edetate is present.

The dosage of the compounds according to the invention is naturally highly dependent on the method of administration and the complaint which is being treated. When administered by inhalation the compounds of formula 1 or the co-crystal or salt forms of formulae 2 and 2a are characterized by a high potency even at doses in the µg range. The compounds of formula 1 or the co-crystal or salt forms of formulae 2 and 2a may also be used effectively above the µg range. The dosage may then be in the gram range, for example.

In another aspect the present invention relates to the above-mentioned pharmaceutical formulations as such which are characterized in that they contain a compound of formula 1 or a co-crystal or salt form of formulae 2 and 2a, particularly the above-mentioned pharmaceutical formulations which can be administered by inhalation.

The following examples of formulations illustrate the present invention without restricting its scope:

i. Examples of Pharmaceutical Formulations

| A) Tablets | per tablet |
|---|---|
| active substance 1, 2, or 2a | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) Tablets | per tablet |
|---|---|
| active substance 1, 2, or 2a | 80 mg |
| lactose | 55 mg |
| maize starch | 190 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance 1, 2, or 2a | 50 mg |
| sodium chloride | 50 mg |
| water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg and 50 mg of active substance.

| D) Metering aerosol | |
|---|---|
| active substance 1, 2, or 2a | 0.005 |
| sorbitan trioleate | 0.1 |
| monofluorotrichloromethane and TG134a:TG227 2:1 | ad 100 |

The suspension is transferred into a conventional aerosol container with metering valve. Preferably 50 µl suspension are released on each actuation. The active substance may also be released in higher doses if desired (e.g. 0.02 wt.-%).

| E) Solutions (in mg/100 ml) | |
|---|---|
| active substance 1, 2, or 2a | 333.3 mg |
| benzalkonium chloride | 10.0 mg |
| EDTA | 50.0 mg |
| HCl (1N) | ad pH 2.4 |

This solution can be prepared in the usual way.

| F) Inhalable powder | |
|---|---|
| active substance 1, 2, or 2a | 12 µg |
| lactose monohydrate | ad 25 mg |

The inhalable powder is prepared in the usual way by mixing the individual ingredients.

j. Indications

Methods of improving cognition or other symptoms of cognitive disease through treating a subject/patient diagnosed with cognitive-associated disease are provided. Aspects of the methods include modulating CCR3, e.g. with a CCR3 modulating agent, in a manner sufficient to treat the patient for the cognitive-associated disease. The methods include treating the cognitive-associated disease with an orally administrable and bioavailable composition, including a composition of compound of formula 1, a co-crystal or salt of formulae 2 or 2a, or a formulation of formula 3, described above. As summarized above and described below in greater detail, a variety of aging associated impairments, e.g., cognitive-associated diseases may be treated by embodiments of the invention. In some instances, the target condition is a cognitive-associated disease condition that is associated with neurodegeneration, e.g., as evidenced by neural compromise, such as one of more of, reduced neurogeneration, e.g., as manifested by decreased numbers of BrdU or EdU positive cells, Ki67 positive cells, and Dcx positive cells when compared to non-diseased tissue. The composition, which modulates CCR3, can be administered to a patient/subject diagnosed with the cognitive-associated disease, such as (by way of example and not limitation): mild cognitive impairment (MCI); Alzheimer's disease; Parkinson's disease; frontotemporal dementia (FTD); Huntington's disease; amyotrophic lateral sclerosis (ALS); multiple sclerosis (MS); glaucoma; myotonic dystrophy; dementia; progressive supranuclear palsy (PSP); ataxia; multiple-system atrophy; and frailty; which are further described below. The methods of the invention can further comprise monitoring improvement in the progression of the neurodegenerative disease through measuring cognitive or physical improvement.

Methods of improving motor coordination, function, or other symptoms of motor disorders through treating a subject/patient diagnosed with motor disorders are provided. Aspects of the methods include modulating CCR3, e.g. with a CCR3 modulating agent, in a manner sufficient to treat the patient for the motor disorder. The methods include treating the motor disorder with an orally administrable and bioavailable composition, including a composition of compound of formula 1, a co-crystal or salt of formulae 2 or 2a, or a formulation of formula 3, described above. As summarized above and described below in greater detail, a variety of aging associated impairments, e.g., motor disorders may be treated by embodiments of the invention. In some instances, the target condition is a motor disorder that is associated with neurodegeneration, e.g., as evidenced by neural compromise, such as one of more of, reduced neurogeneration, e.g., as manifested by decreased numbers of BrdU or EdU positive cells, Ki67 positive cells, and Dcx positive cells when compared to non-diseased tissue. The composition, which modulates CCR3, can be administered to a patient/subject diagnosed with the motor disorder, such as (by way of example and not limitation): Parkinson's disease; Parkinsonism; Dementia with Lewy Bodies; ataxia; dystonia; cervical dystonia; chorea; Huntington's disease, multiple system atrophy; spasticity; progressive supranuclear palsy; Tardive dyskinesia; Tourette syndrome; and tremor; which are further described below. The methods of the invention can further comprise monitoring improvement in the progression of the neurodegenerative disease through measuring cognitive or physical improvement.

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function. Individuals suffering from or at risk of developing an aging-associated cognitive impairment who will benefit from treatment with the subject compounds of the invention, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include by way of not of limitation, those listed below.

Alzheimer's disease. Alzheimer's disease is characterized by a progressive, inexorable loss of cognitive function associated with an excessive number of senile plaques in the cerebral cortex and subcortical gray matter, in addition to excessive β-amyloid and neurofibrillary tangles consisting of tau protein. The common form affects persons >60 years old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic associations. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus coeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease. Parkinson's Disease (PD) is an idiopathic, slowly progressive, degenerative CNS disorder characterized by slow and decreased movement (bradykinesia), muscular rigidity, resting tremor (dystonia), muscle freezing, and postural instability. Originally considered primarily a motor disorder, PD is now recognized to also cause depression and emotional changes. PD also can affect cognition, behavior, sleep, autonomic function, and sensory function. The most common cognitive impairments include an impairment in attention and concentration, working memory, executive function, producing language, and visuospatial function. A characteristic of PD is symptoms related to reduced motor function usually precede those related to cognitive impairment, which aids in diagnosis of the disease.

In primary Parkinson's disease, the pigmented neurons of the substantia nigra, locus coeruleus, and other brain stem dopaminergic cell groups degenerate. The cause is not known. The loss of substantia nigra neurons, which project to the caudate nucleus and putamen, results in depletion of the neurotransmitter dopamine in these areas. Onset is generally after age 40, with increasing incidence in older age groups.

Parkinson's disease is newly diagnosed in about 60,000 Americans each year and currently affects approximately one million Americans. Even though PD is not fatal in itself, its complications are the fourteenth leading cause of death in the United States. At present, PD cannot be cured, and treatment is generally prescribed to control symptoms, with surgery prescribed in later, severe cases.

Treatment options for PD include administration of pharmaceuticals to help manage motor deficits. These options increase or substitute for the neurotransmitter, dopamine, of which PD patients have low brain concentrations. Such medications include: carbidopa/levodopa (which create more dopamine in the brain); apomorphine, pramipexolole, ropinirole, and rotingotine (dopamine agonists); selegiline and rasagiline (MAO-B inhibitors which prevent breakdown of dopamine); entacapone and tolcapone (Catechol-O-methyltransferase [COMT] inhibitors which make more levodopa available in the brain); benztropine and trihexyphenidyl (anticholinergics); and amantadine (controls tremor and stiffness). Exercise/physical therapy is also commonly prescribed to help maintain physical and mental function.

Current treatment options, however treat the symptoms of PD, are not curative, and fail to prevent disease progression. Additionally, current medications tend to lose efficacy in late stage PD. The most prescribed drug, levodopa, commonly results in adverse effects within 5 to 10 years after commencing the medication. These adverse effects can be severe and can result in motor fluctuations and unpredictable swings in motor control between doses as well as jerking/twitching (dyskinesia) which are difficult to manage and are even as disabling as PD's own symptoms. Thus, there remains a need for new therapies with new mechanisms of action which can either be administrated along or in combination with current PD medications.

Parkinsonism. Secondary parkinsonism (also referred to as atypical Parkinson's disease or Parkinson's plus) results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including nigrostriatal degeneration. Certain disorders like Progressive Supranuclear Palsy (PSP), Multiple System Atrophy (MSA), Corticobasal degeneration (CBD) and Dementia with Lewy Bodies (DLB) can exhibit Parkinsonism symptoms before the cardinal symptoms necessary to the specific diagnosis can be made, and thus may be labeled as "Parkinsonism."

Assessing Progression of PD

Several rating scales have been utilized for evaluating the progression of PD. The most widely-used scales include the Unified Parkinson's Disease Rating Scale (UPDRS, which was introduced in 1987) (J. Rehabil Res. Dev., 2012 49(8): 1269-76), and the Hoehn and Yahr scale (Neruology, 1967 17(5): 427-42). Additional scales include the Movement Disorder Society (MDS)'s updated UPDRS scale (MDS-UPDRS) as well as the Schwab and England Activities of Daily Living (ADL) Scale.

The UPDRS scale evaluates 31 items that contributed to three subscales: (1) mentation, behavior, and mood; (2) activities of daily living; and (3) motor examination. The Hoehn and Yahr scale classifies PD into five stages with discreet substages: 0—no signs of disease; 1—symptoms on one side only; 1.5—symptoms on one side but also involving neck and spine; 2—symptoms on both sides with no balance impairment; 2.5—mild symptoms on both sides, with recovery when the 'pull' test is given; 3—balance impairment with mild to moderate disease; 4—severe disability, but ability to walk or stand unassisted; and 5—need a wheelchair or bedridden without assistance. The Schwab and England scale classifies PD into several percentages (from 100%—complete independent to 10%—total dependent). Frontotemporal dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected:

Behavioral variant FTD (bvFTD), with symptoms including lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies." Symptoms include loss of speech (aphasia) and dementia. Patients with orbitofrontal dysfunction can become aggressive and socially inappropriate.

They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning.

Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic lateral sclerosis. Amyotrophic lateral sclerosis (ALS) is a rapidly progressive, invariably fatal, neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years.

Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia. Dementia describes a class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy Bodies.

Dementia with Lewy bodies (DLB), also known under a variety of other names including Lewy body dementia, diffuse Lewy body disease, cortical Lewy body disease, and senile dementia of Lewy type, is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short-term memory will rise and fall.

Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Treating DLB is a complex process and requires a multifaceted approach. (Neurology, 2017 89:1-13). Typical Parkinsonism therapies like dopaminergic and anticholinergic drugs can exacerbate cognition and behavior symptoms. Optimal treatment commonly utilizes both pharmacologic (exercise, cognitive training, and caregiver-oriented training) and non-pharmacologic approaches. For cognitive symptoms, acetylcholinesterase inhibitors can be administered (e.g. rivastigmine, donepezil) as can the NMDA receptor antagonist, memantine. For neuropsychiatric symptoms, acetylcholinesterase inhibitors can improve apathy and hallucinations. Antipsychotics unfortunately increase mortality risk in DLB patients. Motor symptoms are less responsive to dopaminergic treatments in DLB patients and can exacerbate the risk of psychosis. Levodopa can be used, but only a low threshold doses, hence a distinct need in the field for new agents to treat DLB.

Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive) and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-system atrophy. Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation.

The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

Dystonia. Dystonia is a condition which involves sustained involuntary muscle contractions. Such contracts can exhibit twisting, repetitive movements. This disorder may affect the entire body or specific parts of the body, referred to as generalized dystonia or focal dystonia (respectively). Cervical dystonia can cause long-lasting or intermittent contractions in the neck muscles. There is no cure for dystonia. Current therapies include carbidopa-levodopa, trihexyphenidyl, benztropine, tetrabenazine, diazepam, clonazepam, baclofen, physical therapy, speech therapy, stretching, massage, and invasive surgery.

Frailty. Frailty Syndrome ("Frailty") is a geriatric syndrome characterized by functional and physical decline including decreased mobility, muscle weakness, physical slowness, poor endurance, low physical activity, malnourishment, and involuntary weight loss. Such decline is often accompanied and a consequence of diseases such as cognitive dysfunction and cancer. However, Frailty can occur even without disease. Individuals suffering from Frailty have an increased risk of negative prognosis from fractures, accidental falls, disability, comorbidity, and premature mortality. (C. Buigues, et al. Effect of a Prebiotic Formulation on Frailty Syndrome: A Randomized, Double-Blind Clinical Trial, Int. J. Mol. Sci. 2016, 17, 932). Additionally, individuals suffering from Frailty have an increased incidence of higher health care expenditure. (Id.)

Common symptoms of frailty can be determined by certain types of tests. For example, unintentional weight loss involves a loss of at least 10 lbs. or greater than 5% of body weight in the preceding year; muscle weakness can be determined by reduced grip strength in the lowest 20% at baseline (adjusted for gender and BMI); physical slowness can be based on the time needed to walk a distance of 15 feet; poor endurance can be determined by the individual's self-reporting of exhaustion; and low physical activity can be measured using a standardized questionnaire. (Z. Palace et al., The Frailty Syndrome, Today's Geriatric Medicine 7(1), at 18 (2014)).

In some embodiments, the subject methods and compositions find use in slowing the progression of aging-associated cognitive, motor or other age-related impairment. In other words, cognitive, motor, or other abilities in the individual will decline more slowly following treatment by the disclosed methods than prior to or in the absence of treatment by the disclosed methods. In some such instances, the subject methods of treatment include measuring the progression of cognitive, motor or other age-related ability decline after treatment, and determining that the progression of decline is reduced. In some such instances, the determination is made by comparing to a reference, e.g., the rate of decline in the individual prior to treatment, e.g., as determined by measuring cognitive, motor, or other age-related abilities prior at two or more time points prior to administration of the subject blood product.

The subject methods and compositions also find use in stabilizing the cognitive, motor or other abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive, motor, or other age-related impairment in an individual suffering from an aging-associated impairment. In other words, the affected ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-old or more, following treatment by the subject methods relative to the cognitive ability that is observed in the individual prior to treatment by the subject methods.

In some instances, treatment by the subject methods and compositions restores the cognitive, motor, or other ability in the individual suffering from aging-associated cognitive or motor decline, e.g., to their level when the individual was about 40 years old or less. In other words, cognitive or motor impairment is abrogated.

k. Methods of Diagnosing and Monitoring for Improvement of Neurodegenerative-Associated Disease One having ordinary skill in the art would recognize that among the variety of methods to diagnose and monitor disease progression and improvement in neurodegenerative-associated disease, the following types of assessments could be used alone or in combination with subjects suffering from neurodegenerative disease. The following types of methods are presented as examples and are not limited to the recited methods. One having ordinary skill in the art would recognize that other methods to monitor disease would be useful in practicing the invention. Those methods are also contemplated by the methods of the invention.

i. General Cognition

The methods of the invention further comprise methods of monitoring the effect of a medication or treatment on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy.

In one embodiment, examinations of peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

ii. Multiple Sclerosis

In addition to monitoring improvement for symptoms associated with cognition, the progression or improvement of neurodegeneration associated with multiple sclerosis (MS) can be monitored using techniques well-known to those having ordinary skill in the art. By way of example, and not limitation, monitoring can be performed through techniques such as: cerebrospinal fluid (CSF) monitoring;

magnetic resonance imaging (MRI) to detect lesions and development of demyelinating plaques; evoked potential studies; and gait monitoring.

CSF analysis may be performed, for example, through lumbar puncture to obtain pressure, appearance, and CSF content. Normal values typically range as follows: pressure (70-180 mm $H_2O$); appearance is clear and colorless; total protein (15-60 mg/100 mL); IgG is 3-12% of the total protein; glucose is 50-80 mg/100 mL; cell count is 0-5 white blood cells and no red blood cells; chloride (110-125 mEq/L). Abnormal results may indicate the presence or progression of MS.

MRI is another technique that may be performed to monitor disease progression and improvement. Typical criteria for monitoring MS with MRI include the appearance of patchy areas of abnormal white matter in cerebral hemisphere and in paraventricular areas, lesions present in the cerebellum and/or brain stem as well as in the cervical or thoracic regions of the spinal cord.

Evoked potentials may be used to monitor the progression and improvement of MS in subjects. Evoked potentials measure slowing of electrical impulses such as in Visual Evoked Response (VER), Brain Stem Auditory Evoked Responses (BAER), and Somatosensory Evoked Responses (SSER). Abnormal responses help to indicate that there is a decrease in the speed of conduction in central sensory pathways.

Gait monitoring can also be used to monitor disease progression and improvement in MS subjects. MS is often accompanied by an impairment in mobility and an abnormal gait due in part to fatigue. Monitoring may be performed, for example, with the use of mobile monitoring devices worn by subjects. (Moon, Y., et al., *Monitoring gait in multiple sclerosis with novel wearable motion sensors*, PLOS One, 12(2):e0171346 (2017)).

iii. Huntington's

In addition to monitoring improvement for symptoms associated with cognition, the progression or improvement of neurodegeneration associated with Huntington's Disease (HD) can be monitored using techniques well-known to those having ordinary skill in the art. By way of example, and not limitation, monitoring can be performed through techniques such as: motor function; behavior; functional assessment; and imaging.

Examples of motor function that may be monitored as an indication of disease progression or improvement include chorea and dystonia, rigidity, bradykinesia, oculomotor dysfunction, and gait/balance changes. Techniques for performing the monitoring of these metrics are well-known to those having ordinary skill in the art. (See Tang C, et al., *Monitoring Huntington's disease progression through preclinical and early stages*, Neurodegener Dis Manag 2(4):421-35 (2012)).

The psychiatric effects of HD present opportunities to monitor disease progression and improvement. For example, psychiatric diagnoses may be performed in order to determine whether the subject suffers from depression, irritability, agitation, anxiety, apathy and psychosis with paranoia. (Id.)

Functional assessment may also be employed to monitor disease progression or improvement. Total functional score techniques have been reported (Id.), and often declines by one point per year in some HD groups.

MRI or PET may be employed also to monitor disease progression or improvement. For example, there is a loss of striatal projection neurons in HD, and change in number of these neurons may be monitored in subjects. Techniques to determine neuronal change in HD subjects include imaging Dopamine $D_2$ receptor binding. (Id.)

iv. ALS

In addition to monitoring improvement for symptoms associated with cognition, the progression or improvement of neurodegeneration associated with Amyotrophic Lateral Sclerosis (ALS) can be monitored using techniques well-known to those having ordinary skill in the art. By way of example, and not limitation, monitoring can be performed through techniques such as: functional assessment; determining muscle strength; measuring respiratory function; measuring lower motor neuron (LMN) loss; and measuring upper motor neuron (UMN) dysfunction.

Functional assessment can be performed using a functional scale well-known to those having ordinary skill in the art, such as the ALS Functional Rating Scale (ALSFRS-R), which evaluates symptoms related to bulbar, limb, and respiratory function. The rate of change is useful in predicting survival as well as disease progression or improvement. Another measure includes the Combined Assessment of Function and Survival (CAFS), ranking subjects' clinical outcomes by combining survival time with change in ALSFRS-R. (Simon N G, et al., *Quantifying Disease Progression in Amyotrophic Lateral Sclerosis*, Ann Neurol 76:643-57 (2014)).

Muscle strength may be tested and quantified through use of composite Manual Muscle Testing (MMT) scoring. This entails averaging measures acquired from several muscle groups using the Medical Research Council (MRC) muscle strength grading scale. (Id.) Hand-held dynamometry (HHD) may also be used, among other techniques. (Id.)

Respiratory function can be performed using portable spirometry units, used to obtain Forced Vital Capacity (FVC) at baseline to predict the progression or improvement of the disease. Additionally, maximal inspiratory pressure, sniff nasal inspiratory pressure (SNIP), and supping FVC may be determined and used to monitor disease progression/improvement. (Id.)

Loss in lower motor neurons is another metric which can be utilized to monitor disease progression or improvement in ALS. The Neurophysiological Index may be determined by measuring compound muscle action potentials (CMAPs) on motor nerve conduction studies, of which parameters include CMAP amplitude and F-wave frequency. (Id. and de Carvalho M, et al., *Nerve conduction studies in amyotrophic lateral sclerosis*. Muscle Nerve 23:344-352, (2000)). Lower motor neuron unit numbers (MUNE) may be estimated as well. In MUNE, the number of residual motor axons supplying a muscle through estimation of the contribution of individual motor units to the maximal CMAP response is estimated, and used to determine disease progression or improvement. (Simon N G, et al., supra). Additional techniques for determining loss of LMN include testing nerve excitability, electrical impedance myography, and using muscle ultrasound to detect changes in thickness in muscles. (Id.)

Dysfunction of upper motor neurons is another metric which can be utilized to monitor disease progression or improvement in ALS. Techniques for determining dysfunction include performing MRI or PET scans on the brain and spinal cord, transcranial magnetic stimulation; and determining levels of biomarkers in the cerebrospinal fluid (CSF).

v. Glaucoma

In addition to monitoring improvement for symptoms associated with cognition, the progression or improvement of neurodegeneration associated with glaucoma can be monitored using techniques well-known to those having ordinary skill in the art. By way of example, and not limitation, monitoring can be performed through techniques such as: determining intraocular pressure; assessment of the optic disc or optic nerve head for damage; visual field testing for peripheral vision loss; and imaging of the optic disc and retina for topographic analysis.

vi. Progressive Supranuclear Palsy (PSP)

In addition to monitoring improvement for symptoms associated with cognition, the progression or improvement of neurodegeneration associated with Progressive Supranuclear Palsy (PSP) can be monitored using techniques well-known to those having ordinary skill in the art. By way of example, and not limitation, monitoring can be performed through techniques such as: functional assessment (activities of daily living, or ADL); motor assessment; determination of psychiatric symptoms; and volumetric and functional magnetic resonance imaging (MRI).

The level of function of a subject in terms of independence, partial dependence upon others, or complete dependence can be useful for determining the progression or improvement in the disease. (See Duff, K, et al., *Functional impairment in progressive supranuclear palsy,* Neurology 80:380-84, (2013)). The Progressive Supranuclear Palsy Rating Scale (PSPRS) is a rating scale that comprises twenty-eight metrics in six categories: daily activities (by history); behavior; bulbar, ocular motor, limb motor and gait/midline. The result is a score ranging from 0-100. Six items are graded 0-2 and twenty-two items graded 0-4 for a possible total of 100. The PSPRS scores are practical measures, and robust predictors of patient survival. They are also sensitive to disease progression and useful in monitoring disease progression or improvement. (Golbe L I, et al., *A clinical rating scale for progressive supranuclear palsy,* Brain 130:1552-65, (2007)).

The ADL section from the UPDRS (Unified Parkinson's Disease Rating Scale) can also be used to quantify functional activity in subjects with PSP. (Duff K, et al., supra). Similarly, the Schwab & England Activities Daily Living Score (SE-ADL) can be used for evaluate independence. (Id.) Additionally, the motor function sections of the UPDRS are useful as a reliable measure for assessing disease progression in PSP patients. The motor section may contain, for example, 27 different measures for quantifying motor function in PSP patients. Examples of these include resting tremor, rigidity, finger tapping, posture, and gait). A subject's disease progression or improvement may also be assessed by performing a baseline neuropsychological evaluation completed by trained medical personnel, the assessment using the Neuropsychiatric Inventory (NPI) to determine the frequency and severity of behavior abnormalities (e.g. delusions, hallucinations, agitation, depression, anxiety, euphoria, apathy, disinhibition, irritability, and aberrant motor behavior). (Id.)

Functional MRI (fMRI) can be employed to monitor disease progression and improvement as well. fMRI is a technique using MRI to measure changes in brain activity in certain regions of the brain, usually based on blood flow to those regions. Blood flow is considered to correlate with brain region activation. Patients with neurodegenerative disorders like PSP can be subjected to physical or mental tests before or during being scanned in an MRI scanner. By way of example, and not limitation, tests can be a well-established force control paradigm where patients as asked to produce force with the hand most affected by PSP and maximum voluntary contraction (MVC) is measured by fMRI immediately after the test takes place. Burciu, R G, et al., *Distinct patterns of brain activity in progressive supranuclear palsy and Parkinson's disease*, Mov. Disord. 30(9): 1248-58 (2015)).

Volumetric MRI is a technique where MRI scanners determine volume differences in regional brain volume. This may be done, for example, by contrasting different disorders, or by determining differences in volume of a brain region in a patient over time. Volumetric MRI may be employed to determine disease progression or improvement in neurodegenerative disorders like PSP. The technique is well-known to those having ordinary skill in the art. (Messina D, et al., *Patterns of brain atrophy in Parkinson's disease, progressive supranuclear palsy and multiple system atrophy*, Parkinsonism and Related Disorders, 17(3):172-76 (2011)). Examples of cerebral regions which may be measured include, but are not limited to, intracranial volume, cerebral cortex, cerebellar cortex, thalamus, caudate, putamen, pallidum, hippocampus, amygdala, lateral ventricles, third ventricle, fourth ventricle, and brain stem.

vii. Neurogenesis

Noninvasive techniques for evaluating neurogenesis have been reported. (Tamura Y. et al., J. Neurosci. (2016) 36(31): 8123-31). Positron emission tomography (PET) used with the tracer, [$^{18}$F]FLT, in combinations with the BBB transporter inhibitor probenecid, allows for accumulation of the tracer in neurogenic regions of the brain. Such imaging allows for an evaluation of neurogenesis in patients being treated for neurodegenerative disease.

viii. Parkinson's Disease and Motor Function

Several rating scales have been utilized for evaluating the progression of PD. The most widely-used scales include the Unified Parkinson's Disease Rating Scale (UPDRS, which was introduced in 1987) (J. Rehabil. Res. Dev., 2012 49(8): 1269-76), and the Hoehn and Yahr scale (Neurology, 1967 17(5): 427-42). Additional scales include the Movement Disorder Society (MDS)'s updated UPDRS scale (MDS-UPDRS) as well as the Schwab and England Activities of Daily Living (ADL) Scale.

The UPDRS scale evaluates 31 items that contributed to three subscales: (1) mentation, behavior, and mood; (2) activities of daily living; and (3) motor examination. The Hoehn and Yahr scale classifies PD into five stages with discreet substages: 0—no signs of disease; 1—symptoms on one side only; 1.5—symptoms on one side but also involving neck and spine; 2—symptoms on both sides with no balance impairment; 2.5—mild symptoms on both sides, with recovery when the 'pull' test is given; 3—balance impairment with mild to moderate disease; 4—severe disability, but ability to walk or stand unassisted; and 5—need a wheelchair or bedridden without assistance. The Schwab and England scale classifies PD into several percentages (from 100%—complete independent to 10%—total dependent).

General motor function can be evaluated using widely-used scales including the General Motor Function Scale (GMF). This tests three components: dependence, pain, and insecurity. (Aberg A. C., et al. (2003) Disabil. Rehabil. 2003 May 6; 25(9):462-72.). Motor function can also be assessed using home-monitoring or wearable sensors. For example: gait (speed of locomotion, variability, leg rigidity) can be sensed with an accelerometer; posture (trunk inclination) by a gyroscope; leg movement by an accelerometer; hand movement by an accelerometer and gyroscope; tremor (amplitude, frequency, duration, asymmetry) by an accelerometer; falling by an accelerometer; gait freezing by an accelerometer; dyskinesia by an accelerometer, gyroscope, and inertial sensors; bradykinesia (duration and frequency) by an accelerometer plus gyroscope, and aphasia (pitch) using a microphone. (Pastorino M, et al., Journal of Physics: Conference Series 450 (2013) 012055).

l. Reagents, Devices, and Kits

Also provided are reagents, devices, and kits thereof for practicing one or more of the above-described methods. The subject reagents, devices, and kits thereof may vary greatly. Reagents and devices of interest include those mentioned above with respect to the methods of administering the compounds for formula 1 in the subject.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g. diskette, CD, portable flash drive, etc., on which the information has been recorded. Yet another means that may be present is a website address which may be used via the internet to access the information at a remote site. Any convenient means may be present in the kits.

VII. EXAMPLES

The following examples are provided by way of illustration and not by way of limitation.

a. Pharmaceutical Preparation

The pharmaceutical compositions that are administered to subjects with cognitive or neurodegenerative disease that are comprised of the compounds, co-crystals, and salts described above can be synthesized, made, and formulated using the examples disclosed in U.S. Patent Application Publication Nos. 2013/0266646, 2016/0081998, U.S. Pat. Nos. 8,278,302, 8,653,075, RE 45,323, 8,742,115, 9,233,950, and 8,680,280, which are herein incorporated by reference in their entirety. Further, the pharmaceutical compositions may be prepared as described in the examples below:

1. Tablet Formulation—Wet Granulation

Copovidone is dissolved in ethanol at ambient temperature to produce a granulation liquid. An active CCR3 antagonist ingredient, lactose and part of the crospovidone are blended in a suitable mixer, to produce a pre-mix. The pre-mix is moistened with the granulation liquid and subsequently granulated. The moist granulate is optionally sieved through a sieve with a mesh size of 1.6-3.0 mm. The granulate is dried at 45° C. in a suitable dryer to a residual moisture content corresponding to 1-3% loss on drying. The dried granulate is sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 28.000 | 29.5 |
| Copovidone | 3.000 | 3.2 |
| Total (granulate) | 61.000 | 64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

2. Tablet Formulation—Melt Granulation

An active CCR3 antagonist ingredient, lactose, part of the mcc, polyethylene glycole, lactose and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and microcrystalline cellulose in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Lactose | 11.000 | 11.6 |
| Polyethylene glycole | 14.300 | 15.1 |
| MCC | 5.700 | 6.0 |
| Total (granulate) | 61.000 | 64.3 |
| Microcrystalline cellulose | 31.000 | 32.6 |
| Crospovidone | 2.500 | 2.6 |
| Magnesium stearate | 0.500 | 0.5 |
| Total | 95.000 | 100.000 |

3. Tablet Formulation—Hot Melt Granulation

An active CCR3 antagonist ingredient, mannit, polyethylene glycole and part of the crospovidone are blended in a suitable mixer, to produce a pre-mix. The pre-mix is heated in a high shear mixer and subsequently granulated. The hot granulate is cooled down to room temperature and sieved through a sieve with a mesh size of 1.0 mm. The granulate is blended with part of the crospovidone and mannit in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
| --- | --- | --- |
| Active ingredient | 28.500 | 30.0 |
| Crospovidone | 1.500 | 1.6 |
| Mannit | 16.700 | 17.6 |
| Polyethylene glycole | 14.300 | 15.1 |
| Total (granulate) | 61.000 | 64.3 |
| Mannit | 31.000 | 32.6 |

| Component | mg/tablet | %/tablet |
|---|---|---|
| Crospovidone | 2.500 | 2.6 |
| Magnesium stearate | 0.500 | 0.5 |
| Total | 95.000 | 100.000 |

4. Tablet Formulation—Hot Melt Extrusion

An active CCR3 antagonist ingredient and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is blended with mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 28.500 | 30.0 |
| Stearic-palmitic acid | 27.500 | 28.9 |
| Total (granulate) | 56.000 | 58.9 |
| Mannit | 32.600 | 34.3 |
| Crospovidone | 5.600 | 5.9 |
| Magnesium stearate | 0.800 | 0.9 |
| Total | 95.000 | 100.000 |

5. Tablet Formulation—Hot Melt Extrusion

An active CCR3 antagonist ingredient and stearic-palmitic acid are blended in a suitable mixer, to produce a pre-mix. The pre-mix is extruded in a twin-screw-extruder and subsequently granulated. The granulate is sieved through a sieve with a mesh size of 1.0 mm. The granulate is directly filled into hard capsules. The following capsule composition can be obtained:

| Component | mg/tablet | %/tablet |
|---|---|---|
| Active ingredient | 70.000 | 70.0 |
| Stearic-palmitic acid | 30.000 | 30.0 |
| Total (granulate) | 100.000 | 100.0 |
| Capsule | 90.000 | — |
| Total | 190.000 | 100.000 |

6. Tablet Formulation—Roller Compaction

An active CCR3 antagonist ingredient, part of mannit and crospovidone and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with part of mannit and crospovidone in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 28.500 | 30.0 |
| Crospovidone | 1.400 | 1.5 |
| Mannit | 34.600 | 36.4 |
| Magnesium stearate | 0.500 | 0.5 |
| Total (granulate) | 65.000 | 68.4 |
| Mannit | 27.000 | 28.4 |
| Copovidone | 1.600 | 1.7 |
| Crospovidone | 0.950 | 1.0 |
| Magnesium stearate | 0.450 | 0.5 |
| Total | 95.000 | 100.000 |

7. Tablet Formulation—Roller Compaction

An active CCR3 antagonist ingredient and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with mannit and croscarmellose sodium in a suitable mixer. Magnesium stearate is added to this blend after passing through a 1.0 mm sieve for delumping. Subsequently the final blend is produced by final blending in a suitable mixer and compressed into tablets. The following tablet composition can be obtained:

| Component | mg/tablet | %/tablet |
|---|---|---|
| Active ingredient | 114.200 | 66.0 |
| Magnesium stearate | 1.800 | 1.0 |
| Total (granulate) | 116.000 | 67.0 |
| Mannit | 51.000 | 29.5 |
| Croscarmellose sodium | 3.500 | 2.0 |
| Magnesium stearate | 2.500 | 1.5 |
| Total | 173.000 | 100.000 |

8. Tablet Formulation—Roller Compaction

An active CCR3 antagonist ingredient and magnesium stearate are blended in a suitable mixer, to produce a pre-mix. The pre-mix is compacted with a roller compactor and subsequently granulated. Optionally, the granulate is sieved through a sieve with a mesh size of 0.8 mm. The granulate is blended with microcrystalline cellulose and crospovidone in a suitable mixer. Magnesium stearate is added to this blend after passing through a 1.0 mm sieve for de-lumping. Subsequently the final blend is produced by final blending in a suitable mixer and compressed into tablets. The following tablet composition can be obtained:

| Component | mg/tablet | %/tablet |
|---|---|---|
| Active ingredient | 114.200 | 66.0 |
| Magnesium stearate | 1.800 | 1.0 |
| Total (granulate) | 116.000 | 67.0 |
| MCC | 51.000 | 29.5 |
| Crospovidone | 3.500 | 2.0 |
| Magnesium stearate | 2.500 | 1.5 |
| Total | 173.000 | 100.000 |

9. Coated Tablet Formulation

Tablet cores according above mentioned formulations can be used to produce film-coated tablets. Hydroxypropyl methylcellulose, polyethylene glycol, talc, titanium dioxide and iron oxide are suspended in purified water in a suitable mixer at ambient temperature to produce a coating suspension. The tablet cores are coated with the coating suspension to a weight gain of about 3% to produce film-coated tablets. The following film coating composition can be obtained:

| Component | mg/tablet | %/tablet |
| --- | --- | --- |
| Hypromellose | 2.40 | 48.0 |
| Polyethylene glycol 6000 | 0.70 | 14.0 |
| Titanium dioxide | 0.90 | 18.0 |
| Talcum | 0.90 | 18.0 |
| Iron oxide red | 0.10 | 2.0 |
| Purified water (volatile component) | — | — |
| Total | 5.00 | 100.0 | b. Drug Formulation and Administration

The investigational product of the invention (Compound 1) conformed to the following chemical structure:

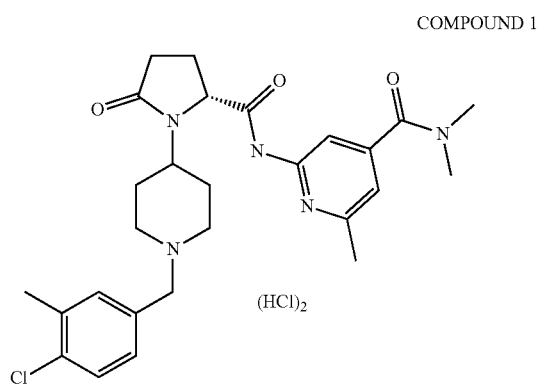

COMPOUND 1

(HCl)₂

Those having ordinary skill in the relevant art would recognize that the compounds, co-crystals, salts, and formulations described previously in the sections above could also be used in these examples.

Compound 1 was made available as 100 mg, 200 mg, and 400 mg film-coated tablets with a biconvex, round or oval shape and a dull red color. The tablets were produced by a dry granulation process and contained microcrystalline cellulose, hydrogen phosphate, croscarmellose sodium, magnesium stearate, polyvinyl alcohol, titanium dioxide, polyethylene glycol, talc, iron oxide red and iron oxide yellow as inactive ingredients. Placebo tablets matching the investigational product were produced by a direct compression process and contained the same inactive ingredients.

c. Pre-Clinical Examples

1. Materials and Methods
(a) Subcutaneous Osmotic Pump Implantation

Alzet mini-pumps were filled, prepared, and numbered by mouse ID the day previous to implantation to allow for priming at 37° C. and to allow for blindness of treatment. Pumps were implanted on the back, slightly posterior to the scapulae and slightly lateral to the midline. Mice were anesthetized with 3-5% isoflurane using a vaporizer and regulator in an induction chamber, then moved to the procedure area and fitted with a nose cone to maintain anesthesia at 1-3% isoflurane. An ophthalmic ointment was applied to the eyes to prevent drying. Mice were injected with meloxicam 5 mg/kg subcutaneously. Fur was removed from the incision area using small sharp scissors, and the area was cleaned with alternating applications of 70% isopropanol and butadiene. An incision 0.5-1 cm was made, and a hemostat was inserted to spread the subcutaneous tissue to create a pocket for the pump. The pump was inserted into the pocket and the wound was closed with wound clips. All surgical tools were autoclaved prior to first use on a surgery day. Subsequently, instruments were sterilized with a glass bead sterilizer between animals. Mice were placed in a clean recovery cage placed partially atop a warming pad until full recovery and ambulation. Mice were tested for anesthesia induction by toe pinch method and monitoring of respiration. Mice were monitored post-operatively every 15 minutes until recovery. Mice were administered a second dose of meloxicam the following day. If signs of infection were observed, mice received 5 mg/kg Baytril subcutaneously per day until infection cleared.

(b) Open Field Test

Open Field is used to evaluate general locomotor activity and exploratory behavior in a novel environment. Mice are brought to the experimental room for at least 30 min for acclimation to the experimental room conditions (dim lighting) prior to testing. The testing arena consists of a 50 cm×50 cm square arena. Mice are placed in the center of an arena and tracked for 15 minutes. Time spent in the peripheral and centers zones is analyzed, along with rearing behavior. 70% ethanol is used to clean all surfaces between trials.

(c) Y-Maze

A large Y-maze test assesses short-term memory of the familiarity of a specific context. Mice are brought to the experimental room for at least 30 min of acclimation to the experimental room conditions (dim lighting) prior to testing. For the initial training trial, the mouse is placed at the end of one arm of a large Y-maze designated "start arm" (arm length: 15 inches). The third arm of the maze is blocked off, allowing the mouse to explore two of the three arms freely ("start arm" and "familiar arm") for 5 min. Each arm contains spatial cues. One hour later, the mouse is placed back into the maze in the "start arm" and allowed to explore all three arms with the third arm unblocked ("novel arm"). Movements in and out of each arm are tracked using automated tracking software (CleverSys). Testing is performed under dim lighting, and the apparatus is cleaned with 70% ethanol between trials.

(d) Barnes Maze

A modified Barnes maze was used to assess spatial working/episodic like learning and memory. The Barnes maze apparatus consists of a 122 cm diameter circular platform with 40 escape holes, each with a diameter of 5 cm placed along three rings of varying distances from the center of the platform. An escape box is attached to one of the holes and all holes are left uncovered. Bright lights and a fan are trained on the maze to provide adverse stimuli to encourage escape. Visual cues are placed on all four sides of the maze. Mice are given a series of 4 or 5 trials with inter-trial intervals of approximately 10 min, and the maximum duration of each trial is 90 or 120 sec. For each trial, mice are placed in the center of the maze. After 10 seconds, mice are allowed to explore, and the trial is ended if the mouse has found and entered an escape box before the end of the trial. Mice that cannot find the escape box are led to it and allowed to enter and given 30 sec to remain before being returned to its home cage. Training is done for 4 days. Data that is recorded and analyzed include velocity, escape latency, and distance moved.

Mice are divided into groups of 4-5 mice each, with balanced treatment groups. For example, Group 1 mice are run for 4 trials, then Group 2 mice are run for 4 trials, and so on until all groups finish testing. 70% ethanol is used to clean the arenas between trials.

(e) Rotarod

The mice were trained in the rotarod for 3 trials up to 100 seconds each, the rotarod being a test of motor coordination. Success or failure was recorded on the last trial, with success defined by a latency to fall of >90 seconds. A binomial test was conducted to compare success rates between control and compound-treated mice.

(f) T maze

The Water Maze was filled with water at least 24 hours prior to the test to allow it to reach room temperature. The water was dyed with white latex paint to make the animals visible for tracking and to allow for the use of a hidden platform. Two distinct visual cues were placed at the end of both T-arms of the T-Maze insert. On day 1 animals were given 4 trials each with a visible platform and a 30 min inter-trial interval. Animals were given 60 seconds to reach the platform. If they did not reach the platform in that time they were guided to it and allowed to remain for 5 seconds before being removed from the tank. The goal arm was switched after every third mouse and both treatment groups had equal numbers of right and left turn goal arms. After each trial the mice were placed in an empty cage with blue pads and allowed to dry off under a red light lamp before being placed back into their home cage. Day 2 is the testing day, where animals are subjected to the same test of 4 trials each and a 30 min inter trial interval, but with a hidden platform. Animals were scored for right or wrong choice and for latency to reach the platform, and a binomial test was conducted to compare success rates between control and compound-treated mice. All trials were recorded using Top-Scan.

(g) Protein Quantification

CCL11 protein levels were measured from mouse plasma by sandwich ELISA Plasma was diluted 1:10 for the assay. (Mouse CCL11/Eotaxin Duo Set ELISA kit, R&D Systems, Minneapolis, Minn.).

Human CCL11 from human plasma was measured by a SomaLogic aptamer-based assay (SOMAscan from Soma-Logic, Inc., Boulder, Colo.). (Gold L, et al. (2010). Aptamer-Based Multiplexed Proteomic Technology for Biomarker Discovery. PLOS ONE 5(12): e15004.

Panels of circulating cytokines from mouse plasma were analyzed by Luminex. Luminex Assay Service performed by Eve Technologies (Calgary, Alberta, Canada).

(h) mRNA Quantification

Snap-frozen hemibrains were dissected out into cortex, hippocampus, striatum, and thalamus. The cortex was split into three homogeneous parts and one part was used for RNA isolation. RNA was isolated using the Prolink RNA Mini Kit (Thermo Fisher Scientific #12183025). cDNA was made using Taqman RT Kit (Thermo Fisher Sci #N8080234). qPCR was run on a Quant Studio 6 using custom made Taqman Multiplex Primers for IL-1beta and GAPDH. All samples were run together on a single plate and analyzed for ddCT relative to their endogenous control first and then relative to the control group.

(i) HPLC/MS Quantification of Compound 1

Compound levels were measured by MS/MS by Quintara (Hayward, Calif.).

(j) Flow Analyses

Eosinophil Count 200 uL of whole blood was collected during perfusion and shipped to Charles River Clinical Pathology Services (Shrewsbury, Mass.) for hematology analysis of eosinophil count by FACS (fluorescence activated cell sorter).

Eosinophil Shape Change (ESC)

The ESC determines the shape change of human eosinophils activated by human eotaxin-1 (PreProTech, Rocky Hill, N.J.) compared to native eosinophils. The change is detected as the change in the forward-scatter measured by FACS (fluorescence activated cell sorter). The mean forward scatter of the autofluorescence (eosinophil) population for each sample was determined in conjunction with the mean of each set of sample triplicates. Methods of determining ESC have been previously described and are known in the art.

CCR3 Receptor Internalization

The CCR3 receptor internalization assay is FACS-based and uses human Eotaxin-1 (PreProTech, Rocky Hill, N.J.) and an anti-human CCR3 antibody labeled with APC (R&D Systems, Minneapolis, Minn.) or isotype control $IgG_2A$ antibody to monitor CCR3 receptor internalization in human eosinophils induced by human eotaxin-1 compared to naïve eosinophils. The median APC fluorescent intensity units for each sample were determined along with the mean of each set of sample triplicates. Methods of monitoring CCR3 receptor internalization have been previously described and are known in the art.

(k) Histology

Mice were taken down on the day following the end of behavior testing. Anesthesia was induced by 2,2,2-tribromo-ethanol and mice were subsequently perfused with 0.9% saline trans-cardially. The brains were dissected and cut sagitally in two even halves. One half was snap frozen for later use in dry ice, and the other was fixed in 4% paraformaldehyde in PBS for use in immunohistochemistry. After two days of fixation, the hemibrains were transferred to a 30% sucrose in PBS solution and changed after two days. Hemibrains were sectioned at 30 um on a microtome at −22° C. Brain sections were stored in cryoprotectant media at −20° C. until needed for staining. Blocking was done on free floating sections in the appropriate serum at 10% serum in PBST 0.5%. Primary antibodies were incubated overnight at 4 C. For light microscopy, the following antibodies were used in the given concentrations: DCX, 1:200, Santa Cruz BioTech, CD68, 1:1000. AbD Serotec. Secondary biotinylated antibodies were applied the next day at a concentration of 1:300. Staining visualization was achieved by reaction with the ABC kit (Vector) and diaminobenzidine (Sigma). Dehydration of the mounted slides was achieved using ethanol and xylene dips. Images were acquired on a Leica light microscope at 5× magnification.

For fluorescent microscopy, the following antibodies were used in the given concentrations: GFAP, 1:500, DAKO; Iba1, 1:1000, Wako; and BrdU, 1:500, AbCam. Antigen retrieval protocol was required for BrdU (2N HCl, 37 C, 30 min) prior to blocking. The appropriate fluorescent secondary antibodies were applied the next day at a concentration of 1:300 for one hour at room temperature. Prolong Gold Mounting Media was used to coverslip the slides. Images were acquired on a light microscope at 5× magnification.

2. Experimental Groups

First Experimental Group (See FIGS. 1-2):

Two-month-old or 18-month-old C57Bl/6 mice were dosed with either IgG antibody control by IP injection or Compound 1 subcutaneously by Alzet osmotic pump for either 2 or 4 weeks. During the last week of treatment, mice were subjected to behavior testing prior to perfusion on the last day of treatment. All mice received 5 consecutive days of BrdU injection at 150 mg/kg IP immediately prior to treatment start.

Drug Formulation.

Control rat IgG2A clone 54447 (MAB006, R&D Systems) was administered at 50 ug/kg in sterile saline. Compound 1 was formulated in 40% HP-β-cyclodextrin, and adjusted to pH 6.5 with NaOH (1M). Solutions were prepared fresh weekly and stored at 4° C.

Treatment Groups.

Treatment Group 1, Young Controls: Young C57BL/6 mice (n=18), aged 1-2 months, received 5 injections of control IgG by intraperitoneal (IP) injection, one injection every 3 days, over a period of 14 days.

Treatment Group 2, Old Controls: Aged C57BL/6 mice (n=18), aged 18 months, received 5 injections of control IgG by IP injection, one injection every 3 days, over a period of 14 days.

Treatment Group 3, Compound 1 (dose 1) in Old: Aged C57BL/6 mice (n=16), aged 18 months, received infusion of ~50 mg/ml Compound 1 by Alzet mini-pump, model 2001 (1 uL/hr), for two weeks with one replacement.

Treatment Group 4, Compound 1 (dose 2) in Old: Aged C57BL/6 mice (n=16), aged 18 months, received infusion of ~50 mg/ml Compound 1 by Alzet mini-pump, model 2002 (0.5 uL/hr), for two weeks.

Treatment Group 5, Compound 1 (dose 2) in Old: Aged C57BL/6 mice (n=16), aged 18 months, received infusion of ~50 mg/ml Compound 1 by Alzet mini-pump, model 2002 (0.5 uL/hr), for four weeks with one replacement.

Figure 1A:
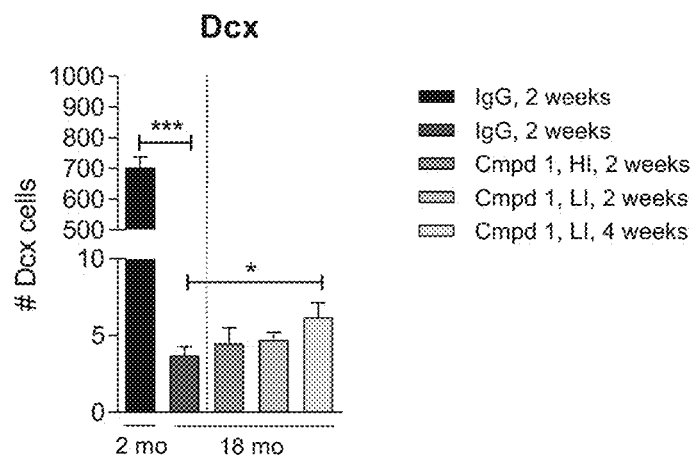
Figure 1B:
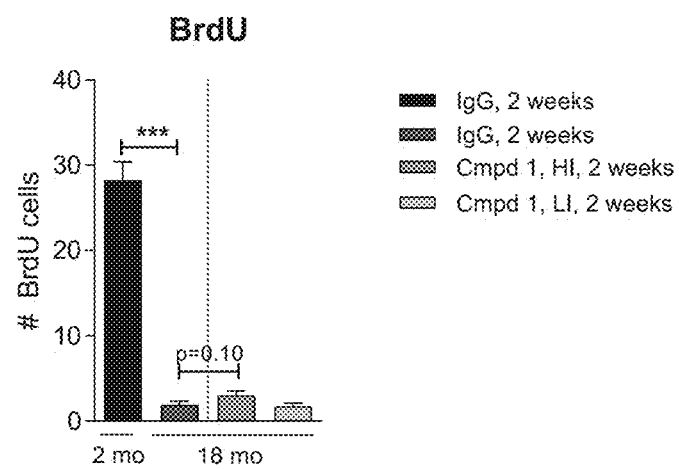
Figure 3:
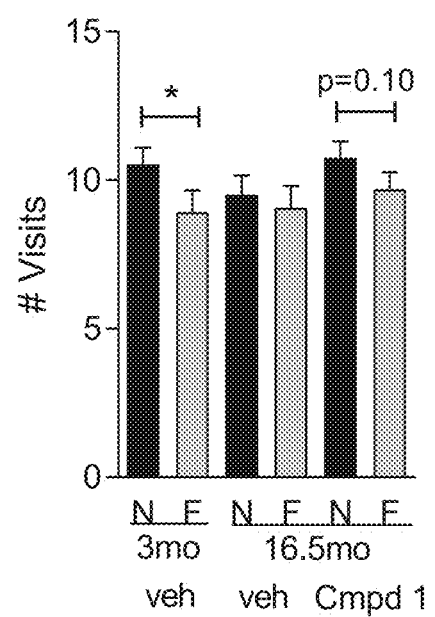

Four-week subcutaneous dosing of Compound 1 in 18-month-old mice increased the numbers of doublecortin-positive cells in the hippocampus, an indicator of neurogenesis (see FIG. 1A). Higher dosing of Compound 1 for 2 weeks led to a trend in increased BrdU-positive cells in the hippocampus, a marker for cell proliferation (see FIG. 1B). Low or high infusion of Compound 1 for 2 or 4 weeks led to improvement in the cued Y-maze, a test for memory (see FIG. 2 reporting percent of time normalized to total interaction time and number of visits—similar effects were also seen when evaluating total time spent). Comparisons are made to control groups (Treatment groups 1 & 2) which were treated with IgG antibody with no compound, and dosing and behavior were performed in parallel.

Thus, administration of Compound 1 increased the number of Dcx and BrdU positive cells, which indicates that Compound 1 increased neurogenesis and cell survival, respectively. Compound 1 was able to improve memory (cognition) as evidenced by performance in the Y-Maze test.

Second Experimental Group (See FIGS. 3-6):

Three-month-old or 16.5-month-old C57Bl/6 mice were dosed with either vehicle control or Compound 1 subcutaneously by Alzet osmotic pump for 4 weeks. During the last week of treatment, mice were subjected to behavior testing prior to perfusion on the last day of treatment. All mice received 5 consecutive days of BrdU injection at 150 mg/kg IP immediately prior to treatment start.

Drug Formulation.

Compound 1 was formulated in 40% HP-β-cyclodextrin, and adjusted to pH 6.5 with NaOH (1M). Vehicle solution was formulated and adjusted for pH similarly. Solutions were prepared fresh weekly and stored at 4° C.

Treatment Groups:

Treatment Group 1, Young Controls: Young C57BL/6 mice (n=19), aged 3 months, received infusion of vehicle by Alzet mini-pump, model 2002 (0.5 uL/hr), for four weeks with one replacement.

Treatment Group 2, Old Controls: Aged C57BL/6 mice (n=19), aged 16 months, received infusion of vehicle by Alzet mini-pump, model 2002 (0.5 uL/hr), for four weeks with one replacement.

Treatment Group 3, Compound 1 (dose 2) in Old: Aged C57BL/6 mice (n=19), aged 16 months, received infusion of ~50 mg/ml Compound 1 by Alzet mini-pump, model 2002 (0.5 uL/hr), for four weeks with one replacement.

Figure 4A:
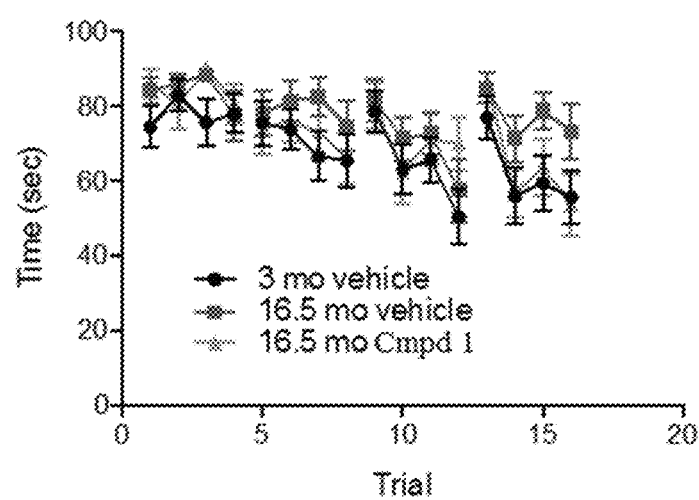
Figure 4B:
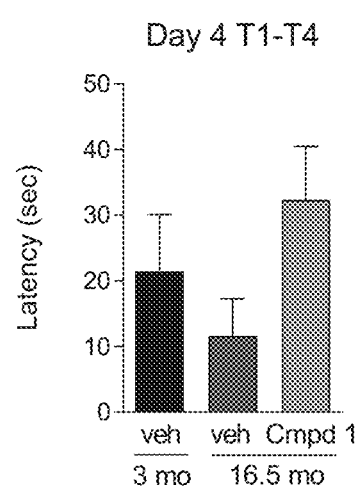
Figure 5:
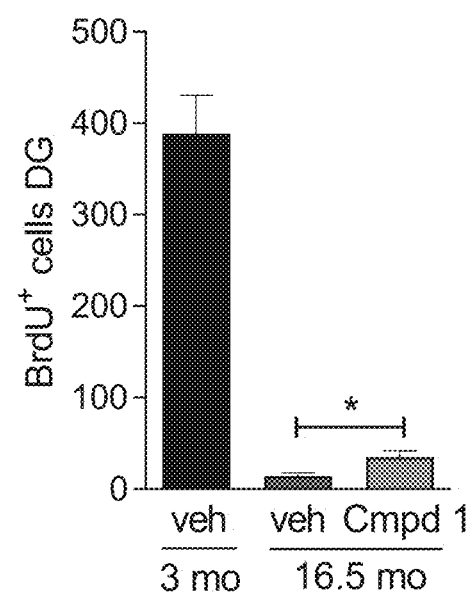

Four-week subcutaneous dosing of Compound 1 in 16.5-month-old mice improved cognitive performance in the cued Y-maze test for memory (see FIG. 3). 4-week dosing of Compound 1 also trended towards improved performance in the Barnes maze, a test for hippocampus-dependent spatial memory (see FIG. 4). Trends for improved memory were also observed upon analysis of the average of the latency for day 4 trials as well as in the difference between the latencies of trials 13 and 16. Four-week dosing of Compound 1 also significantly increased the number of BrdU-positive cells in the hippocampus, an indicator of neurogenesis (see FIG. 5). Thus, Compound 1 was able to both improve cell survival and improve memory (cognition) as evidenced by the results obtained using the Y-Maze and Barnes Maze tests.

Compound Cerebrospinal Fluid Levels in Mice

Figure 6:
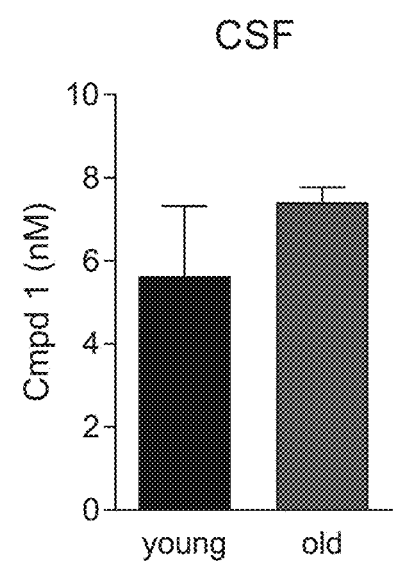
FIG. 6 depicts the levels of Compound 1 detected in the CSF of C57BL/6 mice in both young (n=2) and old groups (n=3) (levels were both below 10 nM). Levels of Compound 1 were detected using mass spectrometry.

Cerebrospinal fluid (CSF) from both the 2-month-old "young" and 16.5-month-old "old" groups was collected and levels of Compound 1 were determined by mass spectroscopy. FIG. 6 depicts the levels of the compound of the invention that were detected in mouse CSF for both the young and old groups (both below 10 nM). These CSF levels do not approach the Ki for the compound in mice (124 nM, determined by cell line receptor binding), and therefore do not cross the blood-brain barrier (BBB) in significant concentrations. For comparison, the levels of the compound of the invention that were measured in the plasma of young (2-month-old) and old (18-month-mice) perfused for 2 and 4 weeks respectively at 0.5 µL/hr of 50 mg/mL solution were significantly higher (352±31 nM and 355±43 nM, respectively; values are mean±s.e.m.), further indicating that the compound of the invention fails to cross the BBB in significant amounts.

This data shows that Compound 1 does not act directly in the CNS, and therefore acts peripherally. Additionally, what does cross the BBB is insufficient in concentration to be effective. Further, there is no difference in BBB penetration between young and old mice, indicating that the effects Compound 1 displays on cognition and neurodegeneration are not due to differences in the BBB between the two groups.

Compound Tissue Distribution Levels

The distribution of Compound 1 in mouse tissues was determined after oral administration of which was [$^{14}$C]-radiolabeled ("Labeled Compound") to male pigmented C57BL/6JOlaHsd mice (Harlan Labs, BV). The Labeled Compound was administered at 10 mg/kg of body weight, corresponding to 17 µmol/kg. One animal was sacrificed after 1, 24, and 168 hours post-administration. Blood, plasma, and eye radioactivity concentrations were measured using liquid scintillation counting (LSC). Tissue and organ concentrations were determined by whole body autoradiography technique (QWBA). Preparation of the whole-body animal sections was performed according to known techniques (see S. Ullberg, et al., Autoradiography in Pharmacology in: The Int. Encyclopedia of Pharmacology, J. Cohen (Ed.), 1(78):221-39 (1971)), using a crystat microtome Reichert-Jung CRYO MACROCUT or a CRYO MACROCUT LEICA CM 3600$^3$.

The following sections were taken at different levels through the embedded animal, and whole body sections selected at 5-7 levels in order to allow for quantitative evaluation of radioactivity: adrenal glands; blood; bone marrow; brain; eye (lens); epididymis; fat (white and brown); Harderian gland; heart; kidneys; liver; lung; muscle; pituitary; pancreas; prostate, spinal cord; spleen salivary gland; skin; testis; thyroid; thymus; uveal tract. Two sections of each chosen level were taken per animal, and those sections lyophilized in the microtome at −20 to −25° C. for a minimum of 48 hours.

FIG. 7 depicts a chart of values reporting the area under the curve (AUC) for all three time points, and quantifies each tissue's exposure to the Labeled POI after administration of the compound. FIG. 7 shows that Compound 1 does not cross the blood-brain barrier (BBB) at significant levels.

Again, these results show that, because Compound 1 cannot cross the BBB at appreciable levels, it acts in a peripheral fashion. As such, Compound 1's effects do not directly act on the central nervous system, and it overcomes difficulties that have caused the failure of many CNS disease-targeting pharmaceutical candidates.

Pharmacokinetic Profiles in P.O. Dosing

Plasma from male 2-month-old C57Bl/6 mice was measured for concentrations of Compound 1 at time points of 20 minutes, 2 hours, 8 hours, and 12 hours after oral gavage at 2 doses: 30 mg/kg and 150 mg/kg. A dose of 30 mg/kg was found to be sufficient to achieve a greater than 100 nM concentration of Compound 1 for 8 hours (FIG. 8).

Third Experimental Group (See FIGS. 9-11):

Two-month-old C57Bl/6 mice were dosed with either vehicle control or Compound 1 by oral gavage twice daily for 18 days. During the last week of treatment, mice were subjected to behavior testing prior to perfusion on the last day of treatment. All mice received 5 consecutive days of BrdU injection at 150 mg/kg IP immediately prior to treatment start.

Drug Formulation:

Compound 1 was formulated in 40% HP-β-cyclodextrin, and adjusted to pH 6.5 with NaOH (1M). Vehicle solution was formulated and adjusted for pH similarly. Solutions were prepared fresh weekly and stored at 4° C.

Treatment Groups:

Treatment Group 1a, Vehicle treatment: Young C57BL/6 mice (n=15), aged 7 weeks, received twice daily (BID) oral (PO) treatment of vehicle solution for 18 days, with only 1 injection on the last day, for a total of 35 injections.

Treatment Group 1b, Compound 1 treatment: Young C57BL/6 mice (n=15), aged 7 weeks, received twice daily (BID) oral (PO) treatment of Compound 1, 30 mg/kg, for 18 days, with only 1 injection on the last day for a total of 35 injections.

Treatment Group 2a, Vehicle treatment with rmCCL11: Young C57BL/6 mice (n=15), aged 7 weeks, received twice daily (BID) oral (PO) treatment of vehicle solution for 18 days, with only 1 injection on the last day for a total of 35 injections. Mice concurrently received peripheral injections (IP) of rmCCL11 starting on day 1 of treatment, every 3 days, for a total of 5 injections.

Treatment Group 2b, Compound 1 treatment with rmCCL11: Young C57BL/6 mice (n=15), aged 7 weeks, received twice daily (BID) oral (PO) treatment of Compound 1, 30 mg/kg, for 18 days, with only 1 injection on the last day for a total of 35 injections. Mice concurrently received peripheral injections (IP) of rmCCL11 starting on day 1 of treatment, every 3 days, for a total of 5 injections.

Recombinant mouse CCL11 ("rmE") treatment significantly worsened anxiety in the Open Field, but 2 weeks of treatment with Compound 1 twice daily orally improved anxiety (see FIG. 9). rmCCL11 impaired memory in the Y-maze; however, mice treated with Compound 1 were no longer significantly different from control mice (see FIG. 10). rmCCL11 also impaired memory in the Barnes maze, and treatment with Compound 1 significantly improved memory performance (see FIG. 11). Thus, rmE worsened both anxiety via the Open Field test and memory as evidenced by performance measured in the Y-Maze and Barnes Maze tests. However, Compound 1 treatment was able to attenuate these effects.

Fourth Experimental Group (See FIG. 12):

23-month-old C57Bl/6 mice were dosed with either vehicle control or Compound 1 by oral gavage twice daily for 19 days. After 11 days of treatment, mice were subjected to Y maze testing.

Drug Formulation:

Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:

Treatment Group 1, Vehicle treatment: Aged C57Bl/6 mice (n=8), aged 23 months, received twice daily (BID) oral gavage (PO) treatment of vehicle solution for 19 days.

Treatment Group 2, Compound 1 treatment: Aged C57Bl/6 mice (n=11), aged 23 months, received twice daily (BID) oral gavage (PO) treatment of Compound 1, 30 mg/kg, for 19 days.

Compound 1 treatment significantly improved memory in the Y-maze. Mice treated with Compound 1 exhibited intact memory for the novel arm in the number of visits (FIG. 12A). Treatment with Compound 1 also significantly increased the distance travelled of mice during the test (FIG. 12B).

Fifth Experimental Group (See FIGS. 13-17):

23-month-old C57Bl/6 mice were dosed with either vehicle control or Compound 1 subcutaneously twice daily for 21 days. Three weeks later, mice were subjected to behavior testing, and sacrificed the day following the last behavior test.

Drug Formulation:

Compound 1 was formulated in 40% HP-β-cyclodextrin and adjusted to pH 6.5 with NaOH (1M). Vehicle solution was formulated and adjusted for pH similarly. Kolliphor was added to each solution at 10% every week and stored at 4° C.

Treatment Groups:

Treatment Group 1b, Vehicle treatment: Aged C57Bl/6 mice (n=9), aged 23 months, received twice daily (BID) subcutaneous (SQ) treatment of vehicle solution for 21 days.

Treatment Group 4, Compound 1 treatment: Aged C57Bl/6 mice (n=17), aged 23 months, received twice daily (BID) subcutaneous (SQ) treatment of Compound 1, 30 mg/kg, for 21 days.

Compound 1 treatment significantly improved memory in the Y-maze and the Barnes Maze. Mice treated with Compound 1 exhibited intact memory for the novel arm in both the number of visits (FIGS. 13A-B) and in the duration of time spent in the novel arm (FIGS. 13C-D). Treatment with Compound 1 also significantly increased the velocity of mice during the test (FIG. 13E). Mice treated with Compound 1 performed significantly better on the Barnes Maze for spatial memory (FIG. 14A) and also exhibited increased velocity during the test (FIG. 14B). Locomotor activity was also improved in the Open Field, where there were strong trends towards improvement in both distance travelled and velocity (FIGS. 15A and 15B, respectively).

Levels of inflammatory cytokines were measured by Luminex assay from the plasma of mice (FIG. 16). There were strong trends in decrease in several inflammatory markers, including TNFa, IL6, IL1beta, IL5, and IL17. Activated microglia was also quantified by IHC staining in the hippocampus of mice (FIG. 17). Compound 1 treatment resulted in a strong trend towards decreased microgliosis.

Sixth Experimental Group (See FIG. 18):

23-month-old C57Bl/6 mice were dosed with either vehicle control or Compound 1 subcutaneously twice daily for 30 days, and then sacrificed on the day of the last injection.

Drug Formulation:

Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:

Treatment Group 1a, Vehicle treatment: Aged C57Bl/6 mice (n=9), aged 23 months, received twice daily (BID) subcutaneous (SQ) treatment of vehicle solution for 30 days.

Treatment Group 3, Compound 1 treatment: Aged C57Bl/6 mice (n=18), aged 23 months, received twice daily (BID) subcutaneous (SQ) treatment of Compound 1, 30 mg/kg, for 30 days.

Compound 1 treatment resulted in a strong trend towards decreased blood eosinophils in the blood by FACS analysis in a subset of animals (n=2, 5) (FIG. 18).

Seventh Experimental Group (See FIG. 19):

3-month-old hairless mice were treated with oxazolone (Ox) every other day and treated with control saline or 30 mg/kg Compound 1 for 2 weeks BID, PO.

Drug Formulation:

Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:

Treatment Group 1, Vehicle treatment: 3-month-old Hairless mice (n=3) received twice daily (BID) oral gavage (PO) treatment of vehicle solution for 2 weeks.

Treatment Group 2, Vehicle treatment and Oxazolone treatment: 3-month-old Hairless mice (n=6) received twice daily (BID) oral gavage (PO) treatment of vehicle solution for 2 weeks.

Treatment Group 3, Compound 1 treatment and Oxazolone treatment: 3-month-old Hairless mice (n=6) received twice daily (BID) oral gavage (PO) treatment of Compound 1, 30 mg/kg, for 2 weeks.

Compound 1 decreased the oxazolone-induced increase in blood eosinophils by complete blood count (CBC) analysis. N=3, 6, 8. *p<0.05, **p<0.01. Compound 1 dramatically reduced numbers of blood eosinophils in an oxazolone-induced model of eosinophilia (FIG. 19). This shows that inhibition of CCR3 can be sufficient to decrease eosinophil levels and function especially in diseased states, demonstrating a second mechanism (in addition to decreased brain inflammation) by which Compound 1 can be effective in treating neuronal loss and associated motor and cognitive deficits.

Eighth Experimental Group (See FIGS. 20-22):

Twenty-four-month-old C57 mice were treated for 4 weeks with continuous infusion of Compound 1 or vehicle by Alzet osmotic pump, which were implanted to continuously deliver the two treatments.

Drug Formulation:

Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:

Treatment Group 1, Old Controls: Aged C57BL/6 mice (n=15), aged 23 months, received infusion of vehicle by Alzet mini-pump, model 2002 (0.5 uL/hr), for four weeks with one replacement.

Treatment Group 2, Compound 1 (dose 2) in Old: Aged C57BL/6 mice (n=15), aged 23 months, received infusion of ~50 mg/ml Compound 1 by Alzet mini-pump, model 2002 (0.5 uL/hr), for four weeks with one replacement.

The mice were tested in the Rotarod for motor coordination. Success or failure was recorded on the last trial, with success defined by a latency to fall of >90 seconds. Compound 1-treated mice succeeded more than vehicle-treated mice by binomial test. N=15 each, *p<0.05. A greater proportion of mice treated with Compound 1, 47%, were able to stay on the rod for longer than 90 seconds, a threshold where only 20% of control-treated mice could stay on after 3 successive trials (FIG. 20). These results suggest that there is a consistent effect of Compound 1 on motor function in models of eotaxin elevation.

Mice were tested in the T maze for cognitive function (FIG. 21). The number of successes or failures to turn down the correct arm was recorded. Compound 1-treated mice succeeded more than vehicle-treated mice by binomial test. *p<0.05.

Fecal output was measured by weighing the dry weight of fecal pellets overnight (FIG. 22). Gastric function is a well-known symptom of Parkinson's disease. Water and food intake were measured over the same time period. Mice treated with Compound 1 had significantly lower fecal output compared to control mice. They also had significantly higher water intake overnight compared to control mice. *p<0.05. These results indicate that deficits in gastric function may be altered by Compound 1 treatment.

Ninth Experimental Group (See FIG. 23):

Three-month-old C57 mice were given one dose of lipopolysaccharide (LPS) 10 mg/kg IP to induce inflammation and treated with Compound 1 for 18 days.

Drug Formulation:

Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:
Treatment Group 1, Vehicle treatment: Young C57BL/6 mice (n=15), aged 3 months, received a single injection of LPS and were treated with vehicle, BID, for 18 days by oral gavage.
Treatment Group 2, Compound 1 treatment: Young C57BL/6 mice (n=15), aged 3 months, received a single injection of LPS and were treated with Compound 1, 30 mg/kg, BID, for 18 days by oral gavage.

Brain sections were immunostained for detection of CD68+ activated microglia. Compound 1-treated mice exhibited significantly decreased CD68+ immunoreactivity (decreased activated microglia) in contrast to vehicle (saline)-treated mice (FIG. 23). N=9, 10, 8. *p<0.05 by one-way ANOVA.

These data indicate a potent anti-neuroinflammatory effect of Compound 1, with therapeutic potential for reducing neuroinflammation-induced toxicity to neurons in diseases exhibiting neurodegeneration or cognitive or motor decline.

Tenth Experimental Group (See FIG. 24-29):
Three-month-old C57 mice were given daily doses of lipopolysaccharide (LPS) 0.5 mg/kg IP to induce inflammation and treated with Compound 1 for up to 4 weeks.

Drug Formulation:
Compound 1 was formulated in 40% HP-β-cyclodextrin, and adjusted to pH 6.5 with NaOH (1M). Vehicle solution was formulated and adjusted for pH similarly. Kolliphor was added to each solution at 10% every week and stored at 4° C.

Treatment Groups:
Treatment Group 1, Vehicle treatment: 3-month-old C57 mice (n=10) received daily IP injection of LPS for 7 weeks and twice daily (BID) oral gavage (PO) treatment of vehicle solution for up to 4 weeks.
Treatment Group 2, Vehicle treatment and Oxazolone treatment: 3-month-old C57 mice (n=10) received daily IP injection of LPS for 7 weeks and twice daily (BID) oral gavage (PO) treatment of vehicle solution for up to 4 weeks.
Treatment Group 3, Compound 1 treatment and Oxazolone treatment: 3-month-old C57 mice (n=9) received daily IP injection of LPS for 7 weeks and twice daily (BID) oral gavage (PO) treatment of Compound 1, 30 mg/kg, for up to 4 weeks.

FIG. 24A describes the dosing paradigm for the tenth experimental group. The section of the paradigm highlighted by the square represents the time points at which the assay in FIG. 24B was performed. Anxiety was tested in the Open Field test after 1 week of Compound 1 treatment (FIG. 24B). LPS treatment significantly increased anxiety in the Open Field, and Compound 1 strongly decreased the increased anxiety, *p<0.05.

FIG. 25A describes the dosing paradigm for the tenth experimental group. The section of the paradigm highlighted by the square represents the time points at which the assay in FIG. 25B was performed. Cognition was tested in the Y maze after 3 weeks of Compound 1 treatment (FIG. 25B). Mice treated with LPS did not show a significant preference for the novel arm. However, mice treated with Compound 1 showed a significant preference for the novel arm, similar to vehicle treated mice, *p<0.05, **p<0.01.

FIG. 26A describes the dosing paradigm for the tenth experimental group. The section of the paradigm highlighted by the square represents the time points at which the assay in FIG. 26B was performed. mRNA levels of the inflammatory cytokine IL-1beta were measured by quantitative PCR 4 weeks after Compound 1 treatment (FIG. 26B). LPS treated mice showed a trend towards increased levels of IL-1beta, and mice treated with Compound 1 showed a significant decrease in IL-1beta expression, *p<0.05.

FIG. 27A describes the dosing paradigm for the tenth experimental group. The section of the paradigm highlighted by the square represents the time points at which the assay in FIG. 27B was performed. Brain sections were immunostained for detection of CD68+ activated microglia. Compound 1-treated mice exhibited dramatically decreased CD68+ immunoreactivity (decreased activated microglia) in contrast to LPS-only-treated mice (FIG. 27B).

FIG. 28A describes the dosing paradigm for the tenth experimental group. The section of the paradigm highlighted by the square represents the time points at which the assay in FIG. 28B was performed. Brain sections were immunostained for detection of Iba1-positive microglia. Compound 1-treated mice exhibited dramatically decreased Iba1+ immunoreactivity (decreased total microglia) in contrast to LPS-only-treated mice (FIG. 28B).

FIG. 29A describes the dosing paradigm for the tenth experimental group. The section of the paradigm highlighted by the square represents the time points at which the assay in FIG. 29B was performed. Brain sections were immunostained for detection of GFAP-positive astroglia. Compound 1-treated mice exhibited dramatically decreased GFAP+ immunoreactivity (decreased total astrocytes) in contrast to LPS-only-treated mice (FIG. 29B).

These data indicate a potent anti-neuroinflammatory effect of Compound 1, with therapeutic potential for reducing neuroinflammation-induced toxicity to neurons in diseases exhibiting neurodegeneration or cognitive or motor decline.

3. Mouse MPTP Model of Parkinson's Disease

A mouse model using MPTP (1-methyl-4-phenyl-1,2,3,6-tetrahydropyridine) is used to determine the level of alleviation of MPTP-induced Parkinsonian deficits. MPTP is a prodrug of MPP+, which can cause permanent Parkinson's symptoms. MPP+ works by killing dopaminergic neurons in the brain's substantia nigra region.

Eight-week-old male C57Bl/6J mice receive either vehicle (saline) or 20 mg/kg MPTP twice per day (BID) at 3-hour intervals for two consecutive days, on Days 1 and 2. On Day 3, mice receive either vehicle or 30 mg/kg Compound 1 twice per day by oral gavage and continue to receive BID PO dosing of Compound 1 through Day 12 (study timeline, FIG. 30A). On Day 10, mice are tested for motor function on the Rotarod, and on Day 11, mice are tested in the Motorater test for kinematic gait analysis of motor coordination (Tse Systems, Inc., Chesterfield, Mo.). Mice are sacrificed on Day 12. Thirty (30) mg/kg is a sufficient dose to achieve >100 nM concentration of Compound 1 for 8 hours (FIG. 8) and the $IC_{50}$ for the CCR3 receptor internalization biomarker assay is <100 nM; this dosing paradigm is used successfully in studies in aged mice. An n of 14 animals are used for each group. These numbers are based on prior experience which observed an effect >20% at a significance value of p<0.05. All results are analyzed by one-way ANOVA to determine: 1) statistical difference between the control group and MPTP group treated with vehicle and 2) statistical difference between MPTP groups treated with vehicle and Compound 1. FIG. 30B summarizes the behavioral, biochemical, and histological endpoints from this study.

4. Synuclein Transgenic Mouse Model of Parkinson's Disease

A synuclein transgenic mouse model is used to determine the effects of chronic CCR3 inhibition by Compound 1 and its ability to slow, halt, or reverse the progression of Parkinson's-like symptoms. Thus, this model which over-expresses human α-synuclein tests whether Compound 1 prevents α-synuclein-induced behavioral and pathological effects. To select an optimal model for testing, plasma eotaxin levels were measured as a biomarker in multiple synuclein mouse models at different ages. The models included A53T, DxJ9M, and Line 61. Plasma from 6-month-old Line 61 synuclein transgenic mice were measured by ELISA assay to detect plasma eotaxin levels as a biomarker. Line 61 mice (QPS Neuro, Grambach, Austria) at 6 months of age exhibited a transgene-induced increase in eotaxin levels (FIG. 31), showing that plasma eotaxin levels can serve as an appropriate clinical biomarker to select treatment populations.

Non-transgenic controls are treated with vehicle and transgenic mice treated with vehicle or Compound 1 in drinking water for 6 weeks. Non-transgenic controls can instead be treated with vehicle BID PO and transgenic mice treated with Compound 1 BID PO. An n of 15 animals per group gives statistical significance at p<0.05 with an effect size of 20% based on previous experimentation. During Week 7, mice undergo behavioral testing and are sacrificed at the conclusion of testing when they are 6 months of age. All results are analyzed by one-way ANOVA to determine 1) statistical difference between the non-transgenic and transgenic group treated with vehicle and 2) statistical difference between transgenic groups treated with vehicle and Compound 1. FIG. 32 summarizes behavioral, biochemical, and histological endpoints.

d. Examples in Humans

1. Eotaxin Levels and Aging

Levels of human eotaxin-1 were determined using a commercially-available affinity-based assay (SOMAscan, SomaLogic, Inc., Boulder, Colo.). Blood plasma samples were collected from 18, 30, 45, 55, and 66-year-old donors and for testing by SomaLogic using a SOMAscan aptamer-based affinity assay that tested, among other things, for relative levels of human eotaxin-1. Eotaxin-1 levels were determined and plotted by age group (FIG. 33). Eotaxin-1 relative concentrations increased with age, indicating that the eotaxin-1 pathway, including its primary receptor, CCR3, is a target to treat aging-associated disease such as neurodegenerative disease and cognitive decline.

2. Human Biomarker Assays

Whole blood from humans treated with Compound 1 was incubated with human recombinant eotaxin-1 to trigger eosinophil shape change (FIG. 34A) or CCR3 receptor internalization (FIG. 34B). Both assays showed a robust concentration-dependent effect of Compound 1 on the respective functional biomarker readouts.

Together, the results obtained from the ESC and CCR3 receptor internalization assays confirm Compound 1 acts as an inhibitor of the human eotaxin-1 pathway. In particular, Compound 1 can act as a potent inhibitor of CCR3 by binding to that receptor.

Notwithstanding the appended clauses, the disclosure set forth herein is also defined by the following clauses:

1. A method of treating neurodegenerative disease in a subject diagnosed with the neurodegenerative disease, the method comprising administering a therapeutically effective amount of a compound of formula 1,

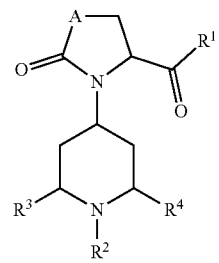

wherein
A is $CH_2$, O or N—$C_{1-6}$-alkyl;
$R^1$ is selected from
  $NHR^{1.1}$, $NMeR^{1.1}$;
  $NHR^{1.2}$, $NMeR^{1.2}$;
  $NHCH_2$—$R^{1.3}$;
  NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl;
  a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, methoxy-phenyl;
  a group selected from $NHCH(pyridinyl)CH_2COO$—$C_{1-6}$-alkyl, $NHCH(CH_2O$—$C_{1-6}$-alkyl)-benzoimidazolyl, optionally substituted with halogen or CN;
  or 1-aminocyclopentyl, optionally substituted with methyl-oxadiazole;
$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}$-alkyl)$_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2$ $CON(C_{1-4}$-alkyl)$_2$)O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl)$_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;
$R^{1.1.1}$ H, $C_{1-6}$-alkyl, $C_{3-6}$-cycloalkyl, $C_{1-6}$-haloalkyl, $CH_2CON(C_{1-6}$-alkyl)$_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;
$R^{1.1.2}$ H, $C_{1-6}$-alkyl, $SO_2C_{1-6}$-alkyl;
or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, $COO$—$C_{1-6}$-alkyl, $CONH_2$, $O$—$C_{1-6}$-alkyl, halogen, CN, $SO_2N(C_{1-6}$-alkyl$)_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

a aromatic or non-aromatic $C_{9\ or\ 10}$-bicyclic-ring, whereas one or two carbon atoms are replaced by N, O or S each optionally substituted with one or two residues selected from the group consisting of $N(C_{1-6}$-alkyl$)_2$, $CONH$—$C_{1-6}$-alkyl, =O;

a heterocyclic non-aromatic ring, optionally substituted with pyridinyl;

4,5-dihydro-naphtho[2,1-d]thiazole, optionally substituted with $NHCO$—$C_{1-6}$-alkyl, $R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, $O$—$C_{1-6}$-alkyl, $O$—$C_{1-6}$-haloalkyl, phenyl, heteroaryl;

$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, $O$—$C_{1-6}$-alkyl, $O$—$C_{1-6}$-haloalkyl, halogen;

$R^3$ is H, $C_{1-6}$-alkyl;

$R^4$ is H, $C_{1-6}$-alkyl;

or $R^3$ and $R^4$ together are forming a $CH_2$—$CH_2$ group;

to treat the subject for the neurodegenerative disease.

2. The method of clause 1 wherein the neurodegenerative disease is from the group consisting of Alzheimer's disease, Parkinson's disease, frontotemporal dementia, Huntington's disease, amyotrophic lateral sclerosis, multiple sclerosis, glaucoma, myotonic dystrophy, vascular dementia, progressive supranuclear palsy.

3. The method of clause 1 or 2 wherein the compound of formula 1,

A is $CH_2$, O or $N$—$C_{1-4}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

$NH$—$C_{3-6}$-cycloalkyl, whereas optionally one carbon atom is replaced by a nitrogen atom, whereas the ring is optionally substituted with one or two residues selected from the group consisting of $C_{1-6}$-alkyl, $O$—$C_{1-6}$-alkyl, $NHSO_2$-phenyl, $NHCONH$-phenyl, halogen, CN, $SO_2$—$C_{1-6}$-alkyl, $COO$—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, $COO$—$C_{1-6}$-alkyl, $C_{1-6}$-haloalkyl, $O$—$C_{1-6}$-alkyl, $NO_2$, halogen, CN, $NHSO_2$—$C_{1-6}$-alkyl, m-methoxyphenyl;

a group selected from $NHCH(pyridinyl)CH_2COO$—$C_{1-6}$-alkyl, $NHCH(CH_2O$—$C_{1-6}$-alkyl)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-6}$-alkyl, $C_{1-6}$-haloalkyl, $CH_2CON(C_{1-6}$-alkyl$)_2$, $CH_2NHCONH$—$C_{3-6}$-cycloalkyl, CN, $CONR^{1.1.1}R^{1.1.2}$, $COO$—$C_{1-6}$-alkyl, $O$—$C_{1-6}$-alkyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}$-alkyl$)_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}$-alkyl$)_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from heteroaryl, optionally substituted with one or two residues selected from the group consisting of $C_{1-6}$-alkyl, $C_{3-6}$-cycloalkyl, $CH_2COO$—$C_{1-6}$-alkyl, $CONR^{1.2.1}R^{1.2.2}$, $COO$—$C_{1-6}$-alkyl, $CONH_2$, $O$—$C_{1-6}$-alkyl, halogen, CN, CO-pyrrolidinyl, CO-morpholinyl or heteroaryl optionally substituted with one or two residues selected from the group consisting of $C_{1-6}$-alkyl;

benzothiazolyl, indazolyl, dihydro-indolyl, indanyl, tetrahydro-quinolinyl, each optionally substituted with one or two residues selected from the group consisting of $N(C_{1-6}$-alkyl$)_2$, $CONH$—$C_{1-6}$-alkyl, =O;

piperidinyl, optionally substituted with pyridinyl;

4,5-dihydro-naphtho[2,1-d]thiazole, optionally substituted with $NHCO$—$C_{1-6}$-alkyl, $R^{1.2.1}$ H, $C_{1-6}$-alkyl;

$R^{1.2.2}$ H, $C_{1-6}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl;

$R^2$ is selected from $CH_2$-phenyl or $CH_2$-naphthyl, both optionally substituted with one or two residues selected from the group consisting of $C_{1-6}$-alkyl, $C_{1-6}$-haloalkyl, O—$C_{1-6}$-alkyl, O—$C_{1-6}$-haloalkyl, halogen; or $CH_2$-thiophenyl, optionally substituted with one or two residues selected from the group consisting of halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

4. The method of clause 1 or 2 wherein the compound of formula 1 is

A is $CH_2$, O or NMe;

$R^1$ is selected from
  $NHR^{1.1}$, $NMeR^{1.1}$;
  $NHR^{1.2}$, $NMeR^{1.2}$;
  $NHCH_2$—$R^{1.3}$;
  NH-cyclohexyl, optionally substituted with one or two residues selected from the group consisting of $C_{1-4}$-alkyl, $NHSO_2$-phenyl, NHCONH-phenyl, halogen;
  NH-pyrrolidinyl, optionally substituted with one or two residues selected from the group consisting of $SO_2$—$C_{1-4}$-alkyl, COO—$C_{1-4}$-alkyl;
  piperidinyl, optionally substituted with one or two residues selected from the group consisting of $NHSO_2$—$C_{1-4}$-alkyl, m-methoxyphenyl;
  dihydro-indolyl, dihydro-isoindolyl, tetrahydro-quinolinyl or tetrahydro-isoquinolinyl, optionally substituted with one or two residues selected from the group consisting of $C_{1-4}$-alkyl, COO—$C_{1-4}$-alkyl, $C_{1-4}$-haloalkyl, O—$C_{1-4}$-alkyl, $NO_2$, halogen;
  a group selected from NHCH(pyridinyl)$CH_2$COO—$C_{1-4}$-alkyl, NHCH($CH_2$O—$C_{1-4}$-alkyl)-benzoimidazolyl, optionally substituted with Cl;
  or 1-aminocyclopentyl, optionally substituted with methyl-oxadiazolyl;

$R^{1.1}$ is phenyl, optionally substituted with one or two residues selected from the group consisting of $C_{1-4}$-alkyl, $C_{1-4}$-haloalkyl, $CH_2CON(C_{1-4}$-alkyl)$_2$, $CH_2NHCONH$—$C_{3-6}$-cycloalkyl, CN, $CONR^{1.1.1}R^{1.1.2}$, COO—$C_{1-4}$-alkyl, O—$C_{1-4}$-alkyl, $SO_2$—$C_{1-4}$-alkyl, $SO_2$—$C_{1-4}$-alkylen-OH, $SO_2$—$C_{3-6}$-cycloalkyl, $SO_2$-piperidinyl, $SO_2NH$—$C_{1-4}$-alkyl, $SO_2N(C_{1-4}$-alkyl)$_2$, halogen, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of $C_{1-4}$-alkyl, $NHC_{1-4}$-alkyl, =O;

$R^{1.1.1}$ H, $C_{1-6}$-alkyl, $C_{3-6}$-cycloalkyl, $C_{1-4}$-haloalkyl, $CH_2CON(C_{1-4}$-alkyl)$_2$, $CH_2$CO-azetindinyl, $C_{1-4}$-alkylen-$C_{3-6}$-cycloalkyl, $CH_2$-pyranyl, $CH_2$-tetrahydrofuranyl, $CH_2$-furanyl, $C_{1-4}$-alkylen-OH or thiadiazolyl, optionally substituted with $C_{1-4}$-alkyl;

$R^{1.1.2}$ H, $C_{1-4}$-alkyl, $SO_2C_{1-4}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2$OH $R^{1.2}$ is selected from
  pyridinyl, pyridazinyl, pyrrolyl, pyrazolyl, isoxazolyl, thiazolyl, thiadiazolyl, optionally substituted with one or two residues selected from the group consisting of $C_{1-4}$-alkyl, $C_{3-6}$-cycloalkyl, $CH_2$COO—$C_{1-4}$-alkyl, $CONR^{1.2.1}R^{1.2.2}$, COO—$C_{1-4}$-alkyl, $CONH_2$, O—$C_{1-4}$-alkyl, halogen, CO-pyrrolidinyl, CO-morpholinyl or pyrazolyl, triazolyl, tetrazolyl, isoxazolyl, oxadiazolyl, each optionally substituted with one or two residues selected from the group consisting of $C_{1-4}$-alkyl;
  benzothiazolyl, indazolyl, dihydro-indolyl, indanyl, tetrahydro-quinolinyl, each optionally substituted with one or two residues selected from the group consisting of $N(C_{1-4}$-alkyl)$_2$, CONH—$C_{1-4}$-alkyl, =O;
  piperidinyl, optionally substituted with pyridinyl;
  4,5-dihydro-naphtho[2,1-d]thiazole, optionally substituted with NHCO—$C_{1-4}$-alkyl, $R^{1.2.1}$ H, $C_{1-4}$-alkyl;

$R^{1.2.2}$ H, $C_{1-4}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-4}$-alkyl, $C_{3-6}$-cycloalkyl, O—$C_{1-4}$-alkyl, O—$C_{1-4}$-haloalkyl;

$R^2$ is selected from $CH_2$-phenyl or $CH_2$-naphthyl, both optionally substituted with one or two residues selected from the group consisting of $C_{1-4}$-alkyl, $C_{1-4}$-haloalkyl, O—$C_{1-4}$-haloalkyl, halogen; or $CH_2$-thiophenyl, optionally substituted with one or two residues selected from the group consisting of halogen;

$R^3$ is H;

$R^4$ is H;

or $R^3$ and $R^4$ together are forming a $CH_2$—$CH_2$ group.

5. The method of clause 1 or 2 wherein formula 1 is

A is $CH_2$, O or NMe;

$R^1$ is selected from
  $NHR^{1.1}$, $NMeR^{1.1}$;
  $NHR^{1.2}$, $NMeR^{1.2}$;
  $NHCH_2$—$R^{1.3}$;
  NH-piperidinyl, optionally substituted with pyridinyl;
  NH-cyclohexyl, optionally substituted with one or two residues selected from the group consisting of t-Bu, $NHSO_2$-phenyl, NHCONH-phenyl, F;
  NH-pyrrolidinyl, optionally substituted with one or two residues selected from the group consisting of $SO_2$Me, COO-t-Bu;
  piperidinyl, optionally substituted with one or two residues selected from the group consisting of $NHSO_2$-n-Bu, m-methoxyphenyl;
  dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br;
  a group selected from NHCH(pyridinyl)$CH_2$COOMe, NHCH($CH_2$OMe)-benzoimidazolyl, optionally substituted with Cl;
  or 1-aminocyclopentyl, optionally substituted with methyl-oxadiazolyl;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2$Me, $SO_2CH_2CH_2OH$, $SO_2$Et, $SO_2$-cyclopropyl, $SO_2$-piperidinyl, $SO_2$NHEt, $SO_2$NMeEt, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

R$^{1.1.1}$ H, Me, Et, t-Bu, i-Pr, cyclopropyl, CH$_2$-i-Pr, CH$_2$-t-Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ H, Me, Et, SO$_2$Me, SO$_2$Et or R$^{1.1.1}$ and R$^{1.1.2}$ together are forming a four-, five- or six-membered carbocyclic ring, optionally containing one O, replacing a carbon atom of the ring, optionally substituted with one or two residues selected from the group consisting of CH$_2$OH R$^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of NMe$_2$, CONHMe, =O;

4,5-dihydro-naphtho[2,1-d]thiazole, optionally substituted with NHCOMe,

R$^{1.2.1}$ H, Me;

R$^{1.2.2}$ H, Me;

R$^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, OCHF$_2$;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et; or CH$_2$-thiophenyl, optionally substituted with one or two residues selected from the group consisting of Cl, Br;

R$^3$ is H;

R$^4$ is H;

or R$^3$ and R$^4$ together are forming a CH$_2$—CH$_2$ group.

6. The method of clause 1 or 2 wherein formula 1 is

A is CH$_2$, O or NMe;

R$^1$ is selected from

NHR$^{1.1}$

NHR$^{1.2}$,

R$^{1.1}$ is phenyl, optionally substituted with one or two residues selected from the group consisting of Me, Et, Bu, CF$_3$, CH$_2$CONMe$_2$, CH$_2$NHCONH-cyclohexyl, CN, CONR$^{1.1.1}$R$^{1.1.2}$, COOMe, COOEt, OMe, SO$_2$Me, SO$_2$CH$_2$CH$_2$OH, SO$_2$Et, SO$_2$-cyclopropyl, SO$_2$-piperidinyl, SO$_2$NHEt, SO$_2$NMeEt, F, Cl, CO-morpholinyl, CH$_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

R$^{1.1.1}$ H, Me, Et, t-Bu, i-Pr, cyclopropyl, CH$_2$-i-Pr, CH$_2$-t-Bu, CH(CH$_3$)CH$_2$CH$_3$, CH$_2$CHF$_2$, CH$_2$CONMe$_2$, CH$_2$CO-azetindinyl, CH$_2$-cyclopropyl, CH$_2$-cyclobutyl, CH$_2$-pyranyl, CH$_2$-tetrahydrofuranyl, CH$_2$-furanyl, CH$_2$CH$_2$OH or thiadiazolyl, optionally substituted with Me;

R$^{1.1.2}$ H, Me, Et, SO$_2$Me, SO$_2$Et or R$^{1.1.1}$ and R$^{1.1.2}$ together are forming a four-, five- or six-membered carbocyclic ring, optionally containing one O, replacing a carbon atom of the ring, optionally substituted with one or two residues selected from the group consisting of CH$_2$OH R$^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, CH$_2$COOEt, CONR$^{1.2.1}$R$^{1.2.2}$, COOMe, COOEt, CONH$_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of NMe$_2$, CONHMe, =O;

4,5-dihydro-naphtho[2,1-d]thiazole, optionally substituted with NHCOMe,

R$^{1.2.1}$ H, Me;

R$^{1.2.2}$ H, Me;

R$^2$ is selected from CH$_2$-phenyl or CH$_2$-naphthyl, both optionally substituted with one or two residues selected from the group consisting of CH$_3$, CF$_3$, OCF$_3$, F, Cl, Br, Et R$^3$ is H;

R$^4$ is H.

7. The method of clause 1 or 2 wherein formula 1 is

A is CH$_2$, O or NMe;

R$^1$ is selected from

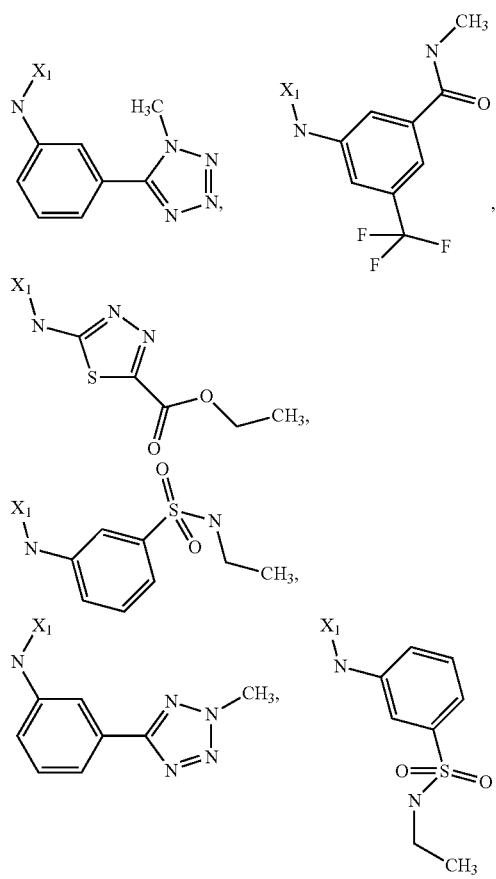

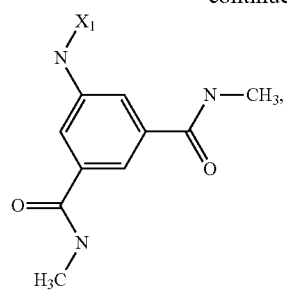
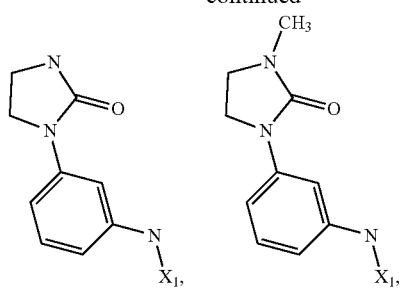
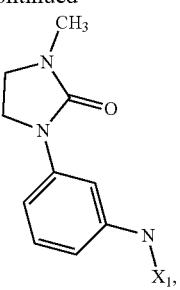
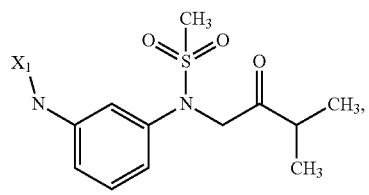
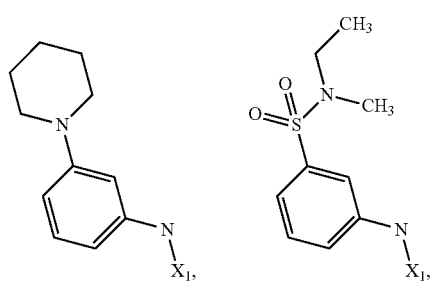
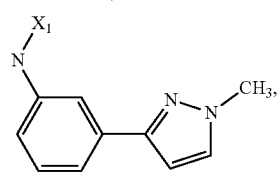
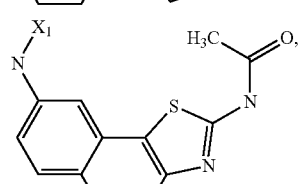
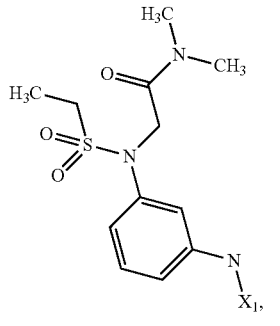
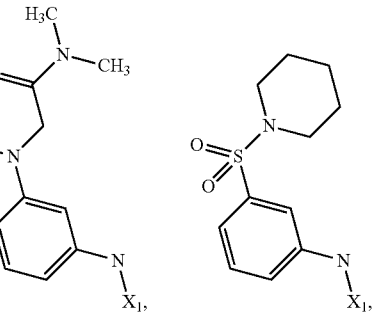
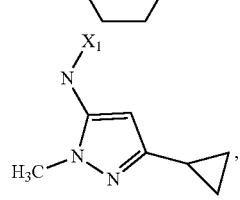
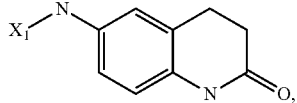
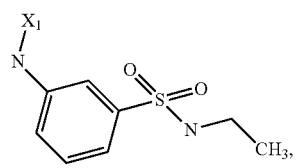
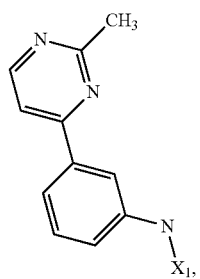
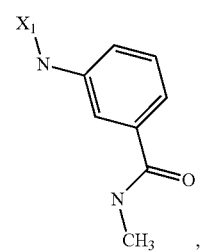
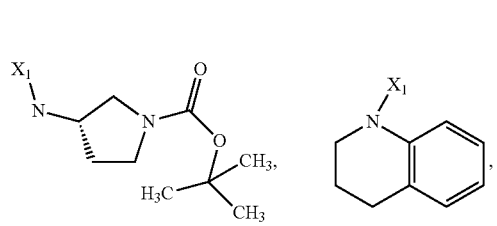
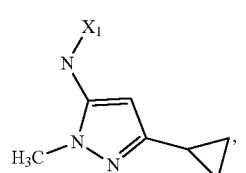
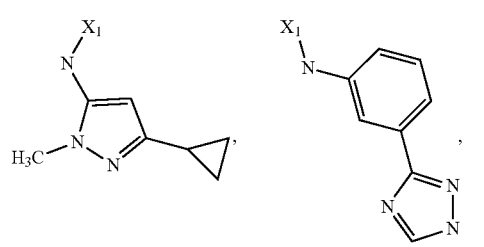
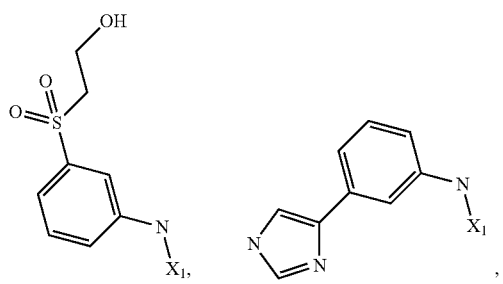

-continued
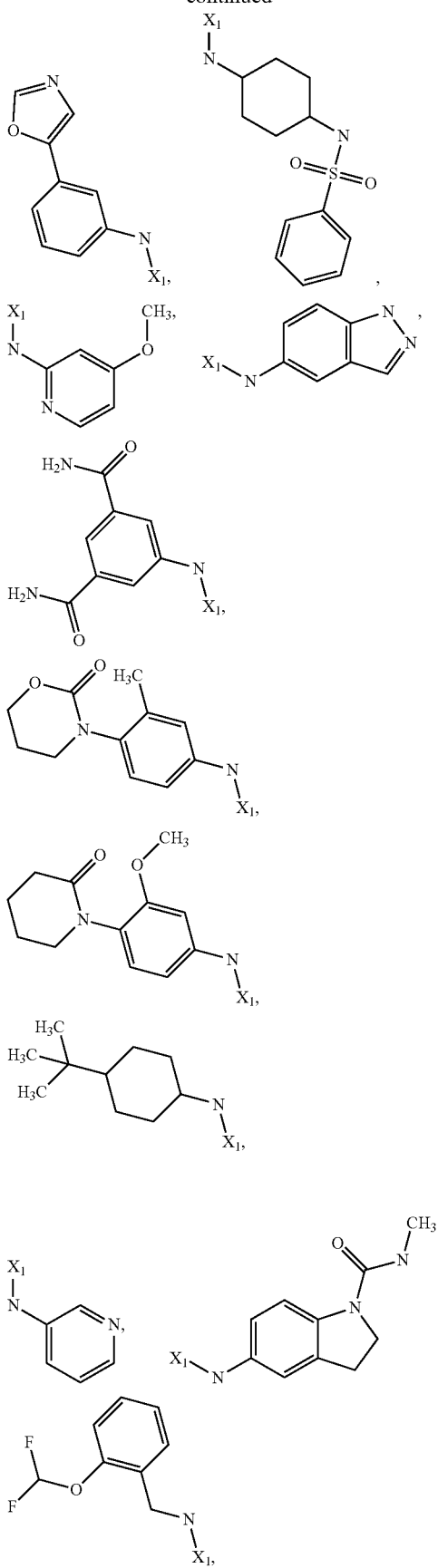
-continued
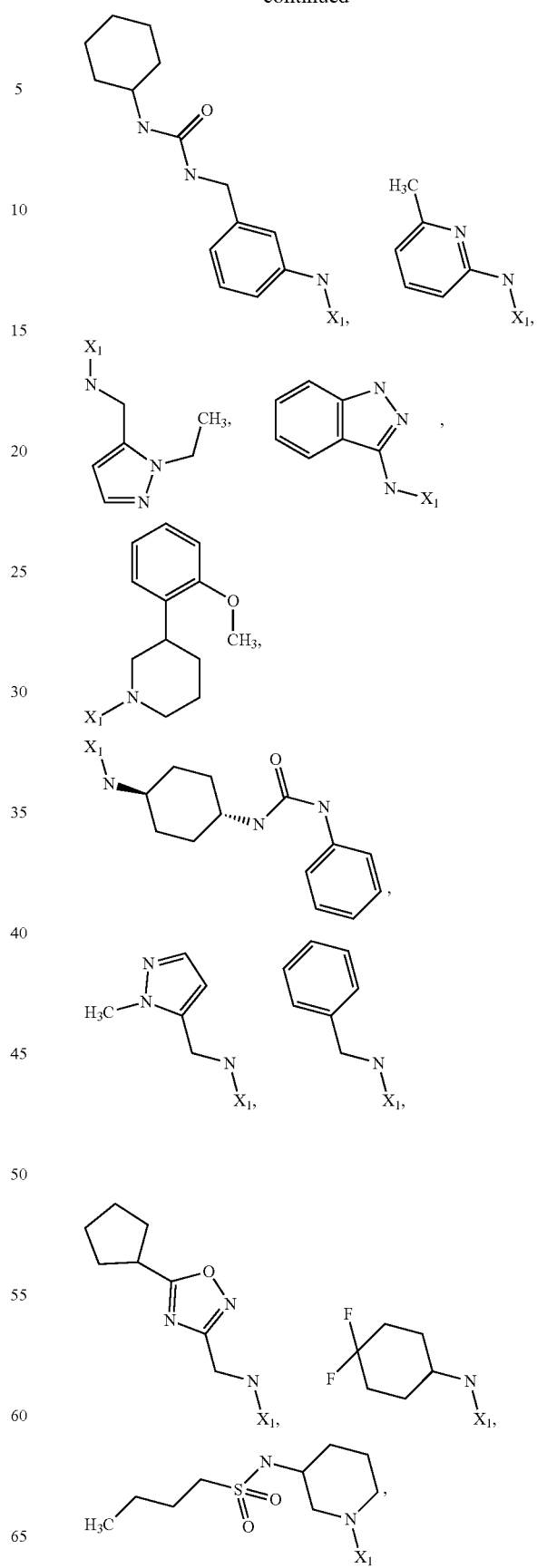

-continued
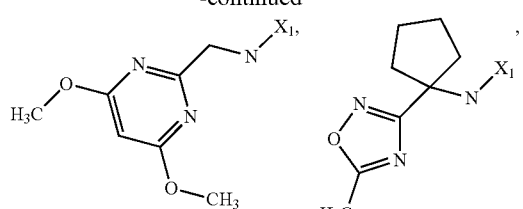
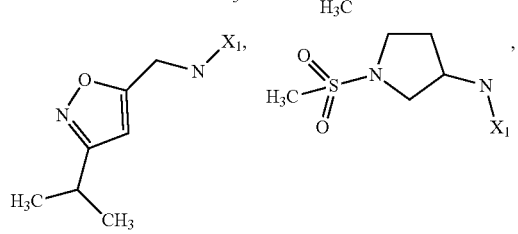
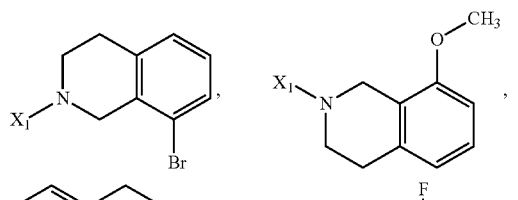
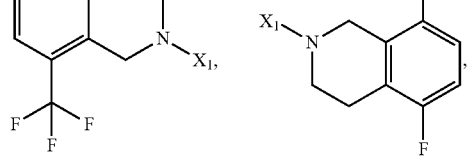
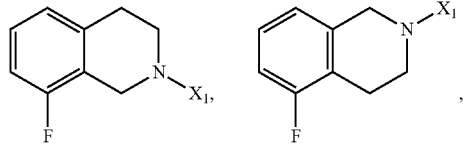
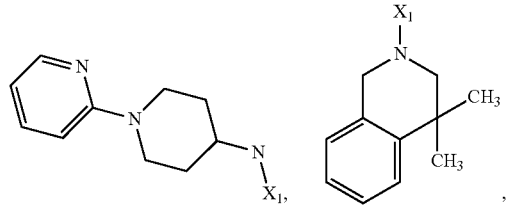
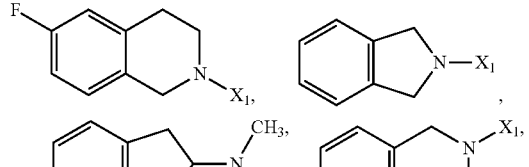
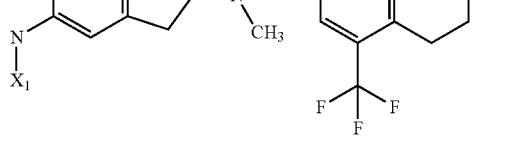
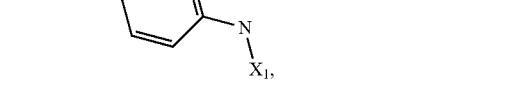
-continued
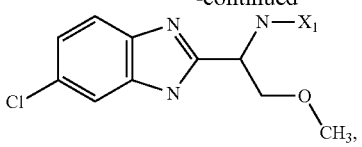
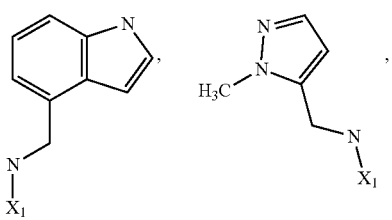
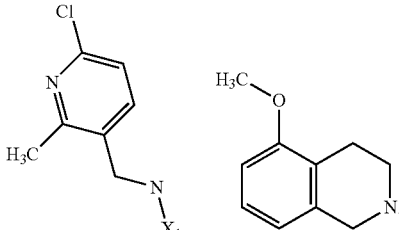
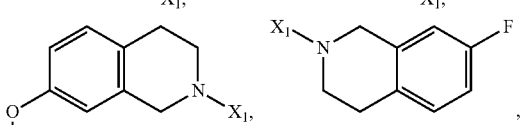
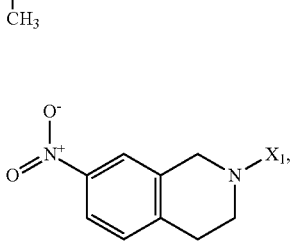
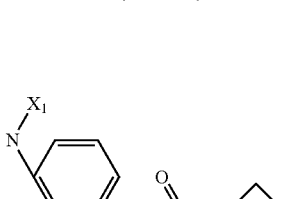
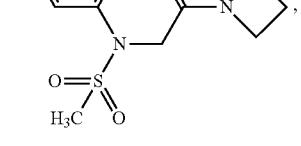
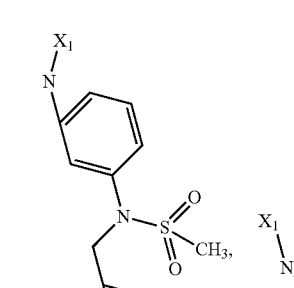
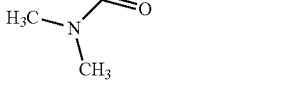
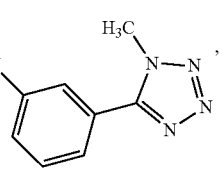

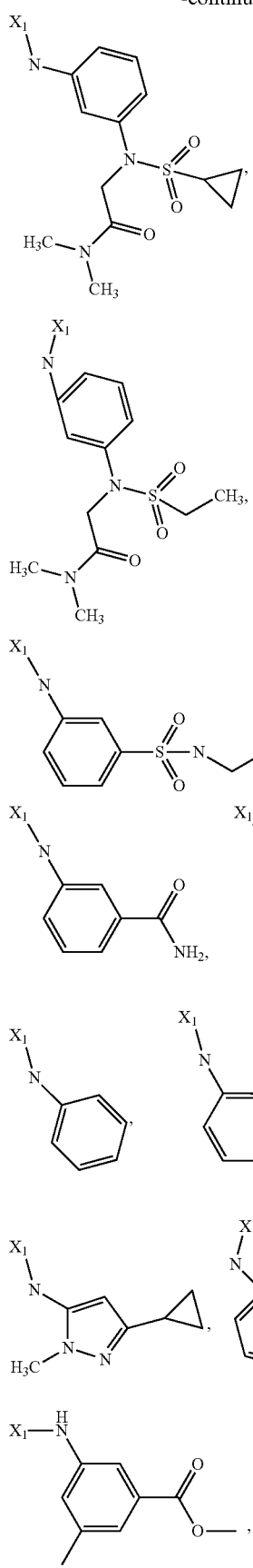
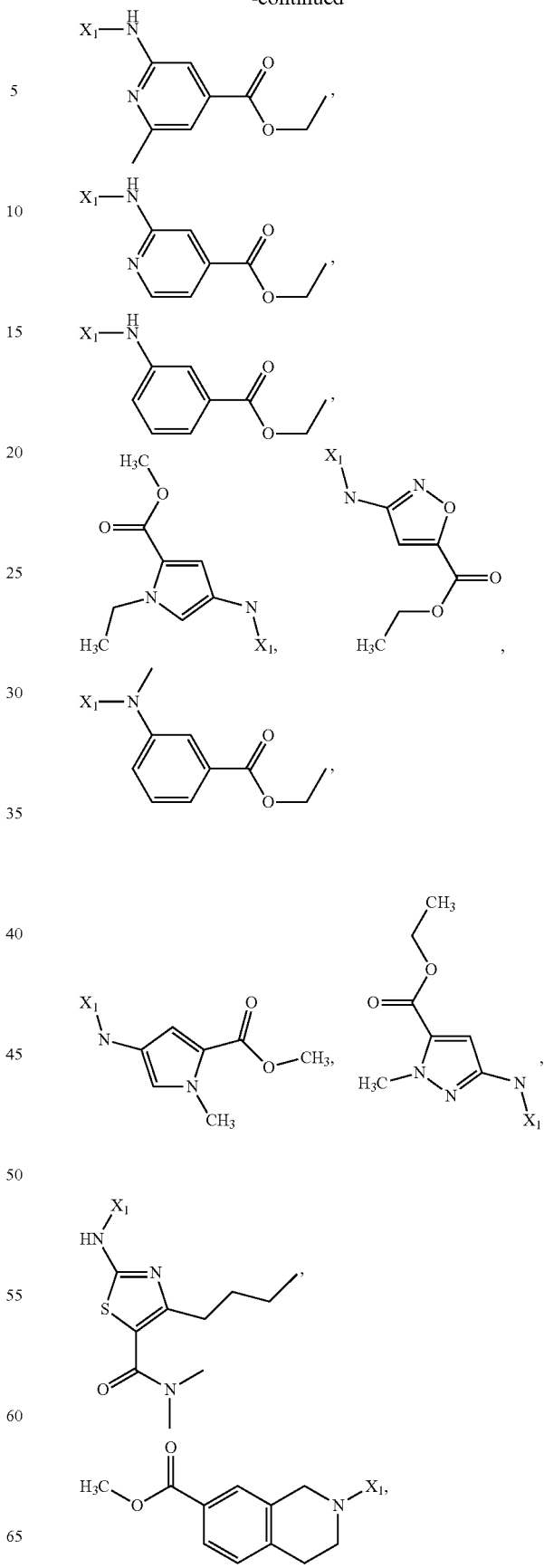

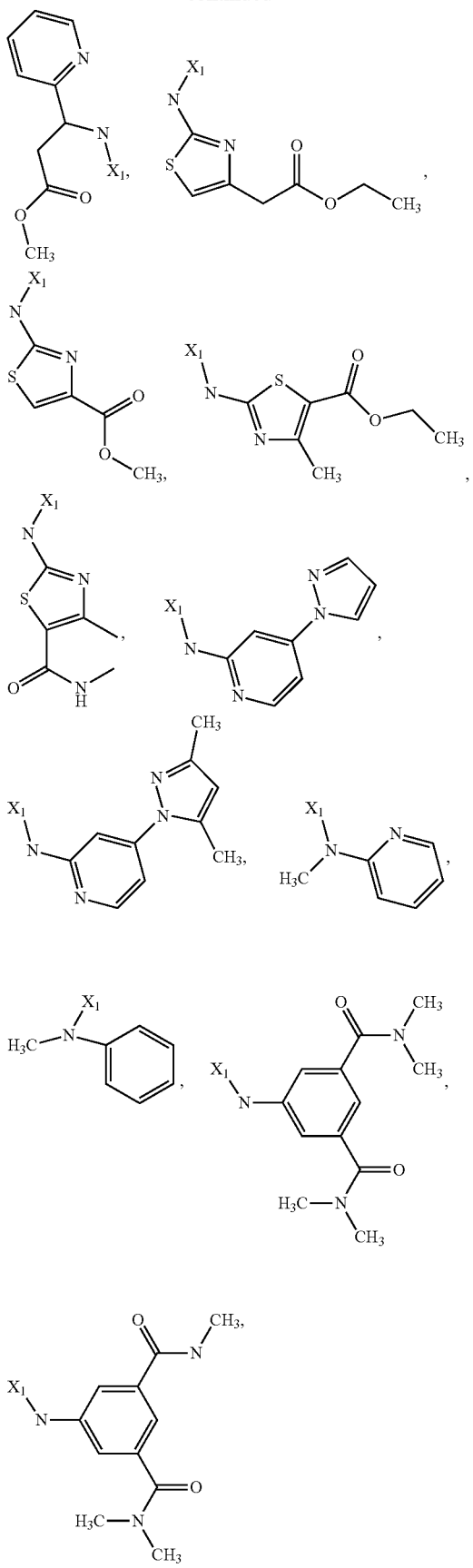
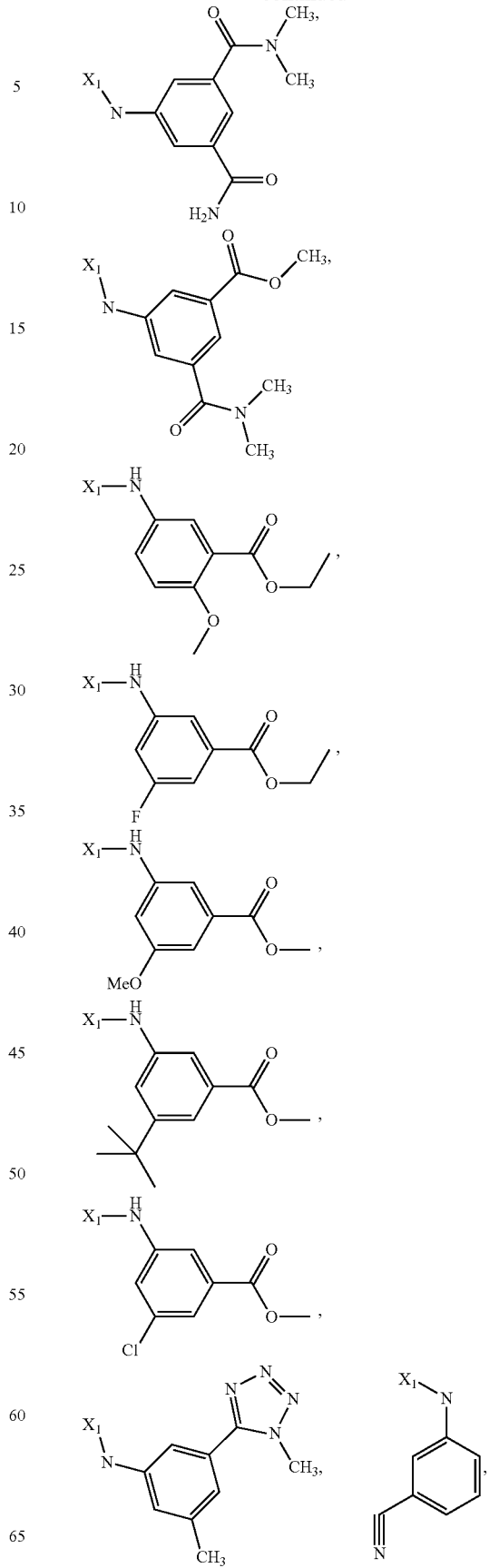

-continued
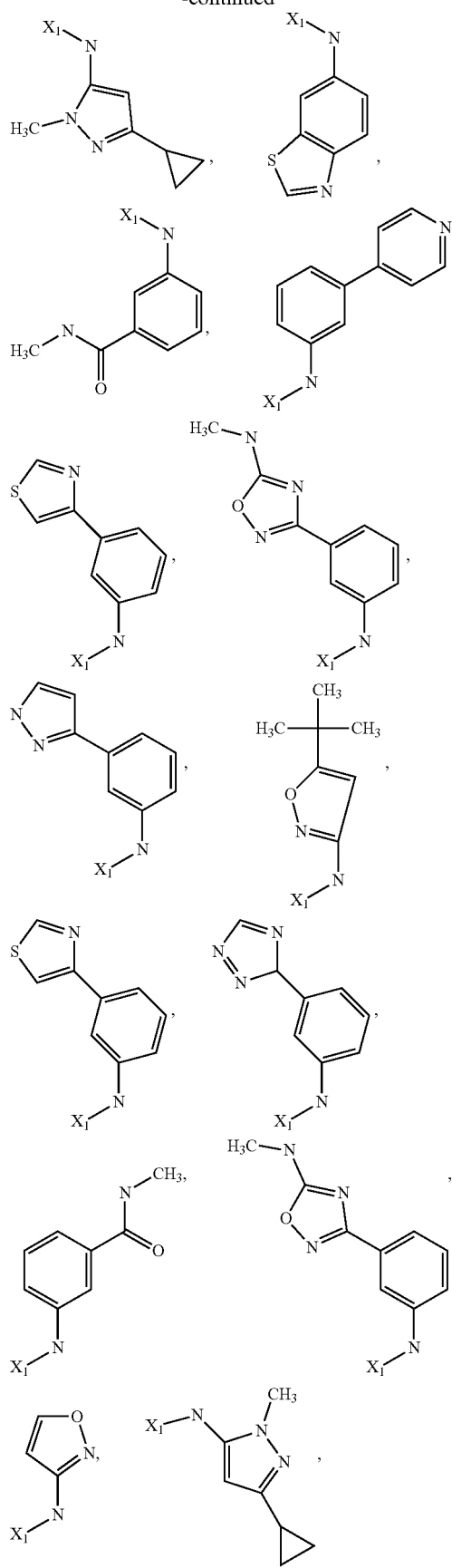
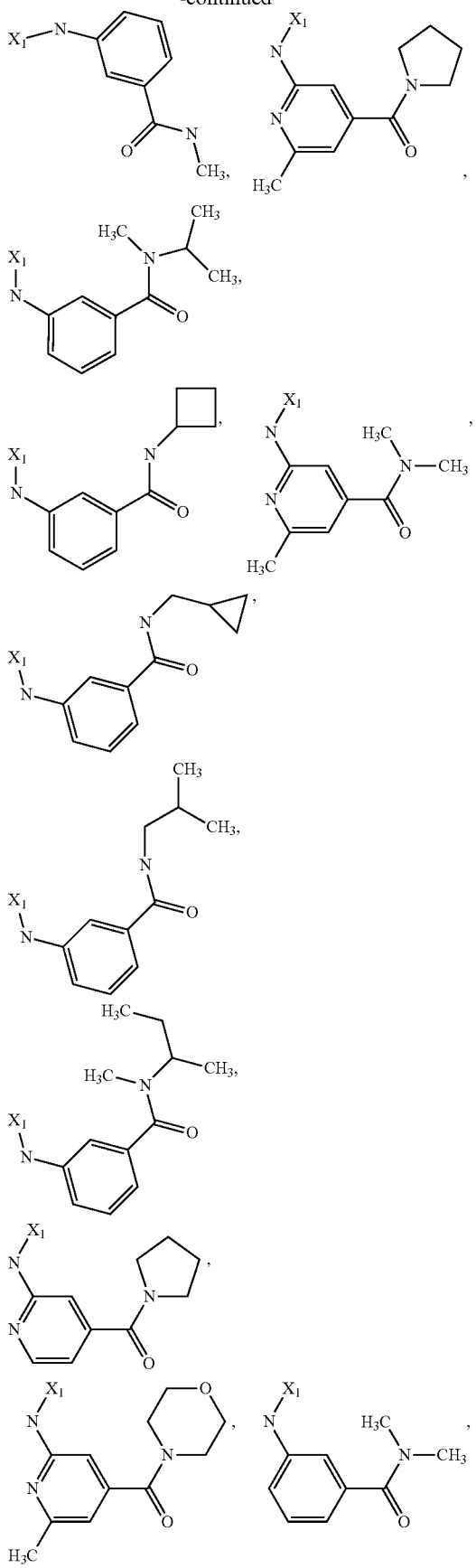

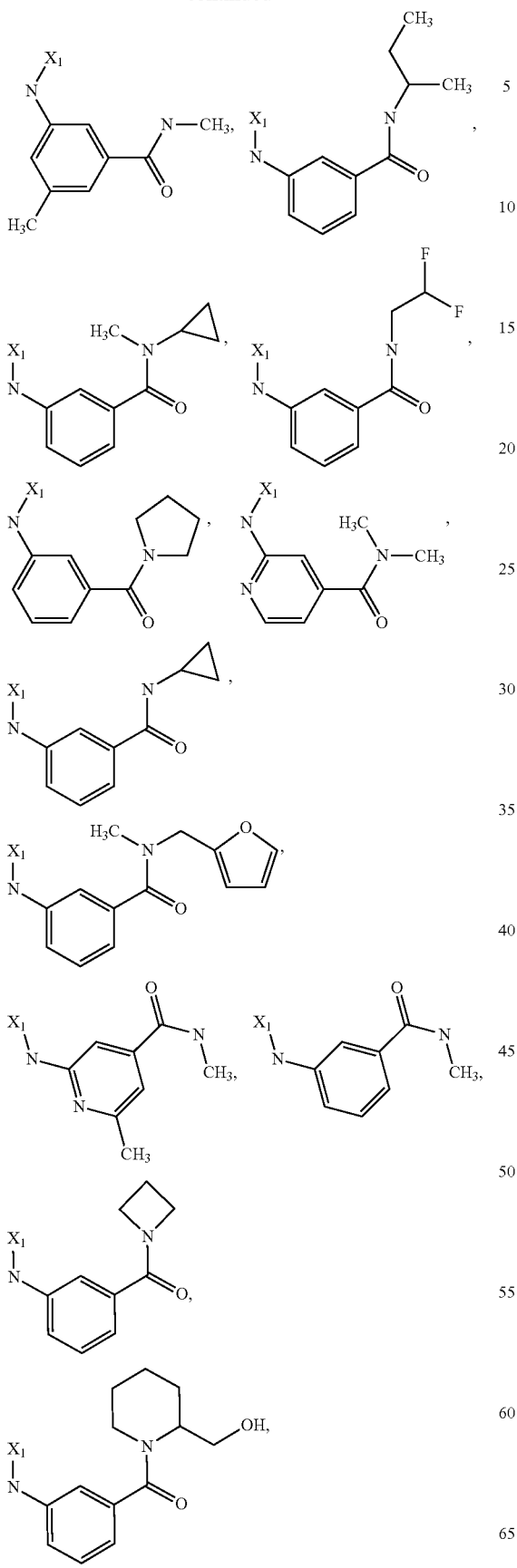
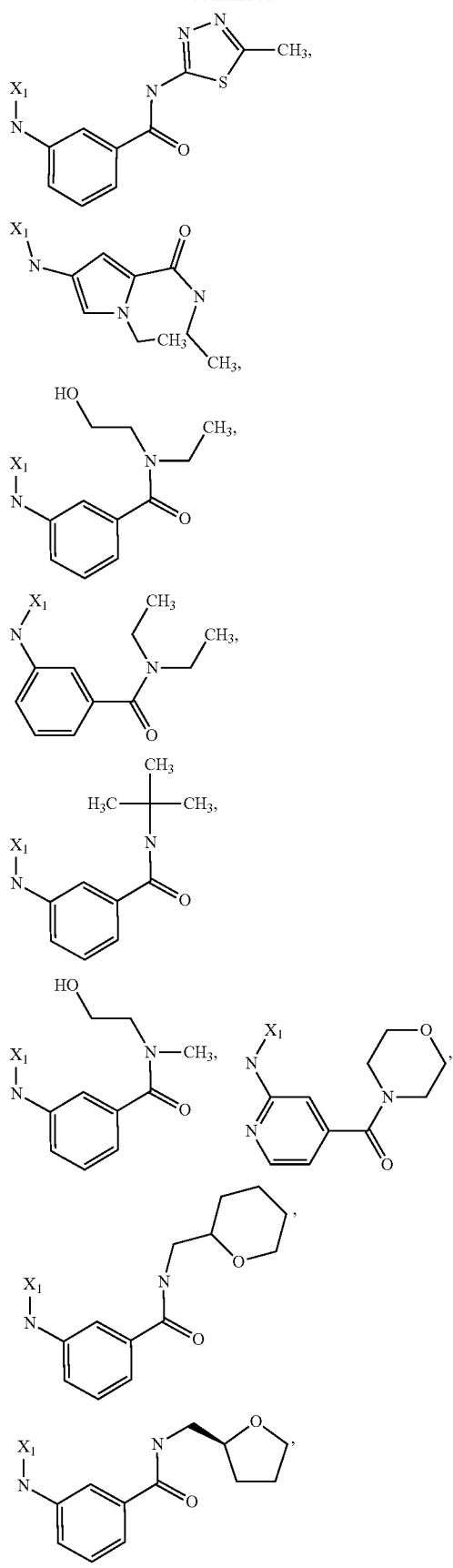

-continued
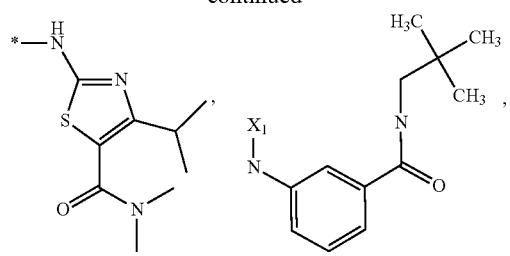
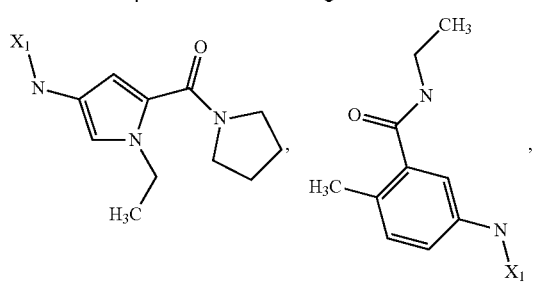
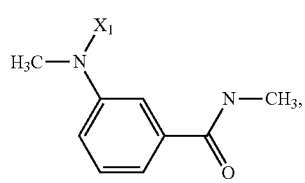
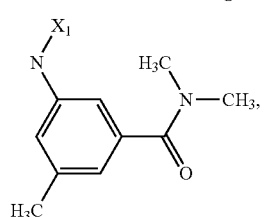
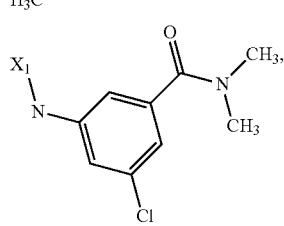
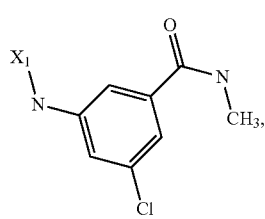
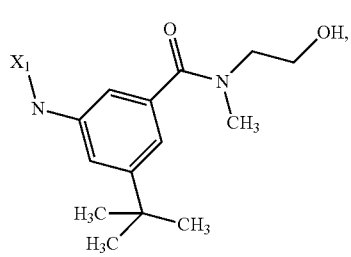
-continued
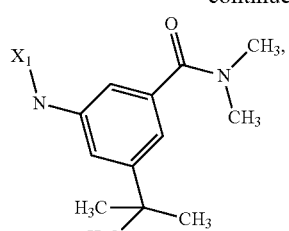
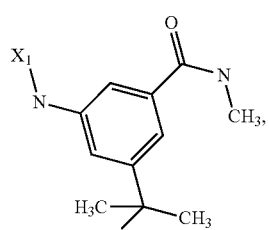
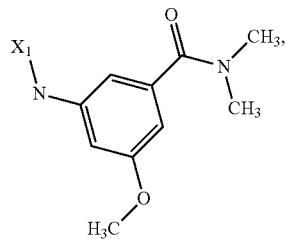
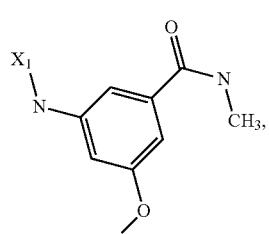
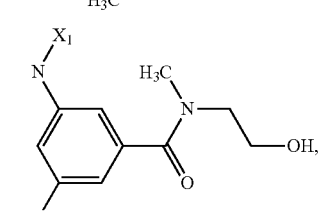
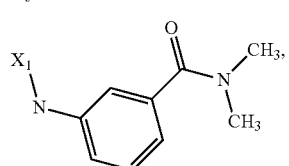
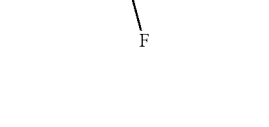

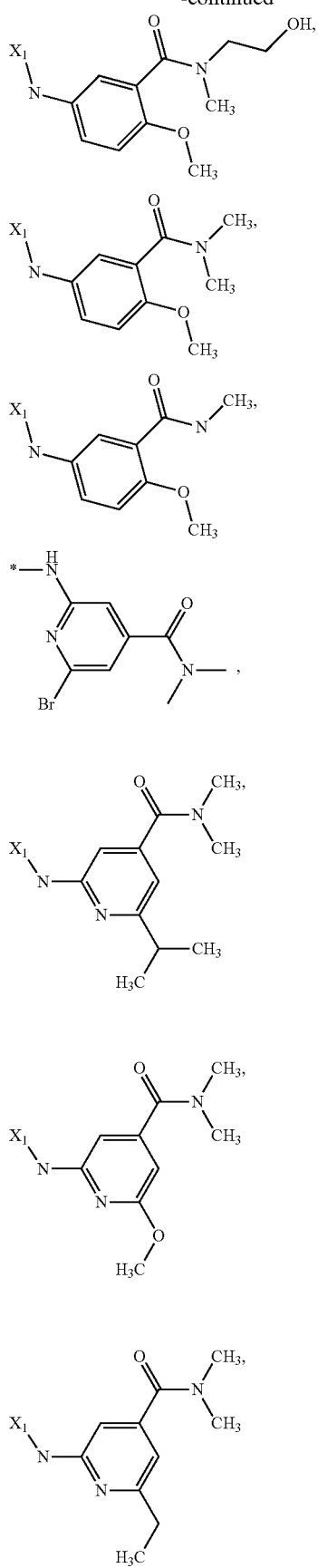

-continued
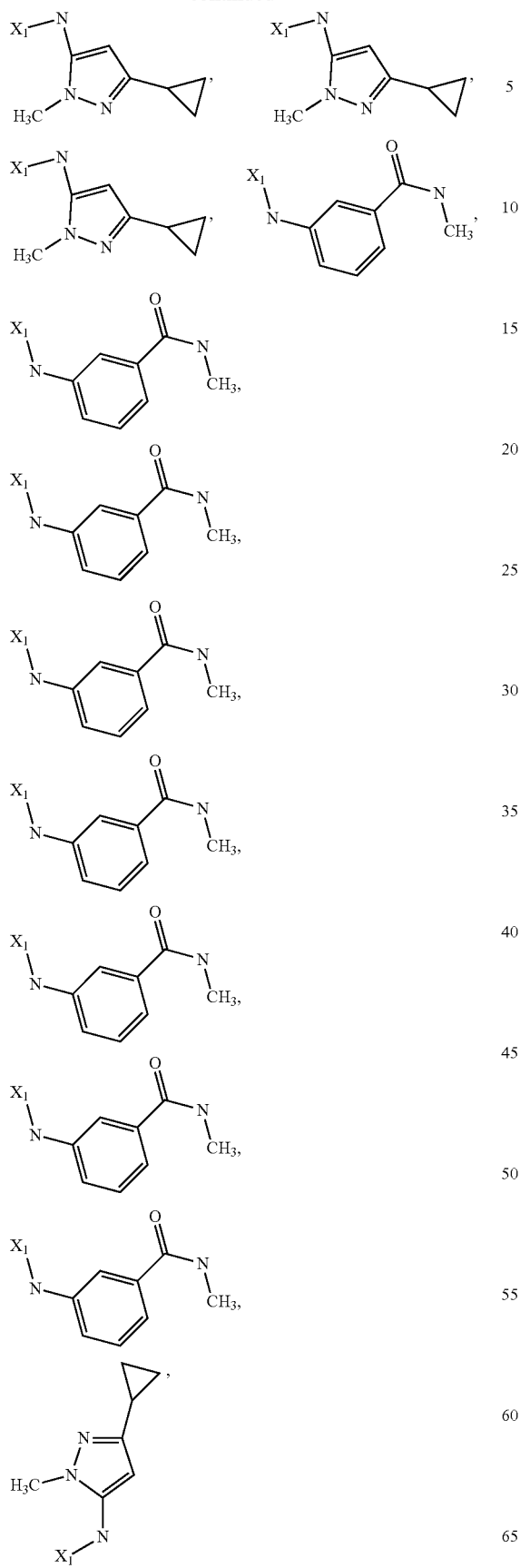
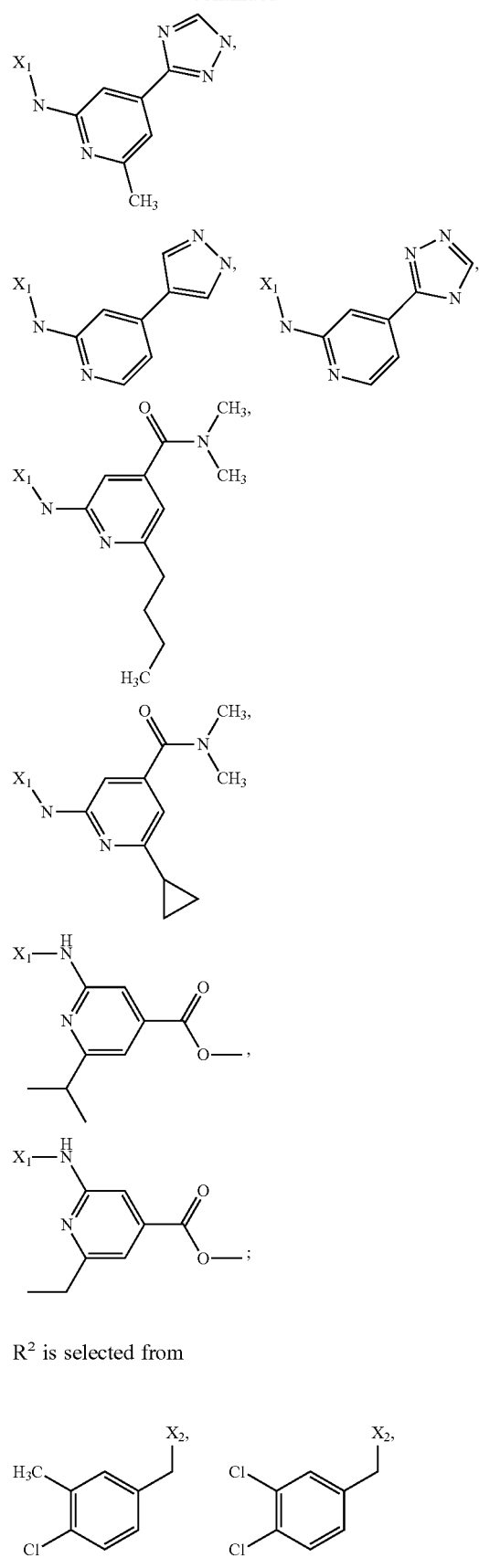
R² is selected from
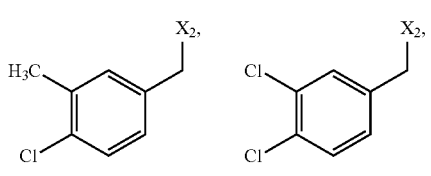

-continued
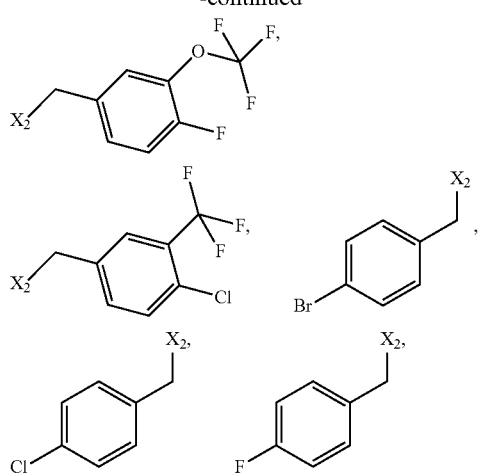
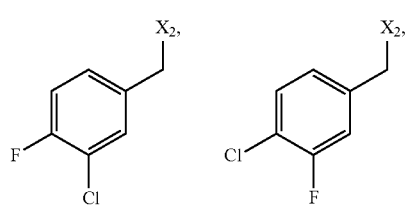
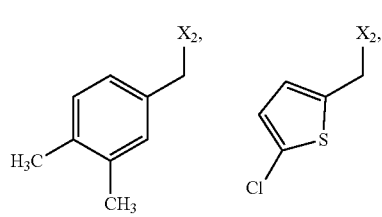
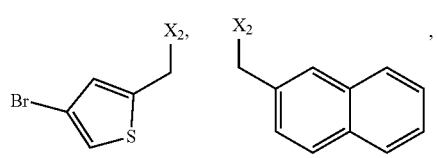
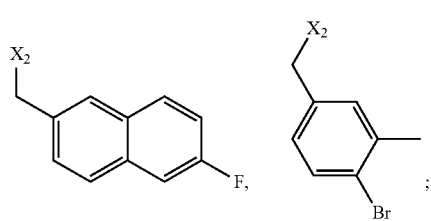
R³ is H;
R⁴ is H;
or R³ and R⁴ together are forming a CH₂—CH₂ group.
8. The method of clause 1 or 2 wherein the compound of formula 1 administered is
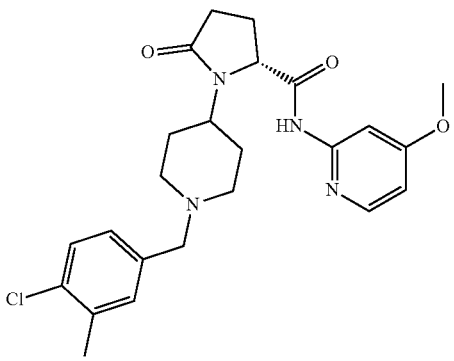 [SMILES: COc1ccnc(NC(=O)[C@H]2CCC(=O)N2C2CCN(Cc3ccc(Cl)c(C)c3)CC2)c1]
9. The method of clause 1 or 2 wherein the compound of formula 1 administered is
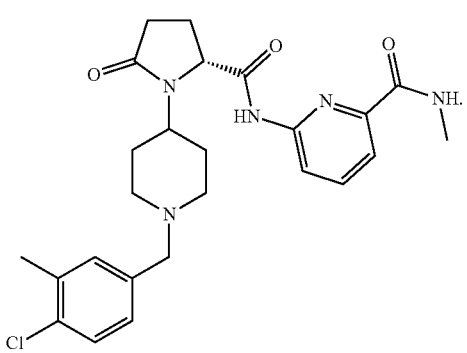
10. The method of clause 1 or 2 wherein the compound of formula 1 administered is
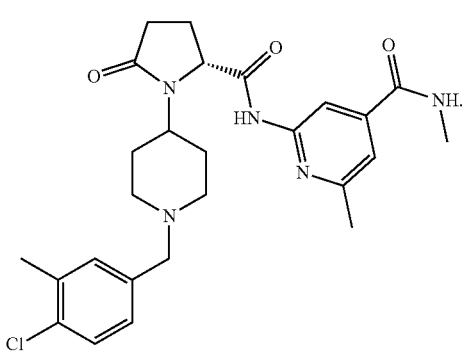
11. The method of clause 1 or 2 wherein the compound of formula 1 administered is 12. The method of clause 1 or 2 wherein the compound of formula 1 administered is

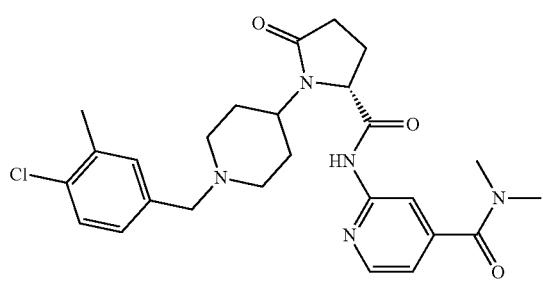 [SMILES: Cc1cc(CN2CCC(N3C(=O)CC[C@@H]3C(=O)Nc3cc(C(=O)N(C)C)ccn3)CC2)ccc1Cl]

13. The method of clause 1 or 2 wherein the compound of formula 1 administered is

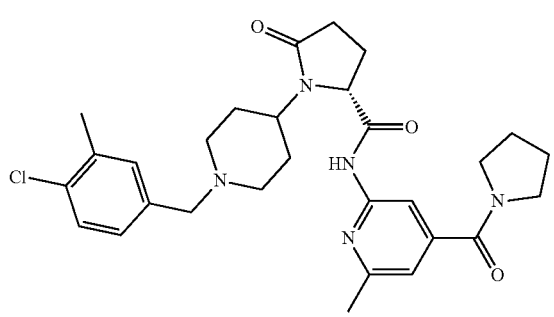 [SMILES: Cc1cc(C(=O)N2CCCC2)cc(NC(=O)[C@H]2CCC(=O)N2C2CCN(Cc3ccc(Cl)c(C)c3)CC2)n1]

14. The method of clause 1 or 2 wherein the compound of formula 1 administered is

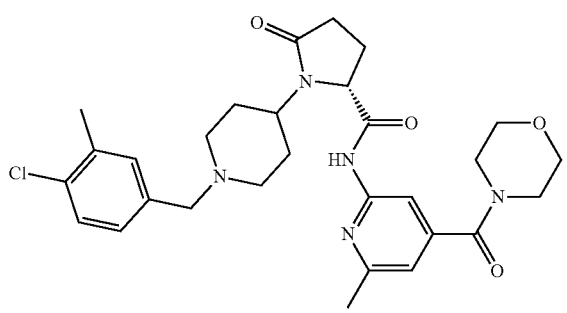 [SMILES: Cc1cc(C(=O)N2CCOCC2)cc(NC(=O)[C@H]2CCC(=O)N2C2CCN(Cc3ccc(Cl)c(C)c3)CC2)n1]

15. The method of clause 1 or 2 wherein the compound of formula 1 administered is 16. The method of clause 1 or 2 wherein the compound of formula 1 administered is

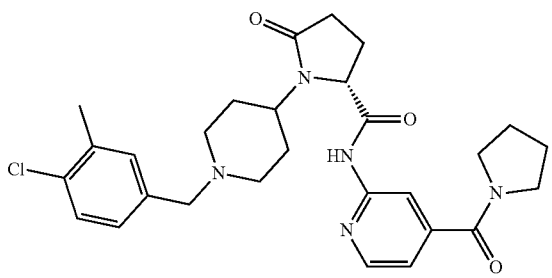 [SMILES: Cc1cc(CN2CCC(N3C(=O)CC[C@@H]3C(=O)Nc3cc(C(=O)N4CCCC4)ccn3)CC2)ccc1Cl]

17. The method of clause 1 or 2 wherein the compound of formula 1 administered is

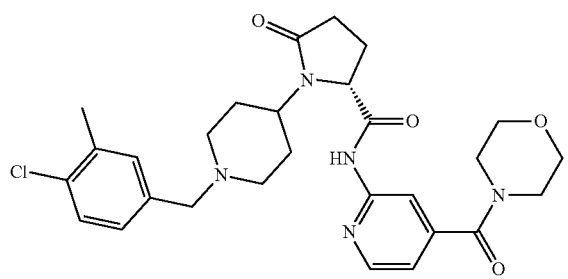 [SMILES: Cc1cc(CN2CCC(N3C(=O)CC[C@@H]3C(=O)Nc3cc(C(=O)N4CCOCC4)ccn3)CC2)ccc1Cl]

18. The method of clause 1 or 2 wherein the compound of formula 1 administered is

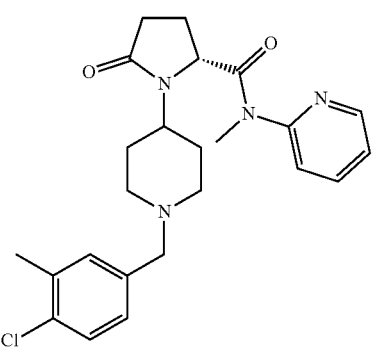 [SMILES: Cc1cc(CN2CCC(N3C(=O)CC[C@@H]3C(=O)N(C)c3ccccn3)CC2)ccc1Cl]

19. The method of clause 1 or 2 wherein the compound of formula 1 administered is

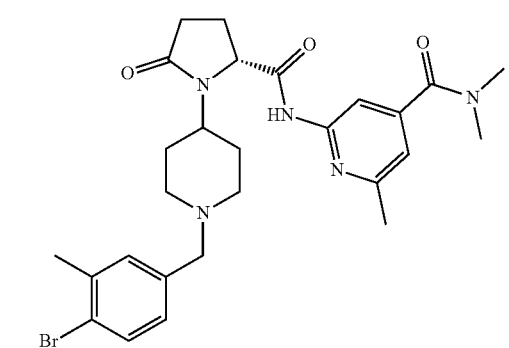

20. The method of clause 1 or 2 wherein the compound of formula 1 administered is

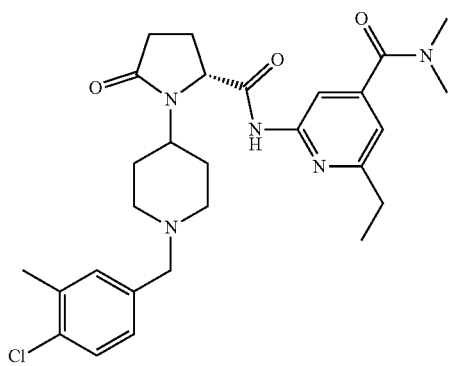

21. The method of clause 1 or 2 wherein the compound of formula 1 administered is

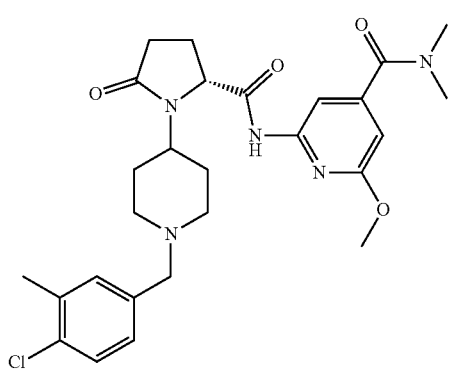

22. The method of clause 1 or 2 wherein the compound of formula 1 administered is 23. The method of clause 1 or 2 wherein the compound of formula 1 administered is

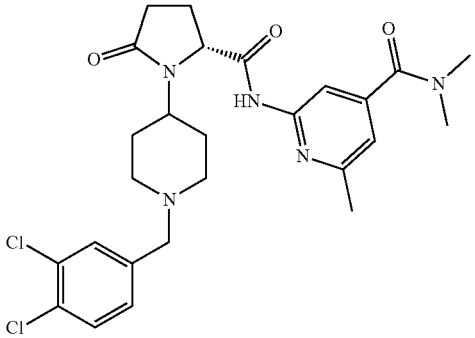 [SMILES: Cc1cc(C(=O)N(C)C)cc(NC(=O)[C@H]2CCC(=O)N2C2CCN(Cc3ccc(Cl)c(Cl)c3)CC2)n1]

24. The method of clause 1 or 2 wherein the compound of formula 1 administered is

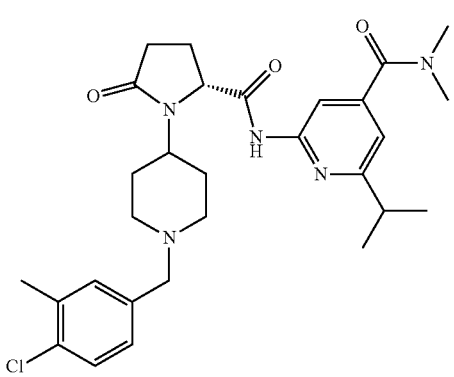

25. The method of clause 1 or 2 wherein the compound is a co-crystal of formula

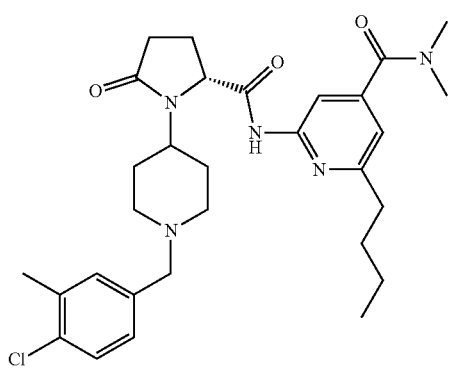

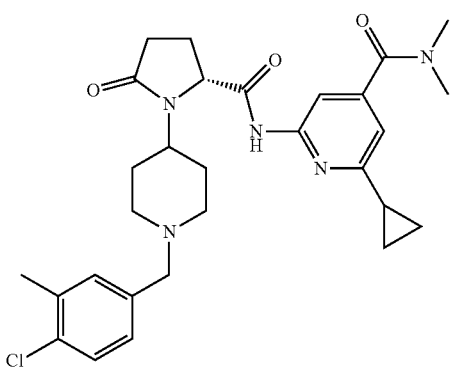

187

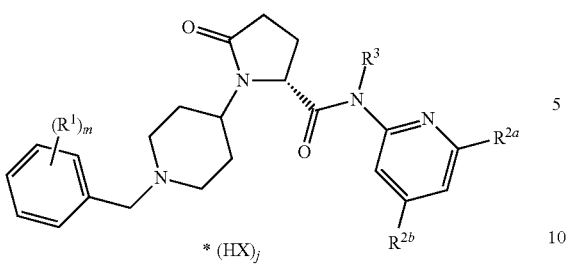

wherein
$R^1$ is $C_{1-6}$-alkyl, $C_{1-6}$-haloalkyl, O—$C_{1-6}$-haloalkyl, halogene;
m is 1, 2 or 3;
$R^{2a}$ and $R^{2b}$ are each independently selected from H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, $CONR^{2b.1}R^{2b.2}$, halogene;
$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
$R^3$ is H, $C_{1-6}$-alkyl;
X is an anion selected from the group consisting of chloride, bromide, iodide, sulphate, phosphate, methanesulphonate, nitrate, maleate, acetate, benzoate, citrate, salicylate, fumarate, tartrate, dibenzoyltartrate, oxalate, succinate, benzoate and p-toluenesulphonate;
j is 0, 0.5, 1, 1.5 or 2;
with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-napthoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, glycine.

26. The method of clause 1 or 2 wherein the compound is a co-crystal of formula

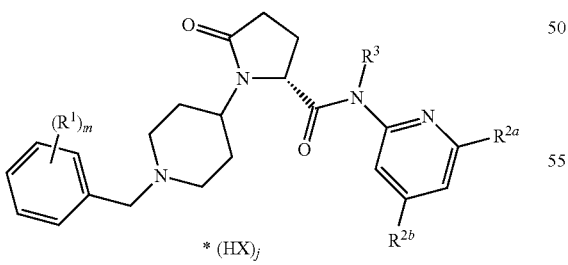

$R^{2a}$ is H, $C_{1-6}$-alkyl, $C_{1-6}$-alkenyl, $C_{1-6}$-alkynyl, $C_{3-6}$-cycloalkyl, O—$C_{1-6}$-alkyl, $CONR^{2a.1}R^{2a.2}$;
$R^{2a.1}$ is H, $C_{1-6}$-alkyl, $C_{1-6}$-haloalkyl;
$R^{2a.2}$ is H, $C_{1-6}$-alkyl;
$R^{2b}$ is H, $C_{1-6}$-alkyl, $C_{1-6}$-alkenyl, $C_{1-6}$-alkynyl, $C_{3-6}$-cycloalkyl, COO—$C_{1-6}$-alkyl, O—$C_{1-6}$-alkyl, $CONR^{2b.1}R^{2b.2}$, halogene;

188

$R^{2b.1}$ is H, $C_{1-6}$-alkyl, $C_{0-4}$-alkyl-$C_{3-6}$-cycloalkyl, $C_{1-6}$-haloalkyl;
$R^{2b.2}$ is H, $C_{1-6}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom.

27. The method of clause 1 or 2 wherein the compound is a co-crystal of formula

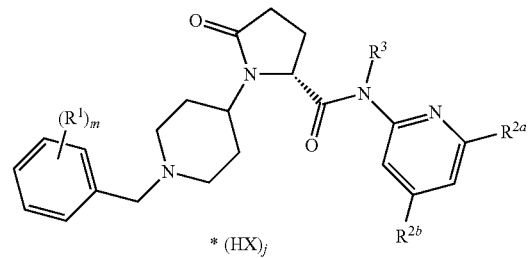

$R^1$ is $C_{1-6}$-alkyl, $C_{1-6}$-haloalkyl, O—$C_{1-6}$-haloalkyl, halogen;
m is 1 or 2;
$R^{2a}$ is H, $C_{1-4}$-alkyl;
$R^{2b}$ is H, $CONR^{2b.1}R^{2b.2}$;
$R^{2b.1}$ is $C_{1-4}$-alkyl, $C_{0-4}$-alkyl-$C_{3-6}$-cycloalkyl, $C_{1-4}$-haloalkyl;
$R^{2b.2}$ is H, $C_{1-4}$-alkyl;
or $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom
$R^3$ is H, $C_{1-6}$-alkyl;
X is an anion selected from the group consisting of chloride or dibenzoyltartrate
j is 1 or 2.

28. The method of clause 1 or 2 wherein the compound is a co-crystal of formula

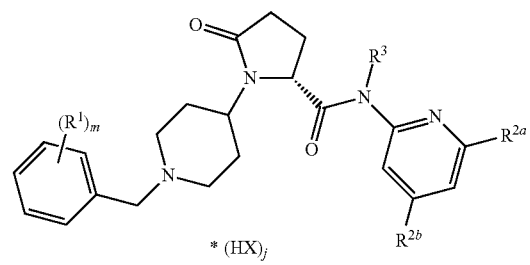

$R^{2a}$ is H, $C_{1-4}$-alkyl;
$R^{2b}$ is H, $CONR^{2b.1}R^{2b.2}$;
$R^{2b.1}$ is $C_{1-4}$-alkyl;
$R^{2b.2}$ is $C_{1-4}$-alkyl.

29. The method of clause 1 or 2 wherein the compound is a co-crystal of formula

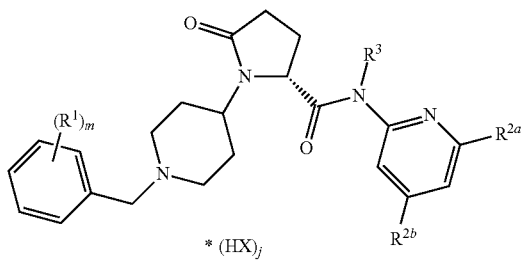

* (HX)$_j$ $R^{2a}$ is H, $C_{1-4}$-alkyl;
$R^{2b}$ is H, $CONR^{2b.1}R^{2b.2}$;
$R^{2b.1}$ is $C_{0-4}$-alkyl-$C_{3-6}$-cycloalkyl;
$R^{2b.2}$ is H, $C_{1-4}$-alkyl.

30. The method of clause 1 or 2 wherein the compound is a co-crystal of formula

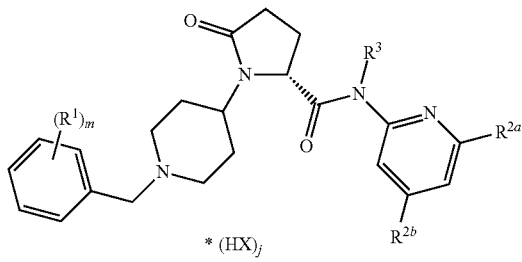

* (HX)$_j$ $R^{2a}$ is H, $C_{1-4}$-alkyl;
$R^{2b}$ is H, $CONR^{2b.1}R^{2b.2}$;
$R^{2b.1}$ is $C_{1-4}$-haloalkyl;
$R^{2b.2}$ is H, $C_{1-4}$-alkyl.

31. The method of clause 1 or 2 wherein the compound is a co-crystal of the formula according to clause 25, wherein $R^{2b.1}$ and $R^{2b.2}$ are together a $C_{3-6}$-alkylene group forming with the nitrogen atom a heterocyclic ring, wherein optionally one carbon atom or the ring is replaced by an oxygen atom.

32. The method of clause 1 or 2 wherein the compound is a co-crystal having the formula shown below,

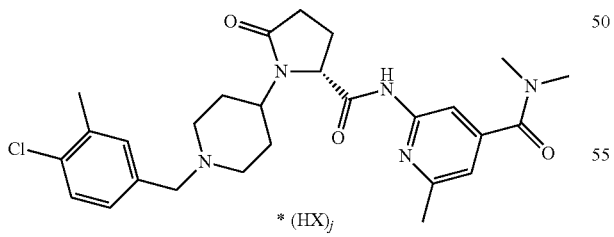

* (HX)$_j$ wherein j is 0,
and the co-crystal former is selected from the group consisting of L-(+)-ascorbic acid, mucic acid, pamoic acid, nicotinic acid, succinamide, nicotinamide, isonicotinamide, L-lysine, and L-proline.

33. The method of clause 1 or 2 wherein the compound is a crystalline salt of the formula below,

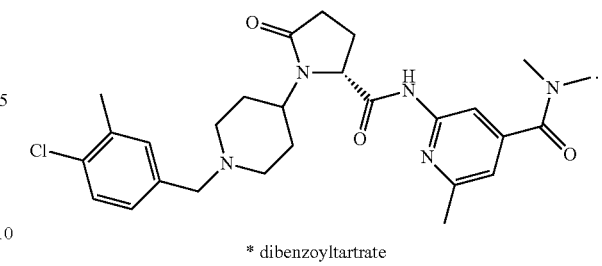

* dibenzoyltartrate

34. The method of clause 1 or 2 wherein the compound is a crystalline salt of the formula below,

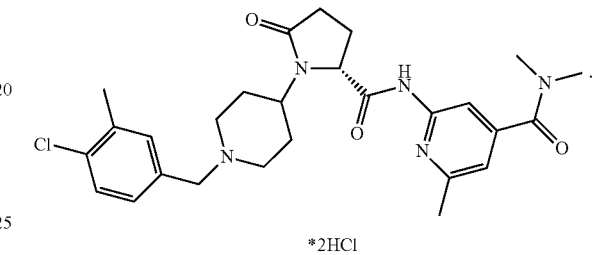

*2HCl

35. The method of clause 33 wherein the crystalline salt is characterized in that the four highest X-ray powder diffraction peaks occur at 3.72, 13.60, 16.89, and 19.34 degrees 2Θ (±0.05 degrees 2Θ) when measured using CuKα radiation.

36. The method of clause 34 wherein the crystalline salt is characterized in that the four highest X-ray powder diffraction peaks occur at 16.02, 16.86, 19.45, and 19.71 degrees 2Θ (±0.05 degrees 2Θ) when measured using CuKα radiation.

37. The method of clause 1 or 2 wherein the compound comprises at least one co-crystal of a compound of the formula according to clause 25 and a pharmaceutically acceptable carrier.

38. The method of clause 1 or 2 wherein the compound of formula 1 is administered in the form of the individual optical isomers, a mixture of the individual enantiomers, a racemate or in the form of the enantiomerically pure compounds.

39. The method of clause 1 or 2 wherein the compound is a pharmaceutical composition comprising as an active ingredient one or more compounds of the formula below,

1

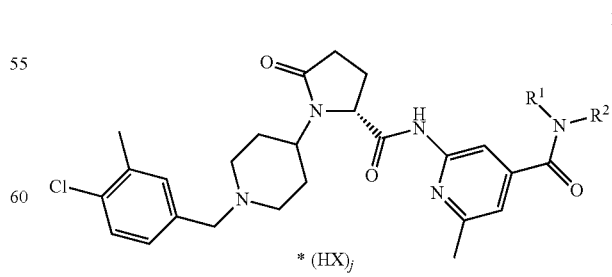

* (HX)$_j$ wherein
$R^1$ is H, $C_{1-6}$-alkyl, $C_{0-4}$-alkyl-$C_{3-6}$-cycloalkyl, $C_{1-6}$-haloalkyl;

$R^2$ is H, $C_{1-6}$-alkyl;

X is an anion selected from the group consisting of chloride or ½ dibenzoyltartrate j is 1 or 2, a first diluent, a second diluent, a binder, a disintegrant and a lubricant.

40. The method of clause 39 wherein $R^1$ is H, Methyl;

$R^2$ is H, Methyl;

X is an anion selected from the group consisting of chloride or ½ dibenzoyltartrate;

j is 1 or 2

41. The method of clause 39 wherein X is chloride and j is 2.

42. The method of clause 39, 40, or 41 wherein the pharmaceutical composition further comprises an additional disintegrant.

43. The method of clause 39, 40, or 41 wherein the pharmaceutical composition further comprises an additional glidant.

44. The method of clause 39, 40, or 41 wherein the diluent of the pharmaceutical composition further comprises cellulose powder, dibasic calciumphosphatae anhydrous, dibasic calciumphosphate dehydrate, erythritol, low substituted hydroxypropyl cellulose, mannitol, pregelantinized starch, or xylitol.

45. The method of clause 39, 40, or 41 wherein the lubricant of the pharmaceutical composition is talc, polyethyleneglycol, calcium behenate, calcium stearate, hydrogenated castor oil or magnesium stearate.

46. The method of clause 39, 40, or 41 wherein the binder of the pharmaceutical composition is copovidone (co-polymerisates of vinylpyrrolidon with other vinylderivates), hydroxypropyl methylcellulose (HPMC), hydroxypropylcellulose (HPC) or polyvinylpyrrolidon (Povidone).

47. The method of clause 39, 40, 41, 42, 43, 44, 45, or 46 wherein the distintegrant of the pharmaceutical composition according to clause is corn starch.

48. The method of clause 39, 40, 41, 42, 43, 44, 45, 46, or 47 wherein the optional glidant of the pharmaceutical composition is colloidal silicon dioxide.

49. The method of clause 39 wherein the pharmaceutical composition further comprises

| | |
|---|---|
| 10-90% | active ingredient |
| 5-70% | diluent 1, |
| 5-30% | diluent 2, |
| 0-30% | binder, |
| 1-12% | disintegrant, and |
| 0.1-3% | lubricant. |

50. The method of clause 39 wherein the pharmaceutical composition further comprises

| | |
|---|---|
| 30-70% | active ingredient |
| 20-75% | diluent 1, |
| 5-30% | diluent 2, |
| 2-30% | binder, |
| 0.5-20% | buffering agent, |
| 1-12% | disintegrant, and |
| 0.1-3% | lubricant. |

51. The method of clause 42 wherein the additional disintegrant of the pharmaceutical composition is crospovidone.

52. The method of clause 39 wherein the pharmaceutical composition is in the dosage form of a capsule, a tablet, or a film-coated tablet.

53. The method of clause 52 wherein the pharmaceutical composition further comprises a 2-4% film coat.

54. The method of clause 53 wherein the film coat comprises a film-forming agent, a plasticizer, a glidant, and optionally one or more pigments.

55. The method of clause 54 wherein the film coat comprises Polyvinyl alcohol (PVA) or hydroxypropylmethylcellulose (HPMC), polyethylene glycol (PEG), talc, titanium dioxide and iron oxide.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A method of treating an aging-associated-neuronal loss, an aging-associated-memory impairment, or an aging-associated-loss of motor coordination in a subject diagnosed with the aging-associated-neuronal loss, the aging-associated-memory impairment, or the aging-associated-loss of motor coordination, the method comprising systemically administering a therapeutically effective amount of a pharmaceutical composition comprising, as an active ingredient, a compound of formula 3, a salt, a co-crystal, an optical isomer, a mixture of enantiomers, a racemate, or an enantiomerically pure form thereof,

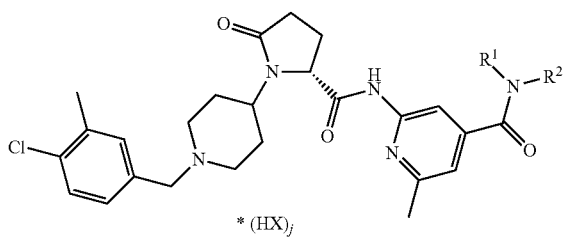

3 wherein
R$^1$ is H, C$_{1-6}$-alkyl, C$_{0-4}$-alkyl-C$_{3-6}$-cycloalkyl, or C$_{1-6}$-haloalkyl;
R$^2$ is H, or C$_{1-6}$-alkyl;
X is an anion selected from the group consisting of chloride and dibenzoyltartrate; and
j is 1 when X is dibenzoyltartrate or 2 when X is chloride;
to treat the subject for the aging-associated-neuronal loss, the aging-associated-memory impairment, or the aging-associated-loss of motor coordination,
wherein the therapeutically effective amount of the pharmaceutical composition produces in the cerebrospinal fluid of the subject the concentration of the compound of formula 3 of below 10 nM.

2. The method of claim 1 wherein the compound of formula 3 is a co-crystal with a co-crystal former selected from the group consisting of orotic acid, hippuric acid, L-pyroglutamic acid, D-pyroglutamic acid, nicotinic acid, L-(+)-ascorbic acid, saccharin, piperazine, 3-hydroxy-2-naphtoic acid, mucic (galactaric) acid, pamoic (embonic) acid, stearic acid, cholic acid, deoxycholic acid, nicotinamide, isonicotinamide, succinamide, uracil, L-lysine, L-proline, D-valine, L-arginine, and glycine.

3. The method of claim 1 wherein the compound is a crystalline salt of the formula below,

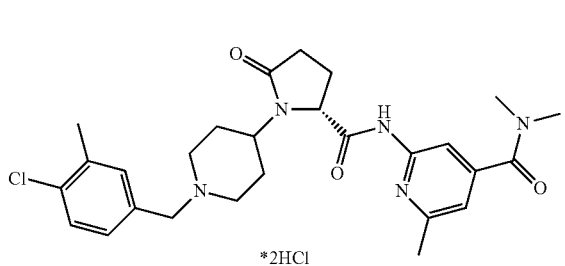

4. The method of claim 1 wherein the composition further comprises a pharmaceutically acceptable carrier.

5. The method of claim 1 wherein the compound of formula 3 is an optical isomer, a mixture of enantiomers, a racemate, or an enantiomerically pure form.

6. The method of claim 1 wherein the pharmaceutical composition further comprises, a diluent, a binder, a disintegrant and a lubricant.

7. The method of claim 6 wherein the pharmaceutical composition further comprises an additional disintegrant.

8. The method of claim 6 wherein the pharmaceutical composition further comprises a glidant.

9. The method of claim 6 wherein the diluent of the pharmaceutical composition comprises cellulose powder, dibasic calciumphosphatae anhydrous, dibasic calciumphosphate dehydrate, erythritol, low substituted hydroxypropyl cellulose, mannitol, pregelantinized starch, or xylitol.

10. The method of claim 1, comprising treating an aging-associated-neuronal loss.

11. The method of claim 1, comprising treating an aging-associated-memory impairment.

12. The method of claim 1, comprising treating an aging-associated-loss of motor coordination.

13. The method of claim 1 wherein the compound acts peripherally to treat the subject for the aging-associated-neuronal loss, the aging-associated-memory impairment, or the aging-associated-loss of motor coordination.

14. The method of claim 1 wherein the subject has Alzheimer's disease (AD).

15. The method of claim 1 wherein the therapeutically effective amount of the pharmaceutical composition produces in the plasma of the subject the concentration of the compound of formula 3 of about 350 nM.

16. The method of claim 1 wherein the therapeutically effective amount of the pharmaceutical composition produces in the plasma of the subject the concentration of the compound of formula 3 that is more than thirty times higher than the concentration of the compound of formula 3 in the cerebrospinal fluid of the subject.

* * * * *

UNITED STATES PATENT AND TRADEMARK OFFICE
CERTIFICATE OF CORRECTION

PATENT NO. : 11,382,907 B2
APPLICATION NO. : 15/945664
DATED : July 12, 2022
INVENTOR(S) : Braithwaite et al.

It is certified that error appears in the above-identified patent and that said Letters Patent is hereby corrected as shown below:

In the Specification

Please replace "3-hydroxy-2-napthoic" with -- 3-hydroxy-2-naphtoic -- (Column 97, Line 61);

Please replace "butadiene" with -- betadine -- (Column 142, Line 6);

Please replace "N" in the chemical structure with -- HN -- (Column 169, Line 23); and Please replace "3-hydroxy-2-napthoic" with -- 3-hydroxy-2-naphtoic -- (Column 187, Lines 40-41).

Signed and Sealed this
Twentieth Day of September, 2022

Katherine Kelly Vidal
*Director of the United States Patent and Trademark Office*